US008273900B2

(12) United States Patent
Beattie et al.

(10) Patent No.: US 8,273,900 B2
(45) Date of Patent: *Sep. 25, 2012

(54) ORGANIC COMPOUNDS

(75) Inventors: David Beattie, Horsham (GB);
Anny-Odile Colson, Horsham (GB);
Andrew James Culshaw, Horsham (GB); Lisa Sharp, Horsham (GB);
Emily Stanley, Horsham (GB); Lilya Sviridenko, Horsham (GB)

(73) Assignee: Novartis AG, Basel (CH)

( * ) Notice: Subject to any disclaimer, the term of this patent is extended or adjusted under 35 U.S.C. 154(b) by 252 days.

This patent is subject to a terminal disclaimer.

(21) Appl. No.: 12/462,318

(22) Filed: Jul. 31, 2009

(65) Prior Publication Data

US 2010/0035898 A1    Feb. 11, 2010

(30) Foreign Application Priority Data

Aug. 7, 2008   (EP) .................................... 08162006
Jan. 14, 2009  (EP) .................................... 09150543

(51) Int. Cl.
*C07D 231/00* (2006.01)
(52) U.S. Cl. .................................. 548/356.1
(58) Field of Classification Search ................ 548/356.1
See application file for complete search history.

(56) References Cited

U.S. PATENT DOCUMENTS

| 7,491,720 | B2 | 2/2009 | Ohkubo et al. |
| 2003/0069261 | A1 | 4/2003 | Marzabadi et al. |
| 2003/0096843 | A1 | 5/2003 | Moriyama et al. |
| 2004/0038855 | A1 | 2/2004 | Salon et al. |
| 2009/0298834 | A1* | 12/2009 | Pajouhesh et al. ......... 514/237.5 |

FOREIGN PATENT DOCUMENTS

| DE | 2828265 | 1/1980 |
| DE | 3600288 | 7/1987 |
| DE | 3618004 | 12/1987 |
| EP | 370498 | 5/1990 |
| EP | 502595 | 9/1992 |
| EP | 524439 | 1/1993 |
| EP | 641781 | 3/1995 |
| EP | 1034793 | 9/2000 |
| EP | 1163910 | 12/2001 |
| EP | 1174150 | 1/2002 |
| EP | 1177796 | 2/2002 |
| EP | 1217000 | 6/2002 |
| EP | 1295607 | 3/2003 |
| EP | 1378247 | 1/2004 |
| EP | 1 403 255 | 3/2004 |
| EP | 1 464 335 | 3/2004 |
| EP | 1489078 | 12/2004 |
| EP | 1775298 | 4/2007 |
| EP | 1813609 | 8/2007 |
| GB | 1494695 | 12/1977 |
| JP | 3218356 | 9/1991 |
| JP | 4273821 | 9/1992 |
| JP | 8041006 | 2/1996 |
| JP | 2004203748 | 7/2004 |
| JP | 2004238296 | 8/2004 |
| JP | 2004315511 | 11/2004 |
| JP | 2005120080 | 5/2005 |
| JP | 2006124387 | 5/2006 |
| JP | 2007091649 | 4/2007 |
| JP | 2007291087 | 11/2007 |
| WO | WO 93/11731 | 6/1993 |
| WO | WO 98/00401 | 1/1998 |
| WO | WO 99/67203 | 12/1999 |
| WO | WO 99/67206 | 12/1999 |
| WO | WO 01/32634 | 5/2001 |
| WO | WO 01/54731 | 8/2001 |
| WO | WO 01/55132 | 8/2001 |
| WO | WO 01/62718 | 8/2001 |
| WO | WO 02/00650 | 1/2002 |
| WO | WO 02/14267 | 2/2002 |
| WO | WO 02/44126 | 6/2002 |
| WO | WO 03/028641 | 4/2003 |
| WO | WO 03/055866 | 7/2003 |
| WO | WO 03/057212 | 7/2003 |
| WO | WO 03/104233 | 12/2003 |
| WO | WO 2004/046136 | 6/2004 |
| WO | WO 2004/050634 | 6/2004 |
| WO | WO 2004/054581 | 7/2004 |
| WO | WO 2004/062601 | 7/2004 |
| WO | WO 2005/028427 | 3/2005 |
| WO | WO 2005/044797 | 5/2005 |
| WO | WO 2005/077932 | 8/2005 |
| WO | WO 2005/095357 | 10/2005 |
| WO | WO 2006/012226 | 2/2006 |
| WO | WO 2006/014482 | 2/2006 |
| WO | WO 2006/023844 | 3/2006 |
| WO | WO 2006/034341 | 3/2006 |
| WO | WO 2006/035967 | 4/2006 |
| WO | WO 2006035967 | * 4/2006 |
| WO | WO 2006/123257 | 11/2006 |

(Continued)

OTHER PUBLICATIONS

Lanier et al. Expert Opinion, Therapeutic Patents 2002, 12(11), 1619-1630.*
Dorwald F. A. Side Reactions in Organic Synthesis, 2005, Wiley: VCH, Weinheim p. IX of Preface p. 1-15.*
Marion Lanier and John P. Williams, "Small Molecule Corticotropin-Releasing Factor Antagonists" Expert Opinon 12(11):1619-1630.
Yoshiisa Sekiguchi et al., Chem Abstracts Service XP002532271.
Yoshiisa Sekiguchi et al., Chem Abstracts Service XP002509906.
A. Banfi et al., "Synthesis of Rigid Analogues of (D,L)-Arginine Methyl Ester with Antiarrhythmic Activity" Synthetic Communications 19(9-10):1787-1799, 1989.

*Primary Examiner* — Nizal Chandrakumar

(74) *Attorney, Agent, or Firm* — Michael G. Smith

(57) ABSTRACT

There are described cyclohexyl amide derivatives useful as corticotropin releasing factor ($CRF_1$) receptor antagonists.

11 Claims, No Drawings

FOREIGN PATENT DOCUMENTS

| | | |
|---|---|---|
| WO | WO 2006/129199 | 12/2006 |
| WO | WO 2007/063839 | 6/2007 |
| WO | WO 2007/079930 | 7/2007 |
| WO | WO 2007/083689 | 7/2007 |
| WO | WO 2008/002671 | 1/2008 |
| WO | WO 2008/062878 | 5/2008 |
| WO | WO 2008/065500 | 6/2008 |
| WO | WO 2008/073670 | 6/2008 |
| WO | WO 2008/079277 | 7/2008 |
| WO | WO 2008/124000 | 10/2008 |
| WO | WO 2008/154642 | 12/2008 |
| WO | WO 2009/129501 | 10/2009 |
| WO | WO 2009/132136 | 10/2009 |
| WO | WO 2009/138386 | 11/2009 |
| WO | WO 2009/146539 | 12/2009 |
| WO | WO 2009/151800 | 12/2009 |
| WO | WO 2009/153720 | 12/2009 |
| WO | WO 2009/155001 | 12/2009 |
| WO | WO 2010/025043 | 3/2010 |
| WO | WO 2010/048149 | 4/2010 |
| WO | WO 2010/051188 | 5/2010 |
| WO | WO 2010/085246 | 7/2010 |
| WO | WO 2010/092962 | 8/2010 |

* cited by examiner

ORGANIC COMPOUNDS

FIELD OF THE INVENTION

The present invention relates to cyclohexyl amide derivatives, their preparation, their use as pharmaceuticals and pharmaceutical compositions containing them. More particularly the present invention relates to their use as corticotropin releasing factor (CRF-1) receptor antagonists.

SUMMARY OF THE INVENTION

In a first aspect of the invention we provide a compound of formula I;

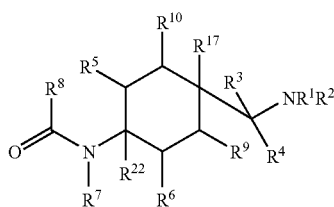

I in which $R^1$ is $-(CH_2)_n(SO_2)_mR^x$;

$R^x$ is phenyl, biphenyl, naphthyl or heteroaryl, each of which may be optionally substituted by one or more substituents selected from the group alkyl C1 to 10, alkoxy C1 to 10, hydroxyalkyl C1 to 10, halogen, haloalkyl C1 to 10, haloalkoxy C1 to 10, nitrile, $-CO_2R^{25}$, $-(CH_2)_pNR^{29}R^{30}$, $-SO_2NR^{31}R^{32}$, alkoxy(C1 to 6)alkyl(C1 to 6)-, a 5- or 6-membered heterocycle, a 5- or 6- membered heteroaryl, phenyl, phenylalkyl(C1 to 6)-aryloxy, each of the 5- or 6-membered heterocycle, 5- or 6-membered heteroaryl, phenyl and aryloxy being optionally substituted by one or more substituents selected from the group, carboxy, alkyl C1 to 6, halogen and hydroxy;

$R^2$ is hydrogen or alkyl C1 to 6 or $R^1$ and $R^2$, together with the nitrogen to which they are attached, form a 5- or 6-membered heteroaryl containing 2, 3 or 4 heteroatoms, the heteroaryl being optionally substituted by one or more substituents selected from the group alkyl C1 to 10, alkoxy C1 to 10, halogen, haloalkyl C1 to 10, haloalkoxy C1 to 10, phenyl or a 5- or 6-membered heterocycle, said heterocycle being optionally substituted by carboxy;

$R^3$, $R^4$, $R^5$, $R^6$, $R^7$, $R^9$, $R^{10}$, $R^{17}$, $R^{22}$, $R^{25}$, $R^{29}$, $R^{30}$, $R^{31}$ and $R^{32}$, which may be the same or different, are each hydrogen or alkyl C1 to 6;

$R^{30}$ is hydrogen, alkyl C1 to 6 or $R^{33}CO-$;

$R^{33}$ is alkyl C1 to 6;

$R^8$ is phenyl or a heteroaryl, each of which may be optionally substituted by one or more substituents selected from the group alkyl C1 to 6, haloalkyl C1 to 6, halogen, alkoxy C1 to 6, nitrile or dialkyl amino C1 to 6 or two adjacent substituents may together form a saturated or unsaturated carbocyclic or heterocyclic ring;

m is an integer 0 or 1;
n is an integer, 0, 1 or 2;
p is an integer from 0 to 6;
and isomers thereof;
in free form or in salt form.

For purposes of interpreting this specification, the following definitions will apply and whenever appropriate, terms used in the singular will also include the plural and vice versa.

As used herein, the term "alkyl" refers to a fully saturated, branched or unbranched hydrocarbon moiety, i.e. primary, secondary or tertiary alkyl or, where appropriate, cycloalkyl or alkyl substituted by cycloalkyl, they may also be saturated or unsaturated alkyl groups. Where not otherwise identified, preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "sulphonyl" refers to $R-SO_2-$, wherein R is hydrogen, alkyl, aryl, heteroaryl, aryl-alkyl, heteroaryl-alkyl, alkoxy, aryloxy, cycloalkyl, or heterocyclyl.

As used herein, the term "heterocyclyl" or "heterocyclo" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1, 2 or 3 substituents selected from the groups consisting of the following:
(a) alkyl;
(b) hydroxy (or protected hydroxy);
(c) halo;
(d) haloalkyl;
(e) oxo, i.e., =O;
(f) amino, alkylamino or dialkylamino;
(g) alkoxy;
(h) cycloalkyl;
(i) carboxyl;

(j) heterocyclooxy, wherein heterocyclooxy denotes a heterocyclic group bonded through an oxygen bridge;
(k) alkyl-O—C(O)—;
(l) mercapto;
(m) nitro;
(n) cyano;
(o) sulfamoyl or sulfonamido;
(p) aryl;
(q) alkyl-C(O)—O—;
(r) aryl-C(O)—O—;
(s) aryl-S—;
(t) aryloxy;
(u) alkyl-S—;
(v) formyl, i.e., HC(O)—;
(w) carbamoyl;
(x) aryl-alkyl-; and
(y) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms, preferably 3-9, or 3-7 carbon atoms, each of which can be optionally substituted by one, or two, or three, or more substituents, such as alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryl" refers to an aromatic carbocyclic ring system containing 6 to 14 ring carbon atoms, which may be unsubstituted or substituted as defined.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or polycyclic-aromatic ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-, naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenanthrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2] benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, 7-benzofuranyl, 2-, 4-, 5-, 6-, or 7-benzo[b]thienyl, 2-, 4-, 5-, 6-, or 7-benzoxazolyl, 2-, 4-, 5-, 6-benzimidazolyl, 2-, 4,5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

The trans arrangement of the 1,4-cyclohexyl substituents —N(R$^7$)C=OR$^8$ and —CR$^3$R$^4$NR$^1$R$^2$ is preferred.

The term alkyl includes straight chain, branched or cyclic alkyl groups. The term haloalkyl includes mono- and polysubstituted e.g. mono-, di- or tri-halo substituted alkyl groups.

When R$^x$ is a heteroaryl examples of such heteroaryls include, pyridine, pyrazole, thiazole, imidazole, pyrazine, pyrimidine, imidazole, triazole, thiadiazole, isoxazole, oxadiazole, quinoline, isoquinoline, indole, benzothiazole, isobenzofuran, benzoimidazole and benzoxazole.

R$^2$ may be hydrogen.

R$^3$ and R$^4$ may each be hydrogen

R$^5$ and R$^6$, which may be the same or different, are each preferably hydrogen or methyl.

R$^7$ may be preferably hydrogen

R$^8$ is preferably phenyl or 3-pyridyl and more preferably substituted phenyl or 3-pyridyl, and especially disubstituted phenyl or disubstituted 3-pyridyl, such as 2,5-disubstituted. Preferred substituents are halogen, such as Cl, or haloalkyl C1 to 10, such as CF$_3$, alkyl C1 to 6, alkoxy C1 to 6, trifluoralkoxy C1 to 6 and dimethylamino.

Specific compounds of formula I which may be mentioned include:

trans-3-methyl-N-(4-phenylaminomethyl-cyclohexyl)-benzamide;

trans-3-chloro-N-(4-phenylaminomethyl-cyclohexyl)-benzamide;

trans-N-(4-Phenylaminomethyl-cyclohexyl)-2-trifluoromethyl-benzamide;

trans-3-cyano-N-(4-phenylaminomethyl-cyclohexyl)-benzamide;

trans-3-methoxy-N-(4-phenylaminomethyl-cyclohexyl)-benzamide;

trans-3-chloro-2-fluoro-N-(4-phenylaminomethyl-cyclohexyl)-6-trifluoromethyl-benzamide;

trans-N-{4-[(4-chloro-phenylamino)-methyl]-cyclohexyl}-3-trifluoromethyl-benzamide;
trans-N-[4-(p-tolylamino-methyl)-cyclohexyl]-3-trifluoromethyl-benzamide;
trans-N-{4-[(3-chloro-4-methoxy-phenylamino)-methyl]-cyclohexyl}-3-trifluoromethyl-benzamide;
trans-N-{4-[(4-isopropyl-phenylamino)-methyl]-cyclohexyl}-3-trifluoromethyl-benzamide;
trans-N-{4-[(4-fluoro-phenylamino)-methyl]-cyclohexyl}-3-trifluoromethyl-benzamide;
trans-3-trifluoromethyl-N-{4-[(4-trifluoromethyl-phenylamino)-methyl]-cyclohexyl}-benzamide;
trans-N-{4-[(4-cyano-phenylamino)-methyl]-cyclohexyl}-3-trifluoromethyl-benzamide;
trans-N-{4-[(3-chloro-cyano-phenylamino)-methyl]-cyclohexyl}-3-trifluoromethyl-benzamide;
trans-N-[4-(naphthalen-1-ylaminomethyl)-cyclohexyl]-3-trifluoromethyl-benzamide;
trans-N-{4-[(3-cyano-phenylamino)-methyl]-cyclohexyl}-3-trifluoromethyl-benzamide;
trans-N-{4-[(3-methoxy-phenylamino)-methyl]-cyclohexyl}-3-trifluoromethyl-benzamide;
trans-N-[4-(quinolin-5-ylaminomethyl)-cyclohexyl]-3-trifluoromethyl-benzamide;
trans-N-[4-(quinolin-6-ylaminomethyl)-cyclohexyl]-3-trifluoromethyl-benzamide;
trans-N-{4-[(4-cyano-3-trifluoromethyl-phenylamino)-methyl]-cyclohexyl}-3-trifluoro methyl-benzamide;
trans-N-{4-[(4-morpholin-4-yl-phenylamino)-methyl]-cyclohexyl}-3-trifluoromethyl-benzamide;
trans-2-chloro-N-(4-phenylaminomethyl-cyclohexyl)-5-trifluoromethyl-benzamide;
trans-2-chloro-N-[4-([1,3,4]thiadiazol-2-ylaminomethyl)-cyclohexyl]-5-trifluoromethyl-benzamide;
trans-2-chloro-N-{4-[(5-methyl-1H-pyrazol-3-ylamino)-methyl]-cyclohexyl}-5-trifluoro methyl-benzamide;
trans-2-chloro-N-{4-[(4-methyl-thiazol-2-ylamino)-methyl]-cyclohexyl}-5-trifluoro methyl-benzamide;
trans-2-chloro-N-{4-[(1H-pyrazol-3-ylamino)-methyl]-cyclohexyl}-5-trifluoromethyl-benzamide;
trans-2-chloro-N-{4-[(2-methyl-1H-indol-5-ylamino)-methyl]-cyclohexyl}-5-trifluoro methyl-benzamide;
trans-2-chloro-5-trifluoromethyl-N-{4-[(1,3,5-trimethyl-1H-pyrazol-4-ylamino)-methyl]-cyclohexyl}-benzamide;
trans-N-[4-(benzothiazol-2-ylaminomethyl)-cyclohexyl]-2-chloro-5-trifluoromethyl-benzamide;
trans-2-chloro-N-(4-{[(5-phenyl-4H-[1,2,4]triazol-3-ylmethyl)-amino]-methyl}-cyclohexyl)-5-trifluoromethyl-benzamide;
trans-2-chloro-N-{4-[(1,3-dihydro-isobenzofuran-5-ylamino)-methyl]-cyclohexyl}-5-trifluoromethyl-benzamide;
trans-2-chloro-N-(4-{[(2-phenyl-2H-[1,2,3]triazol-4-ylmethyl)-amino]-methyl}-cyclohexyl)-5-trifluoromethyl-benzamide; trans-2-chloro-N-(4-{[5-(4-fluoro-phenyl)-2H-pyrazol-3-ylamino]-methyl}-cyclohexyl)-5-trifluoromethyl-benzamide;
trans-2-chloro-N-{4-[(2-methyl-3H-benzoimidazol-5-ylamino)-methyl]-cyclohexyl}-5-trifluoromethyl-benzamide;
trans-2-chloro-N-{4-[(1-methyl-1H-benzoimidazol-2-ylamino)-methyl]-cyclohexyl}-5-trifluoromethyl-benzamide;
trans-2-chloro-N-{4-[(1-methyl-1H-[1,2,4]triazol-3-ylamino)-methyl]-cyclohexyl}-5-trifluoromethyl-benzamide;
trans-2-chloro-N-{4-[(5-propyl-1H-pyrazol-3-ylamino)-methyl]-cyclohexyl}-5-trifluoro methyl-benzamide;
trans-2-chloro-N-{4-[(5-isopropyl-1H-pyrazol-3-ylamino)-methyl]-cyclohexyl}-5-trifluoromethyl-benzamide;
trans-2-chloro-N-{4-[(5-cyclopropyl-2H-pyrazol-3-ylamino)-methyl]-cyclohexyl}-5-trifluoromethyl-benzamide;
trans-2-chloro-N-{4-[(5,6-dimethyl-1H-benzoimidazol-2-ylamino)-methyl]-cyclohexyl}-5-trifluoromethyl-benzamide;
trans-N-(4-{[(benzooxazol-2-ylmethyl)-amino]-methyl}-cyclohexyl)-2-chloro-5-trifluoromethyl-benzamide;
trans-N-{4-[(1H-benzoimidazol-2-ylamino)-methyl]-cyclohexyl}-2-chloro-5-trifluoro methyl-benzamide;
trans-2-chloro-N-[4-(pyridin-3-ylaminomethyl)-cyclohexyl]-5-trifluoromethyl-benzamide;
trans-N-{4-[(4-tert-butyl-phenylamino)-methyl]-cyclohexyl}-2-chloro-5-trifluoromethyl-benzamide;
trans-2-chloro-N-{4-[(3,4-dimethoxy-phenylamino)-methyl]-cyclohexyl}-5-trifluoro methyl-benzamide;
trans-N-{4-[(3-bromo-4-methyl-phenylamino)-methyl]-cyclohexyl}-2-chloro-5-trifluoro methyl-benzamide;
trans-2-chloro-N-(4-{[methyl-(3-phenyl-[1,2,4]oxadiazol-5-ylmethyl)-amino]-methyl}-cyclohexyl)-5-trifluoromethyl-benzamide;
trans-2-chloro-N-(4-{[methyl-(4-methyl-thiazol-2-ylmethyl)-amino]-methyl}-cyclohexyl)-5-trifluoromethyl-benzamide;
trans-2-chloro-N-{4-[(methyl-phenyl-amino)-methyl]-cyclohexyl}-5-trifluoromethyl-benzamide;
trans-2-chloro-N-(4-{[methyl-(5-phenyl-1H-pyrazol-3-ylmethyl)-amino]-methyl}-cyclohexyl)-5-trifluoromethyl-benzamide;
trans-2-chloro-N-(4-{[methyl-(2-methyl-thiazol-4-ylmethyl)-amino]-methyl}-cyclohexyl)-5-trifluoromethyl-benzamide;
trans-2-chloro-N-(4-{[methyl-(3-phenyl-isoxazol-5-ylmethyl)-amino]-methyl}-cyclohexyl)-5-trifluoromethyl-benzamide;
trans-2-chloro-N-{4-[(3-methoxy-4-methyl-phenylamino)-methyl]-cyclohexyl}-5-trifluoromethyl-benzamide;
trans-2-chloro-N-{4-[(6-methyl-quinolin-5-ylamino)-methyl]-cyclohexyl}-5-trifluoro methyl-benzamide;
trans-2-chloro-N-{4-[(2,6-dimethyl-quinolin-5-ylamino)-methyl]-cyclohexyl}-5-trifluoro methyl-benzamide;
trans-2-chloro-N-(4-{[(2,3-dihydro-benzo[1,4]dioxin-2-ylmethyl)-amino]-methyl}-cyclohexyl)-5-trifluoromethyl-benzamide;
trans-2-chloro-N-[4-(quinolin-8-ylaminomethyl)-cyclohexyl]-5-trifluoromethyl-benzamide;
trans-2-chloro-N-[4-(quinolin-6-ylaminomethyl)-cyclohexyl]-5-trifluoromethyl-benzamide;
trans-2-chloro-N-{4-[(2-sulfamoyl-phenylamino)-methyl]-cyclohexyl}-5-trifluoromethyl-benzamide;
trans-2-chloro-N-{4-[(4-methyl-pyridin-2-ylamino)-methyl]-cyclohexyl}-5-trifluoro methyl-benzamide;
trans-2-chloro-N-[4-(isoquinolin-1-ylaminomethyl)-cyclohexyl]-5-trifluoromethyl-benzamide;
trans-2-chloro-N-{4-[(6-chloro-pyridin-3-ylamino)-methyl]-cyclohexyl}-5-trifluoro methyl-benzamide;
trans-2-chloro-N-{4-[(5-ethyl-[1,3,4]thiadiazol-2-ylamino)-methyl]-cyclohexyl}-5-trifluoromethyl-benzamide;
trans-2-chloro-N-{4-[(5-methyl-thiazol-2-ylamino)-methyl]-cyclohexyl}-5-trifluoro methyl-benzamide;
trans-2-chloro-N-{4-[(4,6-dimethyl-pyridin-2-ylamino)-methyl]-cyclohexyl}-5-trifluoro methyl-benzamide;

trans-2-chloro-N-{4-[(6-methoxy-pyridin-3-ylamino)-methyl]-cyclohexyl}-5-trifluoro methyl-benzamide;
trans-2-chloro-N-{4-[(3-methyl-pyridin-2-ylamino)-methyl]-cyclohexyl}-5-trifluoro methyl-benzamide;
trans-2-chloro-N-{4-[(5-methyl-pyridin-2-ylamino)-methyl]-cyclohexyl}-5-trifluoro methyl-benzamide;
trans-2-chloro-N-{4-[(6-methyl-pyridin-2-ylamino)-methyl]-cyclohexyl}-5-trifluoro methyl-benzamide;
trans-2-chloro-N-{4-[(4,6-dimethoxy-pyrimidin-2-ylamino)-methyl]-cyclohexyl}-5-trifluoromethyl-benzamide;
trans-2-chloro-N-[4-(thiazol-2-ylaminomethyl)-cyclohexyl]-5-trifluoromethyl-benzamide;
trans-2-chloro-N-{4-[(5-cyclopropyl-[1,3,4]thiadiazol-2-ylamino)-methyl]-cyclohexyl}-5-trifluoromethyl-benzamide;
trans-2-chloro-N-{4-[(2-fluoro-phenylamino)-methyl]-cyclohexyl}-5-trifluoromethyl-benzamide;
trans-2-chloro-N-{4-[(2,4-difluoro-phenylamino)-methyl]-cyclohexyl}-5-trifluoromethyl-benzamide;
trans-2-chloro-N-{4-[(2-fluoro-5-methyl-phenylamino)-methyl]-cyclohexyl}-5-trifluoro methyl-benzamide;
trans-2-chloro-N-{4-[(2-chloro-5-methyl-phenylamino)-methyl]-cyclohexyl}-5-trifluoro methyl-benzamide;
trans-2-chloro-N-{4-[(2-methoxy-phenylamino)-methyl]-cyclohexyl}-5-trifluoromethyl-benzamide;
trans-2-chloro-N-{4-[(3-cyano-phenylamino)-methyl]-cyclohexyl}-5-trifluoromethyl-benzamide;
trans-2-chloro-N-{4-[(3-fluoro-phenylamino)-methyl]-cyclohexyl}-5-trifluoromethyl-benzamide;
trans-2-chloro-N-{4-[(3-chloro-phenylamino)-methyl]-cyclohexyl}-5-trifluoromethyl-benzamide;
trans-2-chloro-5-trifluoromethyl-N-{4-[(3-trifluoromethyl-phenylamino)-methyl]-cyclohexyl}-benzamide;
trans-2-chloro-N-{4-[(3,4-dimethyl-phenylamino)-methyl]-cyclohexyl}-5-trifluoro methyl-benzamide;
trans-2-chloro-N-{4-[(3,5-dimethyl-phenylamino)-methyl]-cyclohexyl}-5-trifluoro methyl-benzamide;
trans-2-chloro-N-{4-[(4-methoxy-phenylamino)-methyl]-cyclohexyl}-5-trifluoromethyl-benzamide;
trans-2-chloro-N-{4-[(4-ethoxy-phenylamino)-methyl]-cyclohexyl}-5-trifluoromethyl-benzamide;
trans-2-chloro-N-{4-[(2-chloro-phenylamino)-methyl]-cyclohexyl}-5-trifluoromethyl-benzamide;
trans-2-chloro-N-{4-[(3-isopropoxy-phenylamino)-methyl]-cyclohexyl}-5-trifluoro methyl-benzamide;
trans-2-chloro-N-{4-[(1H-indol-5-ylamino)-methyl]-cyclohexyl}-5-trifluoromethyl-benzamide;
trans-N-[4-(benzo[1,3]dioxol-5-ylaminomethyl)-cyclohexyl]-2-chloro-5-trifluoromethyl-benzamide;
trans-2-chloro-N-[4-(quinolin-6-ylaminomethyl)-cyclohexyl]-5-trifluoromethyl-benzamide;
trans-2-chloro-N-{4-[(4-trifluoromethoxy-phenylamino)-methyl]-cyclohexyl}-5-trifluoro methyl-benzamide;
trans-2-chloro-N-{4-[(3-trifluoromethoxy-phenylamino)-methyl]-cyclohexyl}-5-trifluoro methyl-benzamide;
trans-2-chloro-N-{4-[(4,5-dimethyl-thiazol-2-ylamino)-methyl]-cyclohexyl}-5-trifluoro methyl-benzamide;
trans-N-{4-[(2-benzenesulfonyl-ethylamino)-methyl]-cyclohexyl}-2-chloro-5-trifluoro methyl-benzamide;
trans-N-{4-[(5-tert-butyl-isoxazol-3-ylamino)-methyl]-cyclohexyl}-2-chloro-5-trifluoro methyl-benzamide;
trans-2-chloro-N-(4-{[(5-phenyl-isoxazol-3-ylmethyl)-amino]-methyl}-cyclohexyl)-5-trifluoromethyl-benzamide;
trans-2-chloro-N-(4-{[(3-phenyl-[1,2,4]oxadiazol-5-ylmethyl)-amino]-methyl}-cyclohexyl)-5-trifluoromethyl-benzamide;
trans-2-chloro-N-(4-{[(3-phenyl-isoxazol-5-ylmethyl)-amino]-methyl}-cyclohexyl)-5-trifluoromethyl-benzamide;
trans-2-chloro-N-{4-[(3,5-dimethyl-isoxazol-4-ylamino)-methyl]-cyclohexyl}-5-trifluoro methyl-benzamide;
trans-2-chloro-N-{4-[(4-fluoro-3-trifluoromethyl-phenylamino)-methyl]-cyclohexyl}-5-trifluoromethyl-benzamide;
trans-2-chloro-N-{4-[(6-phenoxy-pyridin-3-ylamino)-methyl]-cyclohexyl}-5-trifluoro methyl-benzamide;
trans-2-chloro-N-{4-[(8-methyl-quinolin-5-ylamino)-methyl]-cyclohexyl}-5-trifluoro methyl-benzamide;
2-chloro-N-(2-methyl-4-phenylaminomethyl-cyclohexyl)-5-trifluoromethyl-benzamide;
trans-N-{4-[3-(2-oxo-imidazolidin-1-yl)-pyrazol-1-ylmethyl]-cyclohexyl}-3-trifluoro methyl-benzamide;
trans-2-chloro-N-{4-[3-(2-oxo-imidazolidin-1-yl)-pyrazol-1-ylmethyl]-cyclohexyl}-5-trifluoromethyl-benzamide;
trans-2-chloro-N-methyl-N-(4-phenylaminomethyl-cyclohexyl)-5-trifluoromethyl-benzamide;
trans-2,5-dichloro-N-[4-(pyridin-3-ylaminomethyl)-cyclohexyl]-benzamide;
trans-2,5-dichloro-N-{4-[(6-trifluoromethyl-pyridin-3-ylamino)-methyl]-cyclohexyl}-benzamide;
trans-2,5-dichloro-N-{4-[(6-cyano-pyridin-3-ylamino)-methyl]-cyclohexyl}-benzamide;
trans-N-{4-[(6-acetylamino-pyridin-3-ylamino)-methyl]-cyclohexyl}-2,5-dichloro-benzamide;
trans-2,5-dichloro-N-{4-[(6-methoxy-pyridin-3-ylamino)-methyl]-cyclohexyl}-benzamide;
trans-2,5-dichloro-N-{4-[(6-chloro-pyridin-3-ylamino)-methyl]-cyclohexyl}-benzamide;
trans-2,5-dichloro-N-{4-[(6-morpholin-4-yl-pyridin-3-ylamino)-methyl]-cyclohexyl}-benzamide;
trans-2,5-dichloro-N-(4-{[5-(4-fluoro-phenyl)-2H-pyrazol-3-ylamino]-methyl}-cyclohexyl)-benzamide;
trans-2-chloro-N-{4-[(4,5-dimethyl-thiazol-2-ylamino)-methyl]-cyclohexyl}-5-methyl-benzamide;
trans-N-[4-(benzothiazol-2-ylaminomethyl)-cyclohexyl]-2,5-Dichloro-benzamide;
trans-2,5-dichloro-N-{4-[(1-methyl-1H-benzoimidazol-2-ylamino)-methyl]-cyclohexyl}-benzamide;
trans-2-chloro-N-{4-[(2-methyl-pyridin-3-ylamino)-methyl]-cyclohexyl}-5-trifluoro methyl-benzamide;
trans-2-chloro-N-{4-[(6-methyl-pyridin-3-ylamino)-methyl]-cyclohexyl}-5-trifluoro methyl-benzamide;
trans-2-chloro-N-{4-[(5-methyl-pyridin-3-ylamino)-methyl]-cyclohexyl}-5-trifluoro methyl-benzamide;
trans-2-chloro-N-{4-[(4-methyl-pyridin-3-ylamino)-methyl]-cyclohexyl}-5-trifluoro methyl-benzamide;
trans-2,5-dichloro-N-{4-[(5-cyclopropyl-2H-pyrazol-3-ylamino)-methyl]-cyclohexyl}-benzamide;
trans-2,5-dichloro-N-{4-[(4,5-dimethyl-thiazol-2-ylamino)-methyl]-cyclohexyl}-nicotinamide;
trans-2,5-dichloro-N-(4-{[methyl-(5-phenyl-2H-pyrazol-3-ylmethyl)-amino]-methyl}-cyclohexyl)-benzamide;
trans-2-chloro-N-{4-[(4,5-dimethyl-thiazol-2-ylamino)-methyl]-cyclohexyl}-5-methoxy-benzamide;
trans-2-chloro-N-[4-(pyridin-2-ylaminomethyl)-cyclohexyl]-5-trifluoromethyl-benzamide;
trans-2-chloro-N-{4-[(5-chloro-pyridin-2-ylamino)-methyl]-cyclohexyl}-5-trifluoro methyl-benzamide;
trans-2-chloro-5-trifluoromethyl-N-{4-[(5-trifluoromethyl-pyridin-2-ylamino)-methyl]-cyclohexyl}-benzamide;

trans-2,5-dichloro-N-{4-[(5-propyl-2H-pyrazol-3-ylamino)-methyl]-cyclohexyl}-benzamide;
trans-2-chloro-5-trifluoromethyl-N-{4-[(6-trifluoromethyl-pyridin-2-ylamino)-methyl]-cyclohexyl}-benzamide;
trans-2,5-dichloro-N-{4-[(6-trifluoromethyl-pyridin-2-ylamino)-methyl]-cyclohexyl}-benzamide;
trans-2,5-dichloro-N-{4-[(6-methyl-pyridin-2-ylamino)-methyl]-cyclohexyl}-benzamide;
trans-2,5-dichloro-N-{4-[(5-methyl-pyridin-2-ylamino)-methyl]-cyclohexyl}-benzamide;
trans-2,5-dichloro-N-{4-[(4,6-dimethyl-pyridin-2-ylamino)-methyl]-cyclohexyl}-benzamide;
trans-2-chloro-N-{4-[(6-methoxy-pyridin-2-ylamino)-methyl]-cyclohexyl}-5-trifluoro methyl-benzamide;
trans-2,5-dichloro-N-[4-(pyrazin-2-ylaminomethyl)-cyclohexyl]-benzamide;
trans-2-chloro-6-methyl-N-(4-phenylaminomethyl-cyclohexyl)-nicotinamide;
trans-5-methyl-N-(4-phenylaminomethyl-cyclohexyl)-nicotinamide;
trans-3H-indole-5-carboxylic acid (4-phenylaminomethyl-cyclohexyl)-amide;
trans-2-methyl-N-(4-phenylaminomethyl-cyclohexyl)-benzamide;
trans-2,3-dimethyl-N-(4-phenylaminomethyl-cyclohexyl)-benzamide;
trans-3-chloro-4-methyl-N-(4-phenylaminomethyl-cyclohexyl)-benzamide;
trans-2,5-dichloro-N-(4-phenylaminomethyl-cyclohexyl)-benzamide;
trans-4-fluoro-N-(4-phenylaminomethyl-cyclohexyl)-3-trifluoromethyl-benzamide;
trans-5-fluoro-N-(4-phenylaminomethyl-cyclohexyl)-2-trifluoromethyl-benzamide;
trans-2,5-dichloro-N-(4-phenylaminomethyl-cyclohexyl)-isonicotinamide;
trans-benzofuran-5-carboxylic acid (4-phenylaminomethyl-cylcohexyl)-amide;
trans-3-fluoro-N-(4-phenylaminomethyl-cyclohexyl)-benzamide;
trans-N-{4-[(4-Methoxy-phenylamino)-methyl]-cyclohexyl}-3-trifluoromethyl-benzamide;
trans-N-(4-phenylaminomethyl-cyclohexyl)-3-trifluoromethyl-benzamide;
trans-2,5-dichloro-N-{4-[3-(2-oxo-imidazolidin-1-yl)-pyrazol-1-ylmethyl]-cyclohexyl}-benzamide;
trans-2-chloro-N-{4-[(5-ethyl-2H-pyrazol-3-ylamino)-methyl]cyclohexyl}-5-trifluoro methyl-benzamide;
trans-5-chloro-N-{4-[(4,5-dimethyl-thiazol-2-ylamino)-methyl]-cyclohexyl}-2-methoxy-nicotinamide;
trans-5-chloro-N-{4-[(4,5-dimethyl-thiazol-2-ylamino)-methyl]-cyclohexyl}-2-methyl-nicotinamide;
trans-2-chloro-N-[4-(pyrimidin-2-ylaminomethyl)-cyclohexyl]-5-trifluoromethyl-benzamide;
trans-2,5-dichloro-N-{4-[(5-trifluoromethyl-1H-indazol-3-ylamino)-methyl]-cyclohexyl}-benzamide;
trans-5-chloro-2-dimethylamino-N-{4-[(4,5-dimethyl-thiazol-2-ylamino)-methyl]-cyclohexyl}-nicotinamide;
cis-2-chloro-N-(4-{[5-(4-fluoro-phenyl)-2H-pyrazol-3-ylamino]-methyl}-cyclohexyl)-5-trifluoromethyl-benzamide;
trans-6-chloro-benzofuran-5-carboxylic acid {4-[(4,5-dimethyl-thiazol-2-ylamino)-methyl]-cyclohexyl}-amide;
trans-N-{4-[(4,5-dimethyl-thiazol-2-ylamino)-methyl]-cyclohexyl}-5-trifluoromethyl-nicotinamide;
trans-2,5-dichloro-N-{4-[5-methyl-3-(2-oxo-imidazolidin-1-yl)-pyrazol-1-ylmethyl]-cyclohexyl}-benzamide;
cis-2-chloro-N-{4-[(4-methyl-pyridin-3-ylamino)-methyl]-cyclohexyl}-5-trifluoromethyl-benzamide;
trans-N-{4-[(4,5-dimethyl-thiazol-2-ylamino)-methyl]-cyclohexyl}-2-fluoro-5-trifluoro methyl-benzamide;
trans-5-chloro-N-{4-[(4,5-dimethyl-thiazol-2-ylamino)-methyl]-cyclohexyl}-2-fluoro-benzamide;
trans-2-chloro-N-[4-(1-phenylamino-ethyl)-cyclohexyl]-5-trifluoromethyl-benzamide;
trans-2-chloro-N-{4-[(5-fluoro-pyridin-3-ylamino)-methyl]-cyclohexyl}-5-trifluoromethyl-benzamide;
trans-2-chloro-N-{4-[(5-fluoro-pyridin-2-ylamino)-methyl]-cyclohexyl}-5-trifluoromethyl-benzamide;
trans-2-chloro-N-{4-[(3,5-difluoro-pyridin-2-ylamino)-methyl]-cyclohexyl}-5-trifluoro methyl-benzamide;
trans-2-chloro-5-trifluoromethyl-N-{4-[(4-trifluoromethyl-pyridin-2-ylamino)-methyl]-cyclohexyl}-benzamide;
trans-2-chloro-5-trifluoromethyl-N-{4-[(5-trifluoromethyl-pyridin-3-ylamino)-methyl]-cyclohexyl}-benzamide;
trans-2-chloro-N-{4-[(2-methoxy-pyridin-3-ylamino)-methyl]-cyclohexyl}-5-trifluoromethyl-benzamide;
trans-2-chloro-N-{4-[(5-chloro-pyridin-3-ylamino)-methyl]-cyclohexyl}-5-trifluoro methyl-benzamide;
trans-2-chloro-N-{4-[(4-methyl-pyrimidin-2-ylamino)-methyl]-cyclohexyl}-5-trifluoro methyl-benzamide;
trans-2-chloro-N-{4-[(4,6-dimethyl-pyrimidin-2-ylamino)-methyl]-cyclohexyl}-5-trifluoro methyl-benzamide;
trans-2,5-dichloro-N-{4-[(5-fluoro-pyridin-3-ylamino)-methyl]-cyclohexyl}-benzamide;
trans-2,5-dichloro-N-{4-[(5-fluoro-pyridin-2-ylamino)-methyl]-cyclohexyl}-benzamide;
trans-2,5-dichloro-N-{4-[(3,5-difluoro-pyridin-2-ylamino)-methyl]-cyclohexyl}-benzamide;
trans-2-chloro-N-{4-[(6-dimethylamino-pyridin-3-ylamino)-methyl]-cyclohexyl}-5-trifluoromethyl-benzamide;
trans-2-chloro-N-{4-[(5-dimethylamino-pyridin-2-ylamino)-methyl]-cyclohexyl}-5-trifluoromethyl-benzamide;
trans-6-{[4-(2-chloro-5-trifluoromethyl-benzoylamino)-cyclohexylmethyl]-amino}-nicotinic acid methyl ester;
trans-2-chloro-N-(4-{[5-(4-fluoro-phenyl)-1H-pyrazol-3-ylamino]-methyl}-3-methyl-cyclohexyl)-5-trifluoromethyl-benzamide;
trans-2-chloro-N-[4-((S)-1-phenylamino-ethyl)-cyclohexyl]-5-trifluoromethyl-benzamide;
trans-2-chloro-N-[4-((R)-1-phenylamino-ethyl)-cyclohexyl]-5-trifluoromethyl-benzamide;
trans-2-chloro-N-{4-[(3,5-dimethyl-pyrazin-2-ylamino)-methyl]-cyclohexyl}-5-trifluoro methyl-benzamide;
trans-5-chloro-2-dimethylamino-N-{4-[(4,5-dimethyl-thiazol-2-ylamino)-methyl]-cyclohexyl}-benzamide;
trans-chloro-N-{4-[(5-hydroxymethyl-pyridin-2-ylamino)-methyl]-cyclohexyl}-5-trifluoromethyl-benzamide;
trans-2-dimethylamino-N-{4-[(4,5-dimethyl-thiazol-2-ylamino)-methyl]-cyclohexyl}-5-trifluoromethyl-nicotinamide;
trans-6-{[4-(2-chloro-5-trifluoromethyl-benzoylamino)-cyclohexylmethyl]-amino}-nicotinic acid;
trans-5-chloro-N-{4-[(5-cyclopropyl-2H-pyrazol-3-ylamino)-methyl]-cyclohexyl}-2-methyl-nicotinamide;
trans-2-chloro-N-{4-[(5-dimethylaminomethyl-pyridin-2-ylamino)-methyl]-cyclohexyl}-5-trifluoromethyl-benzamide;
trans-2,5-dichloro-N-{4-[(3,5-dimethyl-1H-pyrazol-4-ylamino)-methyl]-cyclohexyl}-benzamide;
trans-2,5-dichloro-N-{4-[(5-cyclopropyl-2-methyl-2H-pyrazol-3-ylamino)-methyl]-cyclohexyl}-benzamide;

trans-2,5-dichloro-N-{4-[(1-propyl-1H-pyrazol-4-ylamino)-methyl]-cyclohexyl}-benzamide;
trans-N-{4-[(6-bromo-pyridin-2-ylamino)-methyl]-cyclohexyl}-2-chloro-5-trifluoro methyl-benzamide;
trans-2-chloro-N-{4-[(5-fluoro-4-methyl-pyridin-2-ylamino)-methyl]-cyclohexyl}-5-trifluoromethyl-benzamide;
trans-5-chloro-2-methyl-N-{4-[(5-methyl-pyridin-3-ylamino)-methyl]-cyclohexyl}-nicotinamide;
trans-5-chloro-N-{4-[(4,6-dimethyl-pyridin-2-ylamino)-methyl]-cyclohexyl}-2-methyl-nicotinamide;
trans-5-chloro-N-{4-[(5-fluoro-pyridin-3-ylamino)-methyl]-cyclohexyl}-2-methyl-nicotinamide;
trans-5-chloro-2-methyl-N-{4-[(3-methyl-pyridin-2-ylamino)-methyl]-cyclohexyl}-nicotinamide;
trans-5-chloro-2-methyl-N-{4-[(1-methyl-1H-benzoimidazol-2-ylamino)-methyl]-cyclohexyl}-nicotinamide;
trans-5-chloro-2-methyl-N-[4-(pyrimidin-2-ylaminomethyl)-cyclohexyl]-nicotinamide;
trans-5-chloro-2-dimethylamino-N-{4-[(5-methyl-pyridin-3-ylamino)-methyl]-cyclohexyl}-nicotinamide;
trans-2-methyl-N-{4-[(5-methyl-pyridin-3-ylamino)-methyl]-cyclohexyl}-5-trifluoro methyl-nicotinamide;
trans-2,5-dimethyl-N-{4-[(5-methyl-pyridin-3-ylamino)-methyl]-cyclohexyl}-nicotinamide;
trans-5-chloro-2-dimethylamino-N-{1,4-[(4,6-dimethyl-pyridin-2-ylamino)-methyl]-cyclohexyl}-nicotinamide;
trans-N-{4-[(4,6-dimethyl-pyridin-2-ylamino)-methyl]-cyclohexyl}-2-methyl-5-trifluoro methyl-nicotinamide;
trans-5-chloro-2-dimethylamino-N-{4-[(5-fluoro-pyridin-3-ylamino)-methyl]-cyclohexyl}-nicotinamide;
trans-N-{4-[(5-fluoro-pyridin-3-ylamino)-methyl]-cyclohexyl}-2-methyl-5-trifluoro methyl-nicotinamide;
trans-N-{4-[(5-fluoro-pyridin-3-ylamino)-methyl]-cyclohexyl}-2,5-dimethyl-nicotinamide;
trans-2,5-dichloro-N-{4-[(5-propyl-2H-[1,2,4]triazol-3-ylamino)-methyl]-cyclohexyl}-benzamide;
trans-2-chloro-N-{4-[5-methyl-3-(2-oxo-imidazolidin-1-yl)-pyrazol-1-ylmethyl]-cyclohexyl}-5-trifluoromethyl-benzamide;
trans-2-chloro-N-{4-[2-(4,6-dimethyl-pyridin-2-ylamino)-ethyl]-cyclohexyl}-5-trifluoro methyl-benzamide;
trans-2-chloro-N-{4-[(5-fluoro-6-methyl-pyridin-2-ylamino)-methyl]-cyclohexyl}-5-trifluoromethyl-benzamide;
trans-2-chloro-N-{4-[(2,6-dimethyl-pyridin-3-ylamino)-methyl]-cyclohexyl}-5-trifluoro methyl-benzamide;
2-dimethylamino-N-{4-[(4,6-dimethyl-pyridin-2-ylamino)-methyl]-cyclohexyl}-5-trifluoromethyl-nicotinamide;
trans-2-chloro-N-{4-[(5-hydroxymethyl-pyridin-3-ylamino)-methyl]-cyclohexyl}-5-trifluoromethyl-benzamide;
trans-2-chloro-N-{4-[(2,4-dimethyl-pyridin-3-ylamino)-methyl]-cyclohexyl}-5-trifluoro methyl-benzamide;
trans-2-chloro-N-{4-[(4,6-dimethyl-pyridin-3-ylamino)-methyl]-cyclohexyl}-5-trifluoro methyl-benzamide;
trans-2-chloro-N-(4-{[5-(4-fluoro-phenyl)-1H-pyrazol-3-ylamino]-methyl}-3-methyl-cyclohexyl)-5-trifluoromethyl-benzamide;
trans-2-chloro-N-{4-[(5-fluoromethyl-pyridin-3-ylamino)-methyl]-cyclohexyl}-5-trifluoro methyl-benzamide;
trans-2-chloro-N-{4-[(4,5,6,7-tetrahydro-1H-indazol-3-ylamino)-methyl]-cyclohexyl}-5-trifluoromethyl-benzamide;
trans-2-chloro-N-{4-[(5-ethyl-pyridin-2-ylamino)-methyl]-cyclohexyl}-5-trifluoromethyl-benzamide;
trans-2-chloro-N-{4-[(1H-pyrazol-4-ylamino)-methyl]-cyclohexyl}-5-trifluoromethyl-benzamide;
trans-2-chloro-N-{4-[(1H-indazol-3-ylamino)-methyl]-cyclohexyl}-5-trifluoromethyl-benzamide;
trans-2-chloro-N-{4-[(5-ethyl-pyridin-3-ylamino)-methyl]-cyclohexyl}-5-trifluoromethyl-benzamide;
trans-5-chloro-N-{4-[(5-fluoro-4-methyl-pyridin-2-ylamino)-methyl]-cyclohexyl}-2-methyl-nicotinamide;
trans-5-chloro-2-methyl-N-{4-[(4,5,6,7-tetrahydro-1H-indazol-3-ylamino)-methyl]-cyclohexyl}-nicotinamide;
trans-2-chloro-N-{4-[(2-methoxy-5-methyl-pyridin-3-ylamino)-methyl]-cyclohexyl}-5-trifluoromethyl-benzamide;
trans-2-chloro-N-{4-[(1H-pyrazolo[3,4-b]pyridin-3-ylamino)-methyl]-cyclohexyl}-5-trifluoromethyl-benzamide;
trans-2-chloro-5-trifluoromethyl-N-{4-[(5-trifluoromethyl-1H-indazol-3-ylamino)-methyl]-cyclohexyl}-benzamide;
trans-2-chloro-N-{4-[(5-methyl-1H-indazol-3-ylamino)-methyl]-cyclohexyl}-5-trifluoro methyl-benzamide;
trans-2-chloro-N-{4-[(5,5-dimethyl-4,5,6,7-tetrahydro-1H-indazol-3-ylamino)-methyl]-cyclohexyl}-5-trifluoromethyl-benzamide;
trans-2-chloro-N-{4-[(6-methyl-1H-indazol-3-ylamino)-methyl]-cyclohexyl}-5-trifluoro methyl-benzamide;
trans-2-chloro-N-{4-[(5-fluoro-1H-indazol-3-ylamino)-methyl]-cyclohexyl}-5-trifluoro methyl-benzamide;
trans-2-chloro-N-{4-[(4-fluoro-1H-indazol-3-ylamino)-methyl]-cyclohexyl}-5-trifluoro methyl-benzamide;
trans-2-chloro-N-{4-[(4,6-dimethyl-pyridin-2-ylamino)-methyl]-cyclohexyl}-5-isopropyl-nicotinamide;
trans-2-chloro-N-{4-[(4-methyl-1H-indazol-3-ylamino)-methyl]-cyclohexyl}-5-trifluoro methyl-benzamide;
trans-2-chloro-N-{4-[(5-chloro-1H-indazol-3-ylamino)-methyl]-cyclohexyl}-5-trifluoro methyl-benzamide;
trans-2-chloro-N-{4-[(5,6-dimethoxy-1H-indazol-3-ylamino)-methyl]-cyclohexyl}-5-trifluoromethyl-benzamide;
trans-2-chloro-N-{4-[(6-methoxy-1H-indazol-3-ylamino)-methyl]-cyclohexyl}-5-trifluoro methyl-benzamide;
trans-2-chloro-N-{4-[(5-chloro-4-methyl-pyridin-2-ylamino)-methyl]-cyclohexyl}-5-trifluoromethyl-benzamide;
trans-2-chloro-N-{4-[(1-methyl-1H-indazol-3-ylamino)-methyl]-cyclohexyl}-5-trifluoro methyl-benzamide;
trans-2-chloro-N-{4-[(5-methyl-4-phenyl-2H-pyrazol-3-ylamino)-methyl]-cyclohexyl}-5-trifluoromethyl-benzamide;
trans-N-{4-[(5-benzyl-4,5,6,7-tetrahydro-1H-pyrazolo[4,3-c]pyridin-3-ylamino)-methyl]-cyclohexyl}2-chloro-5-trifluoromethyl-benzamide;
trans-2-chloro-N-(4-indazol-1-ylmethyl-cyclohexyl)-5-trifluoromethyl-benzamide
trans-2-chloro-N-(4-indazol-2-ylmethyl-cyclohexyl)-5-trifluoromethyl-benzamide
trans-2-chloro-N-{4-[(5-chloro-2-methyl-pyridin-3-ylamino)-methyl]-cyclohexyl}-5-trifluoromethyl-benzamide;
trans-2-chloro-N-{4-[(6-methyl-1H-pyrazolo[3,4-b]pyridin-3-ylamino)-methyl]-cyclohexyl}-5-trifluoromethyl-benzamide;
trans-2-chloro-N-{4-[(5-chloro-6-methyl-pyridin-3-ylamino)-methyl]-cyclohexyl}-5-trifluoromethyl-benzamide;
N-{4-[(4-bromo-5-propyl-1H-pyrazol-3-ylamino)-methyl]-cyclohexyl}-2-chloro-5-trifluoromethyl-benzamide;

N-[4-(3-amino-4-chloro-indazol-1-ylmethyl)-cyclohexyl]-2-chloro-5-trifluoromethyl-benzamide;
trans-2-chloro-N-[4-(imidazo[1,2-b]pyridazin-3-ylaminomethyl)-cyclohexyl]-2-chloro-5-trifluoro methyl-benzamide;
trans-2-chloro-N-{4-[(4,6-dihydro-1H-thieno[3,4c]pyrazol-3-ylamino)-methyl]-cyclohexyl}-5-trifluoromethyl-benzamide;
trans-2-chloro-N-{4-[(4-methyl-5-phenyl-1H-pyrazol-3-ylamino)-methyl]-cyclohexyl}-5-trifluoromethyl-benzamide;
trans-2-chloro-N-(4-{[4-(4-chloro-phenyl)-1H-pyrazol-3-ylamino]-methyl}-cyclohexyl)-5-trifluoromethyl-benzamide;
N-{4-[(7-bromo-[1,2,4]triazolo[1,5-a]pyridin-2-ylamino)-methyl]-cyclohexyl}-2-chloro-5-trifluoromethyl-benzamide;
trans-2-chloro-N-{4-[(1-methyl-1H-pyrazolo[3,4-b]pyridin-3-ylamino)-methyl]-cyclohexyl}-5-trifluoromethyl-benzamide;
trans-5-chloro-N-{4-[(5-chloro-4-methyl-pyridin-2-ylamino)-methyl]-cyclohexyl}-2-methyl-nicotinamide;
trans-2-chloro-N-[4-(pyrazolo[1,5-a]pyridin-3-ylaminomethyl)-cyclohexyl]-5-trifluoro methyl-benzamide;
trans-2-chloro-N-(4-{[4-(2,4-dichloro-phenyl)-1H-pyrazol-3-ylamino]-methyl}-cyclohexyl)-5-trifluoromethyl-benzamide;
trans-5-chloro-2-methyl-N-{4-[(4-trifluoromethyl-pyridin-2-ylamino)-methyl]-cyclohexyl}-nicotinamide;
trans-5-chloro-2-methyl-N-{4-[(5-trifluoromethyl-pyridin-3-ylamino)-methyl]-cyclohexyl}-nicotinamide;
trans-2-chloro-N-{4-[(5-phenyl-4-propyl-2H-pyrazol-3-ylamino)-methyl]-cyclohexyl}-5-trifluoromethyl-benzamide;
trans-2-chloro-N-[4-(3,5-dimethyl-[1,2,4]triazol-1-ylmethyl)-cyclohexyl]-5-trifluoro methyl-benzamide;
N-{4-[(6-bromo-[1,2,4]triazolo[1,5-a]pyridin-2-ylamino)-methyl]-cyclohexyl}-2-chloro-5-trifluoromethyl-benzamide;
trans-2-chloro-N-{4-[(4,6-dimethyl-1H-pyrazolo[3,4-b]pyridin-3-ylamino)-methyl]-cyclohexyl}-5-trifluoromethyl-benzamide;
trans-5-chloro-N-{4-[(1H-indazol-3-ylamino)-methyl]-cyclohexyl}-2-methyl-nicotinamide;
trans-2-chloro-N-[4-(3,5-dimethyl-pyrazol-1-ylmethyl)-cyclohexyl]-5-trifluoromethyl-benzamide;
trans-5-chloro-2-methyl-N-{4-[(1H-pyrazolo[3,4-b]pyridin-3-ylamino)-methyl]-cyclohexyl}-nicotinamide;
trans-2-chloro-N-(4-{[4-(4-chloro-phenyl)-5-methyl-1H-pyrazol-3-ylamino]-methyl}-cyclohexyl)-5-trifluoromethyl-benzamide;
trans-2-chloro-N-(4-{[5-chloro-3-(4-hydroxy-cyclohexyl)-3H-imidazo[4,5-b]pyridin-2-ylamino]-methyl}-cyclohexyl)-5-trifluoromethyl-benzamide;
trans-2-chloro-N-{4-[(1H-pyrazolo[4,3-b]pyridin-3-ylamino)-methyl]-cyclohexyl}-5-trifluoromethyl-benzamide;
trans-2-chloro-N-{4-[(4-phenyl-1H-pyrazol-3-ylamino)-methyl]-cyclohexyl}-5-trifluoro methyl-benzamide;
trans-2-chloro-N-{4-[(6-fluoro-1H-pyrazolo[4,3-b]pyridin-3-ylamino)-methyl]-cyclohexyl}-5-trifluoromethyl-benzamide;
trans-5-chloro-2-methyl-N-{4-[(5-methyl-4-phenyl-2H-pyrazol-3-ylamino)-methyl]-cyclohexyl}-nicotinamide;
trans-2-chloro-N-{4-[(5-pyridin-3-yl-2H-pyrazol-3-ylamino)-methyl]-cyclohexyl}-5-trifluoromethyl-benzamide;
trans-2-chloro-N-{4-[(3-chloro-6-methoxy-pyridin-2-ylamino)-methyl]-cyclohexyl}-5-trifluoromethyl-benzamide;
trans-2-chloro-N-{4-[(5-chloro-6-methoxy-pyridin-2-ylamino)-methyl]-cyclohexyl}-5-trifluoromethyl-benzamide;
trans-2-chloro-N-{4-[(1-phenyl-1H-tetrazol-5-ylamino)-methyl]-cyclohexyl}-5-trifluoro methyl-benzamide;
trans-2-chloro-N-{4-[(1-methyl-4-phenyl-1H-pyrazol-3-ylamino)-methyl]-cyclohexyl}-5-trifluoromethyl-benzamide;
trans-2-chloro-N-[4-(5-methyl-tetrazol-2-ylmethyl)-cyclohexyl]-5-trifluoromethyl-benzamide;
trans-2-chloro-N-[4-(5-cyclopropyl-tetrazol-2-ylmethyl)-cyclohexyl]-5-trifluoromethyl-benzamide;
trans-2-chloro-N-{4-[(3,4-dimethyl-isoxazol-5-ylamino)-methyl]-cyclohexyl}-5-trifluoro methyl-benzamide;
trans-2-chloro-N-{4-[(4-pyridin-3-yl-2H-pyrazol-3-ylamino)-methyl]-cyclohexyl}-5-trifluoromethyl-benzamide;
trans-2-chloro-N-{4-[(5-chloro-6-d3-methyl-pyridin-3-ylamino)-methyl]-cyclohexyl}-5-trifluoromethyl-benzamide;
trans-2-chloro-N-[4-(3-phenyl-pyrazol-1-ylmethyl)-cyclohexyl]-5-trifluoromethyl-benzamide;
trans-5-chloro-N-[4-(3,5-dimethyl-pyrazol-1-ylmethyl)-cyclohexyl]-2-methyl-nicotinamide;
trans-2-chloro-N-(4-{[4-(4-fluoro-phenyl)-5-methyl-1H-pyrazol-3-ylamino]-methyl}-cyclohexyl)-5-trifluoromethyl-benzamide;
trans-2-chloro-N-[4-(4-phenyl-pyrazol-1-ylmethyl)-cyclohexyl]-5-trifluoromethyl-benzamide;
trans-2-chloro-N-{4-[(1H-pyrazolo[3,4-b]pyrazin-3-ylamino)-methyl]-cyclohexyl}-5-trifluoromethyl-benzamide;
trans-5-chloro-2-methyl-N-{4-[(5-trifluoromethyl-2H-pyrazol-3-ylamino)-methyl]-cyclohexyl}-nicotinamide;
trans-2-chloro-N-[4-(4-chloro-3,5-dimethyl-pyrazol-1-ylmethyl)-cyclohexyl]-5-trifluoro methyl-benzamide;
trans-2-chloro-N-[4-(3-ethoxy-5-methyl-[1,2,4]triazol-1-ylmethyl)-cyclohexyl]-5-trifluoromethyl-benzamide;
trans-2-chloro-N-[4-(5-ethoxy-3-methyl-[1,2,4]triazol-1-ylmethyl)-cyclohexyl]-5-trifluoromethyl-benzamide;
trans-2-chloro-5-trifluoromethyl-N-[4-(3,4,5-trimethyl-pyrazol-1-ylmethyl)-cyclohexyl]-benzamide;
trans-5-chloro-N-{4-[(5-fluoro-pyridin-2-ylamino)-methyl]-cyclohexyl}-2-methyl-nicotinamide;
trans-2-chloro-N-{4-[(5-chloro-6-methoxy-pyridin-3-ylamino)-methyl]-cyclohexyl}-5-trifluoromethyl-benzamide;
trans-5-chloro-2-methyl-N-{4-[(5-propyl-1H-pyrazol-3-ylamino)-methyl]-cyclohexyl}-nicotinamide;
trans-2-chloro-5-trifluoromethyl-N-[4-(3-trifluoromethyl-pyrazol-1-ylmethyl)-cyclohexyl]-benzamide;
trans-2-chloro-N-(4-{[4-(4-chloro-phenyl)-3-methyl-isoxazol-5-ylamino]-methyl}-cyclohexyl)-5-trifluoromethyl-benzamide;
trans-2-chloro-N-{4-[(5-methoxymethyl-4H-[1,2,4]triazol-3-ylamino)-methyl]-cyclohexyl}-5-trifluoromethyl-benzamide;
trans-2-chloro-N-{4-[(trans-5-chloro-2-methoxy-pyridin-3-ylamino)-methyl]-cyclohexyl}-5-trifluoromethyl-benzamide;
trans-2-chloro-N-{4-[(4-chloro-5-methyl-2H-pyrazol-3-ylamino)-methyl]-cyclohexyl}-5-trifluoromethyl-benzamide;

trans-2-chloro-N-{4-[(4-cyano-5-methyl-2H-pyrazol-3-ylamino)-methyl]-cyclohexyl}-5-trifluoromethyl-benzamide;
trans-2-chloro-N-(4-{[2-(4-chloro-phenyl)-5-methyl-2H-pyrazol-3-ylamino]-methyl}-cyclohexyl)-5-trifluoromethyl-benzamide;
trans-2-chloro-N-[4-(3-methyl-5-trifluoromethyl-pyrazol-1-ylmethyl)-cyclohexyl]-5-trifluoromethyl-benzamide;
trans-2-chloro-N-[4-(5-methyl-3-trifluoromethyl-pyrazol-1-ylmethyl)-cyclohexyl]-5-trifluoromethyl-benzamide;
trans-2-chloro-N-{4-[(5-ethyl-4-methyl-1H-pyrazol-3-ylamino)-methyl]-cyclohexyl}-5-trifluoromethyl-benzamide;
trans-2-chloro-N-(4-imidazol-1-ylmethyl-cyclohexyl)-5-trifluoromethyl-benzamide;
trans-2-chloro-N-[4-(2-methyl-4-trifluoromethyl-imidazol-1-ylmethyl)-cyclohexyl]-5-trifluoromethyl-benzamide;
trans-2-chloro-N-{4-[(1-methyl-1H-pyrazolo[4,3-b]pyridin-3-ylamino)-methyl]-cyclohexyl}-5-trifluoromethyl-benzamide;
trans-2-chloro-N-[4-([1,2,4]triazolo[4,3-a]pyridin-3-ylaminomethyl)-cyclohexyl]-5-trifluoromethyl-benzamide;
trans-2-chloro-N-(4-{[4-(4-chloro-phenyl)-isoxazol-3-ylamino]-methyl}-cyclohexyl)-5-trifluoromethyl-benzamide;
trans-2-chloro-N-{4-[(5,7-dimethyl-pyrazolo[1,5-a]pyrimidin-3-ylamino)-methyl]-cyclohexyl}-5-trifluoromethyl-benzamide;
trans-5-chloro-N-[4-(4-chloro-3,5-dimethyl-pyrazol-1-ylmethyl)-cyclohexyl]-2-methyl-nicotinamide;
trans-2-chloro-N-[4-(2-methyl-imidazol-1-ylmethyl)-cyclohexyl]-5-trifluoromethyl-benzamide;
trans-5-chloro-N-{4-[(5-chloro-2-methoxy-pyridin-3-ylamino)-methyl]-cyclohexyl}-2-methyl-nicotinamide;
trans-5-chloro-2-methyl-N-[4-(3,4,5-trimethyl-pyrazol-1-ylmethyl)-cyclohexyl]-nicotinamide;
trans-2-chloro-N-(4-{[4-(3,4-dimethoxy-phenyl)-2,5-dimethyl-2H-pyrazol-3-ylamino]-methyl}cyclohexyl)-5-trifluoromethyl-benzamide;
trans-2-chloro-N-(4-{[4-(2-chloro-phenyl)-1H-pyrazol-3-ylamino]-methyl}-cyclohexyl)-5-trifluoromethyl-benzamide;
trans-2-chloro-N-[4-(3,5-di-(d3)-methyl-pyrazol-1-ylmethyl)-5-trifluoro methyl-benzamide;
trans-2-chloro-N-[4-(5-methyl-pyrazol-1-ylmethyl)-cyclohexyl]-5-trifluoromethyl-benzamide;
trans-2-chloro-N-[4-(3-methyl-pyrazol-1-ylmethyl)-cyclohexyl]-5-trifluoromethyl-benzamide;
trans-2-chloro-N-{4-[5-(4-methoxy-phenyl)-pyrazol-1-ylmethyl]-cyclohexyl}-5-trifluoro methyl-benzamide;
trans-2-chloro-N-{4-[3-(4-methoxy-phenyl)-pyrazol-1-ylmethyl]-cyclohexyl}-5-trifluoro methyl-benzamide;
trans-2-chloro-N-(4-{[1-(4-chloro-benzyl)-1H-tetrazol-5-ylamino]-methyl}-cyclohexyl)-5-trifluoromethyl-benzamide;
trans-2-chloro-N-{4-[(4-chloro-5-methoxy-pyridin-2-ylamino)-methyl]-cyclohexyl}-5-trifluoromethyl-benzamide;
trans-5-chloro-2-methyl-N-[4-(3-methyl-5-trifluoromethyl-pyrazol-1-ylmethyl)-cyclohexyl]-nicotinamide; and
trans-5-chloro-2-methyl-N-[4-(5-methyl-3-trifluoromethyl-pyrazol-1-ylmethyl)-cyclohexyl]-nicotinamide;
and isomers thereof;
in free or in salt form.

Therefore, according to a further aspect of the invention we provide a compound of formula I as hereinbefore described as a medicament. More particularly, we provide a compound of formula I as hereinbefore described as a corticotropin releasing factor (CRF-1) receptor antagonist.

According to a further aspect of the invention we provide the use of a compound of formula I as hereinbefore described in the manufacture of a medicament. More particularly, we provide the use as hereinbefore described in the manufacture of a medicament for a corticotropin releasing factor (CRF-1) receptor antagonist.

Furthermore it has now been found that the compounds of formula I, or a salt thereof, behave as CRF-1 receptor antagonists. Representative compounds of the invention have no significant agonist or antagonist activity at melanin concentrating hormone receptor 1 (MCH-1) or MCH-2.

The activity of a compound according to the present invention can be assessed by the following in vitro & in vivo methods.

The CRF-1 or CRF-2α receptor antagonistic activity of the agents of the invention has been determined in vitro in the following assay:

Chinese hamster ovary (CHO) cells expressing either the human recombinant CRF-1 or CRF-2a receptors (Chen et al., Proc Natl Acad Sci USA 90, 8967-8971, 1993; Liaw et al., Endocrinology 137, 72-77, 1996) are propagated in Dulbecco's modified Eagle medium supplemented with 10% foetal calf serum, non-essential amino acids, 100 U/ml penicillin, 100 mg/l streptomycin and 1 g/l geneticin (G418). For cyclic AMP determinations the Homogeneous Time-Resolved Fluoresce (HTRF) cAMP dynamic 2 kit (Cisbio International, France) was used as per manufacturers' instructions. CHO cells, previously cryopreserved, were thawed, centrifuged for 7 mins at 1200 rpm and resuspended in serum free media, then pipetted out onto clear bottomed black tissue culture treated 384-well microtitre plates (Corning Inc, US) at 2,000 cells per well. Compounds of the invention, prepared in DMSO, and subsequently diluted 50 fold in assay buffer (1× Hanks balanced salt solution, 0.2% (w/v) bovine serum albumin, 1.7 mM isobutylmethylxanthine and 10 mM Hepes, pH 7.4) are then added onto the cell containing plate where a further 2 fold dilution is performed and incubated for 15 min. Following incubation, buffer containing a 5 times final concentration of agonist is added to the plate and incubated for 30 min. Finally, d2 dye labelled cAMP and cryptate labeled anti-cAMP antibody, both made in lysis buffer, are added to the plate followed by a settling period of 1 hour. During the settling period cAMP produced by the cells competes with the d2 labelled cAMP for the anti-cAMP cryptate. The plate is read on the Pherastar (BMG, Germany). Increasing levels of endogenous cAMP produced by cells can be followed by a decrease of fluorescent signal and vice versa. Values represented by a change in arbitrary fluorescence units are converted into cAMP concentrations by use of a standard curve the reagents for which are supplied with the kit. Antagonist dose response curves (1 nM-30 μM) are constructed in the presence of 1 nM CRF. IC50 values of antagonists are calculated by fitting the percent inhibition of the effect of CRF by increasing concentrations of the antagonists. The fit is performed using the nonlinear logistic function of the Activitybase software package v 5.4.5.27 (IDBS, UK).

In this test, the agents of the invention show CRF, antagonistic activity with IC50 CRF, values of about 1 nM to 10 μM, preferably about 1 to 500 nM. Specific data are provided in Table 1 herein.

Compounds of the invention are useful for the treatment of any state with increased endogenous levels of CRF (corticotropin releasing factor) or in which the HPA (hypothalamic pituitary axis) is disregulated, or of various diseases induced or facilitated by CRF.

Compounds of the invention are in particular useful for the treatment or prevention of gastrointestinal disorders including irritable bowel syndrome with or without diarrhea, inflammatory bowel diseases, post-operative ileus, reflux disease and infectious diarrhea.

Compounds of the invention are also in particular useful for the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include fatigue syndrome and dysthymic disorder with early or late onset and with or without atypical features, neurotic depression, post traumatic stress disorders, post operative stress and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganized schizophrenia, catatonic schizophrenia, undifferentiated schizophrenia, residual schizophrenia.

Compounds of the invention are also useful in the treatment or prevention of neurodegenerative diseases such as Alzheimer's disease, Parkinson's disease, Huntington's disease, senile dementia of the Alzheimer's type, and multiinfarct dementia.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa, bulimia, obesity and metabolic syndrome.

Compounds of the invention are also useful in the treatment of sleep disorders including dysomnia, insomnia, sleep apnea, narcolepsy, and circadian rhythmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, postoperative gastric ileus (POI), inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of fertility problems, sexual dysfunctions and pre-term birth and non-inflammatory urogenital disorders such as overactive bladder and related urinary incontinence.

Compounds of the invention are also useful in the treatment of allergic disorders, in particular allergic disorders of the skin such as urticaria, and allergic disorders of the airways such as rhinitis.

Compounds of the invention are also useful in the treatment of mast cell activation disorders such as mastocytosis.

Compounds of the invention are also useful the treatment of Cushing's syndrome induced by drugs such as steroids or cancer such as pituitary adenoma.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The utility of the agents of the invention in the above indicated diseases can be confirmed in a range of standard tests. (1) The anxiolytic activity of the agents of the invention can be confirmed in the mouse elevated plus-maze [see for example Rodgers R. J., Behavioural Pharmacology 8: 477-496 (1997) where the relevance of the elevated plus-maze is discussed on p. 486; for the method, see Rodgers R. J. et al. Ethology and Psychopharmacology (Eds S J Cooper and C A Hendrie), pp 9-44 (1994), J. Wiley, Chichester]. (2) The analgesic activity of the agents of the invention can be confirmed in rat visceral hyperalgesia models following colorectal distension [see for example Schwetz I, Am J Physiology 286: G683-G691 (2004); for the method, see Ness T. J., Brain Research 450:153-169 (1988)]. (3) The anti-diarrheal activity of the agents of the invention can be confirmed in rat defecation models during stress or CRF challenge [see for example Maillot C., Gastroenterology 119:1569-1579 (2002)].

In these tests, the agents of the invention show anxiolytic-like, visceral analgesic and anti-diarrheal effects following oral administration of 0.1 to 30 mg/kg.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100 mg/kg, preferably from about 1 to about 30 mg/kg animal body weight. In larger mammals, for example humans, an indicated daily dosage is in the range from about 1 to about 500 mg, preferably from about 1 to about 100 mg of an agent of the invention, conveniently administered, for example, in divided doses up to three times a day or in sustained release form.

The agents of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of diseases induced or facilitated by CRF, such as these indicated above.

Therefore, according to a further aspect of the invention we provide a compound of formula I, or a salt thereof, for the treatment or alleviation of treatment of any state with increased endogenous level of CRF or in which the HPA (hypothalamic pituitary axis) is disregulated, or of various diseases induced or facilitated by CRF.

The agents of the invention can be administered in vivo either alone or in combination with other pharmaceutical agents, e.g. agents effective in the treatment of diseases and conditions in which an increased endogenous level of CRF plays a role or is implicated. A suitable combination consists of a compound of the present invention with one or more compounds selected from the group consisting of dopamine D2 receptor antagonists, serotonin 5-HT4 receptor agonists, serotonin 5-HT3 receptor agonists, serotonin 5-HT3 receptor antagonists, CCK1 receptor antagonists, motilin receptor agonists, μ-opioid receptor antagonists, opioid receptor agonists and opiates, other CRF-1 receptor antagonists, glutamate receptor antagonists, neurokinin receptor antagonists, histamine H2 receptor antagonists, histamine H4 receptor antagonists, proton pump inhibitors, chloride channel activators, guanylate cyclase-c activators, muscarinic receptor antagonists, antispasmodics, stimulant laxatives, osmotic laxatives, faecal softeners, absorbents and fibre supplements, antacids, GI relaxants, bismuth compounds, vanilloid receptor antagonists, anticonvulsants, NSAIDS, COX-2 inhibitors, GABAb receptor modulators, CB receptor ligands, calcium channel blockers, sodium channel blockers, tricyclic antidepressants, serotonin and noradrenaline re-uptake inhibitors, benzodiazepines, alpha-2 receptor agonists and ghrelin receptor agonists.

More specifically, a compound of the present invention may be administered as a combination with one or more compounds selected from the group consisting of dopamine D2 receptor antagonists, such as, chlorpromazine, prochlorperazine, haloperidol, alizapride, domperidone, metoclopramide and itopride; serotonin 5HT4 receptor agonists, such as, cisapride, cinitapride, mosapride, renzapride, prucalopride, tegaserod, velusetrag, ATI-7505 and compounds described in WO 2005068461, US 2005228014, WO 2005080389, US 2006100426, US 2006100236, US 2006135764, US 2005277671, WO 2005092882, WO 2005073222, JP 2005104896, JP 2005082508, WO 2005021539, JP 2004277319, JP 2004277318, WO 2004026869, EP 1362857, WO 2006108127, US 20060183901, WO 2006127815, US 20060276482, WO 2007005951, WO 2007010390, WO 2007005951, WO 2007048643, WO 2007096352, WO 2007068739 and WO 20070117796; serotonin 5-HT3 receptor agonists, such as, pumesotrag and compounds described in WO 2007004041; serotonin 5-HT3 receptor antagonists, such as, alosetron, cilansetron, ramosetron, azasetron, ondansetron, granisetron, tropisetron, DDP225 and compounds described in WO 2006183769, WO 2006105117 and WO 2007004041; CCK1 receptor antagonists, such as, JNJ-17156516, devazepide, loxiglumide and dexloxiglumide; motilin receptor agonists, such as, motilin, atilmotin, erythromycin, alemcinal, mitemcinal, KOS-2187, 1-[4-(3-fluoro-phenylamino)-piperidin-1-yl]-2-[4-((S)-3-methyl-piperazin-1-ylmethyl)-phenyl]-ethanone and compounds described in WO 2005060693, WO 2006127252, WO 2007007018, WO 2007012479 and WO 2008000729; m-opioid receptor antagonists, such as, naxolone, alvimopan, methylnaltrexone and compounds described in US 20050203123, US 2006063792, WO 2007050802, US 2007103187, WO 2009029252, WO 2009029256, WO 2009029257 and WO 2009029253; opioid receptor agonists and opiates, such as, morphine, buprenorphine, diamorphine, dihydrocodeine, fentanyl, pethidine, asimadoline, loperamide and codeine; CRF-1 receptor antagonists, such as, GSK876008, pexacerfont and compounds described in WO 2004069257, WO 9940089, U.S. Pat. No. 6,844,351, WO 2005013997, WO 2005014557, WO 2005023806, WO 2005026126, WO 2005028480, WO 005044793, WO 2005051954, WO 2005051954, WO 2005115399, WO 2005028480, WO 2005023806, WO 2006044958, WO 2006044821 and US 20060211710; glutamate receptor antagonists, such as, AZD9272, AZD2066, AFQ056, ADX-48621 and compounds described in WO 9902497, WO 2000020001, WO 200304758 and WO 2005030723, WO 2005077345, US 2006009443, EP 1716152, WO 2005080397, US 2006019997, WO 2005066155, WO 2005082884, WO 2005044266, WO 2005077373, EP 1713791, EP 1720860, WO 2005080379, EP 1716130, US 2006235024, WO 2005080363 WO 2006114264, WO 2006114260, WO 2006089700, WO 2006114262, WO 2006123257, US 2005272779, WO 2006048771, WO 2006123249, US 2006009477, WO 2006014185, EP 1723144, US 2006025414, US 2006004021, US 2006160857, WO 2006074884, WO 2006129199, WO 2006123244, WO 2006123255, WO 2007040982, WO 2007023290, WO 2007023242, WO 2007050050, WO 2007039781, WO 2007039782 and WO 2007023245; neurokinin receptor antagonists, such as, taletant, osanetant, casopitant, nepadutrent, saredutant, DNK-333, SLV-317, SLV321, SLV317 and compounds described in EP 96-810237, WO 2006137790, WO 2006137791, WO 2006094934, WO 2007037742 and WO 2007037743; histamine H2 receptor antagonists, such as, famotidine, cimetidine, ranitidine and nizatidine; histamine H4 receptor antagonists, such as, JNJ7777120, JNJ10191584 and compounds described in US 2006111416, WO 2006050965, WO 2005092066, WO 2005054239 US 2005070550, US 2005070527, EP 1505064, WO 2007090852, WO 2007090853, WO 2007090854, US 20070232616, US 20070238771, WO 2007117399, WO 2007031529 and WO2007072163; proton pump inhibitors, such as, omeprazole, lansoprazole, rabeprazole, tentoprazole, pantoprazole, esomeprazole, revaprazan, soraprazan and AGN201904; chloride channel activators, such as, lubiprostone; guanylate cyclase-2c activators, such as, linaclotide, guanilib, guanylin, uroguanylin and compounds described in WO 2005087797, WO 2005016244, WO 2007022531, WO 2007101158, WO 2007101161 and U.S. Pat. No. 7,041,786; muscarinic receptor antagonists, such as, darifenacin, solifenacin, atropine, dicycloverine, hycosine butyl bromide, propantheline, oxybutinin, cimetropium bromide and pinaverium bromide; antispasmodics, such as, mebeverine, octylonium bromide, trimebutine, tiropramide, alverine and peppermint oil; stimulant laxatives, such as, bisacodyl; osmotic laxatives, such as, activated charcoal with sorbitol, lactulose, magnesium hydroxide and phosphate buffered saline; faecal softeners, such as, senna concentrate, liquid paraffin and arachis oil; absorbents and fibre suplements; bulk fibre laxatives such as bran, methylcellulose, ispaghula husk and sterculia; antacids, such as, aluminum, magnesium and calcium antacids, simeticone and alginate containing preparations; GI relaxants, such as, cholestyramine resin; bismuth compounds, such as, bismuth subsalicylate; vanilloid receptor antagonists, such as, SB-705498, ABT-102, AZD1386, GRC-6211, MK-2295 and compounds described in WO 2002076946, WO 2004033435, WO 2005121116, WO 2005120510, WO 2006006740, WO 2006006741, WO 2006010445, WO 2006016218, US 2006058308, WO 2006033620, WO 2006038871, US 2006084640, US 2006089360, WO 2006058338, WO 2006063178, US 2006128689, WO 2006062981, WO 2006065646, WO 2006068618, WO 2006068592, WO 2006068593, WO 2006076646, US 2006160872, WO 200608082, US 2006183745, WO 2006095263, WO 2006102645, WO 2006100520, US 2006241296, WO 2006122200, WO 2006120481, WO 2006122250, DE 102005044814, WO 2006122772, WO 2006122777, WO 2006124753, WO 2006122799, WO 2006122770, WO 2006122769, WO 2006136245, WO 2007030761, US 20070088072, US 20070088073, US 20070105920, WO 2007042906, WO 2007045462, WO 2007050732; anticonvulsants, such as, carbemazepine, oxcarbemazepine, lamotrigine, gabapentin and pregabalin; NSAIDS, such as, aspirin, acetometaphen, ibuprofen, diclofenac, naproxen, flurbiprofen, indomethacin, piroxicam, ketoprofen, sulindac and diflunisal; COX-2 inhibitors, such as, celecoxib, rofecoxib, lumiracoxib, valdecoxib, etoricoxib and compounds described in WO 2004048314; GABAb receptor modulators, such as, racemic and (R)-baclofen, AZD3355, XP19986 and compounds described in WO 2006001750 and WO 2004000856; CB receptor ligands, such as, dronabinol, nabilone, cannabidiol, rimonabant and compounds described in WO 2002042248 and WO 2003066603; calcium channel blockers, such as, ziconotide, AGI0-003, PD-217014 and compounds described in WO 2006038594, WO 2006030211 and WO 2005068448; sodium channel blockers, such as, lamotrigine and compounds described in WO 2006023757, WO 2005097136, JP 2005206590 and WO 2005047270; tricyclic antidepressants, such as, clomipramine, amoxapine, nortripyline, amitriptyline, imipramine, desipramine, doxepin, trimipramine and protripyline; serotonin and noradrenaline re-uptake inhibitors, such as, milnaciprane, desvenlafaxine, sibutramine, duloxetine, fluoxetine, paroxetine, citalopram, sertraline and fluvoxamine; benzodiazepines, such as, levotofisopam, diazepam, lorazepam, clonazepam and alprazolam; alpha-2 receptor agonists, such as, clonidine, tizanidine and guanfacine; ghrelin receptor agonists, such as, ghrelin, ibutamoren, capromorelin, tabimorelin, ipamorelin, 2-Methylalanyl-N-[1(R)-formamido-2-(1H-indol-3-yl)ethyl]-D-tryptophanamide, TZP-101, TZP-102, LY-444711, EX-1314 and compounds described in U.S. Pat. No. 6,525,203, US 20050154043, WO 2005097788, WO2006036932, WO 2006135860, US 20060079562, WO 2006010629, WO 2006009674, WO 2006009645, US 20070021331, WO 2007020013, US 20070037857, WO 2007014258, WO 2007113202, WO 2007118852, US 20080194672, US 20080051383 and US 20080051383; corticosteroids, such as, hydrocortisone, cortisone, dexamethasone, betamethasone, beclomethasone, prednisolone, 6-methylprednisolone, budesonide, mometasone furoate, ciclesonide, fluticasone propionate and fluticasone furoate; aminosalicylates, such as, mesalazine, ipsalazide, olsalazine and balsalazide; immunomodulators, such as, azathioprine, 6-mercaptopurine, methotrexate, mycophenolate mofetil, ciclosporin and tacrolimus; PDE4 inhibitors, such as, tetomilast, cilomilast, roflumilast and arofylline; antibiotics, such as, metronidazole, ornidazole and ciprofloxacin; anti-adhesion molecule agents, such as, natalizumab and MLN02; anti IL-2 agents, such as, daclizumab and basiliximab; anti CD-3 agents, such as, visilizumab; and anti-TNF agents, such as, infliximab, adalimumab, fontolizumab and certolizumab pegol; psychiatric medications comprising compounds selected from the group consisting of agomelatine, azapirones, alprazolam, amitriptyline, aniracetam, acetyl-L-carnitine, aripiprazol, acetophenazine, benzodiazepines, barbiturate, buspirone, bupropione, chlordiazepoxide, chlorazepate, clonazepam, chlorpromazine, clozapine, CX614, CX516, chlorprothixene, diphenhydramine hydroxyzine, demoxepam, diazepam, droperidol, duloxetine, donezepil, doxepine, desipramine, flurazepam, fluphenazine, fluoxetine, flupentixol, gabapentin, melatonin, ginkgo-derived compounds, galantamine, haloperidol, Hydergine (ergoloid mesylates), huperzine, isocarboxazid, imipramine, lorazepam, loxapine, meprobamate, medazepam, moclobemide, molindone, maprotiline, modafinil, memantine, methylphenicate, mesoridazine, methotrimeprazine, nortriptyline, naproxen, oxazepam, oxiracetam, olanzapine, prazepam, paroxetine, phenelzine, pipotiazine, perphenazine, promazine, pimozide, PDE4 inhibitors, quazepam, quetiapine, reboxetine, rivastigmine, prochlorperazine, risperidone, sertraline, sertindole, temazepam, triazolam, tranylcypromine, tomoxetine, thiotixene, trifluoperazine, thioridazine, zolpidem and ziprasidone.

A preferred group of compounds which may be mentioned are compounds of formula II:

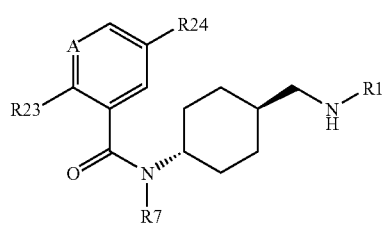

in which $R^{23}$ is hydrogen, alkyl C1 to 6, haloalkyl C1 to 6, dialkylamino C1 to 6, alkoxy C1 to 6 or halogen;
$R^{24}$ is alkyl C1 to 6, haloalkyl C1 to 6 or halogen;
A is —CH— or —N—; and
$R^1$ and $R^7$ are each as hereinbefore described;
and isomers thereof;
in free form or in salt form.

$R^{23}$ is preferably halogen, such as Cl or alkyl, such as methyl or dialkylamino C1 to 6, such as dimethylamino.

$R^{24}$ is preferably haloalkyl C1 to 6, such as $CF_3$ or halogen, such as Cl.

An alternative preferred group of compounds which may be mentioned are compounds of formula III;

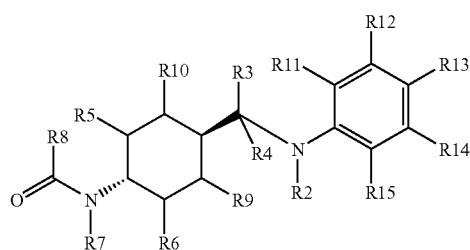

in which $R^2$, $R^3$, $R^4$, $R^5$, $R^6$, $R^7$, $R^8$, $R^9$ and $R^{10}$ are each as hereinbefore described; and
$R^{11}$, $R^{12}$, $R^{13}$, $R^{14}$ and $R^{15}$, which may be the same or different, are each, hydrogen, halogen, alkyl C1 to 6, haloalkyl C1 to 6, alkoxy C1 to 6, halogenated alkoxy C1 to 6, nitrile, morpholinyl, sulphamoyl or $R^{11}$ and $R^{12}$ or $R^{12}$ and $R^{13}$ taken together may form a benzo or heteroaryl fused ring;
and isomers thereof;
in free form or in salt form.

An alternative preferred group of compounds which may be mentioned are compounds of formula IV;

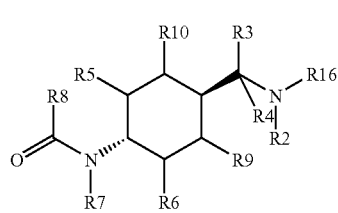

in which $R^2$, $R^3$, $R^4$, $R^5$, $R^6$, $R^7$, $R^8$, $R^9$ and $R^{10}$ are each as hereinbefore defined; and $R^{16}$ is a heteroaryl ring optionally substituted by one or more of alkyl C1 to 10, alkoxy C1 to 10, hydroxyalkyl C1 to 10, halogen, haloalkyl C1 to 10, halogenated alkoxy C1 to 10, nitrile, —$CO_2R^{25}$, alkylamino C1 to 6, dialkylamino C1 to 6, morpholinyl, phenyl, substituted phenyl, aryloxy, substituted phenoxy, imidazolinyl or oxoimidazolinyl;
and isomers thereof;
in free form or in salt form.

The heteroaryl ring of $R^{16}$ may comprise one or more heteroatoms, is preferably aromatic and may optionally be substituted. Examples of heteroaryl rings include, pyridyl, thiazolyl, quinolinyl, thiadiazolyl, pyrimidinyl, oxadiazolyl, indolyl, benzo[1,3]dioxolyl, isoxazolyl, pyrazolyl, oxazolyl, benzimidazolyl, benzothiazolyl, pyrazinyl, triazolyl, benzoxazolyl and imidazolidinyl.

An alternative preferred group of compounds which may be mentioned are compounds of formula XI;

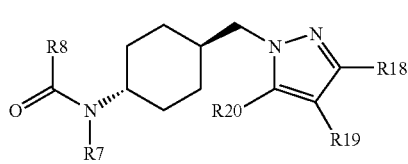

in which $R^7$ and $R^8$ are each as hereinbefore defined; and
$R^{18}$, $R^{19}$ and $R^{20}$, which may be the same or different, are each hydrogen, alkyl C1 to 10, alkoxy C1 to 10, halogen, haloalkyl C1 to 10, halogenated alkoxy, nitrile, morpholinyl, or, optionally substituted, phenyl, phenoxy, imidazolinyl or oxoimidazolinyl, or $R^{18}$ and $R^{19}$ or $R^{19}$ and $R^{20}$ may together form a saturated or unsaturated carbocyclic or heterocyclic ring;
and isomers thereof;
in free form or in salt form.

An alternative preferred group of compounds which may be mentioned are a compound of formula XII;

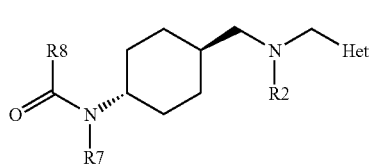

in which $R^2$, $R^7$ and $R^8$ are each as hereinbefore defined; and

Het is a 5-membered heteroaryl ring which may optionally be substituted by one or more of alkyl C1 to 10, alkoxy C1 to 10, halogen, haloalkyl C1 to 10, halogenated alkoxy C1 to 10, nitrile, morpholinyl, or optionally substituted, phenyl, phenoxy, imidazolinyl or oxoimidazolinyl; or Het may optionally be fused to a substituted or unsubstituted benzo or heteroaryl ring;
and isomers thereof;
in free form or in salt form.

In an alternative aspect of the invention we provide a compound of formula IX;

IX

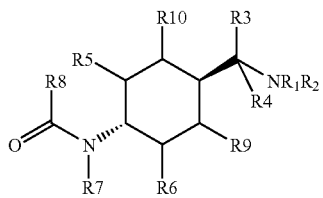

in which $R^1$ is phenyl, biphenyl, naphthyl, 5- or 6-membered heteroaryl, a bicyclic heteroaryl, each of which may optionally be substituted by one or more of alkyl C1 to 10, alkoxy C1 to 10, halogen, haloalkyl C1 to 10, halogenated alkoxy C1 to 10, nitrile, morpholinyl, or optionally substituted phenyl, phenoxy, imidazolinyl or oxoimidazolinyl or together $R^1$ and $R^2$ form a ring, which may be optionally substituted one or more of alkyl C1 to 10, alkoxy C1 to 10, halogen, haloalkyl C1 to 10, halogenated alkoxy, nitrile, morpholinyl, or optionally substituted phenyl, phenoxy, imidazolinyl or oxoimidazolinyl;

$R^2$ is hydrogen or alkyl C1 to 6;

$R^3$, $R^4$, $R^5$, $R^6$, $R^7$, $R^9$ and $R^{10}$, which may be the same or different, are each hydrogen or alkyl C1 to 6;

$R^8$ is phenyl, a 5-membered heteroaryl, a 6-membered heteroaryl or a bicyclic system, each of which may optionally be substituted, by one or more of alkyl C1 to 6, halogenated alkyl C1 to 6, halogen, alkylamino C1 to 6, dialkylamino C1 to 6, alkoxy C1 to 6 or haloalkoxy C1 to 6;

and isomers thereof;

in free form or in salt form.

In an alternative aspect of the invention we provide a compound of formula X;

X

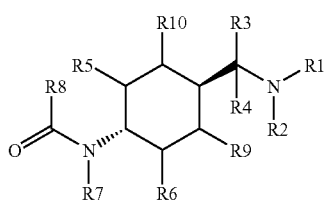

in which $R^1$ is phenyl which may optionally be substituted by one or more of alkyl C1 to 10, alkoxy C1 to 10, halogen, haloalkyl C1 to 10, halogenated alkoxy C1 to 10, nitrile, morpholinyl, or optionally substituted, phenyl, phenoxy, imidazolinyl or oxoimidazolinyl, or $R^1$ may optionally be fused to a substituted or unsubstituted benzo or heteroaryl ring;

$R^2$, $R^3$, $R^4$, $R^5$, $R^6$, $R^7$, $R^9$ and $R^{10}$, which may be the same or different, are each hydrogen or alkyl C1 to 6;

$R^8$ is phenyl, a 5-membered heteroaryl, a 6-membered heteroaryl or a bicyclic system, each of which may optionally be substituted, by one or more of alkyl C1 to 6, halogenated alkyl C1 to 6, halogen, alkylamino C1 to 6, dialkylamino C1 to 6, alkoxy C1 to 6 or haloalkoxy C1 to 6;

and isomers thereof;

in free form or in salt form.

$R^2$ is preferably hydrogen.

In an alternative aspect of the invention we provide a compound of formula X;

X

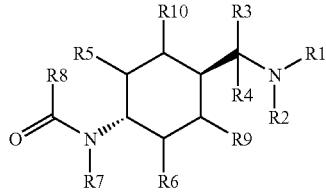

in which $R^1$ is 2-pyridyl, 2-pyrimidinyl or 4-pyrazinyl which may optionally be substituted by one or more of alkyl C1 to 10, alkoxy C1 to 10, halogen, haloalkyl C1 to 10, halogenated alkoxy C1 to 10, nitrile, —$CO_2R^{26}$, —$CH_2NR^{27}R^{28}$, morpholinyl, or optionally substituted phenyl, phenoxy, imidazolinyl or oxoimidazolinyl; or $R^1$ may optionally be fused to a substituted or unsubstituted benzo or heteroaryl ring;

$R^2$, $R^3$, $R^4$, $R^5$, $R^6$, $R^7$, $R^9$, $R^{10}$, $R^{26}$, $R^{27}$ and $R^{28}$, which may be the same or different, are each hydrogen or alkyl C1 to 6;

$R^8$ is phenyl, a 5-membered heteroaryl, a 6-membered heteroaryl or a bicyclic system, each of which may optionally be substituted, by one or more of alkyl C1 to 6, halogenated alkyl C1 to 6, halogen, alkylamino C1 to 6, dialkylamino C1 to 6, alkoxy C1 to 6 or haloalkoxy C1 to 6;

and isomers thereof;

in free form or in salt form.

In an alternative aspect of the invention we provide a compound of formula X;

X

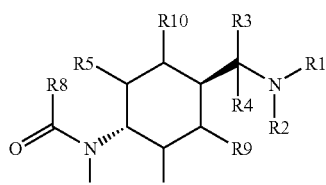

in which $R^1$ is 3-pyridyl which may optionally be substituted by one or more of alkyl C1 to 10, alkoxy C1 to 10, halogen, haloalkyl C1 to 10, halogenated alkoxy C1 to 10, nitrile, morpholinyl, or optionally substituted, phenyl, phenoxy, imidazolinyl or oxoimidazolinyl; or $R^1$ may optionally be fused to a substituted or unsubstituted benzo or heteroaryl ring;

$R^2$, $R^3$, $R^4$, $R^5$, $R^6$, $R^7$, $R^9$ and $R^{10}$, which may be the same or different, are each hydrogen or alkyl C1 to 6;

$R^8$ is phenyl, a 5-membered heteroaryl, a 6-membered heteroaryl or a bicyclic system, each of which may optionally be substituted, by one or more of alkyl C1 to 6, halogenated alkyl C1 to 6, halogen, alkylamino C1 to 6, dialkylamino C1 to 6, alkoxy C1 to 6 or haloalkoxy C1 to 6;

and isomers thereof;

in free form or in salt form.

In an alternative aspect of the invention we provide a compound of formula X;

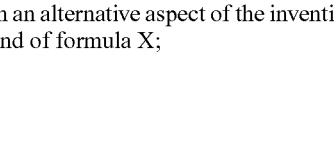

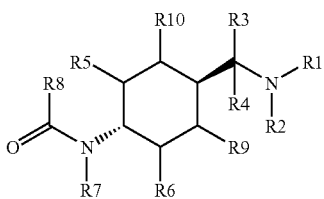

in which $R^1$ is a 5-membered heteroaryl which may optionally be substituted by one or more of alkyl C1 to 10, alkoxy C1 to 10, halogen, haloalkyl C1 to 10, halogenated alkoxy C1 to 10, nitrile or morpholinyl; or phenyl, phenoxy, imidazolinyl or oxoimidazolinyl each of which may be optionally substituted, or $R^1$ may optionally be fused to a substituted or unsubstituted benzo or heteroaryl ring the substituents being selected from the group of alkyl C1 to 6, halo. haloalkyl C1 to 6, alkoxy C1 to 6, or carboxy; or together $R^1$ and $R^2$ form a ring, which may be optionally substituted as hereinbefore described;

$R^2$ is hydrogen or alkyl C1 to 6 or together $R^1$ and $R^2$ form a ring, which may be optionally be substituted as hereinbefore described;

$R^3$, $R^4$, $R^5$, $R^6$, $R^7$, $R^9$ and $R^{10}$, which may be the same or different, are each hydrogen or alkyl C1 to 6;

$R^8$ is phenyl, a 5-membered heteroaryl, a 6-membered heteroaryl or a bicyclic system, each of which may optionally be substituted, by one or more of alkyl C1 to 6, halogenated alkyl C1 to 6, halogen, alkylamino C1 to 6, dialkylamino C1 to 6, alkoxy C1 to 6 or haloalkoxy C1 to 6;

and isomers thereof;

in free form or in salt form.

$R^1$ may contain from 1 to 3 heteroatoms, selected from one or more of N, O or S, for example $R^1$ may be pyrrole, pyrazole, oxazole, isozaxole, thiazole, oxadiazole, triazole or thiadiazole.

$R^2$ is preferably hydrogen.

In an alternative aspect of the invention we provide a compound of formula X;

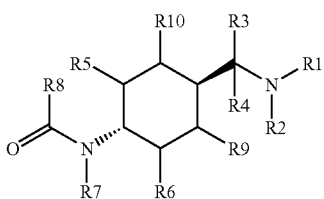

in which together $R^1$ and $R^2$ form a heteroaryl ring, which may be optionally substituted the substituents being selected from the group alkyl C1 to 10, alkoxy C1 to 10, halogen, haloalkyl C1 to 10, halogenated alkoxy C1 to 10, nitrile or morpholinyl; or phenyl, phenoxy, heteroaryl or $R^1$ may optionally be fused to a substituted or unsubstituted benzo or heteroaryl ring, the substituents being selected from the group of alkyl C1 to 6, halo. haloalkyl C1 to 6, alkoxy C1 to 6, or carboxy;

$R^3$, $R^4$, $R^5$, $R^6$, $R^7$, $R^9$ and $R^{10}$, which may be the same or different, are each hydrogen or alkyl C1 to 6;

$R^8$ is phenyl, a 5-membered heteroaryl, a 6-membered heteroaryl or a bicyclic system, each of which may optionally be substituted, by one or more of alkyl C1 to 6, halogenated alkyl C1 to 6, halogen, alkylamino C1 to 6, dialkylamino C1 to 6, alkoxy C1 to 6 or haloalkoxy C1 to 6;

and isomers thereof;

in free form or in salt form.

Together $R^1$ and $R^2$ may form a heteroaryl ring selected from the group consisting of pyrrole, pyrazole, oxazole, isoxazole, thiazole, oxadiazole, triazole or thiadiazole, each of which may be optionally substituted as hereinbefore described.

In an alternative aspect of the invention we provide a compound of formula X;

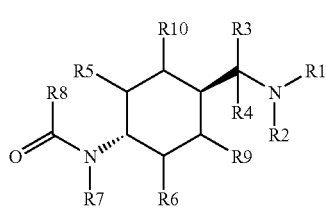

in which $R^1$ is —$CH_2R^{21}$;

$R^2$, $R^3$, $R^4$, $R^5$, $R^6$, $R^7$, $R^9$ and $R^{10}$, which may be the same or different, are each hydrogen or alkyl C1 to 6;

$R^8$ is phenyl, a 5-membered heteroaryl, a 6-membered heteroaryl or a bicyclic system, each of which may optionally be substituted, by one or more of alkyl C1 to 6, halogenated alkyl C1 to 6, halogen, alkylamino C1 to 6, dialkylamino C1 to 6, alkoxy C1 to 6 or haloalkoxy C1 to 6;

$R^{21}$ is a 5-membered heteroaryl which may optionally be substituted by one or more of alkyl C1 to 10, alkoxy C1 to 10, halogen, haloalkyl C1 to 10, halogenated alkoxy C1 to 10, nitrile, morpholinyl, or optionally substituted, phenyl, phenoxy, imidazolinyl or oxoimidazolinyl; or $R^{21}$ may optionally be fused to a substituted or unsubstituted benzo or heteroaryl ring;

and isomers thereof;

in free form or in salt form.

$R^{21}$ may be selected from the group consisting of pyrrole, pyrazole, oxazole, isoxazole, thiazole, oxadiazole, triazole, indole, benzoxazole, benzimidazole, benzothiazole, indazole, oxadiazole or thiadiazole, each of which may be optionally substituted as hereinbefore described.

Acid addition salts may be produced from the free bases in known manner, and vice-versa. A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids) one or more protonated basic groups (e.g. amines), or both (e.g. zwitterions).

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

A prodrug is a compound which is converted to a therapeutically active compound after administration. For example, conversion may occur by hydrolysis of an ester group or some other biologically labile group. Prodrug preparation is well known in the art. For example "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon, sulfur or phosphorus atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of formula (I) in optically pure form, where appropriate, can be obtained from the corresponding racemates according to well-known procedures, e.g., HPLC with chiral matrix. Alternatively, optically pure starting materials can be used.

Stereoisomeric mixtures, e.g., mixtures of diastereomers, can be separated into their corresponding isomers in a manner known per se by means of suitable separation methods. Diastereomeric mixtures, e.g., may be separated into their individual diastereomers by means of fractionated crystallization, chromatography, solvent distribution and similar procedures. This separation may take place either at the level of a starting compound or in a compound of formula (I) itself. Enantiomers may be separated through the formation of diastereomeric salts, e.g., by salt formation with an enantiomer-pure chiral acid, or by means of chromatography, e.g., by HPLC, using chromatographic substrates with chiral ligands.

Any asymmetric atom (e.g., carbon or the like) of the compound(s) of the present invention can be present in racemic or enantiomerically enriched, for example the (R)—, (S)— or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)— or (S)-configuration. Substituents at atoms with unsaturated bonds may, if possible, be present in cis-(Z)— or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

According to a further aspect of the invention we provide a method of treatment or alleviation of any state with increased endogenous level of CRF or in which the HPA (hypothalamic pituitary axis) is disregulated, or of various diseases induced or facilitated by CRF which comprises administering to a mammal a therapeutically effective amount of a compound of formula I as hereinbefore described, or a salt thereof.

We further provide a pharmaceutical composition comprising a compound of formula I as hereinbefore described, in free form or in pharmaceutically acceptable salt form, in association with a pharmaceutically acceptable adjuvant, diluent or carrier.

The pharmaceutical compositions for separate administration of the combination partners and for the administration in a fixed combination, i.e., a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Pharmaceutical compositions contain, e.g., from about 0.1% to about 99.9%, preferably from about 20% to about 60%, of the active ingredients. Pharmaceutical preparations for the combination therapy for enteral or parenteral administration are, e.g., those in unit dosage form, such as tablets including sugar-coated tablets, capsules, suppositories and ampoules. These are prepared in a manner known, per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by CRF, or (ii) associated with CRF activity, or (iii) characterized by abnormal activity of CRF; or (2) reducing or inhibiting the activity of CRF; or (3) reducing or inhibiting the expression of CRF. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CRF; or at least partially reducing or inhibiting the expression of CRF. The meaning of the term "a therapeutically effective amount" as illustrated in the above embodiment for CRF also applies by the same means to any other relevant proteins/peptides/enzymes.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof. In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the α-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

The present invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula I.

According to an additional aspect of the invention we provide a process for the manufacture of a compound of formula I as hereinbefore described which comprises one or more of the following steps;

(i) reacting a compound of formula V;

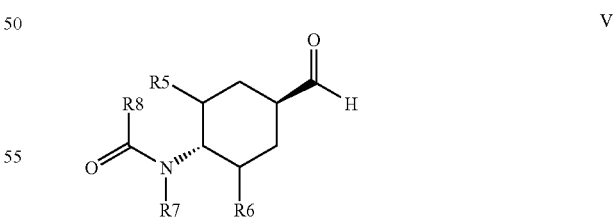

in which $R^5$, $R^6$, $R^7$ and $R^8$, are each as hereinbefore defined;

with a compound of formula VI;

$R^1NH_2$            VI in which $R^1$ is as hereinbefore defined; or (ii) reacting a compound of formula VII;

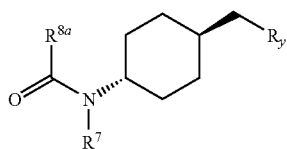

in which $R^{8a}$ is $R^8$ or a protecting group;

$R^5$, $R^6$, $R^7$, $R^8$, $R^9$, $R^{10}$, $R^{17}$ and $R^{22}$, are each as hereinbefore defined; and $R^y$ is a leaving group;

with a compound of formula VIII;

$$R^1R^2NH \quad \text{VIII}$$

in which $R^1$ and $R^2$ are each as hereinbefore defined.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

Other process schemes which may be utilized include:

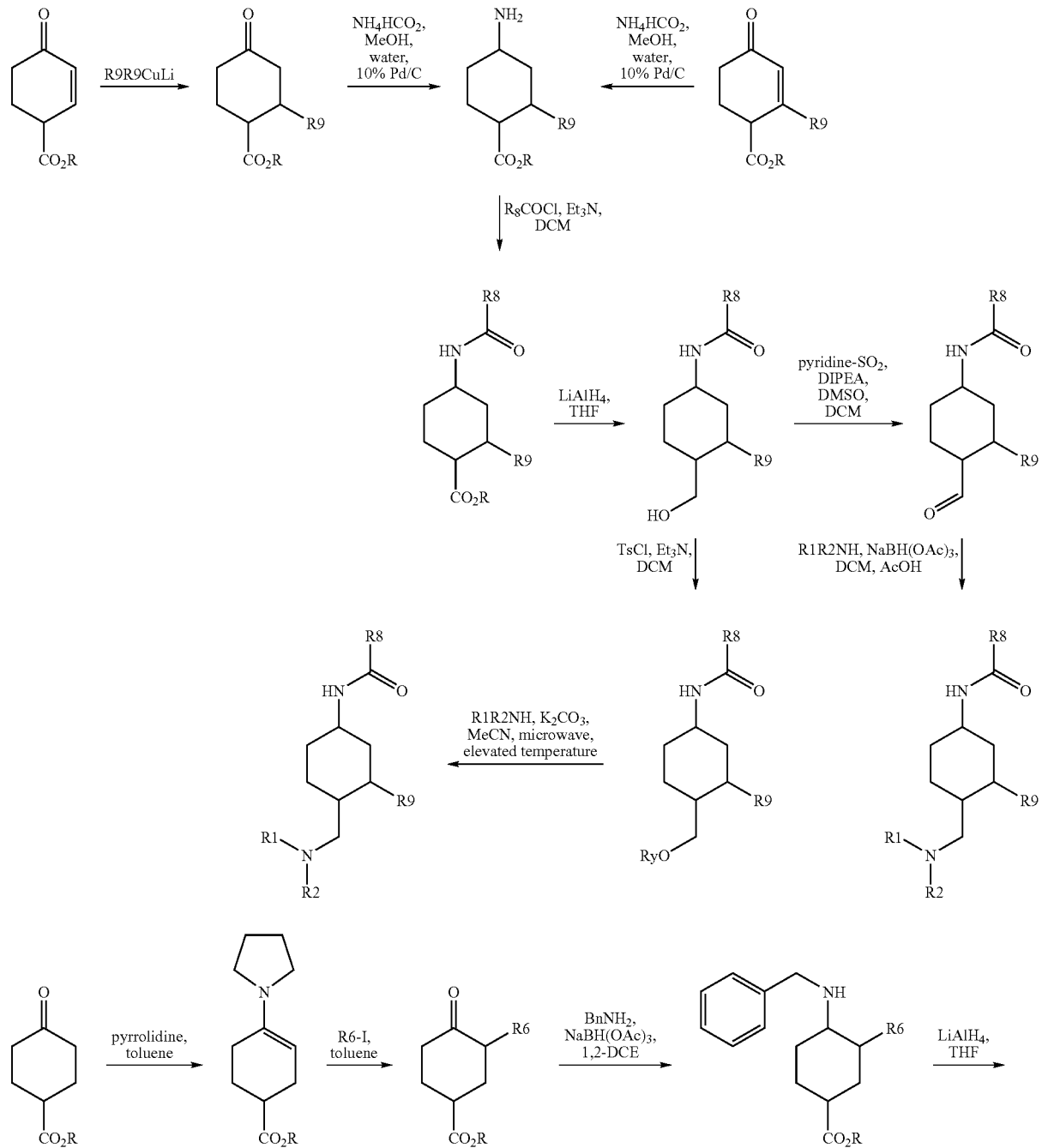

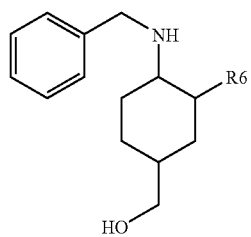 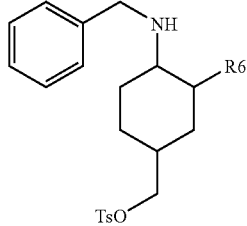
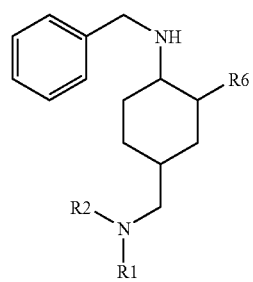 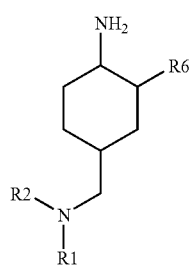 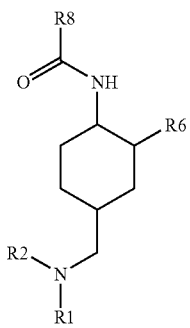
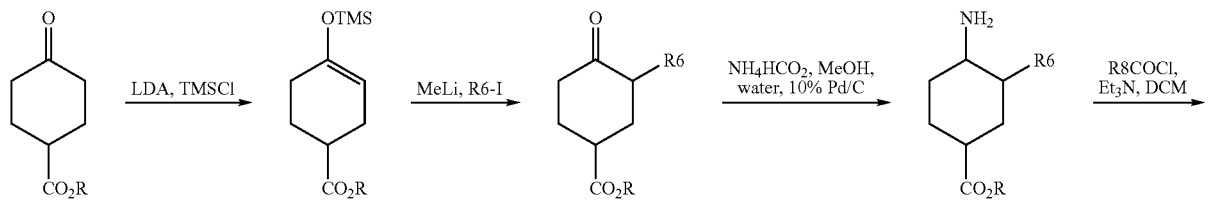
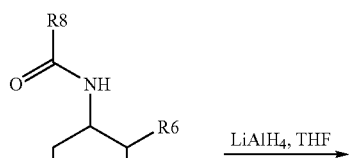
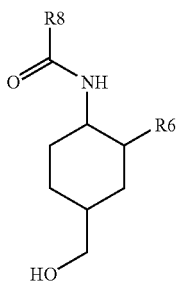 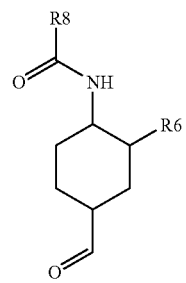
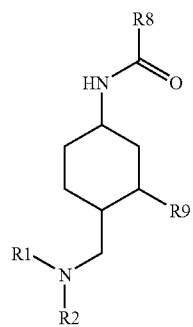 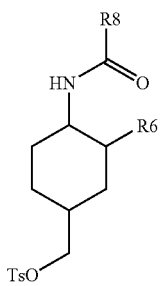 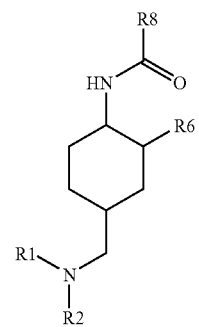

-continued

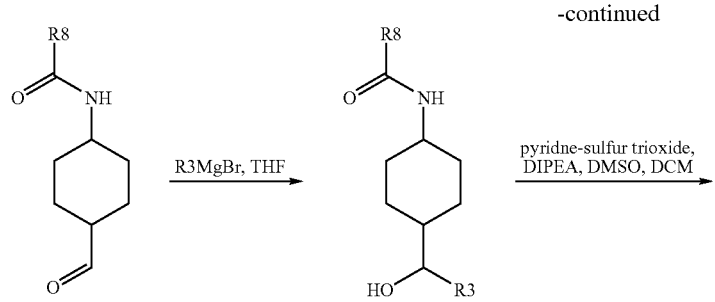

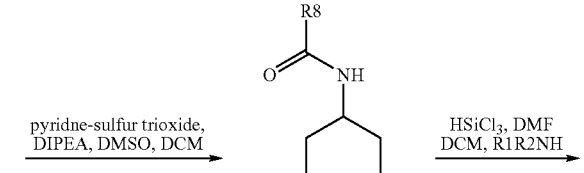

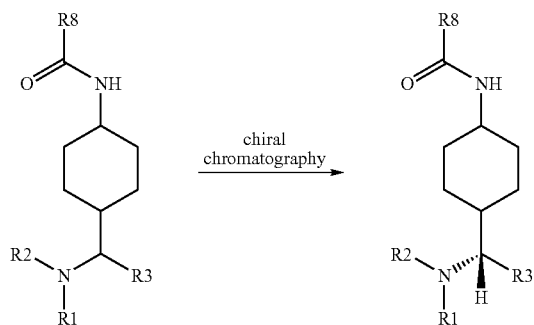

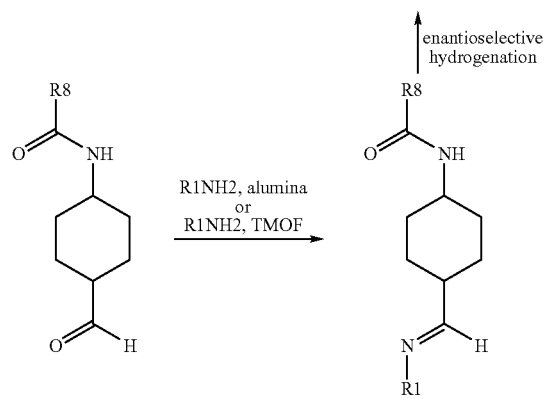

The leaving group $R^y$ may be any conventionally known leaving group, examples of which include, -Ts (tosylate), -Tf (triflate) or Ms (mesylate).

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/1, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Certain of the intermediates used in the processes as hereinbefore described are novel per se. Therefore, according to a further aspect of the invention we provide a compound of formula V;

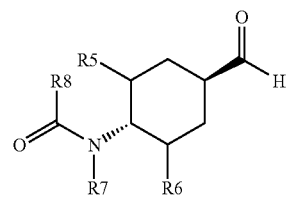

in which $R^5$, $R^6$, $R^7$ and $R^8$, are each as hereinbefore defined.

We also provide a compound of formula VII;

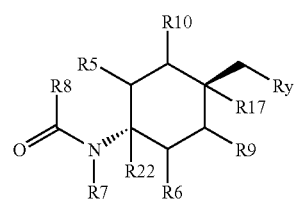

in which $R^5$, $R^6$, $R^7$, $R^8$, $R^9$, $R^{10}$, $R^{17}$, $R^{22}$ and $R^y$, are each as hereinbefore defined.

$R^y$ may be for example, tosylate, triflate or halo.

Compounds of formula I may be prepared by the general reactions (it should be noted that the numbered R groups referred to in the reaction sequences below are for illustrative purposes only and do not precisely correspond to the R groups hereinbefore defined):

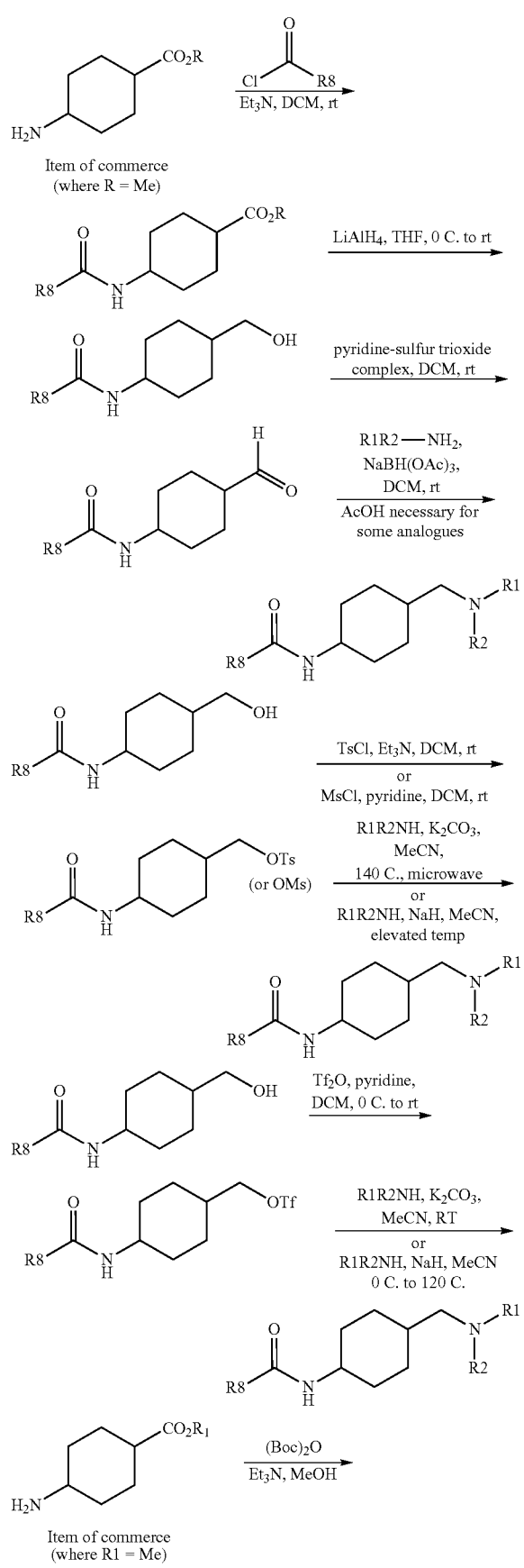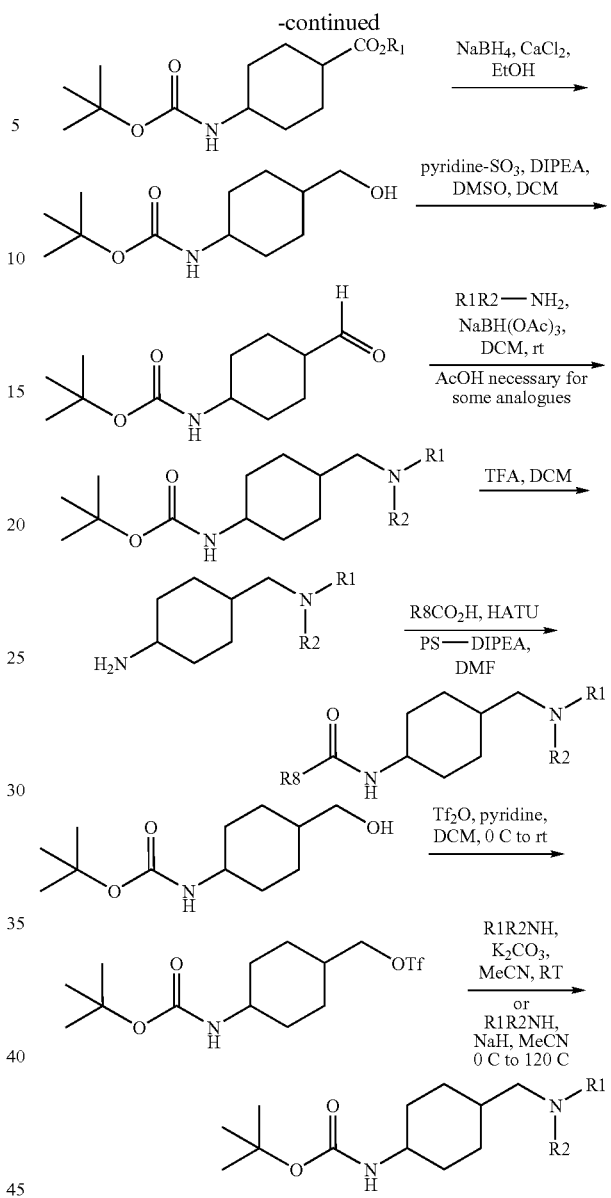

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

General Conditions:

1H-NMR: Spectra are run on either a Bruker Ultrashield™ 400 (400 MHz) spectrometer or on a Bruker AVANCE 400 NMR spectrometer using ICON-NMR. Spectra are measured at 298K and are referenced using the solvent peak, chemical shifts (☐-values) are reported in ppm, coupling constants (J) are given in Hz, spectra splitting pattern are designated as singlet (s), doublet (d), triplet (t), quadruplet (q), multiplet or more overlapping signals (m), broad signal (br), solvent is given in parentheses.

MS: These are either Agilent 1100 HPLC/Micromass Platform Mass Spectrometer combinations or Waters Acquity UPLC with SQD Mass Spectrometer or Waters Alliance HT HPLC system equipped with a MS detector Waters MicromassZQ or Waters Micromass Plattform LCZ system. Mass spectra are run on LCMS systems using electrospray ionization. [M+H]+ refers to mono-isotopic molecular weights.

The various starting materials, intermediates, and compounds of the preferred embodiments may be isolated and purified, where appropriate, using conventional techniques such as precipitation, filtration, crystallization, evaporation, distillation, catch and release, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

In addition various trade reagents and materials available from have been utilized. Such reagents and materials include IST PE-AX/SCX-2 and SCX-2 cartridges and can be readily obtained from the suppliers indicated.

For the examples below as well as throughout the application, the following abbreviations have the following meanings. If not defined, the terms have their generally accepted meanings.

| Abbreviations: | |
|---|---|
| RT | room temperature |
| DMF | N,N-dimethylformamide |
| DIPEA | N,N-diisopropylethylamine |
| MeOH | methanol |
| MeCN | acetonitrile |
| ᵗBuOH | tert-butanol |
| DCM | dichloromethane |
| EtOAc | ethyl acetate |
| HATU | 2-(1H-7-azabenzotriazol-1-yl)-1,1,3,3-tetramethyl uronium hexafluorophosphate |
| PS-NCO | Polymer-supported isocyanate |
| PS-DIEA | Polymer-supported diisopropylethylamine |

PREPARATION OF FINAL COMPOUNDS

Example 1

Trans-2-Chloro-N-{4-[(3-methyl-pyridin-2-ylamino)-methyl]-cyclohexyl}-5-trifluoromethyl-benzamide Step 1

Trans-4-(2-Chloro-5-trifluoromethyl-benzoylamino)-cyclohexane carboxylic acid methyl ester

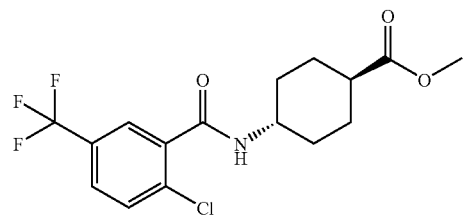

To a stirred suspension of trans-4-amino-cyclohexylcarboxylic acid methyl ester hydrochloride (6.7 g, 34.7 mmol) in dry THF (90 mL) under nitrogen atmosphere is added triethylamine (12 mL, 86.8 mmol). The suspension is cooled to 0° C. and 2-chloro-5-(trifluoromethyl)benzoyl chloride (8.85 g, 36.4 mmol) in dry THF (40 mL) is added dropwise over 20 minutes. The resulting thick, colourless slurry is stirred at 0-5° C. for 30 minutes and then allowed to warm to room temp and stirred at room temp for 1 hour. The reaction is quenched by the dropwise addition of water (5 mL) in THF (45 mL) to give a clear solution. This is diluted with water (100 mL) and ethyl acetate (300 mL). The biphasic mixture is stirred for 5 minutes then the organic phase is separated and washed successively with water (100 mL), saturated sodium bicarbonate (100 mL) and saturated brine (100 mL), dried (MgSO₄), filtered and evaporated to give a colourless solid.; [MH+ 364].

Step 2

Trans-2-Chloro-N-(4-hydroxymethyl-cyclohexyl)-5-trifluoromethyl-benzamide

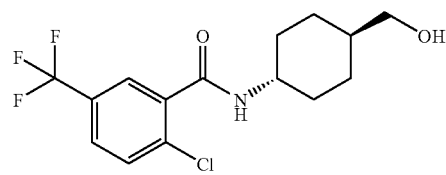

To a solution of trans-4-(2-chloro-5-trifluoromethyl-benzoylamino)-cyclohexane carboxylic acid methyl ester (step 1)(95.2 g, 0.26 mol) in dry THF (1 L) under nitrogen at 0° C. is added lithium aluminum hydride pellets (20 g, 0.53 mol) portion wise over 3 hours. The reaction mixture is stirred at 0° C. for a further 2 hours and then carefully quenched at 0° C. by the addition of water (40 mL) in THF (60 mL) followed by further THF (500 mL) to maintain a mobile suspension. Finally, 1M sodium hydroxide solution (80 mL) is added at 0° C. resulting in a yellow solution containing a colourless suspension. The reaction is filtered through a Celite® pad (filter material) to remove inorganic salts. The Celite® pad/salts are washed with EtOAc (500 mL) then with EtOAc:THF (1:1; 300 mL). The organics are combined and diluted with further EtOAc (600 mL) and then washed with saturated brine (600 mL). The organic layer is dried ($Na_2SO_4$), filtered and concentrated under reduced pressure until a slurry is obtained. $Et_2O$ is added to the slurry, which is then stirred for 5 minutes before being filtered to recover a colourless solid. The solid is washed with isohexane and then dried at 35° C. under vacuum to give the required product.

Step 3

Trans-2-Chloro-N-(4-formyl-cyclohexyl)-5-trifluoromethyl-benzamide

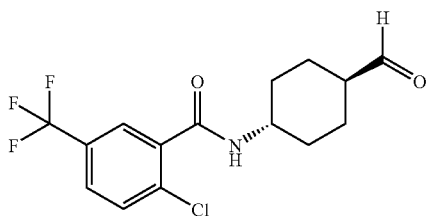

To a stirred suspension of trans-2-chloro-N-(4-hydroxymethyl-cyclohexyl)-5-trifluoromethyl-benzamide (step 2)(24 g, 71.5 mmol) in DCM (72 mL) under $N_2$ supply at RT, is added triethylamine (29.7 mL, 214 mmol) followed by DMSO (24 mL), giving an almost homogenous solution. The mixture is cooled to 0° C. (ice/salt bath), and to this is added dropwise a solution/suspension of sulfur trioxide-pyridine complex (34.1 g, 214 mmol) in DMSO (30 mL): DCM (20 mL) over a period of ~90 min. The mixture is stirred at 0-5° C. over a 1 h period then allowed to warm to RT over 2 h. The mixture is cooled to 0° C. in an ice bath and is quenched by the addition of 1M HCl (aq) (40 mL) dropwise over 30 min. The mixture is then diluted with water (60 mL) and DCM (150 mL). 2 M HCl is added to give pH~1-2. The organic phase is separated, washed again with 2 M HCl (100 mL), followed by sat. $NaHCO_3$ (100 mL). The organic layer is diluted with EtOAc (800 mL) and is vigourously stirred at RT. The mixture is then filtered removing some insoluble material in the process. The now clear two phase mixture is separated, the organic (EtOAc) layer is dried over over $MgSO_4$ and is filtered and concentrated to give an off white solid. The crude solid is suspended in diethylether (500 mL) and is triturated, removing some brown/yellow colour. The solid is allowed to settle, and the liquors are decanted off. The solid is then triturated in iso-hexane (300 mL), using the same procedure twice, then the solid is transferred to a small flask in iso-hexane slurry and is dried in vacuo to give an off-white solid; [MH+ 334]

Step 4

Trans-2-chloro-N-{4-[(3-methyl-pyridin-2-ylamino)-methyl]-cyclohexyl}-5-trifluoromethyl-benzamide

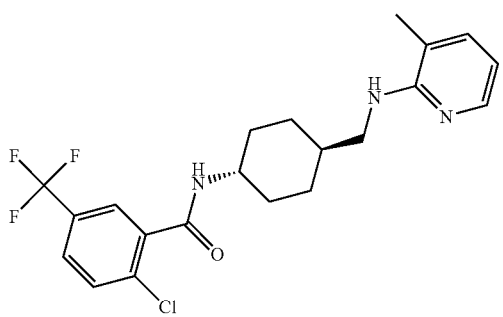

To a 100 mL round-bottomed flask containing trans-2-chloro-N-(4-formyl-cyclohexyl)-5-trifluoromethyl-benzamide (step 3) (900 mg, 2.70 mmol) and 2-amino-3-picoline (306 mg, 2.83 mmol) in dry DCM (30 mL) is added sodium triacetoxyborohydride (857 mg, 4.05 mmol) in one portion. The suspension is stirred at RT overnight. 1N sodium hydroxide (10 mL) is added and the mixture is stirred at RT for 10 min. The mixture is then extracted with DCM (3×75 mL). DCM extracts are combined, washed with sat. brine (50 mL), dried ($MgSO_4$), filtered and evaporated to give a colourless solid. The crude product is redissolved in DCM, absorbed directly onto silica gel and columned on silica gel using a 40 g pre-packed column and isohexane/EtOAc gradient elution (0% to 100% EtOAc). Product is isolated as a colourless solid and is recrystallised from minimum amount of EtOAc containing isohexane (approx 10:1 iHex:EtOAc) to give 487 mg colourless crystals.

The compounds of the following tabulated Examples (Table 1) are prepared by a similar method to that of Example 1 using the appropriate benzamide or pyrazole starting materials (prepared analogously to trans-2-chloro-N-(4-formyl-cyclohexyl)-5-trifluoromethyl-benzamide from trans-4-amino-cyclohexylcarboxylic acid methyl ester hydrochloride and the appropriate benzoyl chloride) and the appropriate amine.

TABLE 1

| Ex. | Structure | Name | [M + H]+ |
| --- | --- | --- | --- |
| 1.1 | 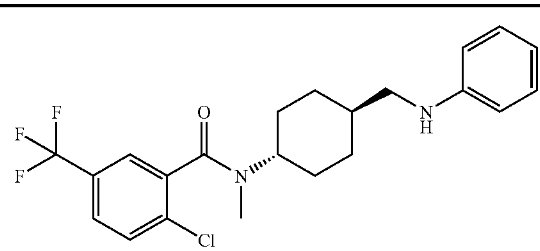 | Trans-2-Chloro-N-methyl-N-(4-phenylaminomethyl-cyclohexyl)-5-trifluoromethyl-benzamide | 425.36 |

TABLE 1-continued

| Ex. | Structure | Name | [M + H]+ |
|---|---|---|---|
| 1.2 | 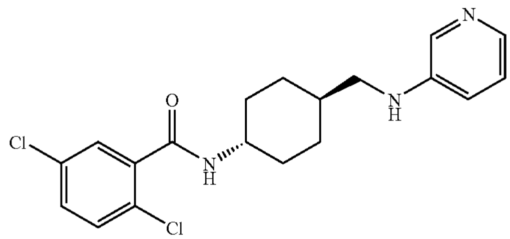 | Trans-2,5-Dichloro-N-[4-(pyridin-3-ylaminomethyl)-cyclohexyl]-benzamide | 378.19 |
| 1.3 | 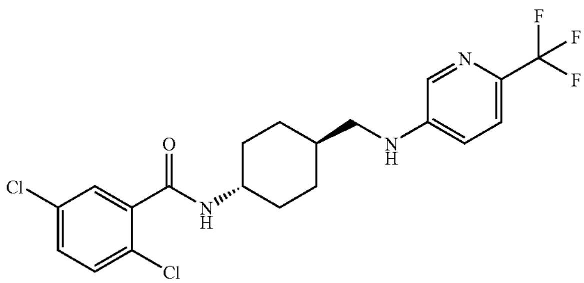 | Trans-2,5-Dichloro-N-{4-[(6-trifluoromethyl-pyridin-3-ylamino)-methyl]-cyclohexyl}-benzamide | 446.23 |
| 1.4 | 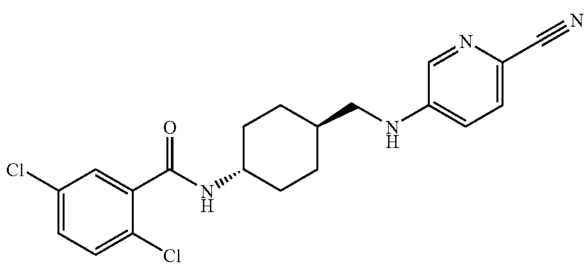 | Trans-2,5-Dichloro-N-{4-{(6-cyano-pyridin-3-ylamino)-methyl]-cyclohexyl}-benzamide | 403.23 |
| 1.5 | 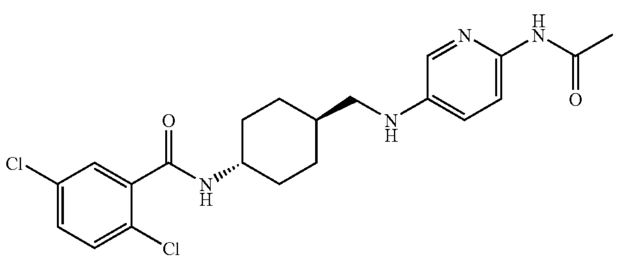 | Trans-N-{4-[(6-Acetylamino-pyridin-3-ylamino)-methyl]-cyclohexyl}-2,5-dichloro-benzamide | 435.28 |
| 1.6 | 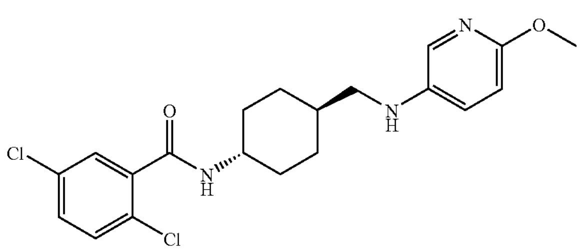 | Trans-2,5-Dichloro-N-{4-[(6-methoxy-pyridin-3-ylamino)-methyl]-cyclohexyl}-benzamide | 408.26 |
| 1.7 | 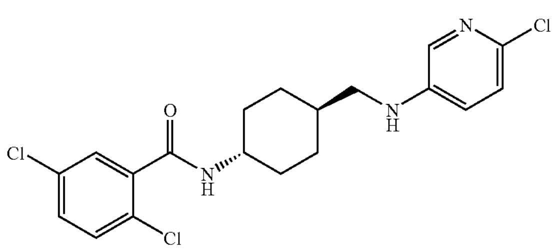 | Trans-2,5-Dichloro-N-{4-[(6-chloro-pyridin-3-ylamino)-methyl]-cyclohexyl}-benzamide | 412.23 |

TABLE 1-continued

| Ex. | Structure | Name | [M + H]+ |
|---|---|---|---|
| 1.8 | 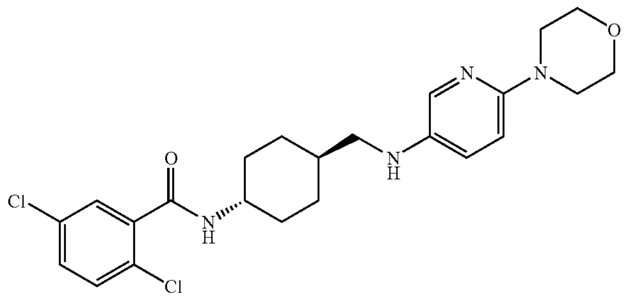 | Trans-2,5-Dichloro-N-{4-[(6-morpholin-4-yl-pyridin-3-ylamino)-methyl]-cyclohexyl}-benzamide | 463.27 |
| 1.9 | 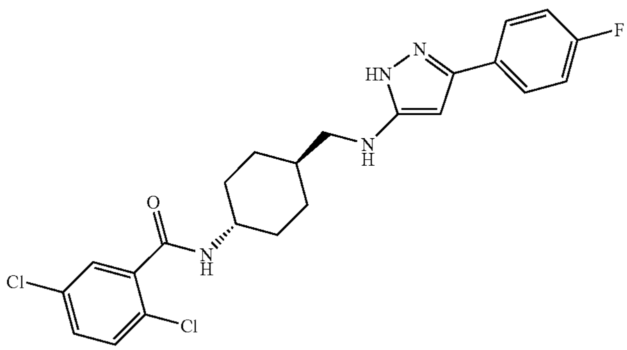 | Trans-2,5-Dichloro-N-(4-{[5-(4-fluoro-phenyl)-2H-pyrazol-3-ylamino]-methyl}-cyclohexyl)-benzamide | 461.3 |
| 1.10 | 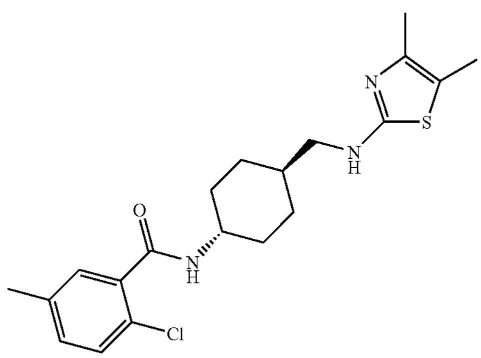 | Trans-2-Chloro-N-{4-[(4,5-dimethyl-thiazol-2-ylamino)-methyl]-cyclohexyl}-5-methyl-benzamide | 392.32 |
| 1.11 | 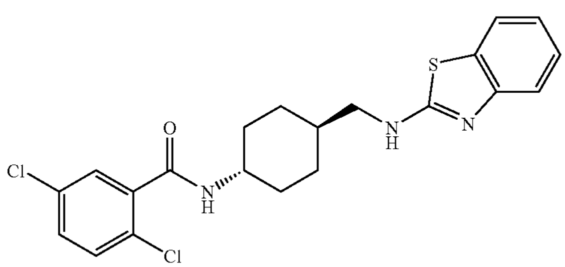 | Trans-N-[4-(Benzothiazol-2-ylaminomethyl)-cyclohexyl]-2,5-dichloro-benzamide | 434.29 |
| 1.12 | 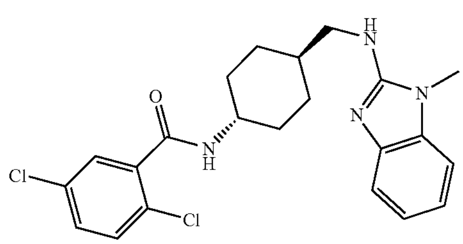 | Trans-2,5-Dichloro-N-{4-[(1-methyl-1H-benzoimidazol-2-ylamino)-methyl]-cyclohexyl}-benzamide | 431.35 |

TABLE 1-continued

| Ex. | Structure | Name | [M + H]+ |
|---|---|---|---|
| 1.13 | 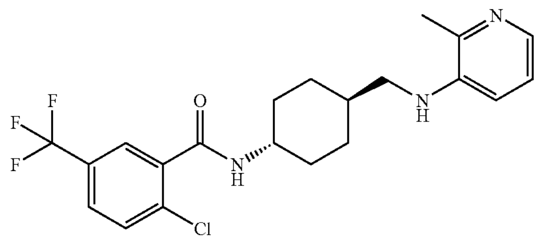 | Trans-2-Chloro-N-{4-[(2-methyl-pyridin-3-ylamino)-methyl]-cyclohexyl}-5-trifluoromethyl-benzamide | 426.4 |
| 1.14 | 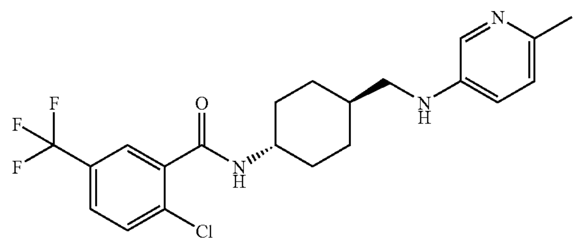 | Trans-2-Chloro-N-{4-[(6-methyl-pyridin-3-ylamino)-methyl]-cyclohexyl}-5-trifluoromethyl-benzamide | 426.42 |
| 1.15 | 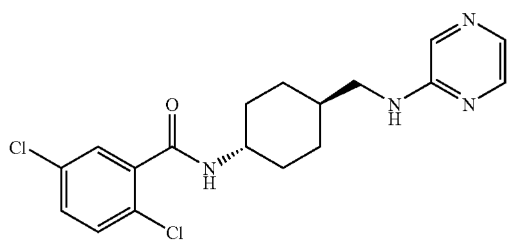 | Trans-2,5-Dichloro-N-[4-(pyrazin-2-ylaminomethyl)-cyclohexyl]-benzamide | 379.21 |
| 1.16 | 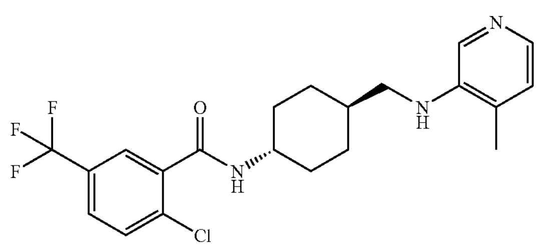 | Trans-2-Chloro-N-{4-[(4-methyl-pyridin-3-ylamino)-methyl]-cyclohexyl}-5-trifluoromethyl-benzamide | 426.42 |
| 1.17 | 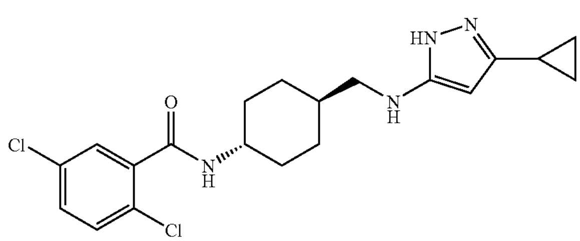 | Trans-2,5-Dichloro-N-{4-[(5-cyclopropyl-2H-pyrazol-3-ylamino)-methyl]-cyclohexyl}-benzamide | 407.32 |
| 1.18 | 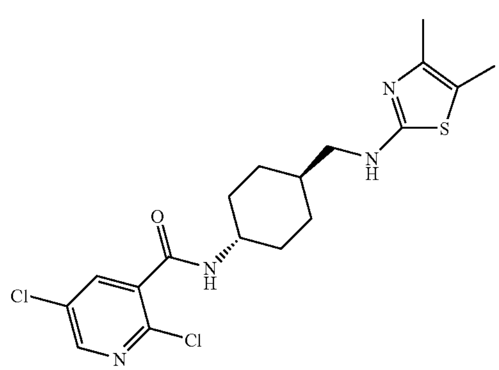 | Trans-2,5-Dichloro-N-{4-[(4,5-dimethyl-thiazol-2-ylamino)-methyl]-cyclohexyl}-nicotinamide | 413.37 |

TABLE 1-continued

| Ex. | Structure | Name | [M + H]+ |
|---|---|---|---|
| 1.19 | 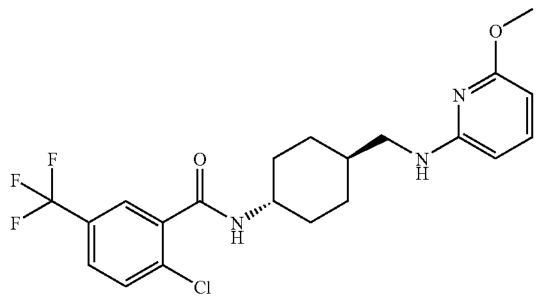 | Trans-2-Chloro-N-{4-[(6-methoxy-pyridin-2-ylamino)-methyl]-cyclohexyl}-5-trifluoromethyl-benzamide | 442.32 |
| 1.20 | 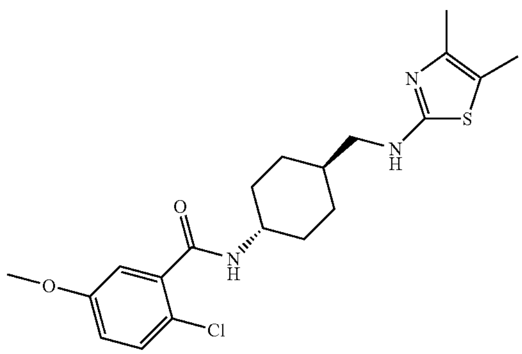 | Trans-2-Chloro-N-{4-[(4,5-dimethyl-thiazol-2-ylamino)-methyl]-cyclohexyl}-5-methoxy-benzamide | 408.33 |
| 1.21 | 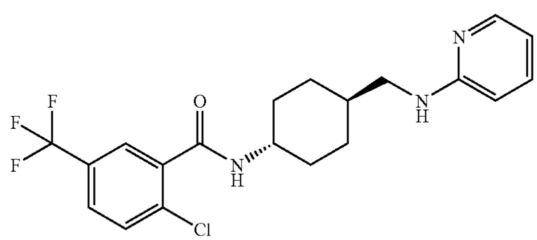 | Trans-2-Chloro-N-[4-(pyridin-2-ylaminomethyl)-cyclohexyl]-5-trifluoromethyl-benzamide | 412.33 |
| 1.22 | 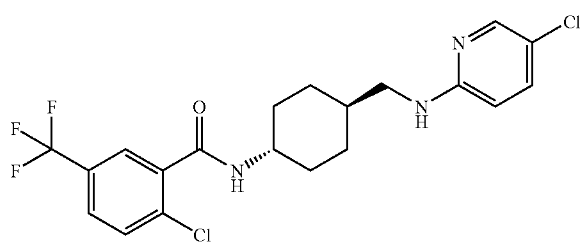 | Trans-2-Chloro-N-{4-[(5-chloro-pyridin-2-ylamino)-methyl]-cyclohexyl}-5-trifluoromethyl-benzamide | 446.28 |
| 1.23 | 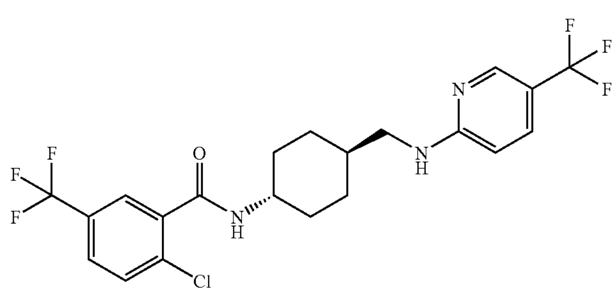 | Trans-2-Chloro-5-trifluoromethyl-N-{4-[(5-trifluoromethyl-pyridin-2-ylamino)-methyl]-cyclohexyl}-benzamide | 480.23 |

TABLE 1-continued

| Ex. | Structure | Name | [M + H]+ |
|---|---|---|---|
| 1.24 | 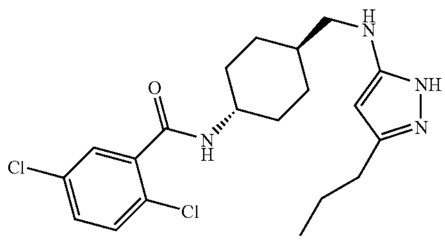 | Trans-2,5-Dichloro-N-{4-[(5-propyl-2H-pyrazol-3-ylamino)-methyl]-cyclohexyl}-benzamide | 409.34 |
| 1.25 | 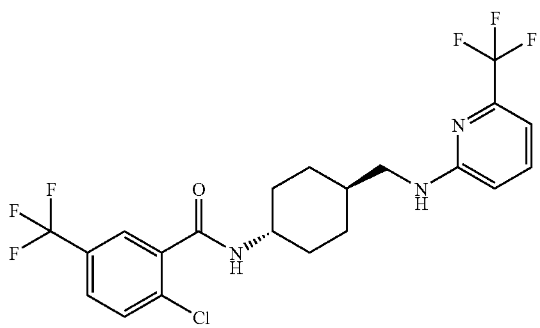 | Trans-2-Chloro-5-trifluoromethyl-N-{4-[(6-trifluoromethyl-pyridin-2-ylamino)-methyl]-cyclohexyl}-benzamide | 480.21 |
| 1.26 | 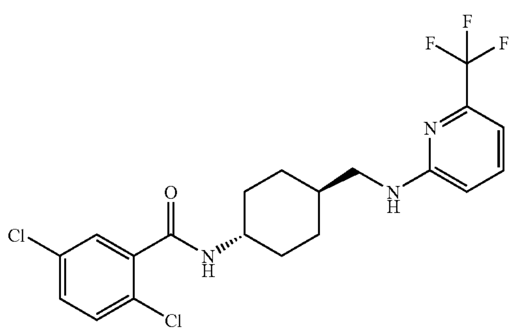 | Trans-2,5-Dichloro-N-{4-[(6-trifluoromethyl-pyridin-2-ylamino)-methyl]-cyclohexyl}-benzamide | 446.25 |
| 1.27 | 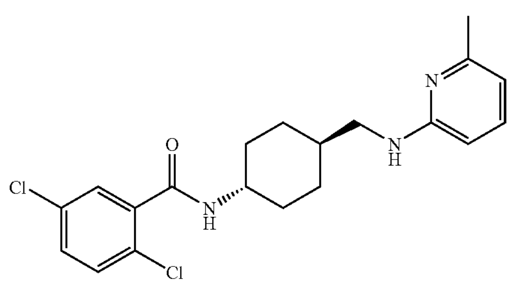 | Trans-2,5-Dichloro-N-{4-[(6-methyl-pyridin-2-ylamino)-methyl]-cyclohexyl}-benzamide | 392.25 |
| 1.28 | 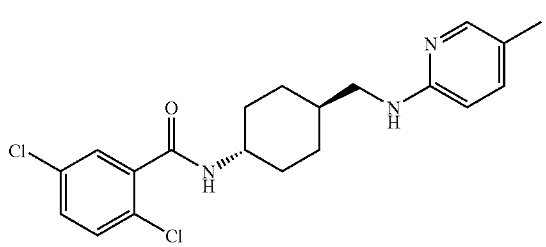 | Trans-2,5-Dichloro-N-{4-[(5-methyl-pyridin-2-ylamino)-methyl]-cyclohexyl}-benzamide | 392.27 |

TABLE 1-continued

| Ex. | Structure | Name | [M + H]+ |
|---|---|---|---|
| 1.29 | 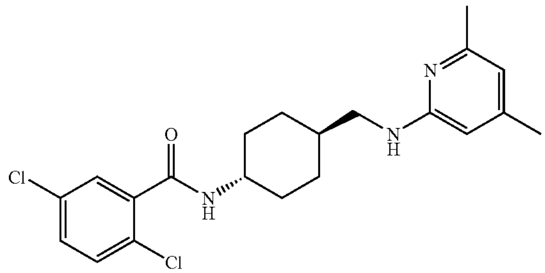 | Trans-2,5-Dichloro-N-{4-[(4,6-dimethyl-pyridin-2-ylamino)-methyl]-cyclohexyl}-benzamide | 406.3 |
| 1.30 | 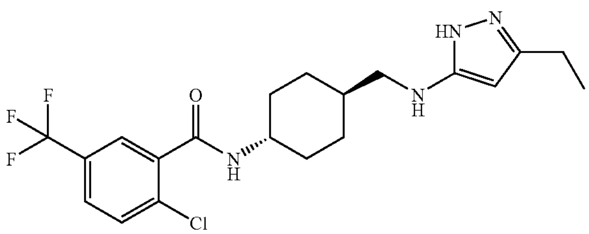 | Trans-2-Chloro-N-{4-[(5-ethyl-2H-pyrazol-3-ylamino)-methyl]cyclohexyl}-5-trifluoromethyl-benzamide | 429.39 |
| 1.31 | 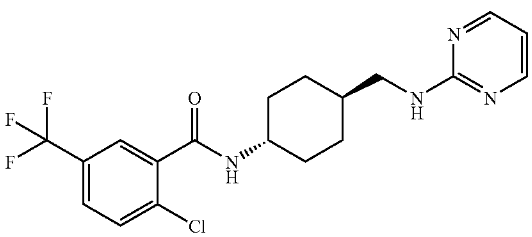 | Trans-2-Chloro-N-[4-(pyrimidin-2-ylaminomethyl)-cyclohexyl]-5-trifluoromethyl-benzamide | 413.34 |
| 1.32 | 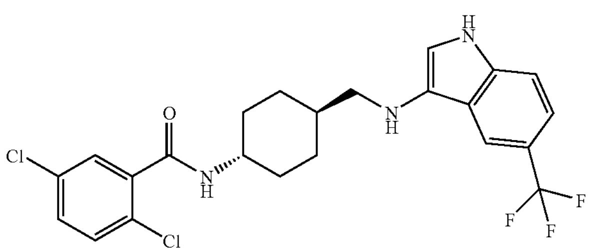 | Trans-2,5-Dichloro-N-{4-[(5-trifluoromethyl-1H-indazol-3-ylamino)-methyl]-cyclohexyl}-benzamide | 485.25 |

Example 1.33

Trans-6-{[4-(2-Chloro-5-trifluoromethyl-benzoylamino)-cyclohexylmethyl]-amino}-nicotinic acid

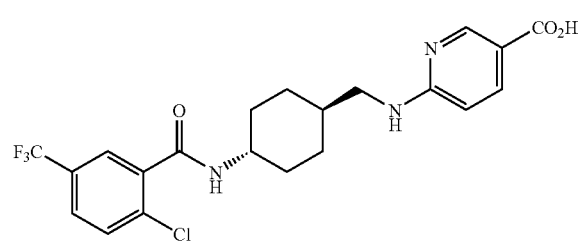

Trans-6-{[4-(2-Chloro-5-trifluoromethyl-benzoylamino)-cyclohexylmethyl]-amino}-nicotinic acid methyl ester (Example 19.15) (30 mg, 0.06 mmol) is placed in a vial with MeOH (2 mL). 1M NaOH (1 mL) is added and the reaction mixture is stirred at RT for 3 days. The reaction mixture is acidified and the resulting precipitate in the aqueous layer which was filtered and dried to afford the title compound. [MH+ 456.31], NMR: δH (400 MHz, DMSO); 12.29 (1H, s), 8.53 (1H, d), 8.48 (1H, d), 7.78 (4H, m) 7.35 (1H, m), 6.50 (1H, d), 3.71 (1H, m), 3.19 (2H, m), 1.96 (2H, m), 1.83 (2H, m), 1.52 (1H, m), 1.23 (2H, m), 1.08 (2H, m).

Example 1.34

Trans-2-Chloro-N-{4-[(5-dimethylaminomethyl-pyridin-2-ylamino)-methyl]-cyclohexyl}-5-trifluoromethyl-benzamide hydrochloride

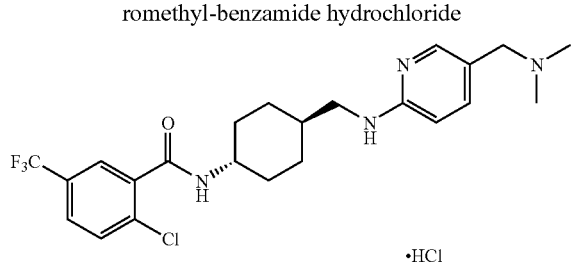

Step 1

Trans-2-Chloro-N-{4-[(5-formyl-pyridin-2-ylamino)-methyl]-cyclohexyl}-5-trifluoromethyl-benzamide Trans-2-Chloro-N-{4-[(5-hydroxymethyl-pyridin-2-ylamino)-methyl]-cyclohexyl}-5-trifluoromethyl-benzamide (Example 19.20) (100 mg, 0.23 mmol) is placed in a flask with DCM (10 mL) and manganese (IV) oxide (297 mg, 3.4 mmol). The reaction mixture is stirred at RT for 4 hours and manganese (IV) oxide is removed by filtration. The solvent was removed in vacuo to afford the title compound; NMR (400 MHz, DMSO-$d_6$) δ 9.66 (1H, s), 8.49 (2H, m), 7.77 (5H, m), 6.58 (1H, d), 3.70 (1H, m), 3.23 (2H, m), 1.93 (2H, m), 1.81 (2H, m), 1.53 (1H, m), 1.23 (2H, m), 1.09 (2H, m).

Step 2

Trans-2-Chloro-N-{4-[(5-dimethylaminomethyl-pyridin-2-ylamino)-methyl]-cyclohexyl}5-trifluoromethyl-benzamide hydrochloride The title compound is prepared from Trans-2-Chloro-N-{4-[(5-formyl-pyridin-2-ylamino)-methyl]-cyclohexyl}-5-trifluoromethyl-benzamide and dimethylamine hydrochloride analogously to Example 1.

[MH]$^+$ 469.30. NMR: δH (400 MHz, DMSO); 11.75 (1H, s), 8.51 (1H, d), 8.10 (1H, s), 7.92 (1H, br), 7.80 (1H, m), 7.81 (1H, m), 7.74 (2H, m), 7.05 (1H, br s), 4.20 (2H, m), 3.71 (1H, m), 3.27 (2H, m), 2.70 (6H, d), 1.92 (4H, m), 1.59 (1H, m), 1.28 (2H, m), 1.12 (2H, m).

Example 1.35

1.35a (+/−)-2-Chloro-N-(1S,3R,4S)-4-{[5-(4-fluoro-phenyl)-1H-pyrazol-3-ylamino]-methyl}-3-methyl-cyclohexyl)-5-trifluoromethyl-benzamide and 1.35b (+/−)-2-Chloro-N-((1S,3S,4S)-4-{[5-(4-fluoro-phenyl)-1H-pyrazol-3-ylamino]-methyl}-3-methylcyclohexyl)-5-trifluoromethyl-benzamide

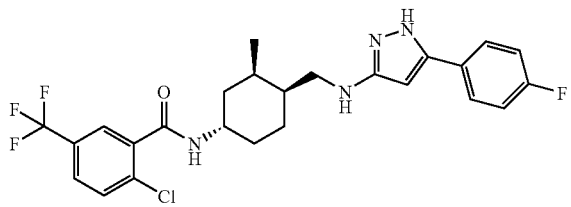

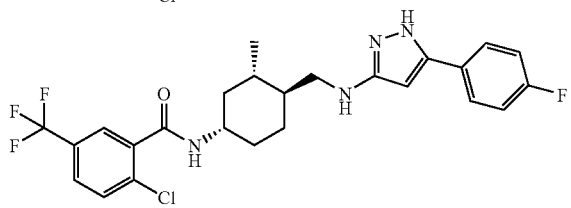

Step 1

Ethyl 4-amino-2-methylcyclohexanecarboxylate

Ethyl 2-methyl-4-oxocyclohex-2-enecarboxylate (2.0 g, 10.98 mmol) is dissolved in MeOH (40 ml) and water (4.0 ml) to give a yellow solution. Ammonium formate (8.31 g, 132 mmol) is added and stirred at RT until the suspension dissolves to form a solution. Palladium on carbon (0.117 g, 1.098 mmol) is added and the reaction mixture is stirred at 70° C. for 1 hour. The mixture is filtered through Celite® (filter material) and washed with MeOH. The filtrate is concentrated in vacuo and the residue is partitioned between EtOAc and water. The aqueous portion is diluted with sat. sodium bicarbonate and washed with EtOAc. The pH is adjusted to pH 14 using 1M NaOH and the aqueous is extracted with EtOAc. The combined organic extracts are dried MgSO$_4$, filtered and concentrated in vacuo to afford the title compound; [MH]$^+$ 186.24.

Step 2

Ethyl 4-(2-chloro-5-(trifluoromethyl)benzamido)-2-methylcyclohexane carboxylate

Ethyl 4-amino-2-methylcyclohexanecarboxylate (780 mg, 4.21 mmol) in THF (10 ml) is treated with TEA (1.174 ml, 8.42 mmol) and the reaction mixture is cooled to 0° C. 2-Chloro-5-(trifluoromethyl)benzoyl chloride (921 mg, 3.79 mmol) is added dropwise and the reaction mixture is stirred and allowed to warm to RT. After 3 hours, the reaction is quenched with water and partitioned between EtOAc and sat. sodium bicarbonate. The organic portion is separated and dried over MgSO$_4$ and concentrated in vacuo to afford the title compound which is used without further purification. [MH]$^+$ 392.26.

Step 3

2-Chloro-N-(4-{[5-(4-fluoro-phenyl)-1H-pyrazol-3-ylamino]-methyl}-3-methyl-cyclohexyl)-5-trifluoromethyl-benzamide The title compound is prepared analogously to Example 1 by replacing trans-4-(2-chloro-5-trifluoromethyl-benzoylamino)-cyclohexane carboxylic acid methyl ester (Ex. 1 Step 2) with ethyl 4-(2-chloro-5-(trifluoromethyl)benzamido)-2-methyl cyclohexane carboxylate (Ex. 1.35 step 2) and by replacing 2-amino-3-picoline (Ex. 1 step 4) with 5-(4-fluorophenyl)-1H-pyrazol-3-amine. [MH]$^+$ 509.40.

Separation and isolation of 1.35a (+/−)-2-Chloro-N-((1S,3R,4S)-4-{[5-(4-fluoro-phenyl)-1H-pyrazol-3-ylamino]-methyl}-3-methyl-cyclohexyl)-5-trifluoromethyl-benzamide and 1.35b (+/−)-2-Chloro-N-((1S,3S,4S)-4-{[5-(4-fluoro-phenyl)-1H-pyrazol-3-ylamino]-methyl}-3-methylcyclohexyl)-5-trifluoromethyl-benzamide from a 90 mg sample of the crude reaction mixture was carried out by Supercritical Fluid Chromatography followed by preparative mass directed reverse phase HPLC, using the following methods:

(1) Supercritical Fluid Chromatography

Mobile Phase: 36% 2-propanol/0.1% DEA/64% $CO_2$

Column: Chiralpak AD-H, 250×10 mm id, 5 μm

Detection: UV @220 nm

Flow rate: 10 ml/min

Sample concentration: 90 mg in 3.0 ml EtOH

Injection volume: 200 μl 7 mg of 1.35a (+/−)-2-Chloro-N-((1S,3R,4S)-4-{[5-(4-fluoro-phenyl)-1H-pyrazol-3-ylamino]-methyl}-3-methyl-cyclohexyl)-5-trifluoromethyl-benzamide was isolated with a retention time of 10.48 min.

Impure fractions centered around retention time 9.15 min were combined and purified by preparative mass directed reverse phase HPLC (2) Preparative Mass Directed Reverse Phase HPLC The impure fractions from the SFC purification above were purified by the following method Column: Sunfire C18, 19×50 mm, 5 um column Mobile phase: A=Water+0.1% TFA B=MeCN+0.1% TFA Gradient: 0-1.0 min 35% B (flow rate 10 ml/min)

1.0-9.0 min 35-42% B (flow rate 30 ml/min)

Detection: single quad electrospray MS

Injection volume: 100 μl

Sample concentration: 20 mg in 2 ml 11 mg of (+/−)-2-Chloro-N-((1S,3S,4S)-4-{[5-(4-fluoro-phenyl)-1H-pyrazol-3-ylamino]-methyl}-3-methyl-cyclo-hexyl)-5-trifluoromethyl-benzamide was isolated with retention time 7.70 min Example 1.36

Trans-2-Chloro-N-(4-{[4-(4-chloro-phenyl)-isox-azol-3-ylamino]-methyl}-cyclohexyl)-5-trifluorom-ethyl-benzamide

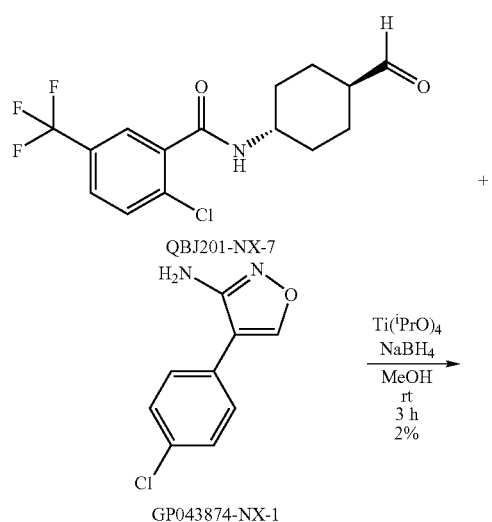

QBJ201-NX-7

GP043874-NX-1

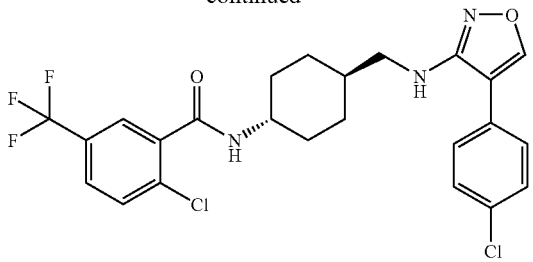

NVP-QBR190-NX-1
E-43746-EXP052
m/z 512.3 [M + H]$^+$

A mixture of trans-2-chloro-N-(4-formyl-cyclohexyl)-5-trifluoromethyl-benzamide (Example 1 Step 3) (100 mg, 0.30 mmol) and 4-(4-chlorophenyl)isoxazol-3-amine (this compound can be prepared according to method described in 'Chemistry of Heterocyclic Compounds' (New York, N.Y., United States) (2007), 43(1), 118-119) (58 mg, 0.300 mmol) is stirred in titanium(IV) isopropoxide (1 ml, 3.4 mmol) for 3 h. A thick slurry results. After 3 h, methanol (5 ml) is added followed by slow addition of sodium borohydride (18 mg, 0.5 mmol). after 5 minutes, sodium hydroxide solution 91 ml, 0.1M) is added to the reaction followed by dilution with ethyl acetate and brine. The organic extract is washed with brine, dried over MgSO4 and the solvent removed in vacuo. Purification by chromatography on silica, eluting with chloroform-ethanol (10:1) affords a sample of product containing minor amounts of starting materials. Trituation with methanol yields a pure sample or the title compound. MS m/z 512.3 [M+H]+; $^1$H NMR (400 MHz, CDCl3) δ 1.25 8H, m), 1.75 (1H, m), 1.95 (2H, m), 2.22 (2H, m), 3.20 (2H, d), 4.00 (1H, m), 5.97 (1H, d), 7.35 (2H, d), 7.45 (2H, d), 7.55 (1H, d), 7.62 (1H, d), 7.90 (1H, s), 8.15 (1H, s).

Examples 2.1 to 2.46

The compounds of the following tabulated Examples are prepared using the following general procedure:

A stock solution of trans-2-chloro-N-(4-formyl-cyclo-hexyl)-5-trifluoromethyl-benzamide (Example 1 Step 3) is made up in dry THF (5.5 g in 88 mL). 800 ul of aldehyde solution is pipetted into each vial of pre-weighed amine (1.2 eq, 0.18 mmol). A stock solution of acetic acid is made up in dry THF (2.56 mL in 22 mL THF). Acetic acid stock solution (200 μl) is pipetted into each vial. MP-triacetoxyborohydride resin (>2.5 eq, >0.374 mmol, ~200 mg) is added to each vial. Vials are sealed and shaken at RT for 16 hours. Crude reaction mixtures are passed onto a 1 g SCX-2 cartridge (Biotage) under gravity, which had been pre-wetted with 1 mL MeOH. The cartridges are washed with 2×2 mL MeOH, then compounds eluted with 2×2 mL 2M ammonia in MeOH. Compounds are analyzed and evaporated in vacuo. Crude mixtures are purified further by prep HPLC (Waters Sunfire C18 5 micron column, 19×50 mm, mobile phases 0.1% TFA in water, 0.1% TFA in acetonitrile, 6 minute gradient dependant on retention time from analytics). Successful purifications are turned into free-based amines by passing prep fraction through a SCX-2 cartridge pre-wetted with MeOH, washed with 5 mL MeOH, and eluted with 2×2 mL 3.5M ammonia in MeOH. Finally, compounds are evaporated in vacuo.

TABLE 2

| Ex. | Structure | Name | [M + H]+ |
|---|---|---|---|
| 2.1 | 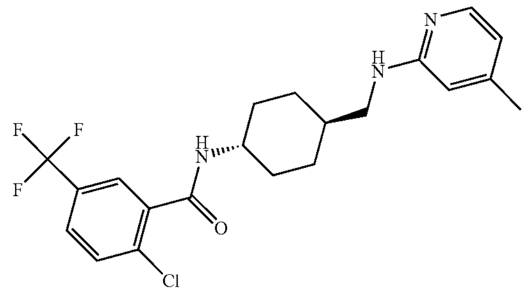 | Trans-2-Chloro-N-{4-[(4-methyl-pyridin-2-ylamino)-methyl]-cyclohexyl}-5-trifluoromethyl-benzamide | 426.34 |
| 2.2 | 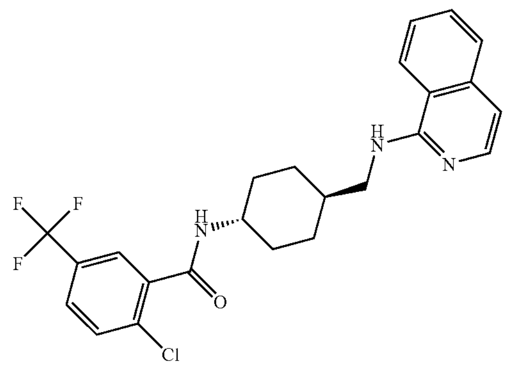 | Trans-2-Chloro-N-[4-(isoquinolin-1-ylaminomethyl)-cyclohexyl]-5-trifluoromethyl-benzamide | 462.36 |
| 2.3 | 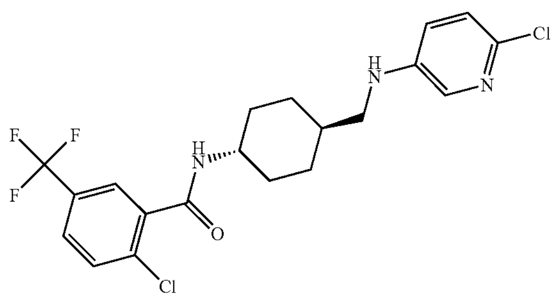 | Trans-2-Chloro-N-{4-[(6-chloro-pyridin-3-ylamino)-methyl]-cyclohexyl}-5-trifluoromethyl-benzamide | 446.29 |
| 2.4 | 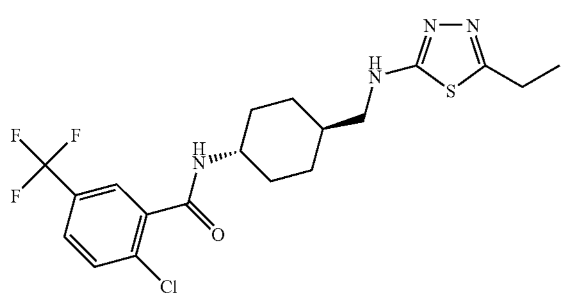 | Trans-2-Chloro-N-{4-[(5-ethyl-[1,3,4]thiadiazol-2-ylamino)-methyl]-cyclohexyl}-5-trifluoromethyl-benzamide | 447.3 |
| 2.5 | 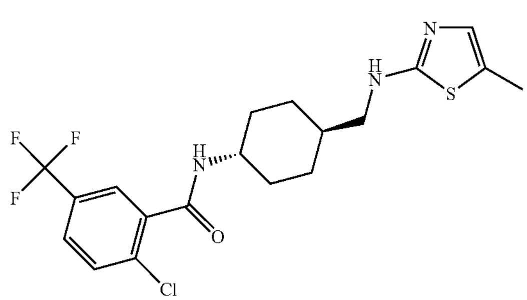 | Trans-2-Chloro-N-{4-[(5-methyl-thiazol-2-ylamino)-methyl]-cyclohexyl}-5-trifluoromethyl-benzamide | 432.3 |

TABLE 2-continued

| Ex. | Structure | Name | [M + H]+ |
|---|---|---|---|
| 2.6 | 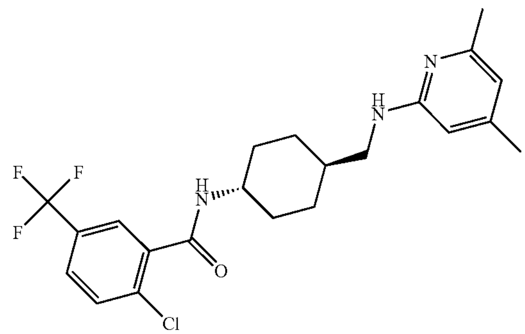 | Trans-2-Chloro-N-{4-[(4,6-dimethyl-pyridin-2-ylamino)-methyl]-cyclohexyl}-5-trifluoromethyl-benzamide | 440.36 |
| 2.7 | 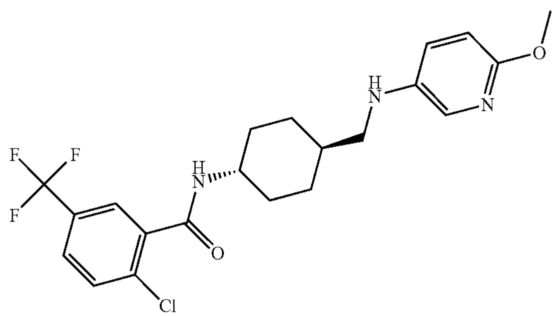 | Trans-2-Chloro-N-{4-[(6-methoxy-pyridin-3-ylamino)-methyl]-cyclohexyl}-5-trifluoromethyl-benzamide | 442.34 |
| 2.8 | 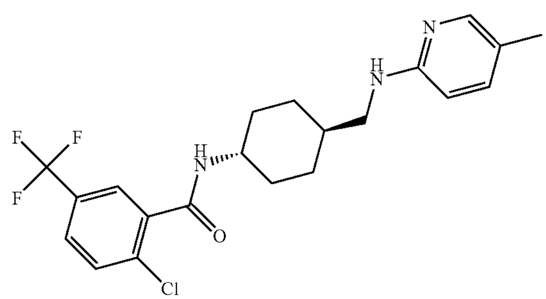 | Trans-2-Chloro-N-{4-[(5-methyl-pyridin-2-ylamino)-methyl]-cyclohexyl}-5-trifluoromethyl-benzamide | 426.32 |
| 2.9 | 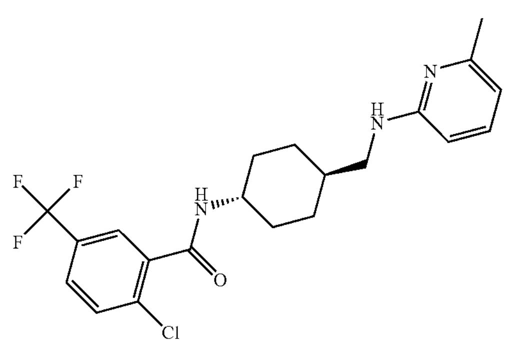 | Trans-2-Chloro-N-{4-[(6-methyl-pyridin-2-ylamino)-methyl]-cyclohexyl}-5-trifluoromethyl-benzamide | 426.32 |

TABLE 2-continued

| Ex. | Structure | Name | [M + H]⁺ |
|---|---|---|---|
| 2.10 | 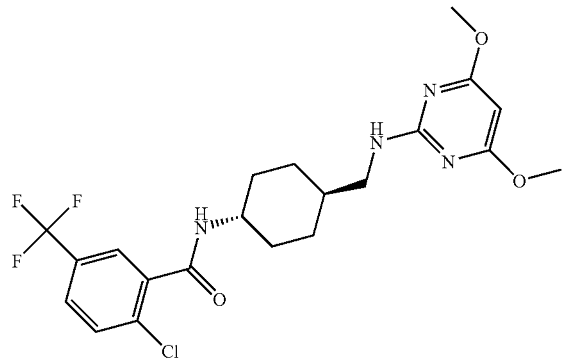 | Trans-2-Chloro-N-{4-[(4,6-dimethoxy-pyrimidin-2-ylamino)-methyl]-cyclohexyl}-5-trifluoromethyl-benzamide | 473.39 |
| 2.11 | 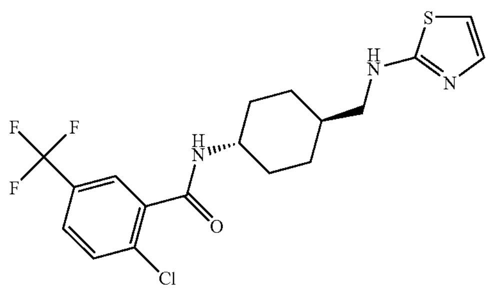 | Trans-2-Chloro-N-[4-(thiazol-2-ylaminomethyl)-cyclohexyl]-5-trifluoromethyl-benzamide | 418.26 |
| 2.12 | 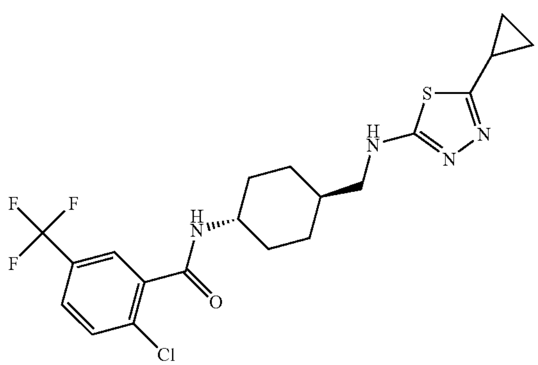 | Trans-2-Chloro-N-{4-[(5-cyclopropyl-[1,3,4]thiadiazol-2-ylamino)-methyl]-cyclohexyl}-5-trifluoromethyl-benzamide | 459.34 |
| 2.13 | 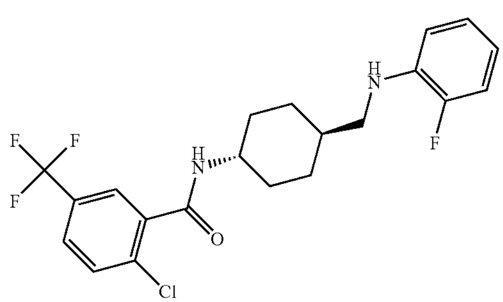 | Trans-2-Chloro-N-{4-[(2-fluoro-phenylamino)-methyl]-cyclohexyl}-5-trifluoromethyl-benzamide | 429.3 |
| 2.14 | 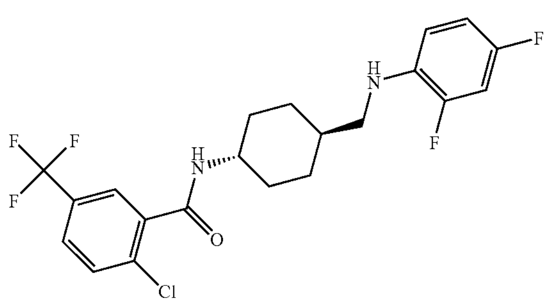 | Trans-2-Chloro-N-{4-[(2,4-difluoro-phenylamino)-methyl]-cyclohexyl}-5-trifluoromethyl-benzamide | 488.36 (MH + MeCN)+ |

TABLE 2-continued

| Ex. | Structure | Name | [M + H]+ |
|---|---|---|---|
| 2.15 | 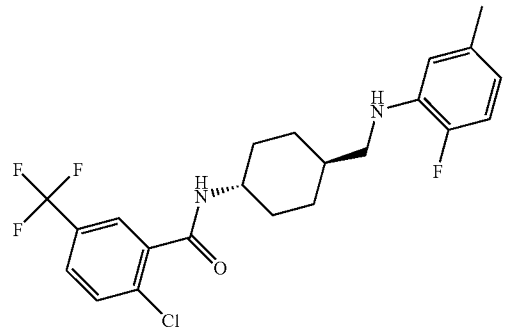 | Trans-2-Chloro-N-{4-[(2-fluoro-5-methyl-phenylamino)-methyl]-cyclohexyl}-5-trifluoromethyl-benzamide | 443.34 |
| 2.16 | 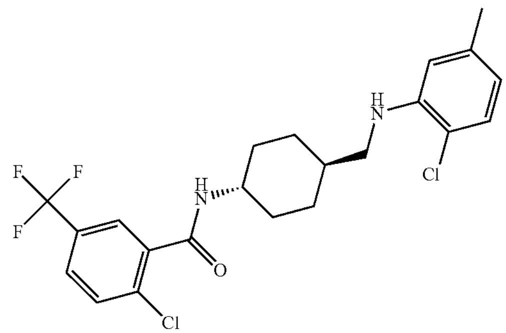 | Trans-2-Chloro-N-{4-[(2-chloro-5-methyl-phenylamino)-methyl]-cyclohexyl}-5-trifluoromethyl-benzamide | 459.34 |
| 2.17 | 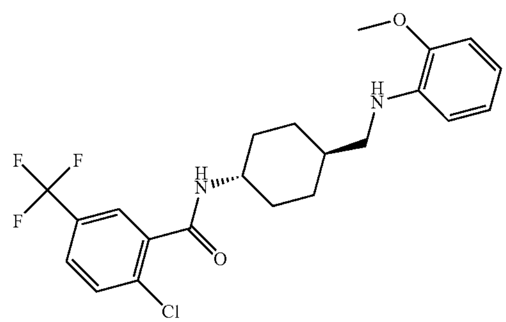 | Trans-2-Chloro-N-{4-[(2-methoxy-phenylamino)-methyl]-cyclohexyl}-5-trifluoromethyl-benzamide | 441.34 |
| 2.18 | 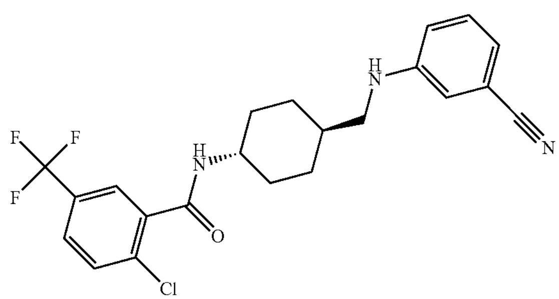 | Trans-2-Chloro-N-{4-[(3-cyano-phenylamino)-methyl]-cyclohexyl}-5-trifluoromethyl-benzamide | 436.33 |
| 2.19 | 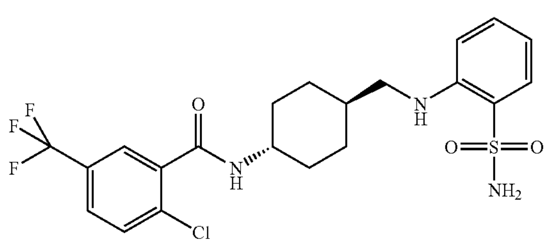 | Trans-2-Chloro-N-{4-[(2-sulfamoyl-phenylamino)-methyl]-cyclohexyl}-5-trifluoromethyl-benzamide | 489.11 |

TABLE 2-continued

| Ex. | Structure | Name | [M + H]+ |
|---|---|---|---|
| 2.20 | 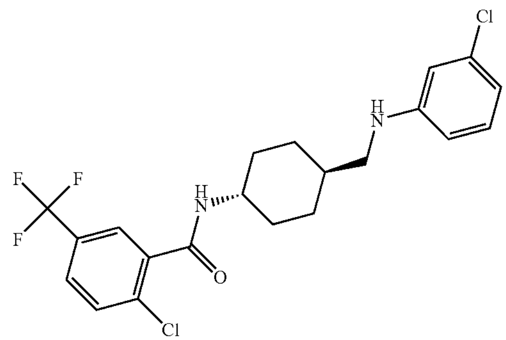 | Trans-2-Chloro-N-{4-[(3-chloro-phenylamino)-methyl]-cyclohexyl}-5-trifluoromethyl-benzamide | 445.29 |
| 2.21 | 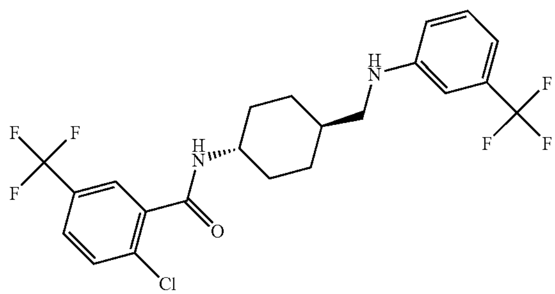 | Trans-2-Chloro-5-trifluoromethyl-N-{4-[(3-trifluoromethyl-phenylamino)-methyl]-cyclohexyl}-benzamide | 479.34 |
| 2.22 | 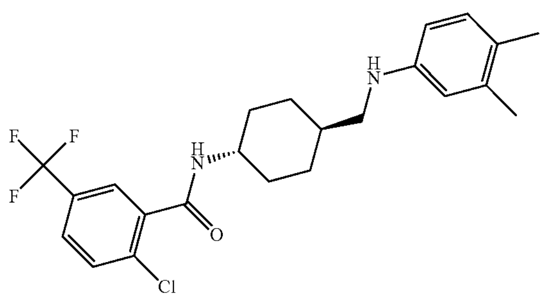 | Trans-2-Chloro-N-{4-[(3,4-dimethyl-phenylamino)-methyl]-cyclohexyl}-5-trifluoromethyl-benzamide | 439.36 |
| 2.23 | 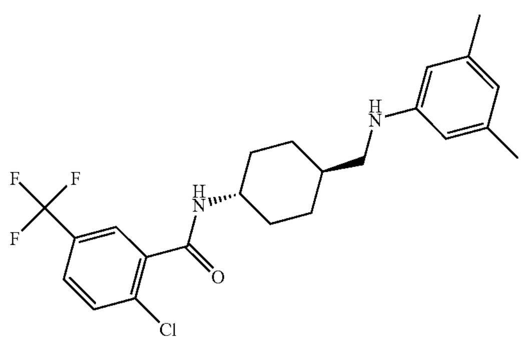 | Trans-2-Chloro-N-{4-[(3,5-dimethyl-phenylamino)-methyl]-cyclohexyl}-5-trifluoromethyl-benzamide | 439.36 |
| 2.24 | 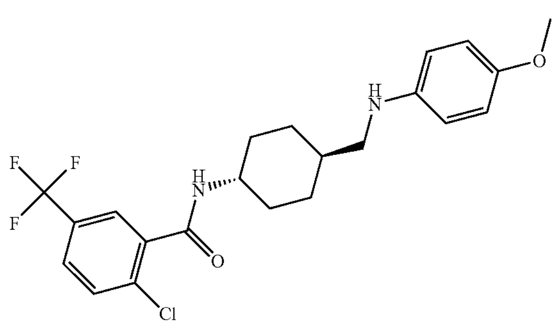 | Trans-2-Chloro-N-{4-[(4-methoxy-phenylamino)-methyl]-cyclohexyl}-5-trifluoromethyl-benzamide | 441.35 |

TABLE 2-continued

| Ex. | Structure | Name | [M + H]+ |
|---|---|---|---|
| 2.25 | 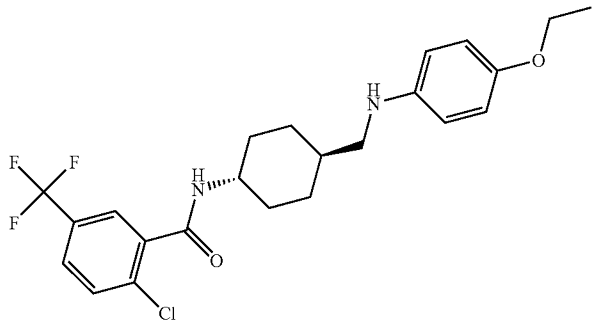 | Trans-2-Chloro-N-{4-[(4-ethoxy-phenylamino)-methyl]-cyclohexyl}-5-trifluoromethyl-benzamide | 455.35 |
| 2.26 | 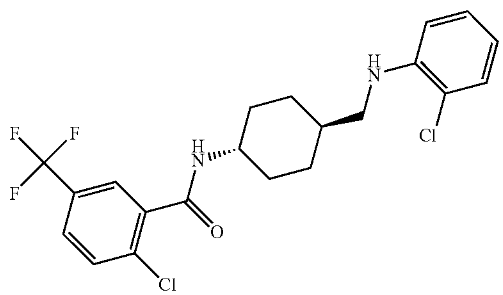 | Trans-2-Chloro-N-{4-[(2-chloro-phenylamino)-methyl]-cyclohexyl}-5-trifluoromethyl-benzamide | 445.3 |
| 2.27 | 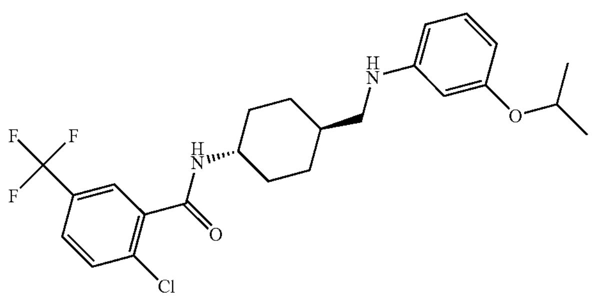 | Trans-2-Chloro-N-{4-[(3-isopropoxy-phenylamino)-methyl]-cyclohexyl}-5-trifluoromethyl-benzamide | 469.39 |
| 2.28 | 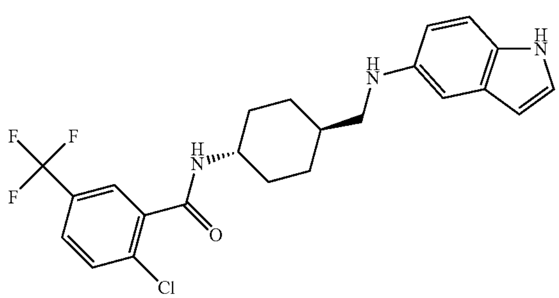 | Trans-2-Chloro-N-{4-[(1H-indol-5-ylamino-methyl]-cyclohexyl}-5-trifluoromethyl-benzamide | 450.34 |
| 2.29 | 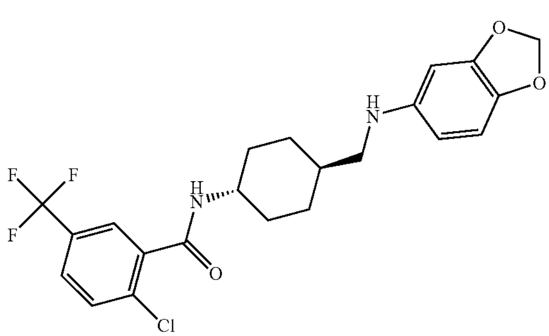 | Trans-N-[4-(Benzo[1,3]dioxol-5-ylaminomethyl)-cyclohexyl]-2-chloro-5-trifluoromethyl-benzamide | 455.32 |

TABLE 2-continued

| Ex. | Structure | Name | [M + H]+ |
|---|---|---|---|
| 2.30 | 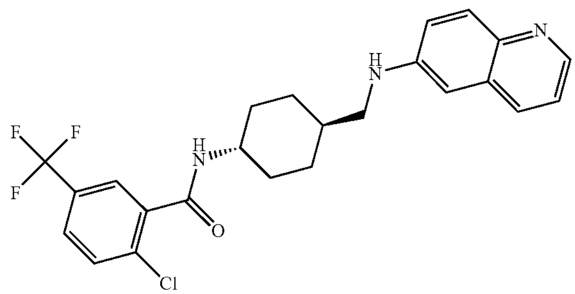 | Trans-2-Chloro-N-[4-(quinolin-6-ylaminomethyl)-cyclohexyl]-5-trifluoromethyl-benzamide | 462.36 |
| 2.31 | 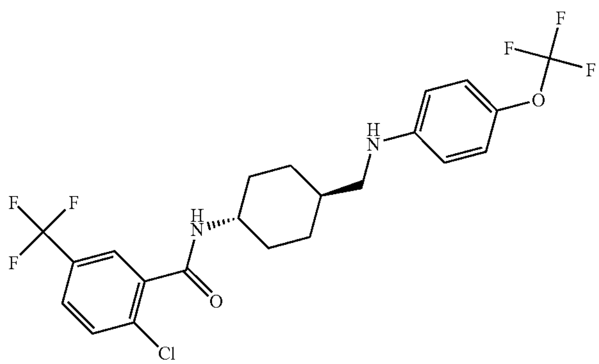 | Trans-2-Chloro-N-{4-[(4-trifluoromethoxy-phenylamino)-methyl]-cyclohexyl}-5-trifluoromethyl-benzamide | 536.38 (MH + MeCN)+ |
| 2.32 | 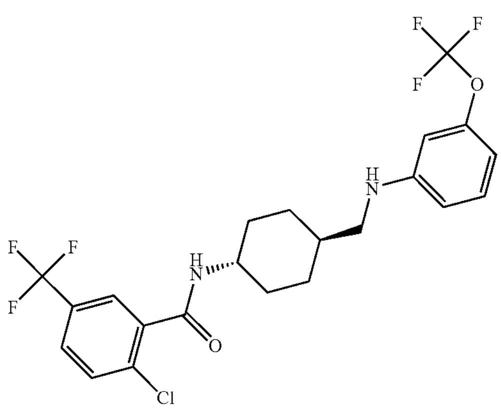 | Trans-2-Chloro-N-{4-[(3-trifluoromethoxy-phenylamino)-methyl]-cyclohexyl}-5-trifluoromethyl-benzamide | 536.38 (MH + MeCN)+ |
| 2.33 | 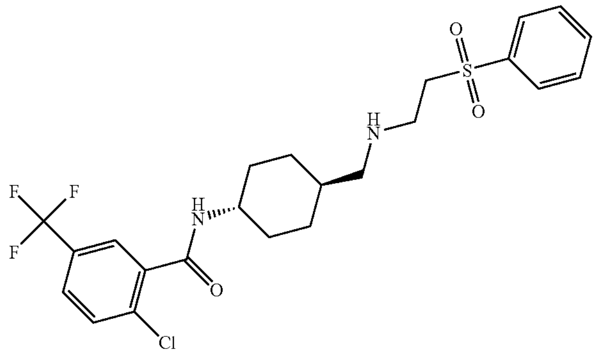 | Trans-N-{4-[(2-Benzenesulfonyl-ethylamino)-methyl]-cyclohexyl}-2-chloro-5-trifluoromethyl-benzamide | 503.34 |

TABLE 2-continued

| Ex. | Structure | Name | [M + H]+ |
|---|---|---|---|
| 2.34 | 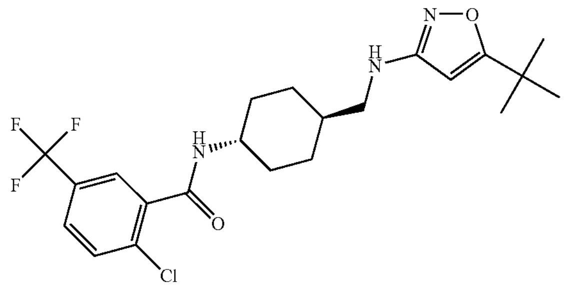 | Trans-N-{4-[(5-tert-Butyl-isoxazol-3-ylamino)-methyl]-cyclohexyl}-2-chloro-5-trifluoromethyl-benzamide | 458.38 |
| 2.35 | 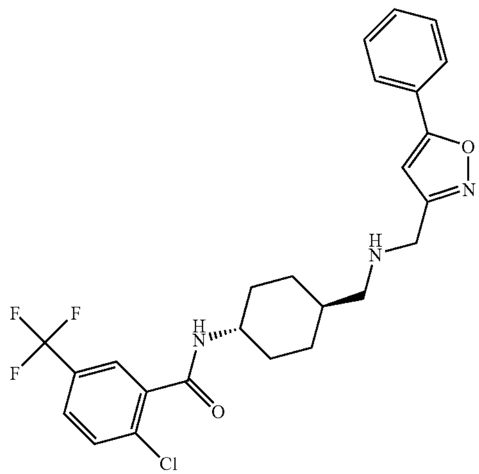 | Trans-2-Chloro-N-(4-{[(5-phenyl-isoxazol-3-ylmethyl)-amino]-methyl}-cyclohexyl)-5-trifluoromethyl-benzamide | 492.37 |
| 2.36 | 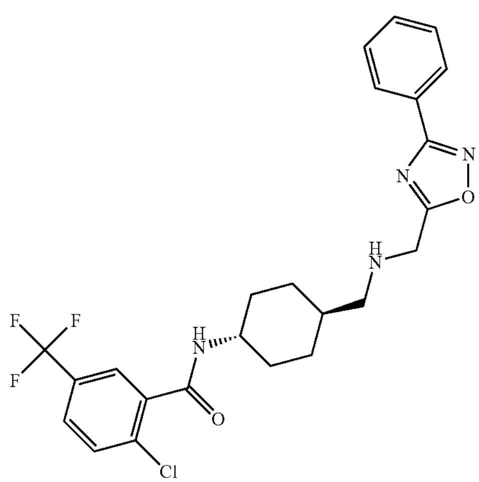 | Trans-2-Chloro-N-(4-{[(3-phenyl-[1,2,4]oxadiazol-5-ylmethyl)-amino]-methyl}-cyclohexyl)-5-trifluoromethyl-benzamide | 493.35 |

TABLE 2-continued

| Ex. | Structure | Name | [M + H]+ |
|---|---|---|---|
| 2.37 | 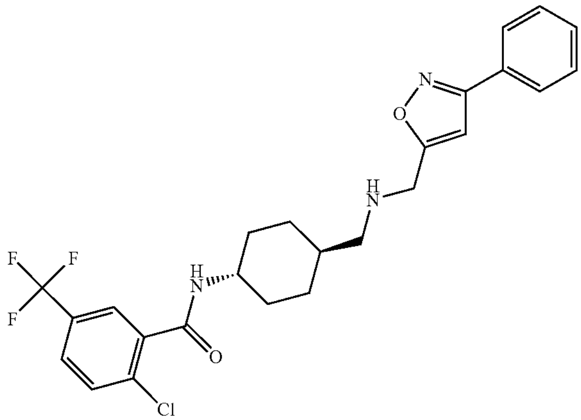 | Trans-2-Chloro-N-(4-{[(3-phenyl-isoxazol-5-ylmethyl)-amino]-methyl}-cyclohexyl)-5-trifluoromethyl-benzamide | 492.35 |
| 2.38 | 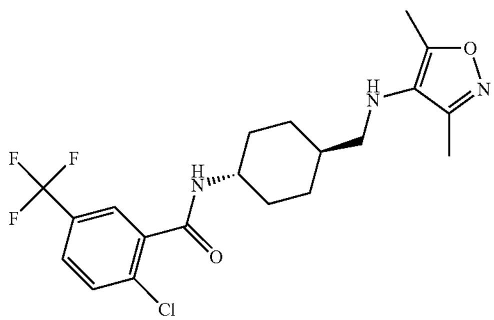 | Trans-2-Chloro-N-{4-[(3,5-dimethyl-isoxazol-4-ylamino)-methyl]-cyclohexyl}-5-trifluoromethyl-benzamide | 430.33 |
| 2.39 | 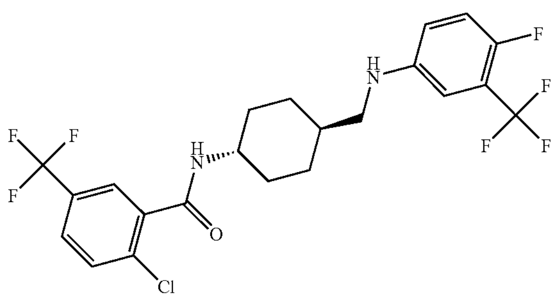 | Trans-2-Chloro-N-{4-[(4-fluoro-3-trifluoromethyl-phenylamino)-methyl]-cyclohexyl}-5-trifluoromethyl-benzamide | 538.38 (MH + MeCN)+ |
| 2.40 | 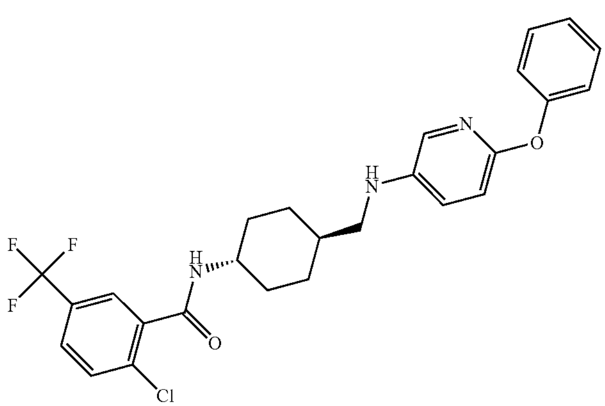 | Trans-2-Chloro-N-{4-[(6-phenoxy-pyridin-3-ylamino)-methyl]-cyclohexyl}-5-trifluoromethyl-benzamide | 504.36 |

TABLE 2-continued

| Ex. | Structure | Name | [M + H]+ |
|---|---|---|---|
| 2.41 | 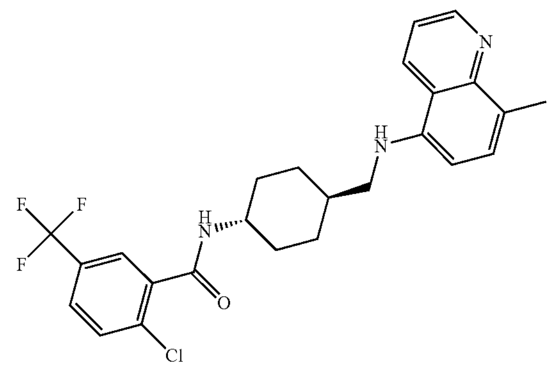 | Trans-2-Chloro-N-{4-[(8-methyl-quinolin-5-ylamino)-methyl]-cyclohexyl}-5-trifluoromethyl-benzamide | 476.38 |
| 2.42 | 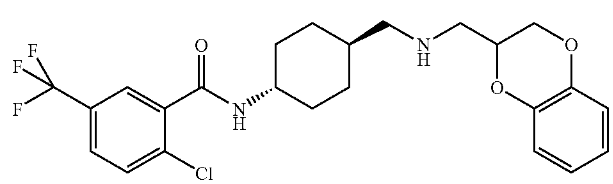 | Trans-2-Chloro-N-(4-{[(2,3-dihydro-benzo[1,4]dioxin-2-ylmethyl)-amino]-methyl}-cyclohexyl)-5-trifluoromethyl-benzamide | 482.16 |
| 2.43 | 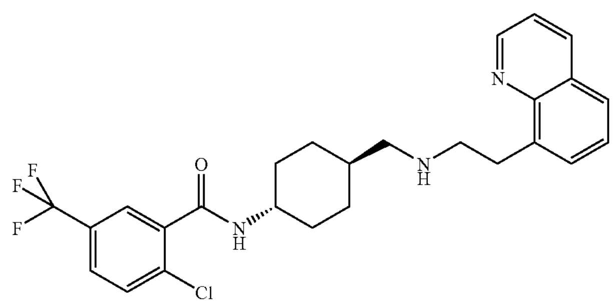 | Trans-2-Chloro-N-[4-(quinolin-8-ylaminomethyl)-cyclohexyl]-5-trifluoromethyl-benzamide | 461.15 |
| 2.44 | 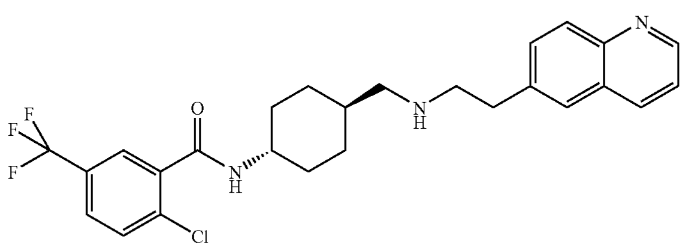 | Trans-2-Chloro-N-[4-(quinolin-6-ylaminomethyl)-cyclohexyl]-5-trifluoromethyl-benzamide | 461.15 |

Example 3

Trans-2-chloro-N-{4-[(4,5-dimethyl-thiazol-2-ylamino)-methyl]-cyclohexyl}-5-trifluoromethyl-benzamide

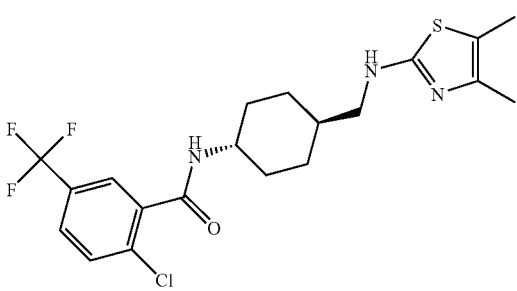

800 mg (2.40 mmol) of trans-2-chloro-N-(4-formyl-cyclohexyl)-5-trifluoromethyl-benzamide (Example 1 Step 3) and 274 mg (2.40 mmol) of 5-methylthiazol-2-amine are placed in a flask with 40 mL of DCM. 191 mg (3.60 mmol) of sodium triacetoxyborohydride is added and the RM is stirred at room temperature overnight 1N sodium hydroxide (2 mL) is added and the mixture is stirred at RT for 10 min. The RM is partitioned between DCM and water. The organic phase is washed with water and brine, dried over MgSO₄, filtered and the solvent is removed in vacuo. The product is purified by ISCO Combiflash Rf (80 g Si, iso-hexane→EtOAc, default setting). The product crystallized out on the column and had to be eluted with EtOAc (10% MeOH). The solvent is removed in vacuo and the product is crystallized from EtOAc, filtered and dried for 4 days under vacuum @50° C.

Examples 4.1 to 4.33

The compounds of the following tabulated Examples are prepared using the following general procedure:
A stock solution of trans-2-chloro-N-(4-formyl-cyclohexyl)-5-trifluoromethyl-benzamide (Example 1 Step 3)

(3.102 g) and acetic acid (1.6 mL) is prepared in 23.5 mL DMF (peptide grade). Each microwave vial is loaded with MP-triacetoxyborohydride resin (~100 mg). 267 µl of the acetic acid/aldehyde solution is added to each microwave vial. Each amine is solubilized in 750 µl DMF and added to the microwave vials. The vials are sealed and heated to 60° C. for 10 minutes in the microwave synthesizer. The crude reactions are passed onto a 1 g SCX-2 cartridge (Biotage) under gravity, which had been pre-wetted with 1 mL MeOH. The cartridges are washed with 2×2 mL MeOH, then compounds eluted with 2×2 mL 2M ammonia in MeOH. Compounds are analyzed and evaporated in vacuo. Crude mixtures are purified further by prep HPLC (Waters Sunfire C18 5 micron column, 19×50 mm, mobile phases 0.1% TFA in water, 0.1% TFA in acetonitrile, 6 minute gradient dependant on retention time from analytics). Successful purifications are turned into free-based amines by passing prep fraction through a SCX-2 cartridge pre-wetted with MeOH, washed with 5 mL MeOH, and eluted with 2×2 mL 3.5M ammonia in MeOH. Compounds are evaporated in vacuo.

TABLE 3

| Ex. | Structure | Name | [M + H]$^+$ |
|---|---|---|---|
| 4.1 | 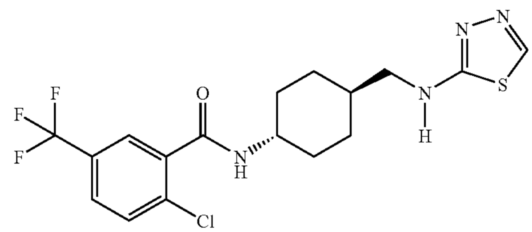 | Trans-2-Chloro-N-[4-([1,3,4]thiadiazol-2-ylaminomethyl)-cyclohexyl]-5-trifluoromethyl-benzamide | 419.04 |
| 4.2 | 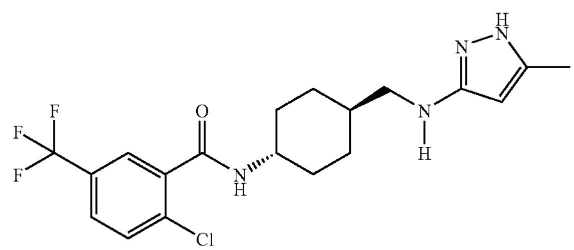 | Trans-2-Chloro-N-{4-[(5-methyl-1H-pyrazol-3-ylamino)-methyl]-cyclohexyl}-5-trifluoromethyl-benzamide | 415.33 |
| 4.3 | 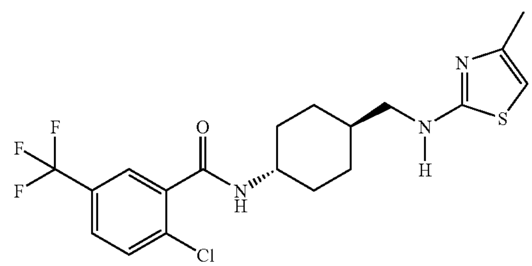 | Trans-2-Chloro-N-{4-[(4-methyl-thiazol-2-ylamino)-methyl]-cyclohexyl}-5-trifluoromethyl-benzamide | 432.29 |
| 4.4 | 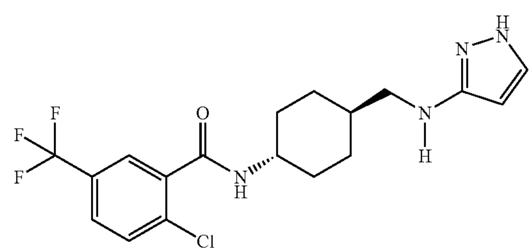 | Trans-2-Chloro-N-{4-[(1H-pyrazol-3-ylamino)-methyl]-cyclohexyl}-5-trifluoromethyl-benzamide | 401.3 |
| 4.5 | 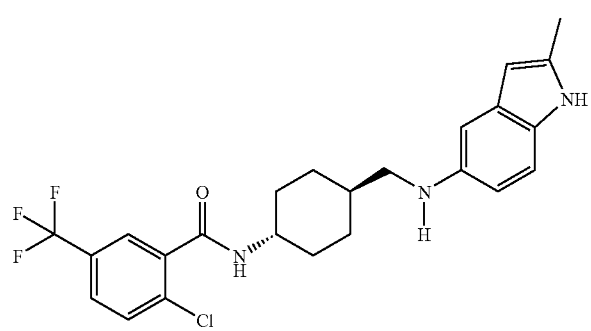 | Trans-2-Chloro-N-{4-[(2-methyl-1H-indol-5-ylamino)-methyl]-cyclohexyl}-5-trifluoromethyl-benzamide | 464.38 |

TABLE 3-continued

| Ex. | Structure | Name | [M + H]+ |
|---|---|---|---|
| 4.6 | 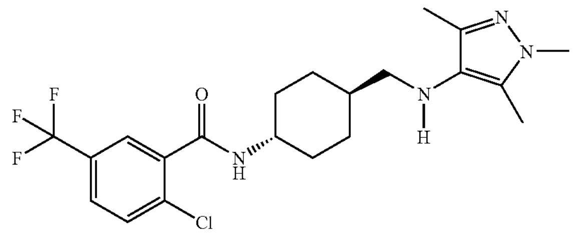 | Trans-2-Chloro-5-trifluoromethyl-N-{4-[(1,3,5-trimethyl-1H-pyrazol-4-ylamino)-methyl]-cyclohexyl}-benzamide | 443.38 |
| 4.7 | 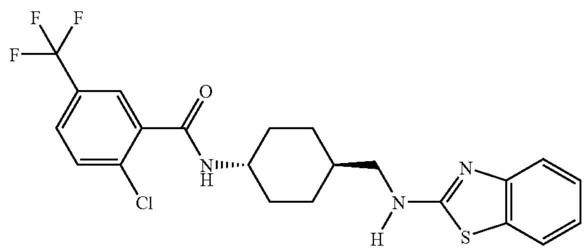 | Trans-N-[4-(Benzothiazol-2-ylaminomethyl)-cyclohexyl]-2-chloro-5-trifluoromethyl-benzamide | 468.31 |
| 4.8 | 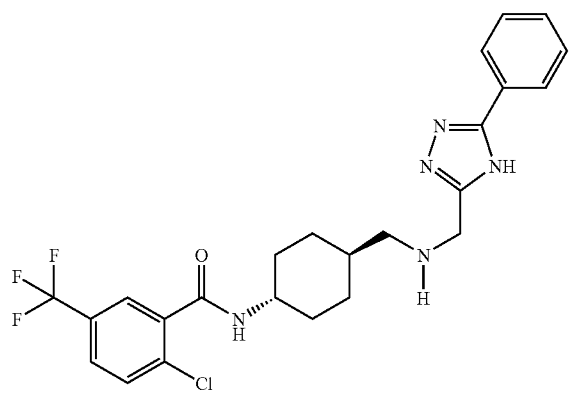 | Trans-2-Chloro-N-(4-{[(5-phenyl-4H-[1,2,4]triazol-3-ylmethyl)-amino]-methyl}-cyclohexyl)-5-trifluoromethyl-benzamide | 492.39 |
| 4.9 | 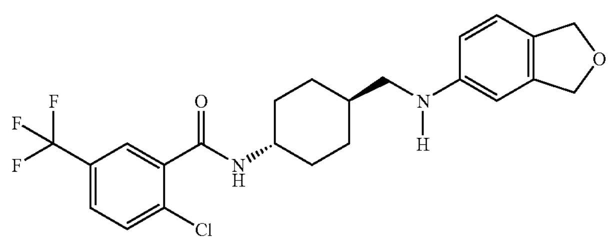 | Trans-2-Chloro-N-{4-[(1,3-dihydro-isobenzofuran-5-ylamino)-methyl]-cyclohexyl}-5-trifluoromethyl-benzamide | 453.35 |
| 4.10 | 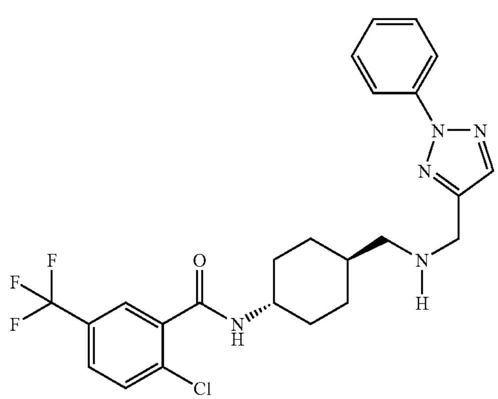 | Trans-2-Chloro-N-(4-{[(2-phenyl-2H-[1,2,3]triazol-4-ylmethyl)-amino]-methyl}-cyclohexyl)-5-trifluoromethyl-benzamide | 492.38 |

TABLE 3-continued

| Ex. | Structure | Name | [M + H]+ |
|---|---|---|---|
| 4.11 | 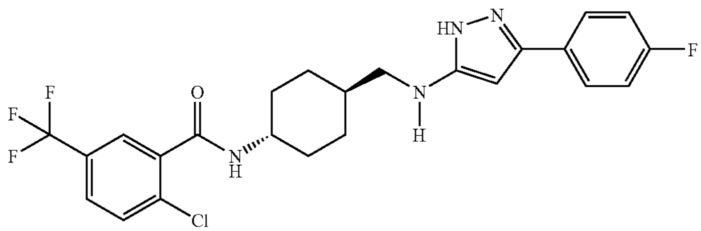 | Trans-2-Chloro-N-(4-{[5-(4-fluoro-phenyl)-2H-pyrazol-3-ylamino]-methyl}-cyclohexyl)-5-trifluoromethyl-benzamide | 495.07 |
| 4.12 | 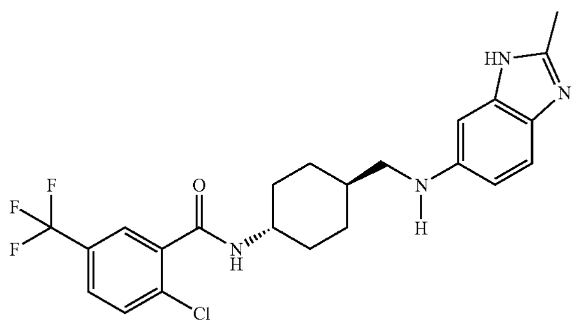 | Trans-2-Chloro-N-{4-[(2-methyl-3H-benzoimidazol-5-ylamino)-methyl]-cyclohexyl}-5-trifluoromethyl-benzamide | 465.38 |
| 4.13 | 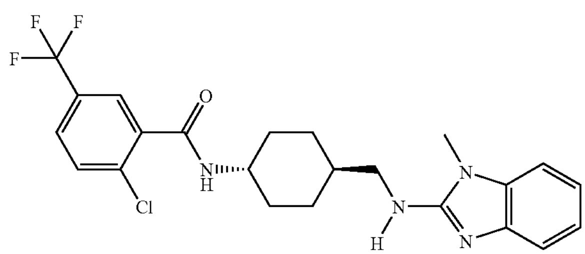 | Trans-2-Chloro-N-{4-[(1-methyl-1H-benzoimidazol-2-ylamino)-methyl]-cyclohexyl}-5-trifluoromethyl-benzamide | 465.09 |
| 4.14 | 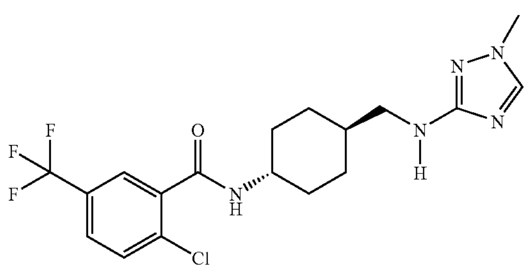 | Trans-2-Chloro-N-{4-[(1-methyl-1H-[1,2,4]triazol-3-ylamino)-methyl]-cyclohexyl}-5-trifluoromethyl-benzamide | 416.33 |
| 4.15 | 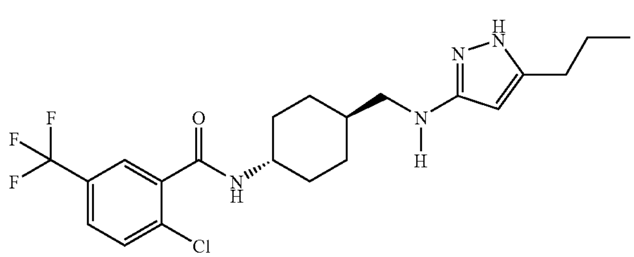 | Trans-2-Chloro-N-{4-[(5-propyl-1H-pyrazol-3-ylamino)-methyl]-cyclohexyl}-5-trifluoromethyl-benzamide | 443.38 |

TABLE 3-continued

| Ex. | Structure | Name | [M + H]+ |
|---|---|---|---|
| 4.16 | 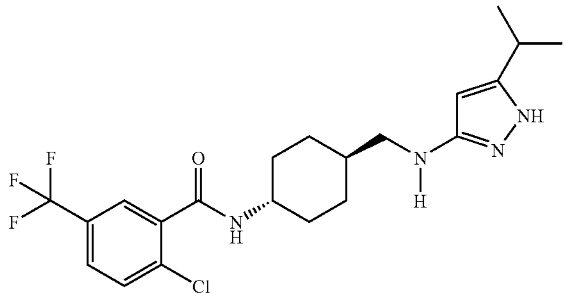 | Trans-2-Chloro-N-{4-[(5-isopropyl-1H-pyrazol-3-ylamino)-methyl]-cyclohexyl}-5-trifluoromethyl-benzamide | 443.38 |
| 4.17 | 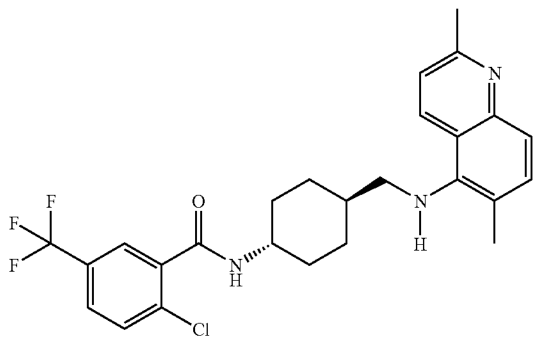 | Trans-2-Chloro-N-{4-[(2,6-dimethyl quinolin-5-ylamino)-methyl]-cyclohexyl}-5-trifluoromethyl-benzamide | 490.38 |
| 4.18 | 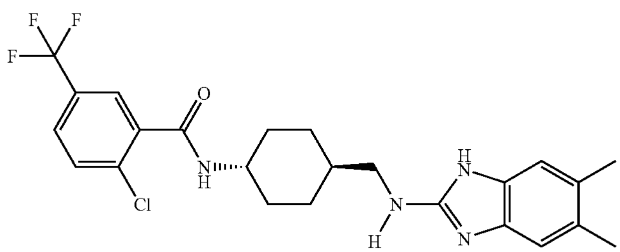 | Trans-2-Chloro-N-{4-[(5,6-dimethyl 1H-benzoimidazol-2-ylamino)-methyl]-cyclohexyl}-5-trifluoromethyl-benzamide | 479.15 |
| 4.19 | 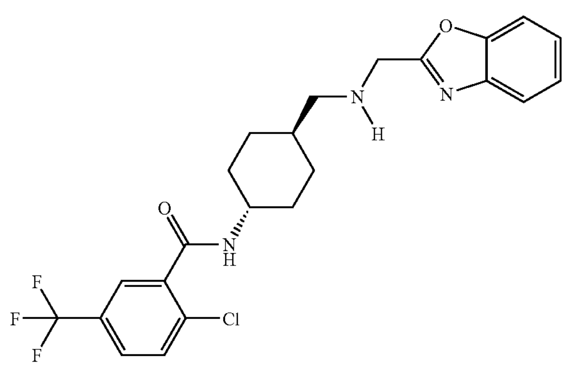 | Trans-N-(4-{[(Benzooxazol-2-ylmethyl)-amino]-methyl}-cyclohexyl)-2-chloro-5-trifluoromethyl-benzamide | 466.36 |
| 4.20 | 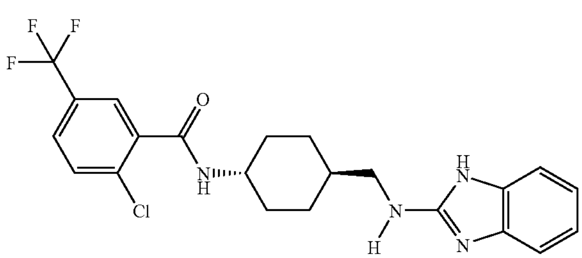 | Trans-N-{4-[(1H-Benzoimidazol-2-ylamino)-methyl]-cyclohexyl}-2-chloro-5-trifluoromethyl-benzamide | 451.34 |

TABLE 3-continued

| Ex. | Structure | Name | [M + H]+ |
|---|---|---|---|
| 4.21 | 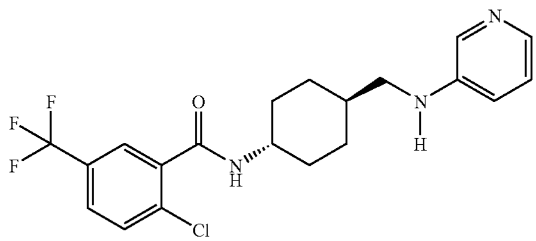 | Trans-2-Chloro-N-[4-(pyridin-3-ylaminomethyl)-cyclohexyl]-5-trifluoromethyl-benzamide | 412.33 |
| 4.22 | 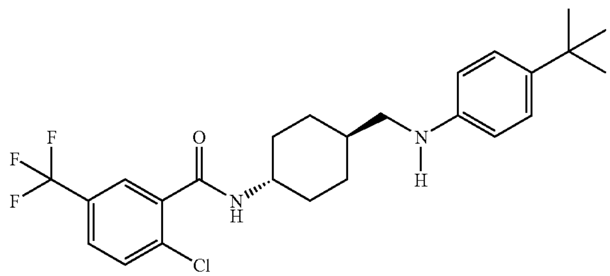 | Trans-N-{4-[(4-tert-Butyl-phenylamino)-methyl]-cyclohexyl}-2-chloro-5-trifluoromethyl-benzamide | 467.13 |
| 4.23 | 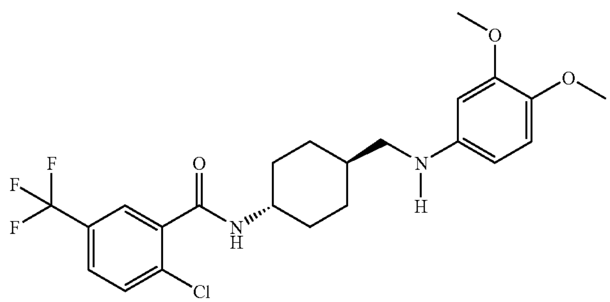 | Trans-2-Chloro-N-{4-[(3,4-dimethoxy-phenylamino)-methyl]-cyclohexyl}-5-trifluoromethyl-benzamide | 471.38 |
| 4.24 | 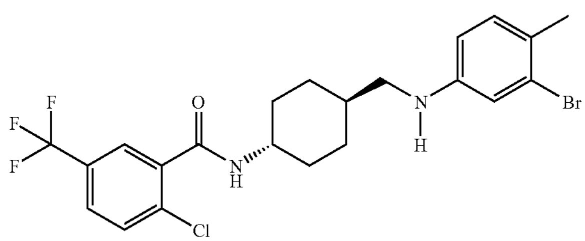 | Trans-N-{4-[(3-Bromo-4-methyl-phenylamino)-methyl]-cyclohexyl}-2-chloro-5-trifluoromethyl-benzamide | 505.01 |
| 4.25 | 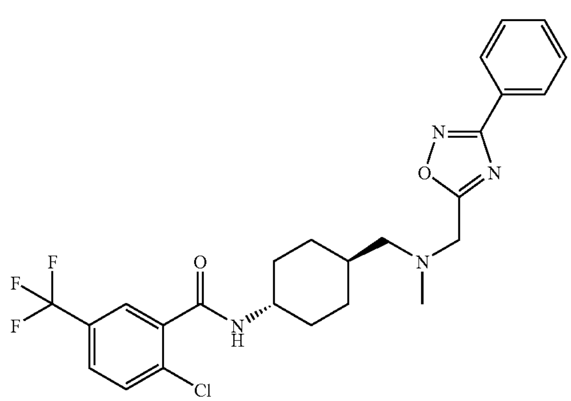 | Trans-2-Chloro-N-(4-{[methyl-(3-phenyl-[1,2,4]oxadiazol-5-ylmethyl)-amino]-methyl}-cyclohexyl)-5-trifluoromethyl-benzamide | 507.38 |

TABLE 3-continued

| Ex. | Structure | Name | [M + H]+ |
|---|---|---|---|
| 4.26 | 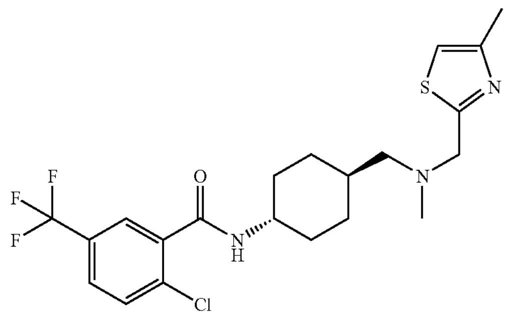 | Trans-2-Chloro-N-(4-{[methyl-(4-methyl-thiazol-2-ylmethyl)-amino]-methyl}-cyclohexyl)-5-trifluoromethyl-benzamide | 460.33 |
| 4.27 | 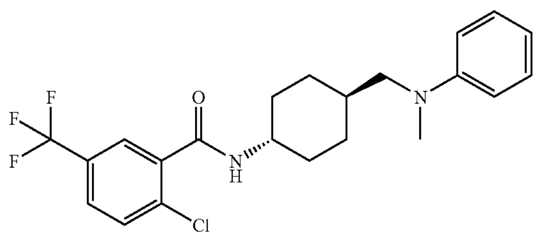 | Trans-2-Chloro-N-{4-[(methyl-phenyl-amino)-methyl]-cyclohexyl}-5-trifluoromethyl-benzamide | 425.33 |
| 4.28 | 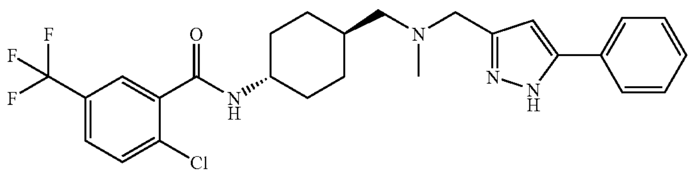 | Trans-2-Chloro-N-(4-{[methyl-(5-phenyl-1H-pyrazol-3-ylmethyl)-amino]-methyl}-cyclohexyl)-5-trifluoromethyl-benzamide | 505.4 |
| 4.29 | 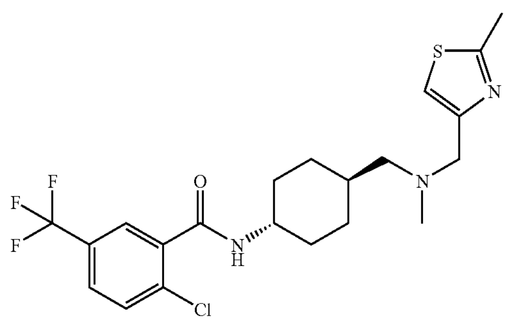 | Trans-2-Chloro-N-(4-{[methyl-(2-methyl-thiazol-4-ylmethyl)-amino]-methyl}-cyclohexyl)-5-trifluoromethyl-benzamide | 460.33 |
| 4.30 | 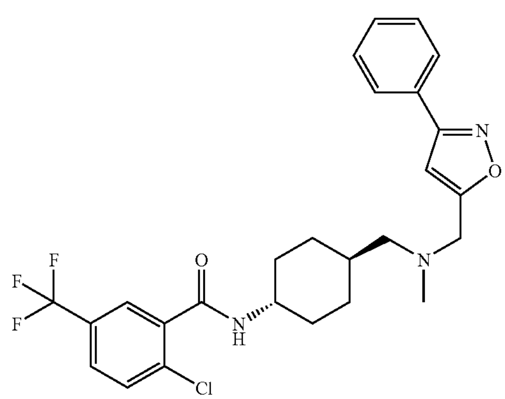 | Trans-2-Chloro-N-(4-{[methyl-(3-phenyl-isoxazol-5-ylmethyl)-amino]-methyl}-cyclohexyl)-5-trifluoromethyl-benzamide | 506.4 |

TABLE 3-continued

| Ex. | Structure | Name | [M + H]+ |
|---|---|---|---|
| 4.31 | 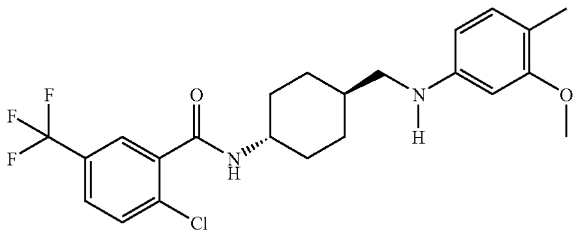 | Trans-2-Chloro-N-{4-[(3-methoxy-4-methyl-phenylamino)-methyl]-cyclohexyl}-5-trifluoromethyl-benzamide | 455.38 |
| 4.32 | 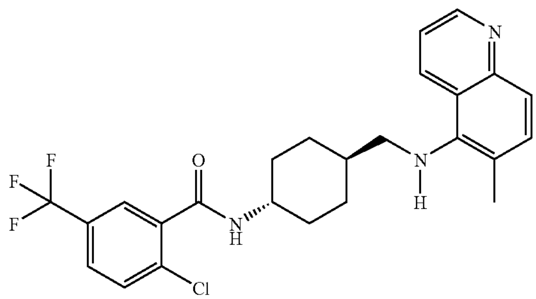 | Trans-2-Chloro-N-{4-[(6-methyl-quinolin-5-ylamino)-methyl]-cyclohexyl}-5-trifluoromethyl-benzamide | 476.38 |
| 4.33 | 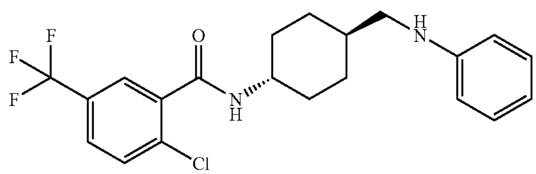 | Trans-2-Chloro-N-(4-phenylaminomethyl-cyclohexyl)-5-trifluoromethyl-benzamide | 411.35 |

Examples 5.1 to 5.17

Preparation of Intermediate Compound
Trans-(4-Amino-cyclohexylmethyl)phenylamine Step 1

Methyl trans-4-(tert-butoxycarbonylamino)cyclohexanecarboxylate

Methyl trans-4-aminocyclohexanecarboxylate (43 g, 222 mmol) is added to MeOH (500 mL) to give a colourless solution. The solution is cooled to 10° C. and triethylamine (46.4 mL, 333 mmol) is added dropwise, followed by a solution of di-tert-butyldicarbonate (53.3 g, 244 mmol) in MeOH (400 mL) over 20 minutes. The reaction is warmed to room temperature and stirred at room temperature overnight. The mixture is evaporated to dryness under reduced pressure. The resulting colourless solid is dissolved in EtOAc (1000 mL) and the solution obtained is washed successively with 10% citric acid solution (100 mL), saturated sodium bicarbonate solution (2×100 mL) and saturated brine (100 mL); dried (MgSO$_4$) and evaporated under reduced pressure to give a colourless solid.

Step 2

Trans-tert-butyl 4-(hydroxymethyl)cyclohexylcarbamate

Methyl trans-4-(tert-butoxycarbonylamino)cyclohexanecarboxylate (55.5 g, 216 mmol) is suspended in ethanol (900 mL) and THF (100 mL) and the mixture is cooled to 5° C. Granular calcium chloride (47.9 g, 431 mmol) is added portionwise to give a milky suspension. Sodium borohydride (32.6 g, 863 mmol) is added portionwise over 25 mins at 5° C. The reaction mixture (white emulsion) is stirred at 5° C. for 1 hour, the water bath is removed and then the reaction mixture is allowed to warm to room temperature and stirred at room temperature overnight. The reaction mixture is cooled to 10° C. and 5% potassium carbonate (200 mL) is added dropwise until the pH of the solution is pH 11. A colourless precipitate formed which is filtered off. The solid is stirred with ethyl acetate (2000 mL) and water (500 mL). The organic layer is separated and washed with 0.5M HCl (200 mL), then washed with water (2×200 mL) and saturated brine (100 mL). The organic solution is dried over anhydrous MgSO$_4$, filtered and evaporated to give a white solid The solid is dried under high vacuum overnight to constant weight; [MH+ 230].

Step 3

Trans-(4-Formyl-cyclohexyl)carbamic acid tert-butyl ester

To trans-tert-butyl-4-(hydroxymethyl)cyclohexylcarbamate (8.0 g, 34.9 mmol) in DCM (180 mL) and DMSO (60 mL) at 0° C. is added DIPEA (24.37 mL, 140 mmol) and pyridine sulfur trioxide (22.21 g, 140 mmol) dissolved in DMSO (60 mL). The mixture is stirred at room temperature for 15 minutes and then is partitioned between 1M HCl and diethylether. The organic phase is separated and washed with 1M HCl, water then saturated brine. The mixture is dried (MgSO$_4$) and solvent evaporated to give the expected product; [MH+ MeCN]+ 269.

Step 4

Trans-(4-Phenylaminomethyl-cyclohexyl)carbamic acid tert-butyl ester

Trans-(4-Formyl-cyclohexyl)carbamic acid tert-butyl ester (3.27 g, 14.38 mmol) and aniline (1.98 mL, 15.81 mmol) are dissolved in dichloromethane (60 mL) at room temperature. Sodium triacetoxyborohydride (4.57 g, 21.57 mmol) is added in one portion and the mixture is stirred at room temperature for 2.5 hours. 1N sodium hydroxide solution (20 mL) is added and the mixture is stirred at room temperature for a further 10 minutes. The DCM layer is separated and washed successively with water and saturated brine, dried ($MgSO_4$), filtered and evaporated to give a colourless solid. This is slurried with iso-hexane, filtered and dried to give a colourless solid; [$MH^+$ 305]

Step 5

Trans-(4-Amino-cyclohexylmethyl)phenylamine

Trans-(4-Phenylaminomethyl-cyclohexyl)carbamic acid tert-butyl ester (4.37 g, 14.35 mmol) is dissolved in dry dichloromethane (200 mL) under a nitrogen atmosphere and trifluoroacetic acid (70 mL) is added dropwise at room temperature. The reaction mixture is stirred at room temperature for 3 hours before the volatiles are removed under reduced pressure. The residue is redissolved in DCM and washed with 1N sodium hydroxide solution. The DCM is then separated, washed sequentially with water and saturated brine and evaporated under reduced pressure, whereupon a beige solid is formed; [$MH^+$ 205]

The compounds of the following tabulated Examples (Table 4) are prepared according from trans-(4-amino-cyclohexylmethyl)phenylamine (Ex. 5.1 step 5) according to the following general procedure:

In each reaction: carboxylic acid (0.147 mmol, 1.47 eq), trans-(4-amino-cyclohexylmethyl)phenylamine (Step 5) (0.1 mmol, 1 eq, 21 mg), HATU (0.147 mmol, 1.47 eq, 56 mg), PS-DIEA 3.4 mmol/g loading (0.2 mmol, 2 eq, 60 mg) are used.

A stock solution of trans-(4-amino-cyclohexylmethyl)phenylamine is made up in DMF (1.428 g in 13.6 mL). A stock solution of HATU is made up in DMF (3.808 g in 20.4 mL DMF). Ca. 60 mg PS-DIEA is added to each pre-weighed carboxylic acid. 200 ul Trans-(4-amino-cyclohexylmethyl)phenylamine solution is pipetted into each vial, followed by 300 μl of HATU solution. Vials are sealed and shaken at RT for 16 hr. Crude reactions are purified by loading onto a 1 g SCX-2 cartridge pre-wetted with MeOH, crude is washed with 3 mL MeOH before compounds are eluted with 2×2 mL 2M ammonia in MeOH. Compounds are analyzed and evaporated in vacuo. Crude mixtures are purified further by prep HPLC (Waters Sunfire C18 5 micron column, 19×50 mm, mobile phases 0.1% TFA in water, 0.1% TFA in acetonitrile, 6 minute gradient dependant on retention time from analytics). Successful purifications are turned into free-based amines by passing prep fraction through a SCX-2 cartridge pre-wetted with MeOH, washed with 5 mL MeOH, and eluted with 2×2 mL 3.5M ammonia in MeOH. Compounds are evaporated in vacuo.

TABLE 4

| Ex. | Structure | Name | [M + H]$^+$ |
| --- | --- | --- | --- |
| 5.1 | 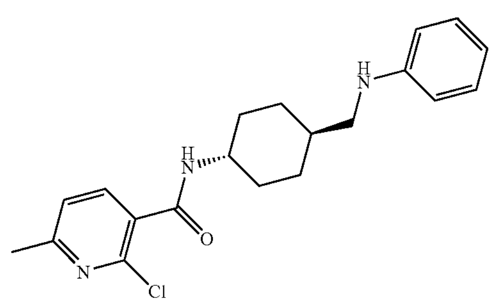 | Trans-2-Chloro-6-methyl-N-(4-phenylaminomethyl-cyclohexyl)-nicotinamide | 358.28 |
| 5.2 | 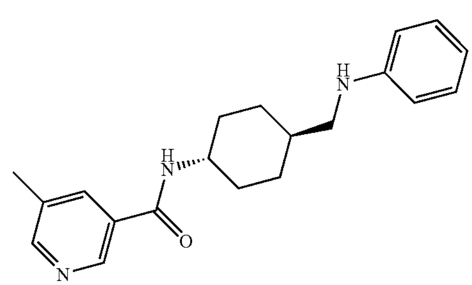 | Trans-5-Methyl-N-(4-phenylaminomethyl-cyclohexyl)-nicotinamide | 324.32 |

TABLE 4-continued

| Ex. | Structure | Name | [M + H]⁺ |
|---|---|---|---|
| 5.3 | 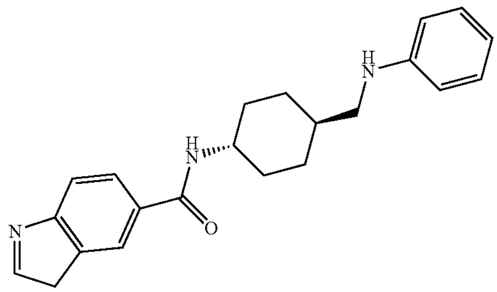 | Trans-3H-Indole-5-carboxylic acid (4-phenylaminomethyl-cyclohexyl)-amide | 348.33 |
| 5.4 | 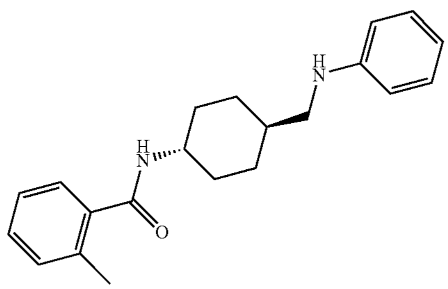 | Trans-2-Methyl-N-(4-phenylaminomethyl-cyclohexyl)-nicotinamide | 323.33 |
| 5.5 | 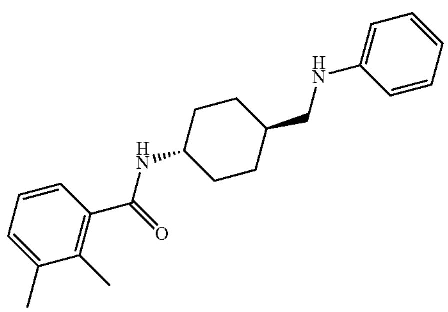 | Trans-2,3-Dimethyl-N-(4-phenylaminomethyl-cyclohexyl)-benzamide | 337.35 |
| 5.6 | 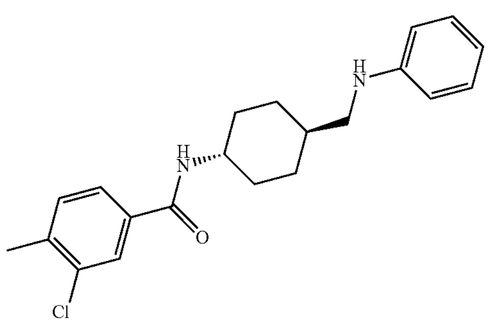 | Trans-3-Chloro-4-methyl-N-(4-phenylaminomethyl-cyclohexyl)-benzamide | 357.3 |
| 5.7 | 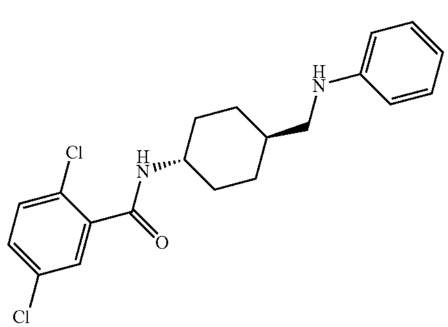 | Trans-2,5-Dichloro-N-(4-phenylaminomethyl-cyclohexyl)-benzamide | 377.26 |

TABLE 4-continued

| Ex. | Structure | Name | [M + H]+ |
|---|---|---|---|
| 5.8 | 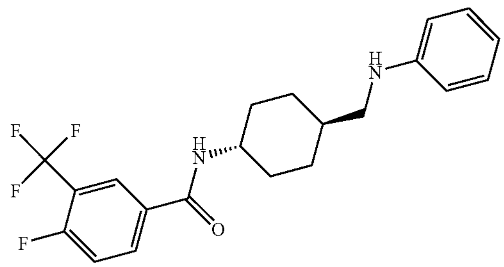 | Trans-4-Fluoro-N-(4-phenylaminomethyl-cyclohexyl)-3-trifluoromethyl-benzamide | 395.32 |
| 5.9 | 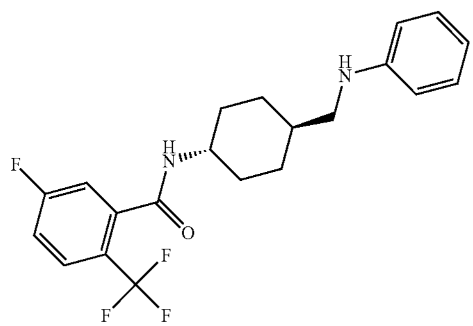 | Trans-5-Fluoro-N-(4-phenylaminomethyl-cyclohexyl)-2-trifluoromethyl-benzamide | 395.32 |
| 5.10 | 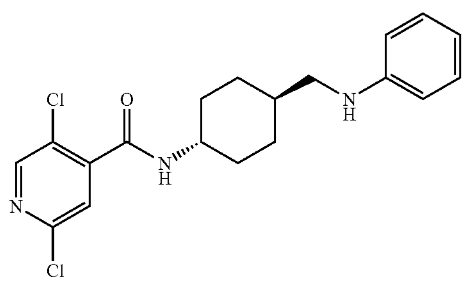 | Trans-2,5-Dichloro-N-(4-phenylaminomethyl-cyclohexyl)-isonicotinamide | 378.24 |
| 5.11 | 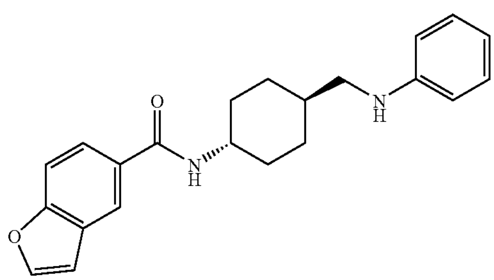 | Trans-Benzofuran-5-carboxylic acid-(4-phenylaminomethyl-cyclohexyl)-amide | 349.31 |
| 5.12 | 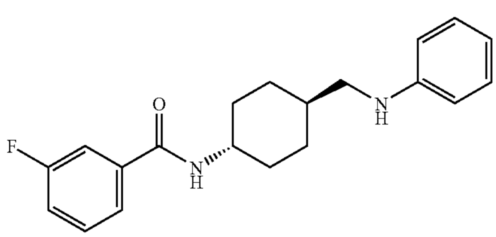 | Trans-3-Fluoro-N-(4-phenylaminomethyl-cyclohexyl)-benzamide | 327.32 |

TABLE 4-continued

| Ex. | Structure | Name | [M + H]+ |
|---|---|---|---|
| 5.13 | 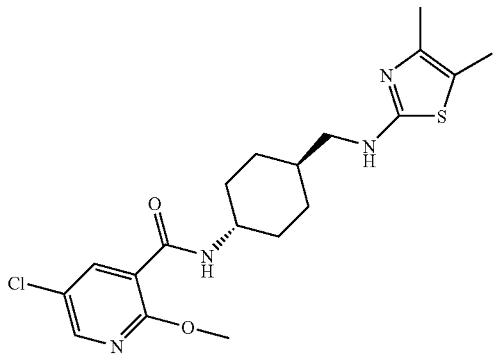 | Trans-5-Chloro-N-{4-[(4,5-dimethyl-thiazol-2-ylamino)-methyl]-cyclohexyl}-2-methoxy-nicotinamide | 409.35 |
| 5.14 | 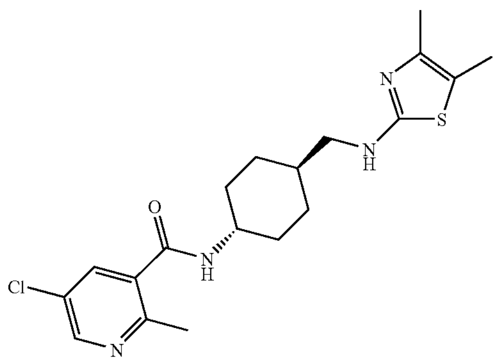 | Trans-5-Chloro-N-{4-[(4,5-dimethyl-thiazol-2-ylamino)-methyl]-cyclohexyl}-2-methyl-nicotinamide | 393.31 |
| 5.15 | 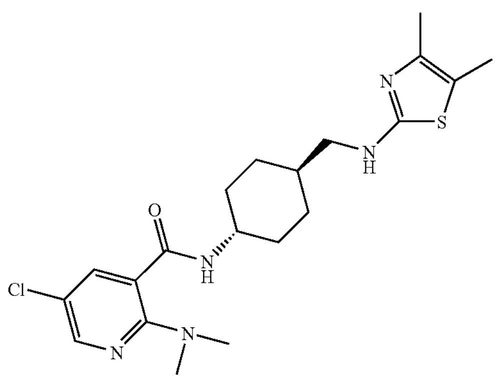 | Trans-5-Chloro-2-dimethylamino-N-{4-[(4,5-dimethyl-thiazol-2-ylamino)-methyl]-cyclohexyl}-nicotinamide | 422.41 |
| 5.16 | 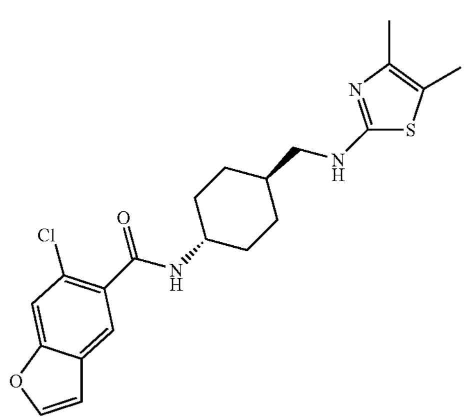 | Trans-6-Chloro-benzofuran-5-carboxylic acid {4-[(4,5-dimethyl-thiazol-2-ylamino)-methyl]-cyclohexyl}-amide | 418.4 |

| Ex. | Structure | Name | [M + H]+ |
|---|---|---|---|
| 5.17 | 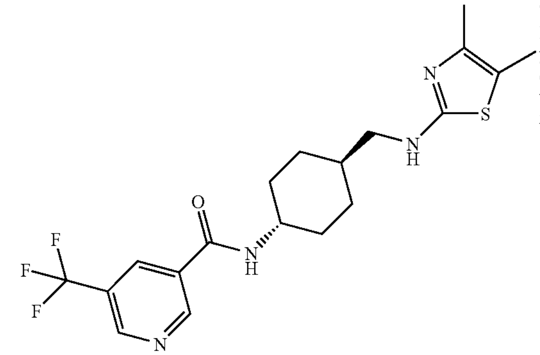 | Trans-N-{4-[(4,5-Dimethyl-thiazol-2-ylamino)-methyl]-cyclohexyl}-5-trifluoromethyl-nicotinamide | 413.38 |

Example 6

Trans-2-chloro-N-(4-((3-(2-oxoimidazolidin-1-yl)-1H-pyrazol-1-yl)methyl)cyclohexyl)-5-(trifluoromethyl)benzamide

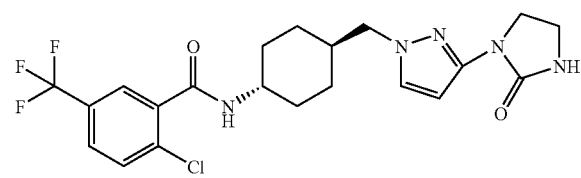

Step 1

Trans-(4-(2-chloro-5-(trifluoromethyl)benzamido)cyclohexyl)methyl 4-methyl benzenesulfonate Trans-2-chloro-N-(4-hydroxymethyl-cyclohexyl)-5-trifluoromethyl-benzamide (Example 1 step 2) 1.00 g (2.98 mmol) is dissolved in DCM (40 mL) and pyridine (10 mL). Tosyl chloride (0.85 g, 4.47 mmol) is added and the reaction mixture is stirred at RT overnight. The mixture is partitioned between DCM and 1M HCl. The organic phase is washed with water and brine, dried over MgSO$_4$, filtered and the solvent is removed in vacuo. Trituration of the resulting solid with iso-hexane:EtOAc—4:1 affords the title compound; $^1$H NMR (400 MHz, DMSO-d$_6$) δ 8.48 (1H, d), 7.80 (3H, m), 7.72 (2H, d), 7.49 (2H, d), 3.85 (2H, d), 3.60 (1H, m), 2.41 (3H, s), 1.89 (2H, m), 1.68 (2H, m), 1.53 (1H, m), 1.20 (2H, m), 1.00 (2H, m).

Step 2

Trans-2-chloro-N-(4-((3-(2-oxoimidazolidin-1-yl)-1H-pyrazol-1-yl)methyl)cyclohexyl)-5-(trifluoromethyl)benzamide 1-(1H-pyrazol-3-yl)imidazolidin-2-one (410 mg, 2.69 mmol) is placed in a microwave vial with acetonitrile (12 mL). NaH (60%, 108 mg, 2.69 mmol) is added and the reaction mixture is stirred at RT for 30 minutes. Trans-(4-(2-chloro-5-(trifluoromethyl)benzamido)cyclohexyl)methyl 4-methylbenzenesulfonate (1.20 g (0.20 mmol) is added and the mixture is heated using microwave radiation at 120° C. for 30 minutes. The mixture is partitioned between DCM and water. The organic phase is washed with water and brine, dried over MgSO$_4$, filtered and the solvent was removed in vacuo. The product is purified by crystallization (EtOAc with a small amount of MeOH) to afford the title compound.

The compounds of the following tabulated Examples (Table 5), or tautomers thereof, are prepared by a similar method to that of Example 6 by replacing 1-(1H-pyrazol-3-yl)imidazolidin-2-one with the appropriate intermediate. One such intermediate is 1-(5-Methyl-1H-pyrazol-3-yl)-imidazolidin-2-one, the preparation of which is described as follows:

Step 1

3-[3-(2-Chloro-ethyl)-ureido]-5-methyl-pyrazole-1-carboxylic acid (2-chloro-ethyl)-amide To a solution of 5-Methyl-1H-pyrazol-3-ylamine (7.5 g, 77.2 mmol) in THF (150 mL) at 0° C. was added 2-chloroethylisocyanate (25 g, 236.9 mmol) and then the reaction mixture was stirred at RT for 18 h. Hexane was added to the reaction mixture, cooled to 0° C. and stirred for ~2 h. The white solid precipitated out was collected by filtration, washed with diethylether and dried.

Step 2

1-(5-Methyl-1H-pyrazol-3-yl)-imidazolidin-2-one

To a solution of 3-[3-(2-Chloro-ethyl)-ureido]-5-methyl-pyrazole-1-carboxylic acid (2-chloro-ethyl)-amide (14.5 g, 47.05 mmol) in THF (100 mL) was added sodium ethoxide solution prepared from sodium (2.2 g, 95.65 mmol) and ethanol (100 mL) and then the reaction mixture was stirred at RT for 20 h. Precipitation of white solid was observed. The reaction mixture was cooled to 0° C. and stirred for ~2 h. The precipitated solid was collected by filtration, washed with ethanol and water, and dried under vacuum.

TABLE 5

| Ex. | Structure | Name | [M + H]+ |
|---|---|---|---|
| 6.1 | 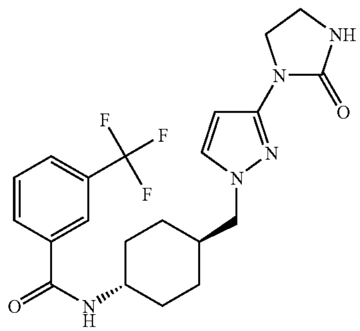 | Trans-N-{4-[3-(2-Oxo-imidazolidin-1-yl)-pyrazol-1-ylmethyl]-cyclohexyl}-3-trifluoromethyl-benzamide | 436.37 |
| 6.2 | 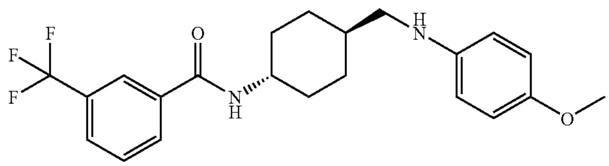 | Trans-N-{4-[(4-Methoxy-phenylamino)-methyl]-cyclohexyl}-3-trifluoromethyl-benzamide | 407.43 |
| 6.3 | 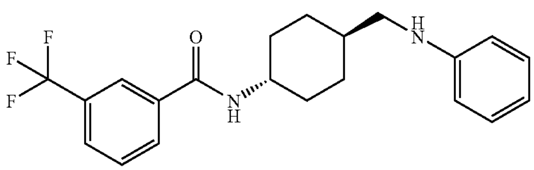 | Trans-N-(4-Phenylaminomethyl-cyclohexyl)-3-trifluoromethyl-benzamide | 377.32 |
| 6.4 | 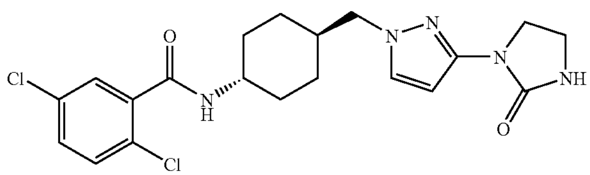 | Trans-2,5-Dichloro-N-{4-{3-(2-oxo-imidazolidin-1-yl)-pyrazol-1-ylmethyl]-cyclohexyl}-benzamide | 436.33 |
| 6.5 | 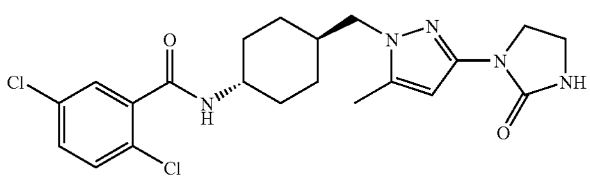 | Trans-2,5-Dichloro-N-{4-[5-methyl-3-(2-oxo-imidazolidin-1-yl)-pyrazol-1-ylmethyl]-cyclohexyl}-benzamide | 450.36 |

Example 7.0

Trans-2-chloro-N-[4-(3,5-dimethyl-pyrazol-1-ylmethyl)-cyclohexyl]-5-trifluoromethyl-benzamide

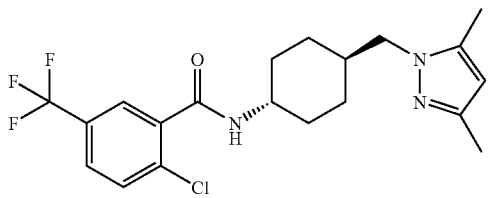

Step 1

Trans-(4-(2-chloro-5-(trifluoromethyl)benzamido)cyclohexyl)methyl trifluoro methanesulfonate Trans-2-chloro-N-(4-hydroxymethyl-cyclohexyl)-5-trifluoromethyl-benzamide (1.00 g, 2.98 mmol) in 25 mL of DCM is treated with pyridine (0.28 g, 3.57 mmol) and the reaction mixture is cooled to 0° C. Trifluoromethanesulfonic anhydride (0.92 g, 3.28 mmol) of is slowly added and the reaction mixture is stirred at 0° C. for 1 hour. The reaction is quenched by the addition of sat. NH$_4$Cl at 0° C. and then extracted with DCM (3×10 mL). The DCM extracts are combined, washed with sat. brine (10 mL), dried (MgSO4), filtered and evaporated to afford the title compound as a pale yellow solid; $^1$H NMR (400 MHz, DMSO-d$_6$) δ 8.50 (1H, d), 7.80 (1H, m) 7.72 (2H, m), 4.11 (2H, d), 3.68 (1H, m), 1.95 (2H, m), 1.78 (2H, m), 1.65 (1H, m), 1.25 (2H, m), 1.11 (2H, m).

Step 2

Trans-2-chloro-N-[4-(3,5-dimethyl-pyrazol-1-ylmethyl)-cyclohexyl]-5-trifluoromethyl-benzamide A solution of 3,5-dimethyl pyrazole (51.4 mg, 0.534 mmol) in MeCN (2 ml) is treated with sodium hydride (14.11 mg, 0.588 mmol) and the reaction mixture is stirred 10 minutes. Trans-4-(2-Chloro-5-(trifluoromethyl)benzamido)cyclohexyl)methyl trifluoromethanesulfonate (250 mg, 0.534 mmol) is added and the mixture is stirred at RT for 2 hrs.

The resulting mixture is diluted with DCM and washed NaHCO$_3$. The organic portion is separated and concentrated in vacuo. Purification of the crude product by chromatography on silica eluting with iso-hexane/EtOAc affords a white solid. The solid is triturated with 9:1 iso-hexane:EtOAc and the resulting white solid is filtered off and dried to give the title compound. [MH+ 414.4]. NMR: δH (400 MHz, DMSO) 8.49 (1H, d), 7.73 (3H, m), 5.77 (1H, s), 3.76 (2H, d), 3.68 (1H, m), 2.18 (3H, s), 2.08 (3H, s), 1.91 (2H, m), 1.73 (1H, m), 1.58 (2H, m), 1.16 (4H, m).

The compounds of the following tabulated Examples (Table 6), or tautomers thereof, are prepared from trans4-(2-chloro-5-(trifluoromethyl)benzamido)cyclohexyl)methyl trifluoromethanesulfonate by a similar method to that of Example 7.0 using the appropriate azole.

TABLE 7

| Ex. | Structure | Name | [M + H]$^+$ |
| --- | --- | --- | --- |
| 7.1 | 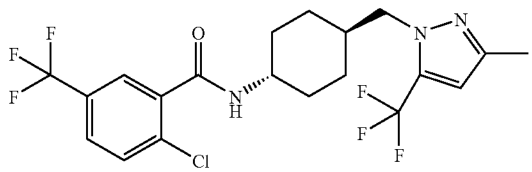 | Trans-2-Chloro-N-[4-(3-methyl-5-trifluoromethyl-pyrazol-1-ylmethyl)-cyclohexyl]-5-trifluoromethyl-benzamide | 368.3 |
| 7.2 | 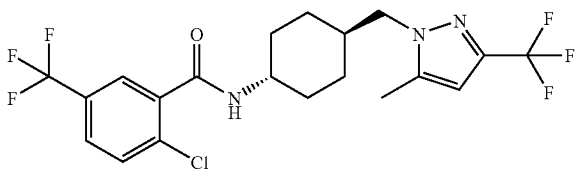 | Trans-2-Chloro-N-[4-(5-methyl-3-trifluoromethyl-pyrazol-1-ylmethyl)-cyclohexyl]-5-trifluoromethyl-benzamide | 368.3 |
| 7.3 | 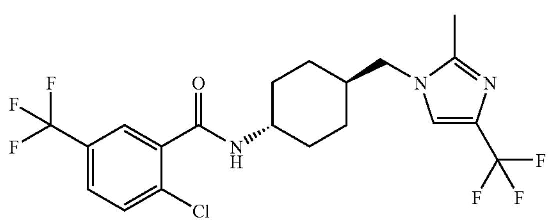 | Trans-2-Chloro-N-[4-(2-methyl-4-trifluoromethyl-imidazol-1-ylmethyl)-cyclohexyl]-5-trifluoromethyl-benzamide | 468.33 |
| 7.4 | 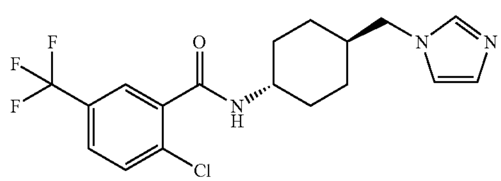 | Trans-2-Chloro-N-(4-imidazol-1-ylmethyl-cyclohexyl)-5-trifluoromethyl-benzamide | 386.30 |
| 7.5 | 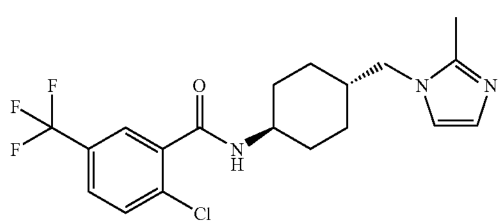 | Trans-2-Chloro-N-[4-(2-methyl-imidazol-1-ylmethyl)-cyclohexyl]-5-trifluoromethyl-benzamide | 400.38 |
| 7.6 | 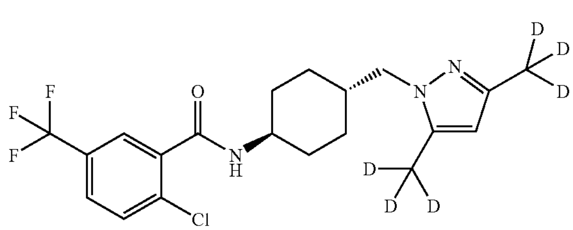 | Trans-2-Chloro-N-[4-(3,5-di-(d3)-methyl-pyrazol-1-ylmethyl)-cyclohexyl]-5-trifluoromethyl-benzamide | 420.45 |

TABLE 7-continued

| Ex. | Structure | Name | [M + H]+ |
|---|---|---|---|
| 7.7 | 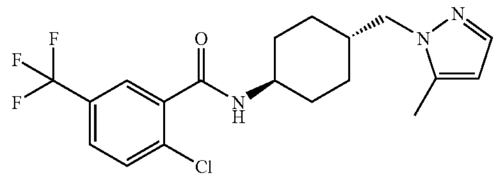 | Trans-2-Chloro-N-[4-(5-methyl-pyrazol-1-ylmethyl)-cyclohexyl]-5-trifluoromethyl-benzamide | 400.35 |
| 7.8 | 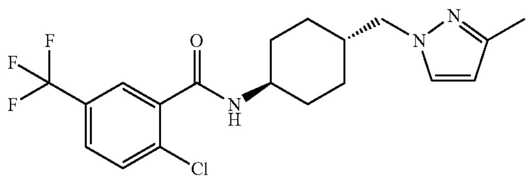 | Trans-2-Chloro-N-[4-(3-methyl-pyrazol-1-ylmethyl)-cyclohexyl]-5-trifluoromethyl-benzamide | 400.35 |
| 7.9 | 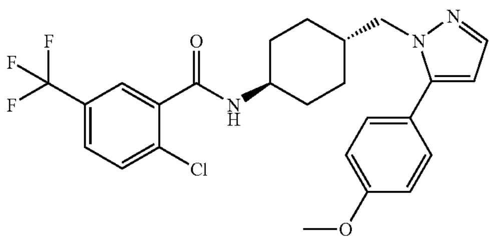 | Trans-2-Chloro-N-{4-[5-(4-methoxy-phenyl)-pyrazol-1-ylmethyl]-cyclohexyl}-5-trifluoromethyl-benzamide | 492.32 |
| 7.10 | 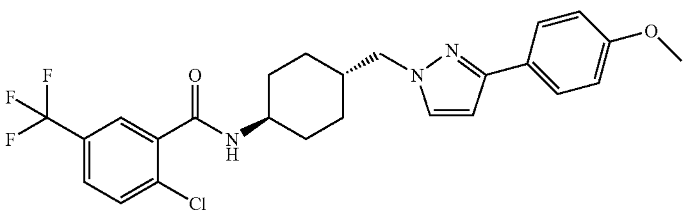 | Trans-2-Chloro-N-{4-[3-(4-methoxy-phenyl)-pyrazol-1-ylmethyl]-cyclohexyl}-5-trifluoromethyl-benzamide | 492.34 |

Example 8

Trans-2-Chloro-N-{4-[(5-cyclopropyl-2H-pyrazol-3-ylamino)-methyl]-cyclohexyl}-5-trifluoromethyl-benzamide

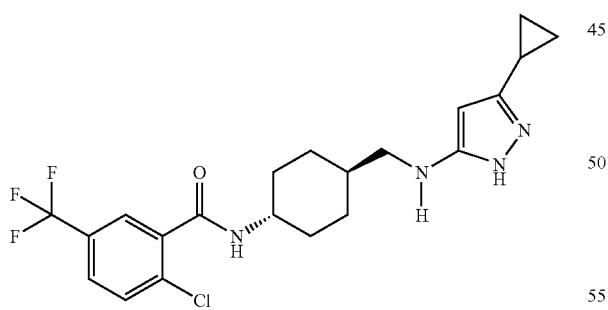

To a 25 mL round-bottomed flask is added trans-2-chloro-N-(4-formyl-cyclohexyl)-5-trifluoromethyl-benzamide (100 mg, 0.300 mmol) and 3-cyclopropyl-1H-pyrazol-5-amine (24.60 mg, 0.200 mmol) in DCM (8 mL) to give a colorless solution. Acetic acid (0.046 mL, 0.799 mmol) and sodium triacetoxyborohydride (127 mg, 0.599 mmol) are added and the mixture is stirred at room temp for 90 minutes.

1M sodium hydroxide solution (2 mL) is added and the mixture is stirred at room temp for 10 minutes. The mixture is passed through a phase separator and evaporated to give a colourless oil. The crude mixture is re-dissolved in the minimum amount of DCM, applied to a prepacked 12 g silica gel column and eluted with 0-100% EtOAc/isohexane gradient elution over 6 minutes, then 100% EtOAc for 8 minutes. Pure product is recovered as a colourless oil. The oil is dissolved in the minimum amount of DCM and triturated/sonicated With 9:1 isohexane/EtOAc to give a colourless solid, 31 mg, [MH+ 441.36].

Example 9

Trans-2-Chloro-N-{4-[(3-fluoro-phenylamino)-methyl]-cyclohexyl}-5-trifluoromethyl-benzamide

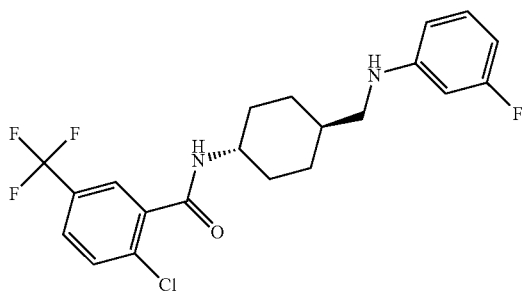

To a 50 mL round-bottomed flask containing trans-2-chloro-N-(4-formyl-cyclohexyl)-5-trifluoromethyl-benzamide (Ex. 1 step 3) (1.0 g, 3.0 mmol) and 3-fluoroaniline (0.29 mL, 3.0 mmol) in dry DCM (25 mL) is added sodium triacetoxyborohydride (953 mg, 4.49 mmol) in three portions over 1-2 minutes. The suspension is stirred at RT for 1 hour. 1N sodium hydroxide (25 mL) is added and the mixture is stirred at RT for 20 min. The mixture is then diluted with DCM (50 mL) and the DCM layer separated and washed with 1M HCl (25 mL) and brine (15 mL), dried (MgSO$_4$), filtered and evaporated to give a colourless solid. The crude product is redissolved in DCM, absorbed directly onto silica gel and columned on silica gel using a 50 g pre-packed column and eluted with 30% EtOAc/isohexane. Product is isolated as a colourless oil which is triturated with diether ether-isohexane to afford the title compound as colourless crystals. [MH+ 429.24].

Example 10

Trans-2-chloro-N-(4-((5-methylpyridin-3-ylamino) methyl)-cyclohexyl)-5-(trifluoromethyl)benzamide

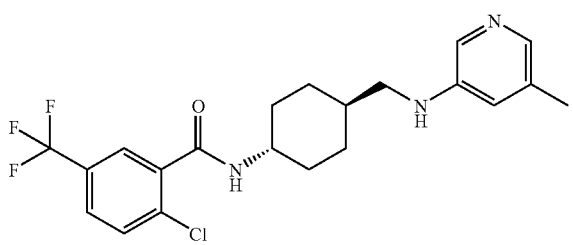

To a 50 mL round-bottomed flask containing trans-2-chloro-N-(4-formyl-cyclohexyl)-5-trifluoromethyl-benzamide (Ex. 1 step 3) (100 mg, 0.3 mmol) and 3-amino-5-methylpyridine (36 mg, 0.3 mmol) in dry DCM (5 mL) is added sodium triacetoxyborohydride (106 mg, 0.45 mmol) in one portion. The suspension is stirred at RT for 4 hours. The mixture is partitioned between DCM and saturated sodium bicarbonate, passed through a phase separator to recover the DCM layer and evaporated to give a colourless solid. The crude product is redissolved in DCM, absorbed directly onto silica gel and columned on silica gel using a 12 g pre-packed column and isohexane/EtOAc gradient elution (0% to 100% EtOAc). Product-containing fractions are combined and evaporated and the product is isolated as a colourless solid after trituration with 20% EtOAc/isohexane, 55 mg, [MH+ 426.40].

Example 11

Trans-2,5-Dichloro-N-(4-{[methyl-(5-phenyl-2H-pyrazol-3-ylmethyl)amino]-methyl}-cyclohexyl)-benzamide

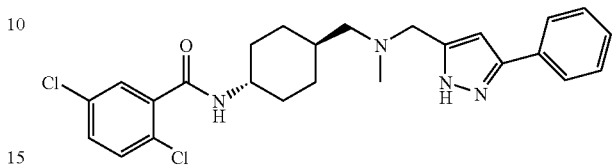

To a 25 mL round-bottomed flask is added trans-2,5-dichloro-N-(4-formylcyclohexyl)benzamide (200 mg, 0.666 mmol) and N-methyl-1-(3-phenyl-1H-pyrazol-5-yl)methanamine oxalate (277 mg, 0.999 mmol) in DCM (15 mL) to give a colorless solution. Acetic acid (0.153 mL, 2.67 mmol) and sodium triacetoxyborohydride (424 mg, 1.999 mmol) are added and the mixture stirred at room temp for 90 minutes. 1M sodium hydroxide solution (4 mL) is added and the mixture is stirred at room temp for 10 minutes. The mixture is passed through a phase separator and evaporated to give a colourless oil. The crude mixture is re-dissolved in the minimum amount of DCM and applied to a pre-packed 12 g silica gel column and eluted with 0-100% EtOAc/isohexane over 6 minutes then 100% EtOAc for 8 minutes. Pure product is recovered as a colourless oil. The oil is dissolved in the minimum amount of DCM and triturated/sonicated with 9:1 isohexane/EtOAc to give a colourless solid 124 mg, [MH+ 471.30].

Example 12

Trans-3-Chloro-N-(4-phenylaminomethyl-cyclohexyl)-benzamide

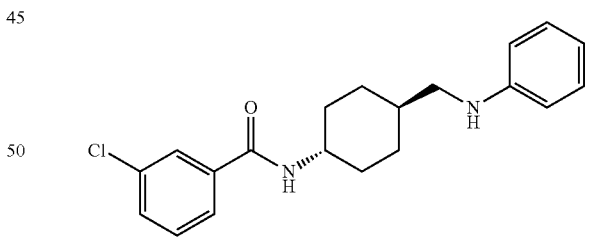

To a 7 mL vial equipped with magnetic stirrer bar is added (4-Amino-cyclohexylmethyl)-phenyl-amine (41 mg, 0.2 mmol), 3-chlorobenzoyl chloride (20 mg, 0.16 mmol) and DCM (2 mL) followed by trethylamine (42 µL, 0.3 mmol). The mixture is stirred at room temperature under nitrogen atmosphere for 3 hours. The mixture was then evaporated to dryness and purified directly by preparative HPLC, [MH+ 343.19].

The compounds of the following tabulated Examples (Table 7), or tautomers thereof, are prepared by a similar method to that of Example 12 using the appropriate acid chloride.

TABLE 7

| Ex. | Structure | Name | [M + H]+ |
|---|---|---|---|
| 12.1 | 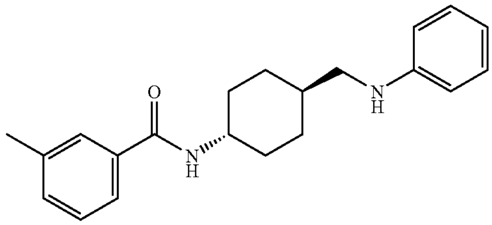 | Trans-3-Methyl-N-(4-phenylaminomethyl-cyclohexyl)-benzamide | 323.33 |
| 12.2 | 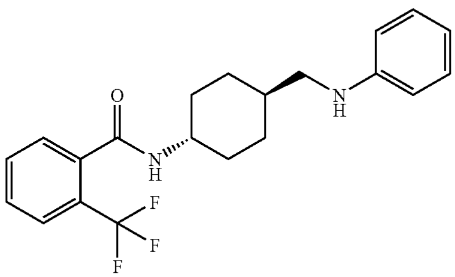 | Trans-N-(4-Phenylaminomethyl-cyclohexyl)-2-trifluoromethyl-benzamide | 377.2 |
| 12.3 | 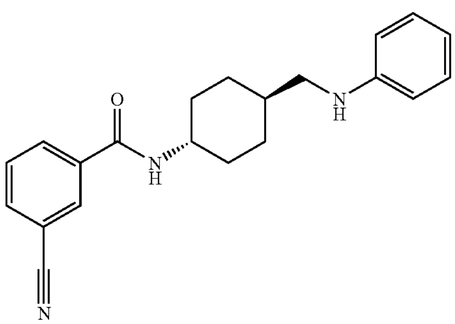 | Trans-3-Cyano-N-(4-phenylaminomethyl-cyclohexyl)-benzamide | 334.24 |
| 12.4 | 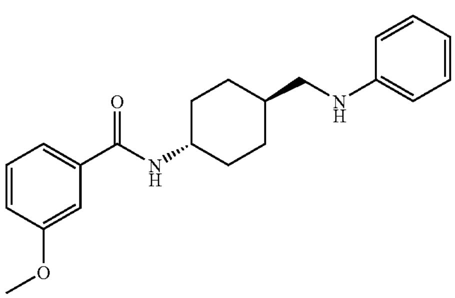 | Trans-3-Methoxy-N-(4-phenylaminomethyl-cyclohexyl)-benzamide | 339.23 |
| 12.5 | 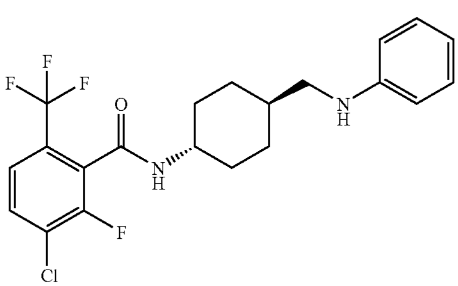 | Trans-3-Chloro-2-fluoro-N-(4-phenylaminomethyl-cyclohexyl)-6-trifluoromethyl-benzamide | 429.27 |

Example 13

Trans-N-[4-(Quinolin-5-ylaminomethyl)-cyclohexyl]-3-trifluoromethyl-benzamide

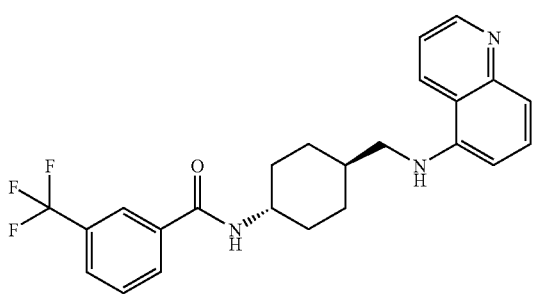

To a solution of trans-N-(4-formyl-cyclohexyl)-3-trifluoromethyl-benzamide (prepared analogously to trans-2-chloro-N-(4-formyl-cyclohexyl)-5-trifluoromethyl-benzamide (Ex. 1 step 3) from the appropriate starting compounds) (100 mg, 0.33 mmol) and 5-aminoquinoline (48 mg, 0.33 mmol) in dry 1,2-dichloroethane (2 mL) in a 2-5 mL capacity microwave tube, is added acetic acid (0.06 mL, 1.0 mmol) and sodium triacetoxyborohydride (178 mg, 0.84 mmol). The tube is sealed with a septum and the mixture is heated at 140° C. for 10 minutes in a Biotage Initiator microwave. After cooling to room temperature, the solvents are removed under reduced pressure and the residue is purified by chromatography on a pre-packed reverse phase column. [MH+428.45].

The compounds of the following tabulated Examples (Table 8) are prepared by a similar method to that of Example 13 using the appropriate amine.

TABLE 8

| Ex. | Structure | Name | [M + H]+ |
|---|---|---|---|
| 13.1 | 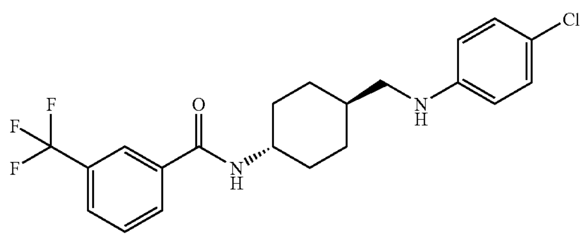 | Trans-N-{4-[(4-Chloro-phenylamino)-methyl]-cyclohexyl}-3-trifluoromethyl-benzamide | 411.36 |
| 13.2 | 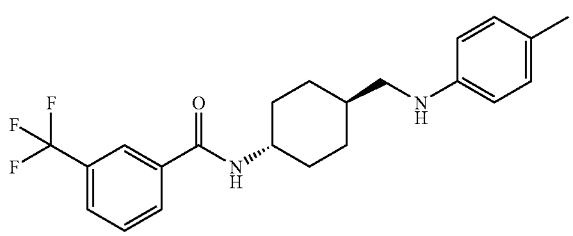 | Trans-N-[4-(p-Tolylamino-methyl)-cyclohexyl]-3-trifluoromethyl-benzamide | 391.37 |
| 13.3 | 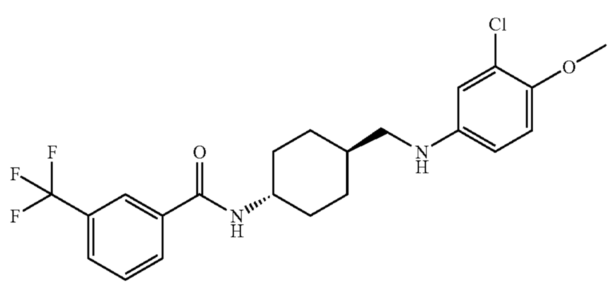 | Trans-N-{4-[(3-Chloro-4-methoxy-phenylamino)-methyl]-cyclohexyl}-3-trifluoromethyl-benzamide | 441.38 |
| 13.4 | 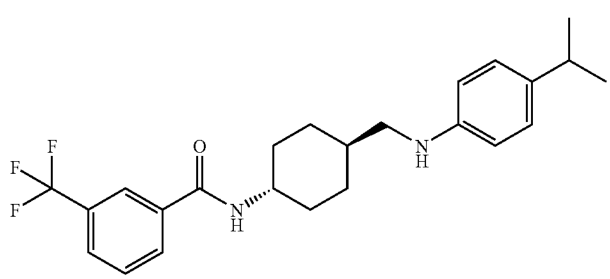 | Trans-N-{4-[(4-Isopropyl-phenylamino)-methyl]-cyclohexyl}-3-trifluoromethyl-benzamide | 419.48 |

TABLE 8-continued

| Ex. | Structure | Name | [M + H]+ |
|---|---|---|---|
| 13.5 | 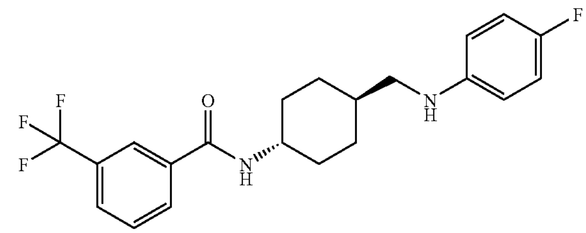 | Trans-N-{4-[(4-Fluoro-phenylamino)-methyl]-cyclohexyl}-3-trifluoromethyl-benzamide | 395.37 |
| 13.6 | 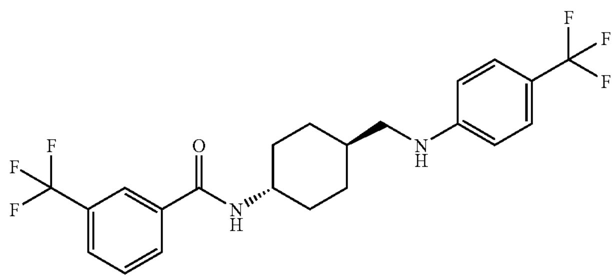 | Trans-3-Trifluoromethyl-N-{4-[(4-trifluoromethyl-phenylamino)-methyl]-cyclohexyl}-benzamide | 445.37 |
| 13.7 | 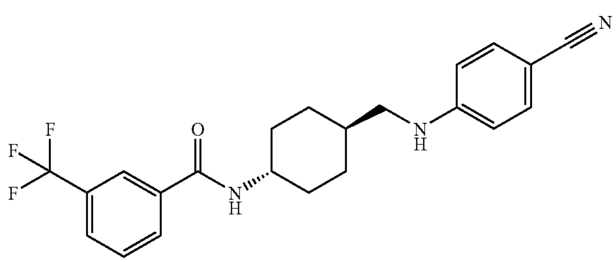 | Trans-N-{4-[(4-Cyano-phenylamino)-methyl]-cyclohexyl}-3-trifluoromethyl-benzamide | 402.35 |
| 13.8 | 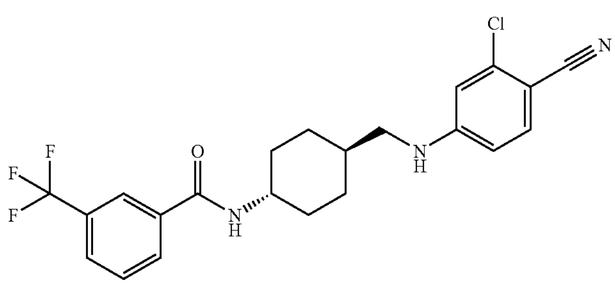 | Trans-N-{4-[(3-Chloro-4-cyano-phenylamino)-methyl]-cyclohexyl}-3-trifluoromethyl-benzamide | 477.42 (MH + MeCN)+ |
| 13.9 | 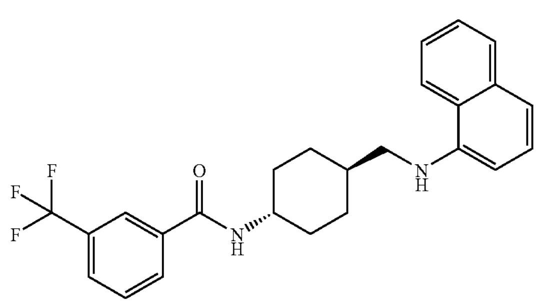 | Trans-N-[4-(Naphthalen-1-ylaminomethyl)-cyclohexyl]-3-trifluoromethyl-benzamide | 427.44 |
| 13.10 | 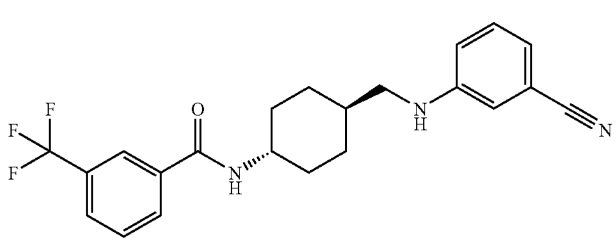 | Trans-N-{4-[(3-Cyano-phenylamino)-methyl]-cyclohexyl}-3-trifluoromethyl-benzamide | 402.37 |

TABLE 8-continued

| Ex. | Structure | Name | [M + H]+ |
|---|---|---|---|
| 13.11 | 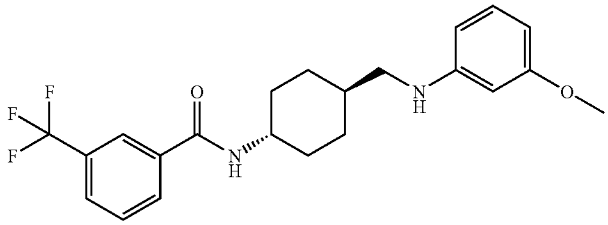 | Trans-N-{4-[(3-Methoxy-phenylamino)-methyl]-cyclohexyl}-3-trifluoromethyl-benzamide | 407.4 |
| 13.12 | 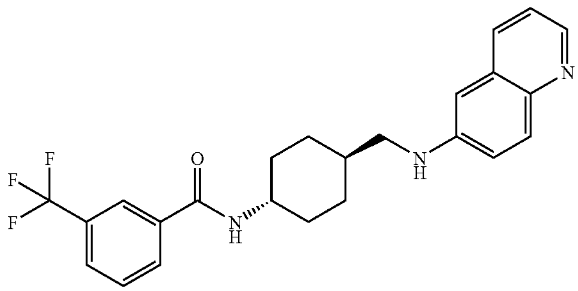 | Trans-N-[4-(Quinolin-6-ylaminomethyl)-cyclohexyl]-3-trifluoromethyl-benzamide | 428.45 |
| 13.13 | 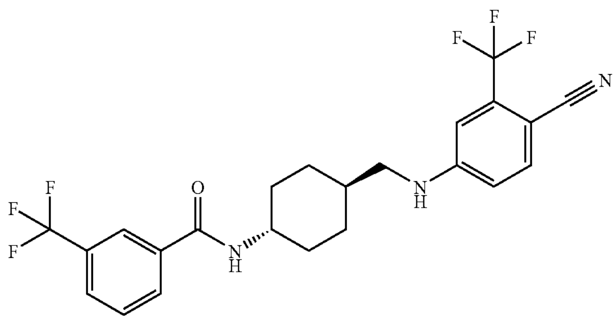 | Trans-N-{4-[(4-Cyano-3-trifluoromethyl phenylamino)-methyl]-cyclohexyl}-3-trifluoromethyl-benzamide | 511.33 (MH + MeCN)+ |
| 13.14 | 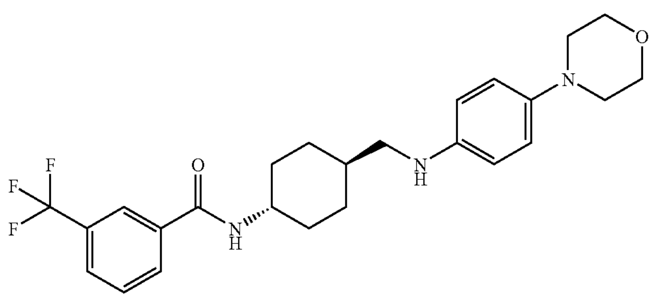 | Trans-N-{4-[(4-Morpholin-4-yl-phenylamino)-methyl]-cyclohexyl}-3-trifluoromethyl-benzamide | 462.42 |

Example 14

Cis-2-Chloro-N-(4-{[5-(4-fluoro-phenyl)-2H-pyrazol-3-ylamino]-methyl}-cyclohexyl)-5-trifluoromethyl-benzamide

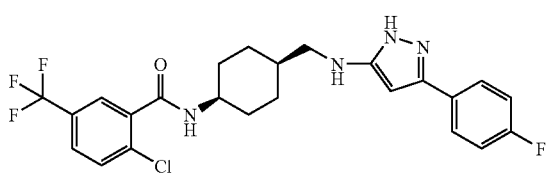

Step 1

Cis-2-chloro-N-(4-(hydroxymethyl)cyclohexyl)-5-(trifluoromethyl)-benzamide

To a solution of cis-(4-Amino-cyclohexyl)-methanol (Tetrahedron Lett., 1970, 11, 4285-4288) (0.75 g, 5.80 mmol) in THF (10 ml) is added water (1.8 mL), triethylamine (2.023 mL, 14.51 mmol) and 2-chloro-5-(trifluoromethyl)benzoyl chloride (1.411 g, 5.80 mmol). The RM is stirred at RT for 1 hour. The reaction mixture is partitioned between EtOAc and water. The organic phase is washed successively with water, saturated sodium bicarbarbonate and saturated brine, dried over MgSO₄, filtered and the solvent removed in vacuo. Purification by chromatography on a pre-packed silica gel column using 0-100% EtOAc in isohexane gradient elution gave the desired product as a colourless solid.

Step 2

Cis-2-Chloro-N-(4-formyl-cyclohexyl)-5-trifluoromethyl-benzamide

To a solution of Cis-2-chloro-N-(-4-(hydroxymethyl)cyclohexyl)-5-(trifluoromethyl)-benzamide (1 g, 2.98 mmol) in DCM (18 mL) is added DIPEA (2.081 mL, 11.91 mmol). The reaction mixture is cooled to 0° C. and pyridine-sulfur trioxide (1.896 g, 11.91 mmol) in DMSO (6 mL) is added. The reaction mixture is stirred at this temperature for 30 mins. The reaction mixture is partitioned between water and DCM and passed through a phase separator. The DCM layer was collected and concentrated under reduced pressure to give a colourless oil. Purification by chromatography on a pre-packed silica gel column using 0-100% EtOAc in isohexane gradient elution gave the desired product as a colourless solid.

Step 3

Cis-2-chloro-N-(4-((3-(4-fluorophenyl)-1H-pyrazol-5-ylamino)methyl)cyclohexyl)-5-(trifluoromethyl)benzamide To a solution of Cis-2-Chloro-N-(4-formyl-cyclohexyl)-5-trifluoromethyl-benzamide (100 mg, 0.300 mmol) in DCM (3 mL) is added 3-(4-fluorophenyl)-1H-pyrazol-5-amine (58.4 mg, 0.330 mmol) to give a pale orange solution. This is stirred for 10 mins at room temperature before sodium triacetoxyborohydride (102 mg, 0.479 mmol) is added. The reaction mixture is stirred at room temperature for 1 hour. The reaction mixture is quenched by the addition of saturated sodium bicarbonate. The DCM layer is separated and further washed with water. The aqueous extracts are combined and re-extracted with DCM. The combined organic extracts are then dried over MgSO4, filtered and concentrated under vacuum. Purification by chromatography on a pre-packed 12 g silica gel column using 0-100% EtOAc in isohexane (gradient elution) gave the desired product as a colourless solid. [MH+ 495.29].

Example 14.1

Cis-2-chloro-N-((1s,4s)-4-((4-methylpyridin-3-ylamino)methyl)cyclohexyl)-5-(trifluoromethyl)benzamide

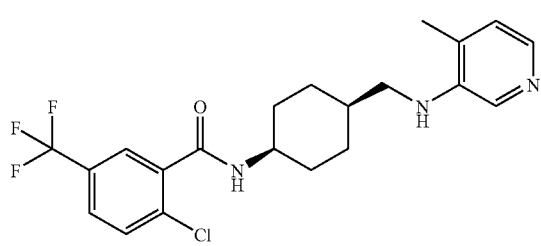

The title compound is prepared analogously to Example 14 using the appropriate amine in step 3; [MH+426.39].

Example 15

Trans-2-Chloro-N-[4-(1RS-phenylamino-ethyl)-cyclohexyl]-5-trifluoromethyl-benzamide

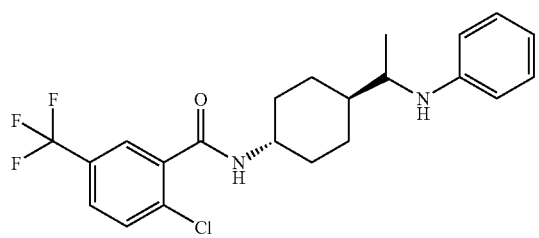

Step 1

Trans-2-chloro-N-(-4-((S)-1-hydroxyethyl)-cyclohexyl)-5-(trifluoromethyl)benzamide To a solution of trans-2-chloro-N-(4-formylcyclohexyl)-5-(trifluoromethyl)-benzamide (1.00 g, 3.00 mmol) in THF (50 mL) is added methylmagnesium bromide 2.5 mL of a 3M solution in THF, 7.49 mmol,) and the reaction mixture is stirred at room temperature for 1 hour. The reaction mixture is quenched with water and partitioned between EtOAc and water. The organic phase is washed with water and brine, dried over MgSO4, filtered and the solvent is removed in vacuo. The mixture is used directly in step 2 without further purification.

Step 2

Trans-N-(4-acetylcyclohexyl)-2-chloro-5-(trifluoromethyl)benzamide

To a solution of Trans-2-chloro-N-(-4-((S)-1-hydroxyethyl)-cyclohexyl)-5-(trifluoromethyl)benzamide (1.00 g, 2.86 mmol) in DCM (20 mL) is added DIPEA (1.48 g, 11.4 mmol) of DIPEA. The reaction mixture is cooled to 0° C. and then a solution of sulfur trioxide-pyridine complex (1.82 g, 11.4 mmol) in DMSO (5 mL) is added. The reaction mixture is stirred at 0° C. for 10 min and then partitioned between DCM and water. The organic phase was washed with water and brine, dried over MgSO4, filtered and the solvent was removed in vacuo. Purification by chromatography on a pre-packed 40 g silica gel column using 0-100% EtOAc in isohexane (gradient elution) gave the desired product as a colourless solid.

Step 3

Trans-2-chloro-N-(-4-(1-(phenylamino)ethyl)-cyclohexyl)-5-(trifluoromethyl)benzamide To a solution of Trans-N-(4-acetylcyclohexyl)-2-chloro-5-(trifluoromethyl)benzamide (200 mg, 0.57 mmol) and aniline (54 mg, 0.57 mmol) in DCM (10 mL) is added DMF (0.1 mL) followed by trichlorosilane (78 mg, 0.57 mmol). After stirring at room temperature for 1 hour, further trichlorosilane (5×78 mg, 5×0.57 mmol) is added at 1 hour intervals

Example 16

2-Chloro-N-(2RS-methyl-4-phenylaminomethyl-cyclohexyl)-5-trifluoromethyl-benzamide

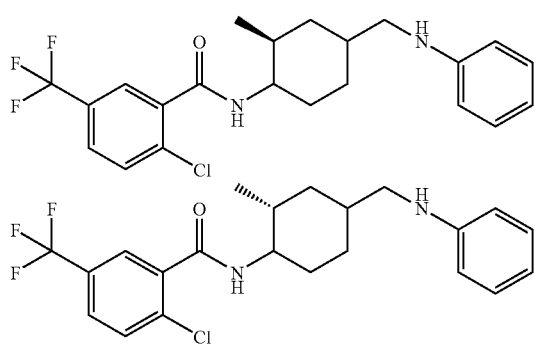

Step 1

3-Methyl-4-oxo-cyclohexanecarboxylic acid ethyl ester

Ethyl 4-oxocyclohexane carboxylate (10.0 g, 58.8 mmol) and pyrrolidine (5.87 g, 82.7 mmol) in toluene (100 mL) and molecular sieves (40 g of 4 Å sieves) are heated to reflux overnight using Dean Stark apparatus. The mixture is filtered and the excess pyrrolidine is removed in vacuo. The resulting mixture is diluted with toluene (50 mL) and treated with methyl iodide (8.96 g, 63.1 mmol). After heating at reflux for 15 hours, the mixture is allowed to cool to RT and silica (3 g) and water (30 mL) are added. The mixture is stirred at RT for 3 hours and partitioned between water and diethyl ether. The organic portion is separated and washed with water, brine, dried ($MgSO_4$) and concentrated in vacuo. Purification by chromatography on silica eluting with iso-hexane: EtOAc (19:1 increasing to 9:1) affords the title compound. $^1$H NMR (400 MHz, DMSO-$d_6$) δ 4.15 (2H, q), 2.89 (1H, m), 2.51 (1H, m), 2.38 (1H, m), 2.21 (3H, m), 1.89 (1H, m), 1.62 (1H, m), 1.22 (3H, t), 0.95 (3H, d).

Step 2

4-Benzylamino-3-methyl-cyclohexanecarboxylic acid ethyl ester

A mixture comprising 3-methyl-4-oxo-cyclohexanecarboxylic acid ethyl ester (1.00 g, 5.43 mmol) and benzylamine (0.58 g, 5.43 mmol) in DCE (50 mL) is treated with sodium triacetoxyborohydride (2.30 g, 10.9 mmol) and stirred at RT for 2 hours. The mixture is partitioned between DCM and water and the organic portion is separated, dried ($MgSO_4$) and concentrated in vacuo. Purification by chromatography on silica eluting with iso-hexane: EtOAc (4:1 increasing to 1:1) affords the title compound. $^1$H NMR (400 MHz, DMSO-$d_6$) δ 7.32 (4H, m), 7.20 (1H, m) 4.04 (2H, q), 3.72 (2H, m), 2.50-1.30 (9H, m), 1.19 (4H, m), 0.89 (3H, d).

Step 3

(4Benzylamino-3-methyl-cyclohexyl)-methanol

A cooled (0° C.) mixture comprising 4-benzylamino-3-methyl-cyclohexanecarboxylic acid ethyl ester (0.90 g, 3.27 mmol) in THF (50 mL) is treated with $LiAlH_4$ (4.09 mL, 8.08 mmol of a 2M solution in THF) and the reaction mixture is stirred at RT for 2 hours. The reaction is quenched with water (5 mL), NaOH (5 mL) followed by water (20 mL). The resulting precipitate is removed by filtration and washed with EtOAc. The organic phase is washed with water, brine, dried ($MgSO_4$) and concentrated in vacuo to afford the title compound which is used in the next step without further purification. $^1$H NMR (400 MHz, DMSO-$d_6$) δ 7.30 (4H, m), 7.19 (1H, m) 4.31 (1H, t), 3.68 (2H, m), 3.29 (0.4H, t), 3.15 (1.6H, t), 2.45 (1H, m), 2.18 (0.2H, m), 2.06 (0.8H, m), 1.69 (2H, m), 1.52 (3H, m), 1.27 (2H, m), 1.03 (1H, m), 0.90 (0.6H, d), 0.88 (2.4H, d), 0.80 (1H, m).

Step 4

Toluene-4-sulfonic acid 4-benzylamino-3-methyl-cyclohexylmethyl ester (4-Benzylamino-3-methyl-cyclohexyl)-methanol (0.1 g, 3.00 mmol) in DCM (30 mL) and pyridine (3 mL) is treated with TsCl (0.86 g, 4.50 mmol) and the resulting mixture is stirred at RT overnight. The reaction mixture is partitioned between DCM and water and the organic portion is separated, dried ($MgSO_4$) and concentrated in vacuo. Purification by chromatography on silica eluting with iso-hexane:EtOAc (1:2 increasing to 1:4) affords the title compound. $^1$H NMR (400 MHz, DMSO-$d_6$) δ 7.78 (2H, d), 7.50 (2H, d), 7.30 (4H, m), 7.20 (1H, m), 3.80 (2H, d), 3.63 (2H, q), 2.41 (4H, m), 2.01 (1H, m), 1.72 (2H, m), 1.58 (1H, m), 1.49 (2H, m), 1.20 (1H, m), 1.02 (1H, m), 0.85 (1H, m), 0.81 (3H, d).

Step 5

(4-Benzylamino-3-methyl-cyclohexylmethyl)-phenyl-amine

A mixture comprising toluene-4-sulfonic acid 4-benzylamino-3-methyl-cyclohexylmethyl ester (350 mg, 0.90 mmol), aniline (126, mg, 1.35 mmol) and potassium carbonate (250 mg, 1.80 mmol) in MeCN (1 mL) is heated using microwave radiation at 180° C. for 1 hour. The reaction mixture is partitioned between DCM and water and passed through a phase separator. The solvent is removed in vacuo and purification of the crude residue by chromatography on silica eluting with iso-hexane: EtOAc (25:1 increasing to 10:1) affords the title compound. [MH+ 309.34].

Step 6

(4-Amino-3-methyl-cyclohexylmethyl)-phenyl-amine (4-Benzylamino-3-methyl-cyclohexylmethyl)-phenyl-amine (160 mg, 0.52 mmol) and ammonium formate (164 mg, 2.60 mmol) in EtOH (5 mL) is treated with 10% Pd/C (30 mg) and heated at reflux for 2 hours. The Pd/C is removed by

131 filtration and washed with MeOH. The filtrate is concentrated in vacuo to afford the title compound which is used without further purification.

Step 7

2-Chloro-N-(2-methyl-4-phenylaminomethyl-cyclohexyl)-5-trifluoromethyl-benzamide (4-Amino-3-methyl-cyclohexylmethyl)-phenyl-amine (113 mg, 0.52 mmol) in dry THF (5 mL) and TEA (105 mg, 1.04 mmol) is treated with 2-chloro-5-(trifluoromethyl)benzoyl chloride (139 mg, 0.57 mmol). After stirring at RT for 2 hours, the solvent is removed in vacuo and the residue is partitioned between water and DCM. The mixture is passed through a phase separator and the organic portion is concentrated in vacuo. Purification of the crude residue by chromatography on silica eluting with iso-hexane: EtOAc (9:1 increasing to 2:1) affords the title compound. $^1$H NMR (400 MHz, DMSO-$d_6$) δ 8.47 (1H, d), 7.82 (1H, d), 7.73 (2H, m), 7.07 (2H, t), 6.56 (2H, d), 6.49 (1H, t), 5.55 (1H, m), 3.93 (1H, m), 2.86 (2H, m), 2.23 (1H, m), 1.88 (1H, m), 1.78 (1H, m), 1.70 (1H, m), 1.59 (2H, m), 1.31 (1H, m), 1.11 (1H, m), 0.92 (3H,d).

Step 8

2-Chloro-N-2-methyl-4-phenylaminomethyl-cyclohexyl)-5-trifluorome thyl-benzamide

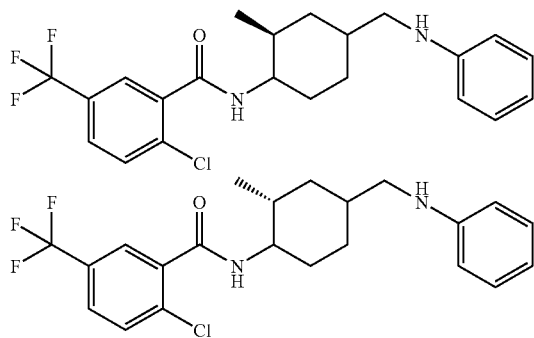

The racemate is separated into the component enantiomers by chiral chromatography on a Daicel Chiralpak AS column, 250 mm×20 mm (serial number AS00CJ-DD004)

The method used is hexane 95%, ethanol 5% (no modifier) at 20 ml/min for 23 minutes. UV trigger at 210 nm.

Example 17

Trans-5-Chloro-N-[4-(4-chloro-3,5-dimethyl-pyrazol-1-ylmethyl)-cyclohexyl]-2-methyl-nicotinamide

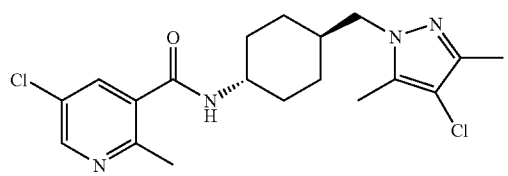

132

Step 1

5-chloro-2-methylnicotinoyl chloride

5-Chloro-2-methyl-nicotinic acid (4.15 g, 24.2 mmol) is placed in a flask with DCM (100 mL) and oxalyl chloride (3.68 g, 29 mmol). DMF (200 µL) is added and the reaction mixture is stirred at r.t. for 1 hour (gas evolution). The mixture is filtered and the solvent is removed in vacuo to afford the title product which is used in the next step without further purification.

Step 2

Trans-4-[(5-Chloro-2-methyl-pyridine-3-carbonyl)-amino]-cyclohexane carboxylic acid methyl ester Trans-4-Amino-cyclohexanecarboxylic acid methyl ester (2.14 g, 11.05 mmol) is suspended in THF (50 mL) and Et$_3$N (2.79 g, 27.6 mmol) and cooled to 0° C. 5-chloro-2-methylnicotinoyl chloride (step 1)(2.20 g, 11.05 mmol) is slowly added portionwise and the RM is stirred at r.t. for 2 hours. LCMS showed mainly product. The reaction mixture is partitioned between EtOAc and 1M HCl. The organic phase is washed with water and brine, dried over MgSO$_4$, filtered and the solvent is removed in vacuo to afford the title product which is used in the next step without further purification. $^1$H NMR (400 MHz, DMSO-$d_6$) δ 8.53 (1H, d), 7.42 (1H, 5), 7.80 (1H, d), 3.70 (1H, m), 3.60 (3H, s), 2.49 (3H, s), 2.29 (1H, m), 1.95 (4H, m), 1.42 (2H, m), 1.29 (2H, m); [MH]$^+$ 311.26.

Step 3

Trans-5-Chloro-N-(4-hydroxymethyl-cyclohexyl)-2-methyl-nicotinamide

Trans-4-[(5-Chloro-2-methyl-pyridine-3-carbonyl)-amino]-cyclohexanecarboxylic acid methyl ester (step 2) (2.20 g, 7.08 mmol) is placed in a flask with dry THF (100 mL). This is cooled to 0° C. and lithium aluminum hydride (0.537 g, 14.16 mmol) is added. The reaction mixture is stirred at r.t. for 2 hours and then quenched with water (0.5 mL), 2M NaOH (0.5 mL) and then water again (1.5 mL). The solids are filtered off through Celite® (filter material) and the filtrate is partitioned between EtOAc and water. The organic phase is washed with water and brine, dried over MgSO$_4$, filtered and the solvent is removed in vacuo to afford the title product which is used in the next step without further purification. $^1$H NMR (400 MHz, DMSO-$d_6$) δ 8.53 (1H, d), 8.38 *1H, d), 7.79 (1H, d), 4.40 (1H, t), 3.66 (1H, m), 3.21 (2H, t), 2.47 (3H, s), 1.92 (2H, m), 1.78 (2H, m), 1.31 (1H, m), 1.22 (2H, m), 0.98 (2H, m). [MH]$^+$ 283.30.

Step 4

Trans-Methanesulfonic acid 4-[(5-chloro-2-methyl-pyridine-3-carbonyl)-amino]-cyclohexylmethyl ester A solution of Trans-5-chloro-N-(hydroxymethyl-cyclohexyl)-2-methyl-nicotinamide (step 1) (100 mg, 0.354 mmol) and pyridine (3.6 ml) in dry DCM (3.5 ml) under nitrogen is cooled to approx. 0° C. using an ice-water bath. Methanesulfonyl chloride (0.030 ml, 0.389 mmol) is added dropwise. The reaction mixture is allowed to warm to room temp and stirred at this temp for 4 hours. The reaction is quenched by the addition of sat. NH$_4$Cl at room temp and then extracted with diethyl ether (3×20 ml). The Et₂O extracts are combined, washed with sat brine (20 mL), dried (MgSO₄), filtered and evaporated to give the title compound as a colourless solid.

MS m/z 361.2/363.2 [M+H]+. ¹H NMR (400 MHz, CDCl₃) δ 8.52 (1H, d), 7.65 (1H, d), 5.68 (1H, br d), 4.09 (2H, d), 3.96 (1H, m), 3.04 (3H, s), 2.65 (3H, s), 2.21 (2H, m), 1.96 (2H, m), 1.79 (1H, m), 1.27 (4H, m).

Step 5a

4-Chloro-3,5-dimethyl-1H-pyrazole 3,5-Dimethyl-1H-pyrazole (1.00 g, 10.4 mmol) is dissolved in chloroform (10 mL). N-Chlorosuccinimide (1.39 g, 10.4 mmol) is added and the reaction mixture is stirred at RT for 1 hour. The mixture is partitioned between chloroform and water. The organic phase is washed with water and brine, dried over MgSO₄, filtered and the solvent is removed in vacuo to afford the title product; ¹H NMR (400 MHz, DMSO-d₆) δ 12.5 (1H, broad), 2.12 (6H, s).

Step 5b

Trans-5-Chloro-N-[4-(4-chloro-3,5-dimethyl-pyrazol-1-ylmethyl)-cyclohexyl]-2-methyl-nicotinamide To a solution of 4-chloro-3,5-dimethyl-1H-pyrazole (step 5a)(37 mg, 0.283 mmol) in dry acetonitrile (4.5 mL) at room temp is added sodium hydride (14 mg of a 60% dispersion in mineral oil, 0.353 mmol). The mixture is stirred at room temp for 10 minutes before trans-methanesulfonic acid 4-[(5-chloro-2-methyl-pyridine-3-carbonyl)-amino]-cyclohexyl-methyl ester (step 4) (85 mg, 0.236 mmol) is added in one portion. The mixture is heated at 120° C. for 30 minutes using microwave radiation. After cooling to RT, the reaction mixture is diluted with water (10 mL) and extracted with EtOAc (3×10 mL). The EtOAc extracts are combined, washed with saturated brine (10 mL), dried (MgSO₄), filtered and evaporated to give a colourless foam. Purification by chromatography on silica gel using a 12 g pre-packed column eluting with 0-100% EtOAc affords the title compound as a colourless solid. MS m/z 395.3/397.3 [M+H]+. ¹H NMR (400 MHz, DMSO-d₆) δ 8.53 (1H, d), 8.39 (1H, d), 7.78 (1H, d), 3.83 (2H, d), 3.67 (1H, m), 2.47 (3H, s), 2.20 (3H, s), 2.09 (3H, s), 1.89 (2H, m), 1.73 (1H, m), 1.57 (2H, m), 1.16 (4H, m).

Example 18

Trans-5-Chloro-2-methyl-N-[4-(3,4,5-trimethyl-pyrazol-1-ylmethyl)-cyclohexyl]-nicotinamide

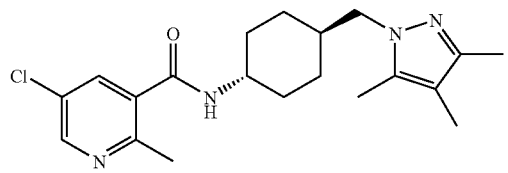

Step 1

Trans-Trifluoro-methanesulfonic acid 4-tert-butoxycarbonylamino-cyclohexylmethyl ester To a stirred solution of trans-tert-butyl 4-(hydroxymethyl)cyclohexylcarbamate (Ex 5.1 step 2) (1 g, 4.36 mmol) and dry pyridine (0.423 mL, 5.23 mmol) in dry DCM (45 mL) at 0° C. is added trifluoromethanesulfonic anhydride (0.81 mL, 4.8 mmol). The mixture is stirred at 0° C. for 1 hour and then allowed to warm to room temp. TLC analysis (isohexane: EtOAc, 1:2; stained with phosphomolybdic acid in EtOH) shows that the starting alcohol had been consumed and a new, less polar product had been formed. The reaction is quenched with saturated ammonium chloride solution (30 mL) and the DCM layer is separated using a phase separator, dried (MgSO4), filtered and evaporated to give the title compound as a pale yellow solid. This is used in the next step without further purification; ¹H NMR (400 MHz, CDCl₃) δ 4.40 (1H, m), 4.35 (2H, d), 3.41 (1H, m), 2.12 (2H, m), 1.89 (2H, m), 1.80 (1H, m), 1.46 (9H, s), 1.16 (4H, m).

Step 2

Trans-[4-(3,4,5-Trimethyl-pyrazol-1-ylmethyl)-cyclohexyl]-carbamic acid tert-butyl ester To a stirred solution of 3,4,5-trimethyl-1H-pyrazole (84 mg, 0.761 mmol) in dry acetonitrile (4 mL) at room temp is added sodium hydride (33 mg of a 60% dispersion on mineral oil, 0.83 mmol). The mixture is stirred at room temp for 10 minutes and then treated with a solution of trans-trifluoromethanesulfonic acid 4-tert-butoxycarbonylamino-cyclohexylmethyl ester (step 1) (250 mg, 0.692 mmol) in dry acetonitrile (3 mL). The reaction mixture is stirred at room temp for 17 hours. The mixture is diluted with water (20 mL) and extracted with EtOAc (3×10 mL). The EtOAc extracts are combined, washed with brine (20 mL), dried (MgSO4), filtered and evaporated to give the title compound as a colourless oil. This is used in the next step without further purification; MS m/z 322.4 [M+H]+.

Step 3

Trans-4-(3,4,5-Trimethyl-pyrazol-1-ylmethyl)-cyclohexylamine

To a stirred solution of trans-[4-(3,4,5-trimethyl-pyrazol-1-ylmethyl)-cyclohexyl]-carbamic acid tert-butyl ester (step 2)(215 mg, 0.669 mmol) in methanol (3 mL) at room temp is added a solution of 4M HCl in dioxane (3 mL). The mixture is stirred at room temp for 1 hour and then concentrated in vacuo. The resulting gum is dried under vacuum overnight to afford the title compound which is used without further purification. ¹H NMR (400 MHz, CDCl₃) δ 8.16 (3H, br s), 4.10 (2H, d), 2.90 (1H, m), 2.29 (3H, s), 2.27 (3H, s), 2.01-1.90 (5H, m including 3H, s), 1.83 (1H, s), 1.54 (2H, m), 1.30 (2H, m), 1.12 (2H, m). (NMR shows contamination with side products and solvents.)

Step 4

Trans-5-Chloro-2-methyl-N-[4-(3,4,5-trimethyl-pyrazol-1-ylmethyl)-cyclohexyl]-nicotinamide To a suspension of 5-chloro-2-methylnicotinoyl chloride (Ex. 17 step 1) and trans-4-(3,4,5-trimethyl-pyrazol-1-ylmethyl)-cyclohexylamine (step 3) (197 mg, ca. 0.67 mmol) in dry DCM (6.5 mL) is added triethylamine (0.37 mL, 2.68 mmol). The mixture is stirred at room temp for 45 minutes. Water (20 mL) is added and the mixture is extracted with EtOAc (3×20 mL). The EtOAc extracts are combined, washed with saturated brine (20 mL), dried (MgSO4), filtered and evaporated to give a pale yellow gum. The mixture is purified by chromatography on silica gel eluting with 0-100% EtOAc to give a colourless solid which was triturated with Et$_2$O to afford the title product. MS m/z 375.3/377.3 [M+H]$^+$ 1H NMR (400 MHz, DMSO-d$_6$) δ 8.54 (1H, d), 8.39 (1H, d), 7.79 (1H, d), 3.74 (2H, d), 3.67 (1H, m), 2.47 (3H, s), 2.10 (3H, s), 2.02 (3H, s), 1.88 (2H, m), 1.83 (3H, m), 1.70 (1H, m), 1.57 (2H, m), 1.14 (4H, m).

Examples 22.6 and 22.7

Trans-5-Chloro-2-methyl-N-[4-(3-methyl-5-trifluoromethyl-pyrazol-1-ylmethyl)-cyclohexyl]-nicotinamide (22.6) and Trans-5-Chloro-2-methyl-N-[4-(5-methyl-3-trifluoromethyl-pyrazol-1-ylmethyl)-cyclohexyl]-nicotinamide (22.7)

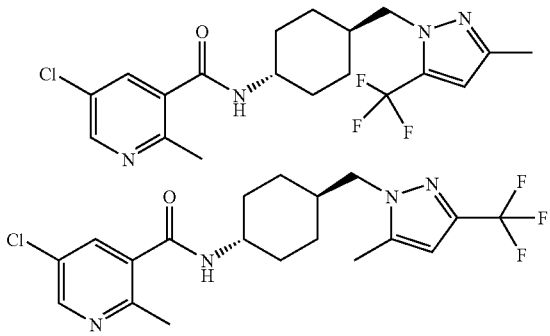

Step 1

Trans-tert-butyl-4-((3-methyl-5-(trifluoromethyl)-1H-pyrazol-1-yl)methyl)cyclohexylcarbamate and trans-tert-butyl-4-((5-methyl-3-(trifluoromethyl)-1H-pyrazol-1-yl)methyl)cyclohexylcarbamate To a stirred solution of 5-methyl-3-(trifluoromethyl)-1H-pyrazole (199 mg, 1.328 mmol) in dry acetonitrile (7 mL) at room temp is added sodium hydride (63 mg of a 60% dispersion on mineral oil, 2.66 mmol). The mixture is stirred at room temp for 10 mins after which the initial effervescence had subsided to leave a colourless solution. A solution of trans-trifluoro-methanesulfonic acid 4-tert-butoxycarbonylamino-cyclohexylmethyl ester (Ex. 18 step 1) (400 mg, 1.107 mmol) in dry acetonitrile (4 mL) is then added and the mixture is stirred at room temp for 17 hours. The crude mixture is diluted with water (20 mL) and extracted with EtOAc (3×15 mL). The EtOAc extracts are combined, washed with sat. brine (30 mL), dried (MgSO4), filtered and evaporated to give a mixture of the title compounds as a pale yellow gum. This is used in the next step without further purification.

Step 2

Trans-4-((3-methyl-5-(trifluoromethyl)-1H-pyrazol-1-yl)methyl)cyclohexanamine and Trans-4-((5-methyl-3-(trifluoromethyl)-1H-pyrazol-1-yl)methyl)cyclohexanamine A crude mixture of step 1 (0.8 g, approx 1.1 mmol) in dry methanol (4 mL) at RT is treated with a solution of 4M HCl in dioxane (4 mL) stirred at RT for 1 hour.

The solvents are evaporated under reduced pressure and the pale yellow gum obtained is placed under high vacuum for 18 hours to ensure complete removal of excess HCl. Due to polar nature of products, no purification is undertaken—crude product is used in the next step without further manipulation or characterization.

Step 3

Trans-5-Chloro-2-methyl-N-[4-(3-methyl-5-trifluoromethyl-pyrazol-1-ylmethyl)-cyclohexyl]-nicotinamide and Trans-5-Chloro-2-methyl-N-[4-(5-methyl-3-trifluoromethyl-pyrazol-1-ylmethyl)-cyclohexyl]-nicotinamide A crude mixture of step 1 (approx. 0.55 mmol of each compound) is suspended in dry DCM (25 mL) at RT. Triethylamine (0.38 mL, 2.75 mmol) is added followed by portion-wise addition of 5-chloro-2-methylnicotinoyl chloride (Ex. 17 step 1)(0.274 g, 1.21 mmol). The mixture is stirred at RT for 3 hours and then quenched with water (50 mL) and extracted with EtOAc (3×25 mL). The EtOAc extracts are combined, washed with sat. brine (25 mL), dried (MgSO$_4$), filtered and evaporated to give a pale yellow gum. The compounds are purified and separated by chromatography on silica gel using ISCO 40 g pre-packed silica column and 0-100% EtOAc in iso-hexane as eluant to afford the title compounds (see Table 12 for characterizing data).

The compounds of the following tabulated Examples (Table 9) are prepared by a similar method to that of Example 1 using the appropriate benzamide or pyrazole starting materials (prepared analogously to trans-2-chloro-N-(4-formyl-cyclohexyl)-5-trifluoromethyl-benzamide from trans-4-amino-cyclohexylcarboxylic acid methyl ester hydrochloride and the appropriate benzoly chloride) and the appropriate amine.

TABLE 9

| Ex. | Structure | IUPAC Name | [M + H]+ | NMR Data |
|---|---|---|---|---|
| 19.1 | 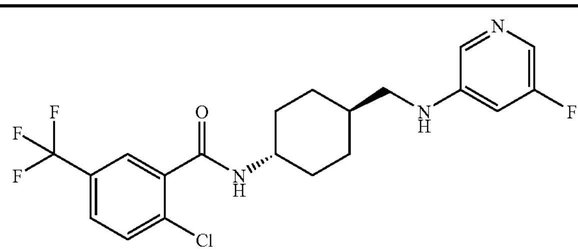 | Trans-2-chloro-N-(4-((5-fluoropyridin-3-ylamino)methyl)cyclohexyl)-5-(trifluoromethyl)benzamide | 430.36 | δH (400 MHz, DMSO); 8.50 (1 H, d), 7.82 (2 H, m) 7.73 (2 H, m), 7.53 (1 H, s), 6.73 (1 H, m), 6.31 (1 H, t), 3.70 (1 H, m), 2.91 (2 H, t), 1.95 (2 H, m), 1.86 (2 H, m), 1.50 (1 H, m), 1.25 (2 H, m), 1.09 (2 H, m). |

TABLE 9-continued

| Ex. | Structure | IUPAC Name | [M + H]+ | NMR Data |
|---|---|---|---|---|
| 19.2 | 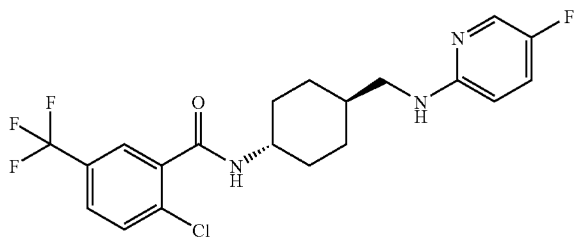 | Trans-2-chloro-N-(4-((5-fluoropyridin-2-ylamino)methyl)cyclohexyl)-5-(trifluoromethyl)benzamide | 430.37 | δH (400 MHz, DMSO) 8.48 (1 H, d), 7.90 (1 H, d), 7.81 (1 H, m), 7.73 (2 H, m), 7.31 (1 H, m), 6.53 (1 H, t), 6.49 (1 H, d of d), 3.70 (1 H, m), 3.08 (2 H, t), 1.92 (2 H, m), 1.81 (2 H, m), 1.50 (1 H, m), 1.22 (2 H, m), 1.04 (2 H, m). |
| 19.3 | 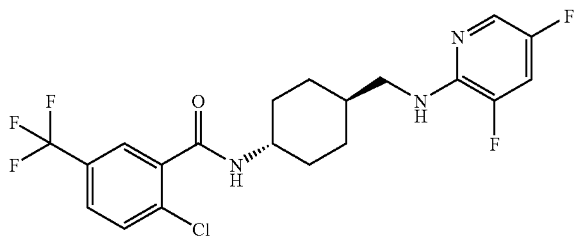 | Trans-2-chloro-N-(4-((3,5-difluoro pyridin-2-ylamino)methyl)cyclohexyl)-5-(trifluoromethyl)benzamide | 448.33 | δH (400 MHz, DMSO); 8.48 (1 H, d), 7.88 (1 H, d), 7.80 (1 H, m), 7.73 (2 H, m), 7.58 (1 H, m), 6.62 (1 H, t), 3.70 (1 H, m, 3.18 (2 H, t), 1.92 (2 H, m), 1.81 (2 H, m), 1.59 (1 H, m), 1.22 (2 H, m), 1.04 (2 H, m). |
| 19.4 | 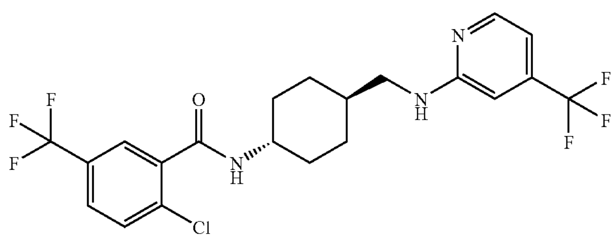 | Trans-2-chloro-5-(trifluoromethyl)-N-(4-((4-(trifluoromethyl)pyridin-2-ylamino)methyl)cyclohexyl)benzamide | 480.32 | δH (400 MHz, DMSO); 8.50 (1 H, d), 8.17 (1 H, d), 7.80 (1 H, m), 7.73 (2 H, m), 7.11 (1 H, t), 6.78 (1 H, s), 6.68 (1 H, d), 3.70 (1 H, m), 3.18 (2 H, t), 1.93 (2 H, m), 1.82 (2 H, m), 1.51 (1 H, m), 1.23 (2 H, m), 1.07 (2 H, m). |
| 19.5 | 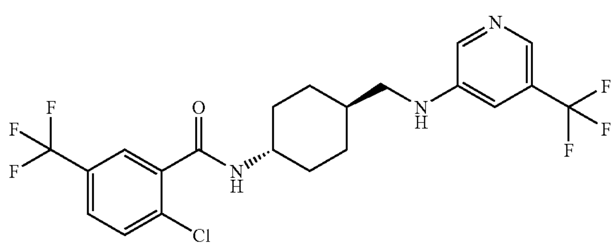 | Trans-2-chloro-5-(trifluoromethyl)-N-(4-((5-(trifluoromethyl)pyridin-3-ylamino)methyl)cyclohexyl)benzamide | 480.33 | δH (400 MHz, DMSO); 8.50 (1 H, d), 8.22 (1 H, s), 8.02 (1 H, s), 7.80 (1 H, m), 7.72 (2 H, m), 7.11 (1 H, s), 6.43 (1 H, t), 3.70 (1 H, m), 2.98 (2 H, t), 1.91 (4 H, m), 1.51 (1 H, m), 1.29 (2 H, m), 1.10 (2 H, m). |
| 19.6 | 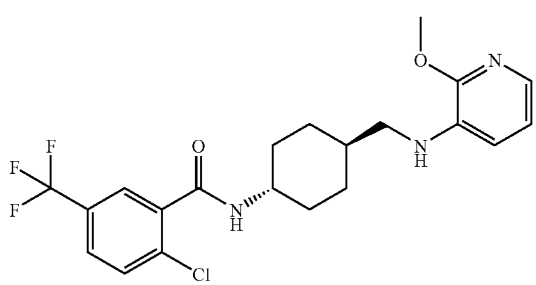 | Trans-2-chloro-N-(4-((2-methoxypyridin-3-ylamino)methyl)cyclohexyl)-5-(trifluoromethyl)benzamide | 442.42 | δH (400 MHz, DMSO); 8.50 (1 H, d), 7.80 (1 H, m), 7.72 (2 H, m), 7.31 (1 H, d), 6.75 (2 H, m), 5.10 (1 H, t), 3.87 (3 H, s), 3.70 (1 H, m), 2.92 (2 H, t), 1.94 (2 H, m), 1.82 (2 H, m), 1.57 (1 H, m), 1.22 (2 H, m), 1.04 (2 H, m). |
| 19.7 | 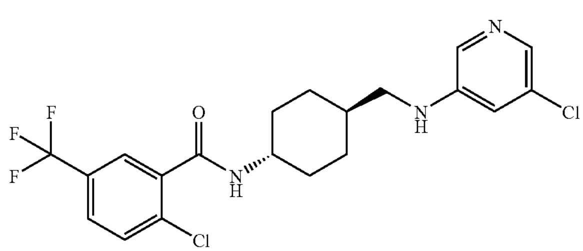 | Trans-2-chloro-N-(4-((5-chloropyridin-3-ylamino)methyl)cyclohexyl)-5-(trifluoromethyl)benzamide | 446.38 | δH (400 MHz, DMSO); 8.49 (1 H, d), 8.17 (1 H, d), 7.91 (1 H, d), 7.80 (1 H, m), 7.73 (2 H, m), 6.83 (1 H, m), 6.51 (2 H, m), 3.70 (1 H, m), 3.10 (2 H, t), 1.92 (2 H, m), 1.81 (2 H, m), 1.49 (1 H, m), 1.22 (2 H, m), 1.05 (2 H, m). |

| Ex. | Structure | IUPAC Name | [M + H]+ | NMR Data |
|---|---|---|---|---|
| 19.8 | 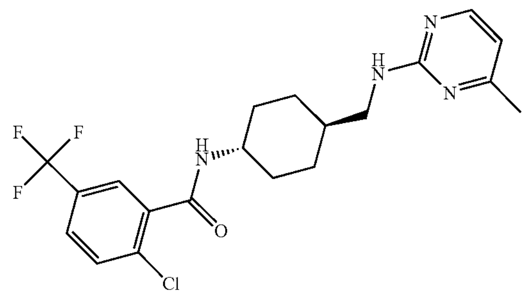 | Trans-2-chloro-N-(4-((4-methylpyrimidin-2-ylamino)methyl)cyclohexyl)-5-(trifluoromethyl)benzamide | 427.41 | δH (400 MHz, DMSO); 8.48 (1 H, d), 8.10 (1 H, d), 7.81 (1 H, m) 7.73 (2 H, m), 7.02 (1 H, m), 6.41 (1 H, d), 3.69 (1 H, m), 3.11 (2 H, t), 2.21 (3 H, s), 1.91 (2 H, m), 1.79 (2 H, m), 1.50 (1 H, m), 1.21 (2 H, m), 1.02 (2 H, m). |
| 19.9 | 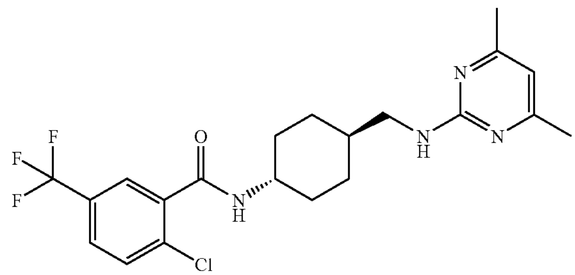 | Trans-2-chloro-N-(4-((4,6-dimethylpyrimidin-2-ylamino)methyl)cyclohexyl)-5-(trifluoromethyl)benzamide | 441.42 | δH (400 MHz, DMSO); 8.48 (1 H, d), 7.80 (1 H, m) 7.73 (2 H, m), 6.88 (1 H, m), 6.30 (1 H, s), 3.68 (1 H, m), 3.11 (2 H, t), 2.18 (6 H, s), 1.91 (2 H, m), 1.80 (2 H, m), 1.50 (1 H, m), 1.21 (2 H, m), 1.02 (2 H, m). |
| 19.10 | 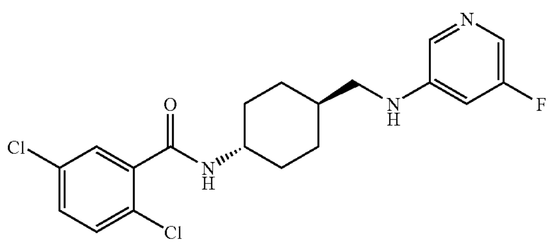 | Trans-2,5-dichloro-N-(4-((5-fluoropyridin-3-ylamino)methyl)cyclohexyl)benzamide | 396.27 | δH (400 MHz, DMSO); 8.40 (1 H, d), 7.82 (1 H, s) 7.63 (1 H, d), 7.50 (3 H, m), 6.72 (1 H, d), 6.31 (1 H, t), 3.70 (1 H, m), 2.901 (2 H, t), 1.89 (4 H, m), 1.50 (1 H, m), 1.22 (2 H, m), 1.08 (2 H, m). |
| 19.11 | 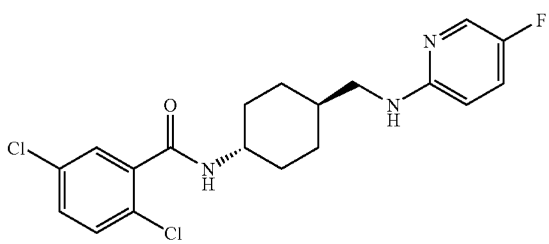 | Trans-2,5-dichloro-N-(4-((5-fluoropyridin-2-ylamino)methyl)cyclohexyl)benzamide | 396.25 | δH (400 MHz, DMSO); 8.39 (1 H, d), 7.90 (1 H, d) 7.50 (3 H, m), 7.30 (1 H, m), 6.50 (2 H, m), 3.68 (1 H, m), 3.04 (2 H, t), 1.90 (2 H, m), 1.80 (2 H, m), 1.50 (1 H, m), 1.21 (2 H, m), 1.02 (2 H, m). |
| 19.12 | 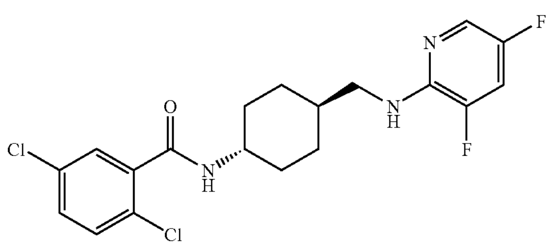 | Trans-2,5-dichloro-N-(4-((3,5-difluoropyridin-2-ylamino)methyl)cyclohexyl)benzamide | 414.31 | δH (400 MHz, DMSO); 8.39 (1 H, d), 7.88 (1 H, d) 7.51 (4 H, m), 6.61 (1 H, t), 3.66 (1 H, m), 3.18 (2 H, t), 1.90 (2 H, m), 1.79 (2 H, m), 1.57 (1 H, m), 1.20 (2 H, m), 1.01 (2 H, m). |
| 19.13 | 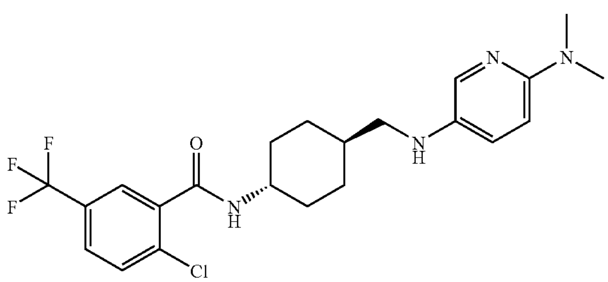 | Trans-2-chloro-N-(4-((6-(dimethylamino)pyridin-3-ylamino)methyl)cyclohexyl)-5-(trifluoromethyl)benzamide | 455.37 | δH (400 MHz, DMSO); 8.48 (1 H, d), 7.80 (1 H, m) 7.73 (2 H, m), 7.56 (1 H, s), 6.93 (1 H, m), 6.52 (1 H, d), 4.92 (1 H, m), 3.70 (1 H, m), 2.87 (6 H, s), 2.81 (2 H, t), 1.93 (2 H, m), 1.88 (2 H, m), 1.48 (1 H, m), 1.22 (2 H, m), 1.05 (2 H, m). |

TABLE 9-continued

| Ex. | Structure | IUPAC Name | [M + H]+ | NMR Data |
|---|---|---|---|---|
| 19.14 | 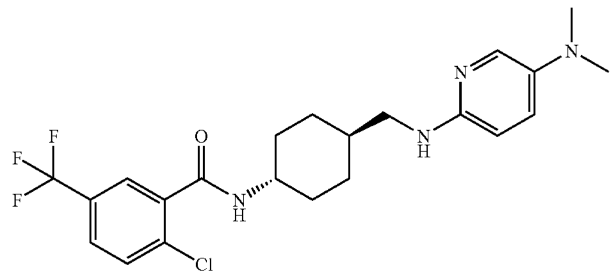 | Trans-2-chloro-N-(4-((5-(dimethylamino)pyridin-2-ylamino)methyl)cyclohexyl)-5-(trifluoromethyl)benzamide | 455.37 | δH (400 MHz, DMSO); 8.48 (1 H, d), 7.80 (1 H, m) 7.72 (2 H, m), 7.55 (1 H, d), 7.08 (1 H, d of d), 6.41 (1 H, d), 5.90 (1 H, t), 3.70 (1 H, m), 3.01 (2 H, t), 2.69 (6 H, s), 1.91 (2 H, m), 1.82 (2 H, m), 1.50 (1 H, m), 1.22 (2 H, m), 1.02 (2 H, m). |
| 19.15 | 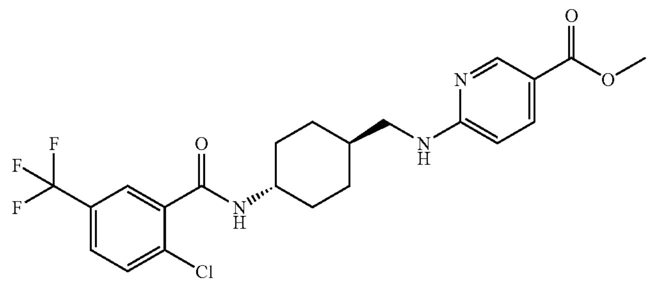 | 6-{[4-(2-Chloro-5-rifluoromethyl-benzoylamino)-cyclohexylmethyl]-amino}-nicotinic acid methyl ester | 470.36 | δH (400 MHz, DMSO); 8.55 (1 H, d), 8.48 (1 H, d), 7.80 (2 H, m) 7.74 (2 H, m), 7.45 (1 H, m), 6.50 (1 H, d), 3.77 (3 H, s), 3.70 (1 H, m), 3.20 (2 H, m), 1.93 (2 H, m), 1.82 (2 H, m), 1.52 (1 H, m), 1.22 (2 H, m), 1.07 (2 H, m). |
| 19.16 | 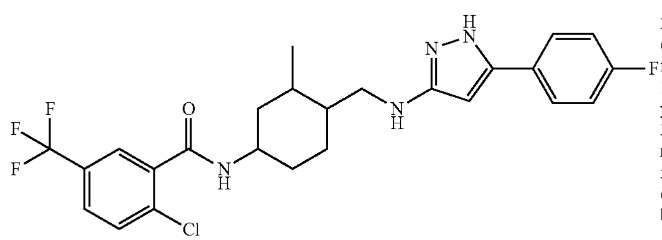 | 2-chloro-N-(4-((5-(4-Ffluorophenyl)-1H-pyrazol-3-ylamino)methyl)-3-methylcyclohexyl)-5-(trifluoromethyl)benazmide | 509.4 | NO NMR data |
| 19.17 | 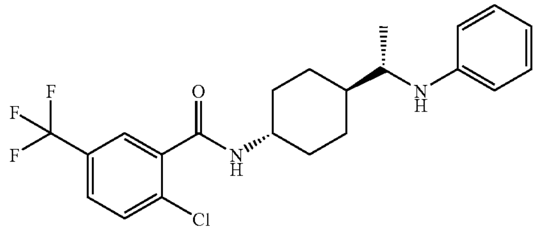 | Trans-2-chloro-N-(-(4-((S)-1-(phenylamino)ethyl)cyclohexyl)-5-(trifluoromethyl)benzamide | 425.46 | δH (400 MHz, DMSO); 8.48 (1 H, d), 7.80 (1 H, m), 7.73 (2 H, m), 7.02 (2 H, t), 6.53 (2 H, d), 6.43 (1 H, t), 5.29 (1 H, d), 3.68 (1 H, m), 3.30 (3 H, s), 3.25 (1 H, m), 1.91 (3 H, m), 1.78 (1 H, m), 1.40 (1 H, m), 1.20 (4 H, m), 1.03 (3 H, d). |
| 19.18 | 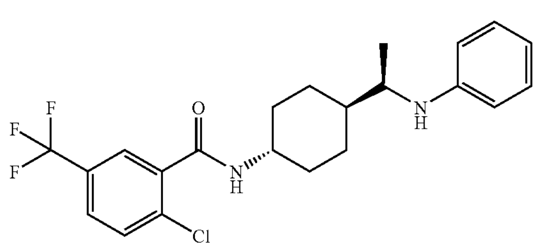 | Trans-2-chloro-N-(4-((R)-1-(phenylamino)ethyl)cyclohexyl)-5-(trifluoromethyl)benzamide | 425.47 | δH (400 MHz, DMSO); 8.48 (1 H, d), 7.80 (1 H, m), 7.73 (2 H, m), 7.02 (2 H, t), 6.53 (2 H, d), 6.43 (1 H, t), 5.29 (1 H, d), 3.68 (1 H, m), 3.30 (3 H, s), 3.25 (1 H, m), 1.91 (3 H, m), 1.78 (1 H, m), 1.40 (1 H, m), 1.20 (4 H, m), 1.03 (3 H, d). |

TABLE 9-continued

| Ex. | Structure | IUPAC Name | [M + H]+ | NMR Data |
|---|---|---|---|---|
| 19.19 | 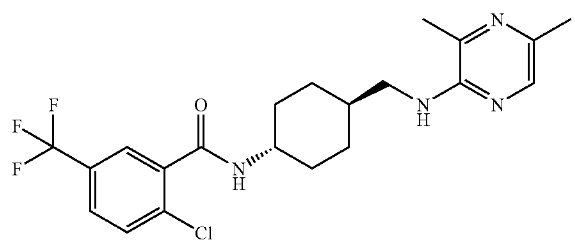 | Trans-2-chloro-N-(4-((3,5-dimethylpyrazin-2-ylamino)methyl)cyclohexyl)-5-(trifluoromethyl)benzamide | 441.41 | δH (400 MHz, DMSO); 8.47 (1 H, d, J 8.0 Hz), 7.82-7.68 (4 H, m), 6.18 (1 H, br t, J 5.5Hz), 3.70 (1 H, m), 3.16 (2 H, t, J 6.2 Hz), 2.27 (3 H, s), 2.21 (3 H, s), 1.92 (2 H, m), 1.82 (2 H, m), 1.59 (1 H, m), 1.23 (2 H, m), 1.06 (2 H, m). |
| 19.20 | 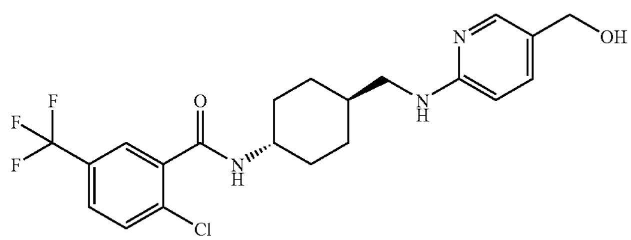 | Trans-2-chloro-N-(4-((5-(hydroxymethyl)pyridin-2-ylamino)methyl)cyclohexyl)-5-(trifluoromethyl)benzamide | 442.42 | δH (400 MHz, DMSO); 8.47 (1 H, d), 7.86 (1 H, d) 7.80 (1 H, m), 7.72 (2 H, m), 7.30 (1 H, d of d), 6.43 (2 H, d), 4.85 (1 H, t), 4.26 (2 H, d), 3.68 (1 H, m), 3.10 (2 H, t), 1.93 (2 H, m), 1.81 (2 H, m), 1.50 (1 H, m), 1.22 (2 H, m), 1.03 (2 H, m). |
| 19.21 | 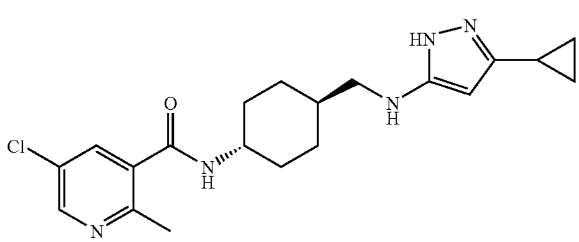 | Trans-5-chloro-N-(4-((3-cyclopropyl-1H-pyrazol-5-ylamino)methyl)cyclohexyl)-2-methyl-nicotinamide | 388.36 | δH (400 MHz, DMSO); 11.1 (1 H, br s), 8.52 (1 H, s), 8.38 91 H, d), 7.80 (1 H, s), 5.10 (1 H, br s), 3.68 (1 H, m), 2.80 (2 H, m), 2.45 (3 H, s), 1.90 (2 H, m), 1.80 (2 H, m), 1.72 (1 H, m), 1.45 (1 H, m), 1.22 (2 H, m), 1.00 (2 H, m), 0.80 (2 H, m), 0.55 (2 H, m) |
| 19.22 | 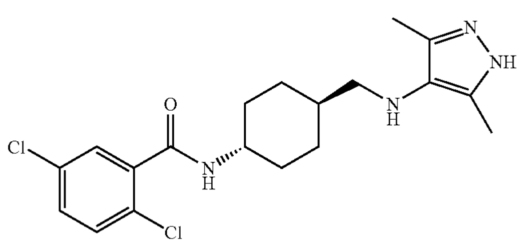 | Trans-2,5-dichloro-N-(4-((3,5-dimethyl-1H-pyrazol-4-ylamino)methyl)cyclohexyl)benzamide | 395.27 | δH (400 MHz, DMSO); 11.59 (1 H, br s), 8.38 (1 H, d, J 7.9 Hz), 7.88-7.38 (3 H, m), 3.66 (1 H, m), 3.17 (1 H, br s), 2.60 (2 H, d, J 6.4 Hz), 2.04 (6 H, s), 1.90 (4 H, m), 1.29-1.18 (3 H, m), 1.04-0.95 (2 H, m). |
| 19.23 | 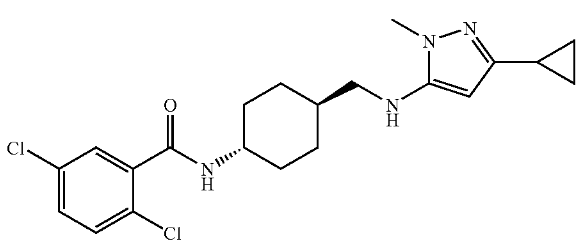 | Trans-2,5-dichloro-N-(4-((3-cyclopropyl-1-methyl-1H-pyrazol-5-ylamino)methyl)cyclohexyl)benzamide | 421.44 | δH (400 MHz, DMSO); 11.25 (1 H, br s), 8.39 (1 H, d, J 7.9 Hz), 7.53-7.45 (3 H, m), 5.22 (1 H, br s), 3.64 (1 H, m), 2.91 (2 H, d, J 7.0 Hz), 2.72 (3 H, s), 1.90-1.59 (6 H, m), 1.23 (2 H, m), 0.99 (2 H, m), 0.83 (2 H, m), 0.61 (2 H, m). |

TABLE 9-continued

| Ex. | Structure | IUPAC Name | [M + H]+ | NMR Data |
|---|---|---|---|---|
| 19.24 | 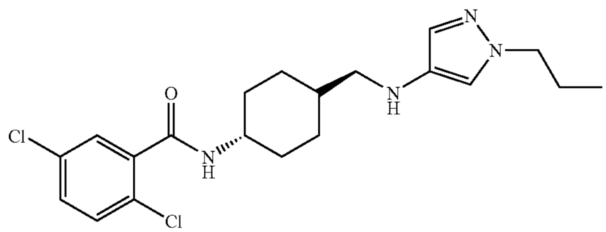 | Trans-2,5-dichloro-N-(4-((1-propyl-1H-pyrazol-4-ylamino)methyl)cyclohexyl)benzamide | 409.4 | δH (400 MHz, DMSO); 8.39 (1 H, d, J 8.0 Hz), 7.54-7.46 (3 H, m), 7.03 (1 H, s), 6.92 (1 H, s), 4.27 (1 H, t, J 6.3 Hz), 3.87 (2 H, t, J 6.9 Hz), 3.66 (1 H, m), 2.67 (2 H, t, J 6.4 Hz), 1.87 (4 H, m), 1.70 (2 H, m), 1.44 (1 H, m), 1.21 (2 H, m), 1.04 (2 H, m), 0.80 (3 H, t, J 7.4 Hz). |
| 19.25 | 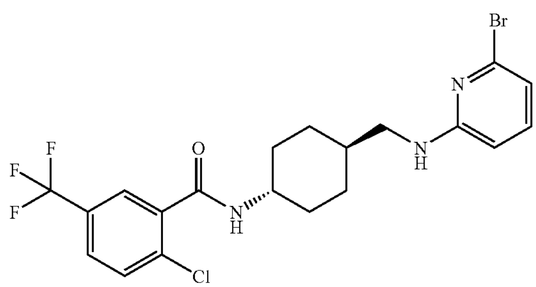 | Trans-N-(4-((6-bromopyridin-2-ylamino)methyl)cyclohexyl)-2-chloro-5-(trifluoromethyl)benzamide | 492.19 | δH (400 MHz, DMSO); 8.48 (1 H, d), 7.81 (1 H, m), 7.73 (2 H, m), 7.27 (1 H, t), 6.97 (1 H, m), 6.60 (1 H, d), 6.45 (1 H, d), 3.70 (1 H, m), 3.04 (2 H, m), 1.93 (2 H, m), 1.81 (2 H, m), 1.49 (1 H, m), 1.24 (2 H, m), 1.09 (2 H, m). |
| 19.26 | 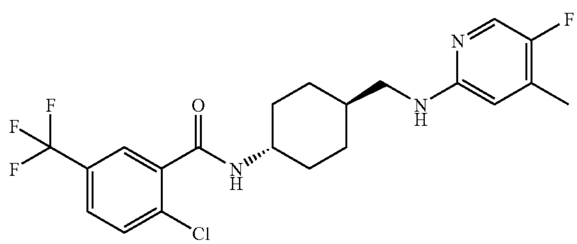 | Trans-2-chloro-N-(4-((5-fluoro-4-methylpyridin-2-ylamino)methyl)cyclohexyl)-5-(trifluoromethyl)benzamide | 444.36 | δH (400 MHz, DMSO); 8.48 (1 H, d), 7.80 (2 H, m), 7.72 (2 H, m), 6.39 (1 H, m), 6.36 (1 H, m), 3.69 (1 H, m), 3.03 (2 H, m), 2.11 (3 H, s), 1.92 (2 H, m), 1.81 (2 H, m), 1.49 (1 H, m), 1.22 (2 H, m), 1.03 (2 H, m). |
| 19.27 | 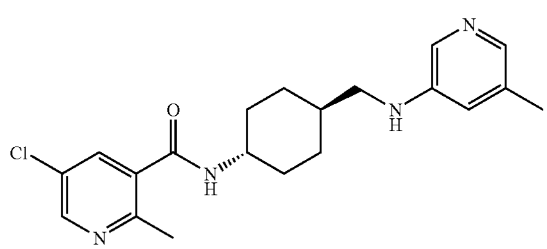 | Trans-5-chloro-2-methyl-N-(4-((5-methylpyridin-3-ylamino)methyl)cyclohexyl)nicotinamide | 373 | NO NMR data |
| 19.28 | 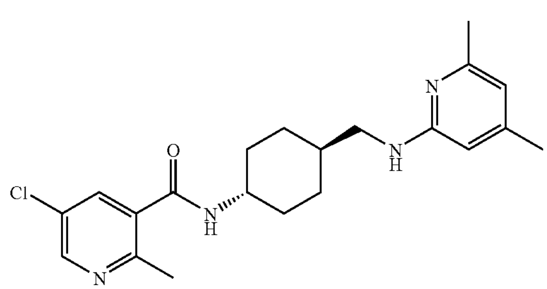 | Trans-5-chloro-N-(4-((4,6-dimethylpyridin-2-ylamino)methyl)cyclohexyl)-2-methyl-nicotinamide | 387.1 | NO NMR data |

TABLE 9-continued

| Ex. | Structure | IUPAC Name | [M + H]+ | NMR Data |
|---|---|---|---|---|
| 19.29 | 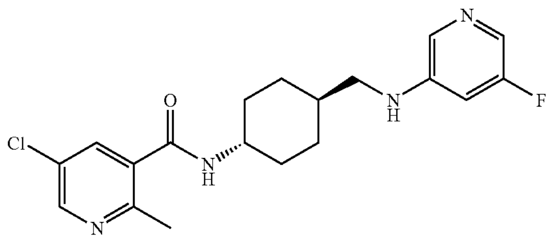 | Trans-5-chloro-N-(4-((5-fluoropyridin-3-ylamino)methyl)cyclohexyl)-2-methyl-nicotinamide | 377 | NO NMR data |
| 19.30 | 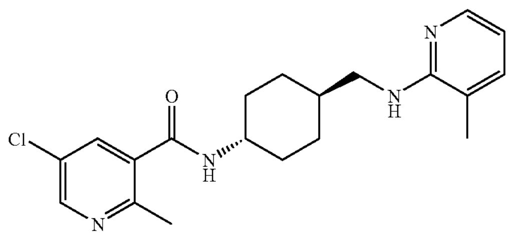 | Trans-5-chloro-2-methyl-N-(4-((3-methylpyridin-2-ylamino)methyl)cyclohexyl)nicotinamide | 373 | NO NMR data |
| 19.31 | 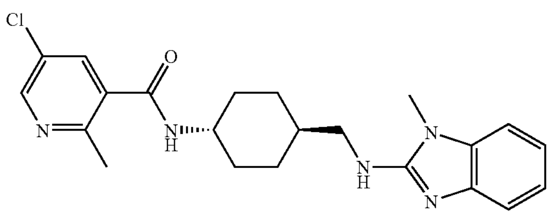 | Trans-5-chloro-2-methyl-N-(4-((1-methyl-1H-benzo[d]imidazol-2-ylamino)methyl)cyclohexyl)nicotinamide | 412.1 | NO NMR data |
| 19.32 | 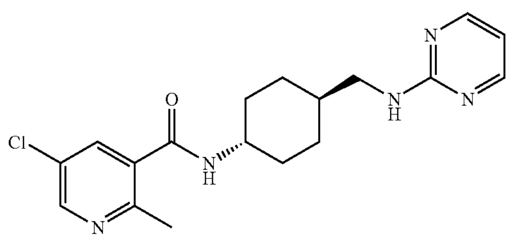 | Trans-5-chloro-2-methyl-N-(4-((pyrimidin-2-ylamino)methyl)cyclohexyl)nicotinamide | 360 | NO NMR data |
| 19.33 | 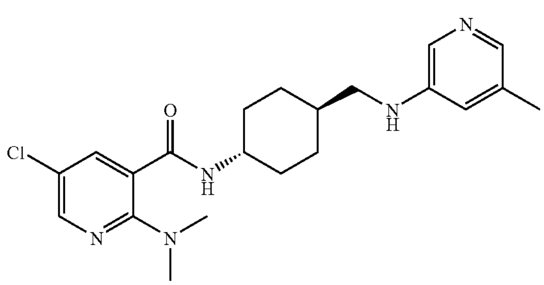 | Trans-5-chloro-2-(dimethylamino)-N-(4-((5-methylpyridin-3-ylamino)methyl)cyclohexyl)nicotinamide | 402.1 | NO NMR data |
| 19.34 | 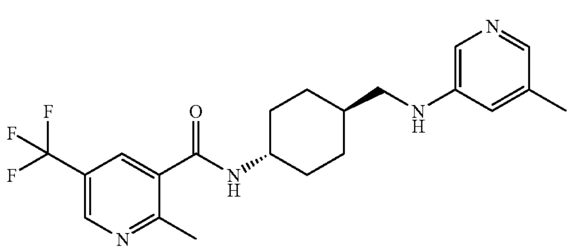 | Trans-2-methyl-N-(4-((5-methylpyridin-3-ylamino)methyl)cyclohexyl)-5-(trifluoromethyl)nicotinamide | 407.1 | NO NMR data |

TABLE 9-continued

| Ex. | Structure | IUPAC Name | [M + H]+ | NMR Data |
|---|---|---|---|---|
| 19.35 | 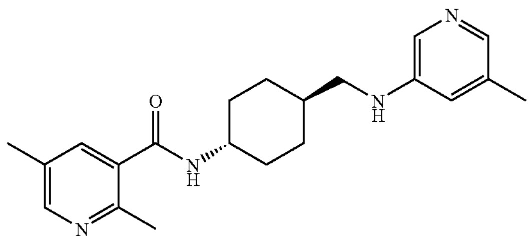 | Trans-2,5-dimethyl-N-(4-((5-methylpyridin-3-ylamino)methyl)cyclohexyl)nicotinamide | 353.1 | NO NMR data |
| 19.36 | 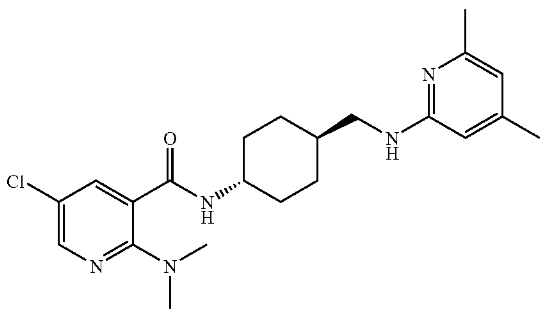 | Trans-5-chloro-2-(dimethylamino)-N-(4-((4,6-dimethyl pyridin-2-ylamino)methyl)cyclohexyl)nicotinamide | 416.1 | NO NMR data |
| 19.37 | 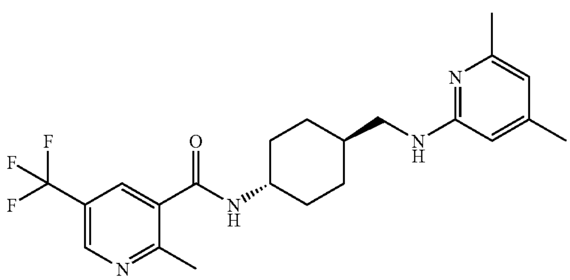 | Trans-N-(4-((4,6-dimethylpyridin-2-ylamino)methyl)cyclohexyl)-2-methyl-5-(trifluoromethyl)nicotinamide | 421.1 | NO NMR data |
| 19.38 | 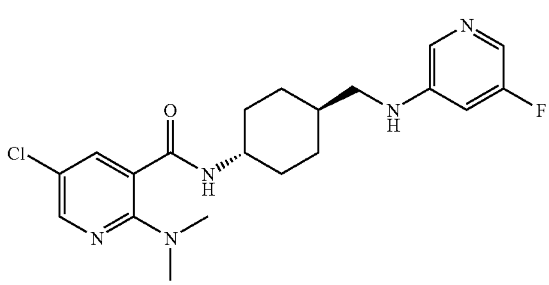 | Trans-5-chloro-2-(dimethylamino)-N-(4-((5-fluoropyridin-3-ylamino)methyl)cyclohexyl)nicotinamide | 406.1 | NO NMR data |
| 19.39 | 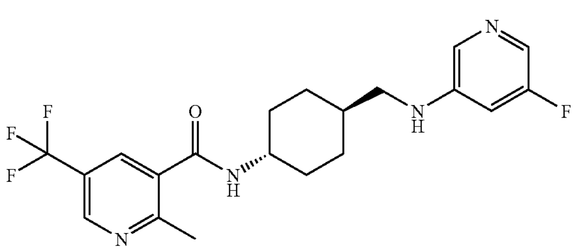 | Trans-N-(4-((5-fluoropyridin-3-ylamino)methyl)cyclohexyl)-2-methyl-5-(trifluoromethyl)nicotinamide | 411.1 | NO NMR data |

TABLE 9-continued

| Ex. | Structure | IUPAC Name | [M + H]+ | NMR Data |
|---|---|---|---|---|
| 19.40 | 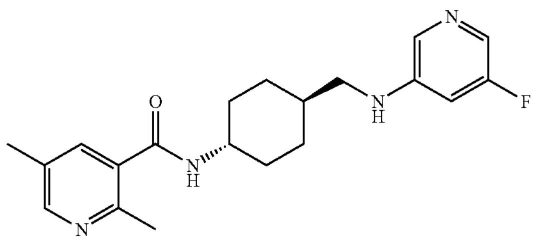 | Trans-N-(4-((5-fluoropyridin-3-ylamino)methyl)cyclohexyl)-2,5-dimethyl nicotinamide | 357.1 | NO NMR data |
| 19.41 | 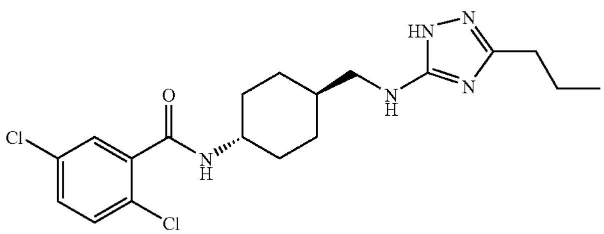 | Trans-2,5-dichloro-N-(4-((3-propyl-1H-1,2,4-triazol-5-ylamino)methyl)cyclohexyl)benzamide | 410.43 | δH (400 MHz, DMSO); 12.28 and 11.66 (1 H, br s, NH tautomers), 8.39 (1 H, d, J 7.8 Hz), 7.88-7.45 (3 H, m), 6.35 and 5.60 (1 H br s NH tautomers), 3.66 (1 H, br m), 2.93 (2 H, br m), 2.39 (2 H, br m), 1.89 (2 H, m), 1.80 (2 H, m), 1.61 (2 H, m), 1.45 (1 H, m), 1.21 (2 H, m), 1.00 (2 H, m), 0.89 (3 H, t, J 7.3 Hz). |
| 19.42 | 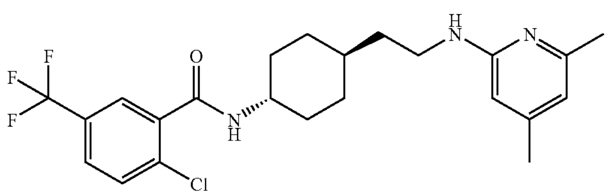 | Trans-2-chloro-N-(4-(2-(4,6-dimethyl pyridin-2-ylamino)ethyl)cyclohexyl)-5-(trifluoromethyl)benzamide | 454.39 | δH (400 MHz, DMSO); 8.48 (1 H, d), 7.80 (1 H, m), 7.74 (2 H, m), 6.15 (2 H, m), 6.02 (1 H, s), 3.68 (1 H, m), 3.20 (2 H, m), 2.19 (3 H, s), 2.09 (3 H, s), 1.91 (2 H, m), 1.80 (2 H, m), 1.41 (2 H, m), 1.30 (1 H, m), 1.23 (2 H, m), 1.02 (2 H, m). |
| 19.43 | 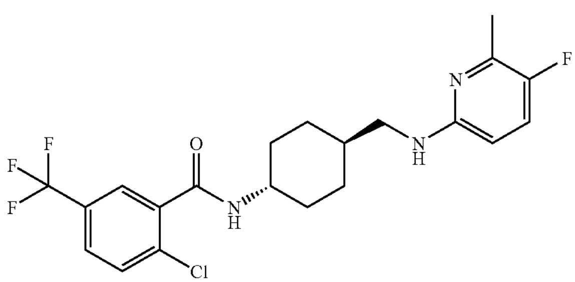 | Trans-2-chloro-N-(4-((5-fluoro-6-methyl pyridin-2-ylamino)methyl)cyclohexyl)-5-(trifluoromethyl)benzamide | 444.48 | δH (400 MHz, DMSO); 8.49 (1 H, d), 7.82 (1 H, m), 7.73 (2 H, m), 7.22 (1 H, m), 6.35 (1 H, m), 6.29 (1 H, m), 3.70 (1 H, m), 3.04 (2 H, m), 2.21 (3 H, d), 1.93 (2 H, m), 1.83 (2 H, m), 1.49 (1 H, m), 1.22 (2 H, m), 1.08 (2 H, m). |
| 19.44 | 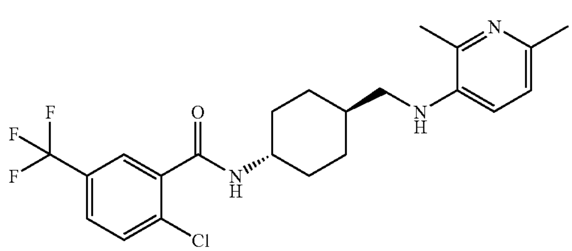 | Trans-2-chloro-N-(4-(2,6-dimethylpyridin-3-ylamino)methyl)cyclohexyl)-5-(trifluoromethyl)benzamide | 440.47 | δH (400 MHz, DMSO); 8.50 (1 H, d), 7.81 (1 H, m), 7.73 (2 H, m), 6.83 (1 H, d), 6.73 (1 H, d), 4.88 (1 H, m), 3.71 (1 H, m), 2.90 (2 H, m), 2.28 (6 H, d), 1.94 (2 H, m), 1.88 (2 H, m), 1.54 (1 H, m), 1.23 (2 H, m), 1.08 (2 H, m). |

TABLE 9-continued

| Ex. | Structure | IUPAC Name | [M + H]+ | NMR Data |
|---|---|---|---|---|
| 19.45 | 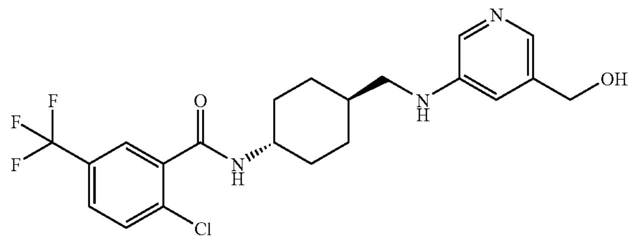 | Trans-2-chloro-N-(4-((5-(hydroxymethyl)pyridin-3-ylamino)methyl)cyclohexyl)-5-(trifluoromethyl)benzamide | 442.43 | δH (400 MHz, DMSO); 8.49 (1 H, d), 7.78 (5 H, m), 6.83 (1 H, s), 5.87 (1 H, t), 5.12 (1 H, t), 4.41 (2 H, d), 3.70 (1 H, m), 2.90 (2 H, t), 1.90 (4 H, m), 1.51 (1 H, m), 1.24 (2 H, m), 1.09 (2 H, m). |
| 19.46 | 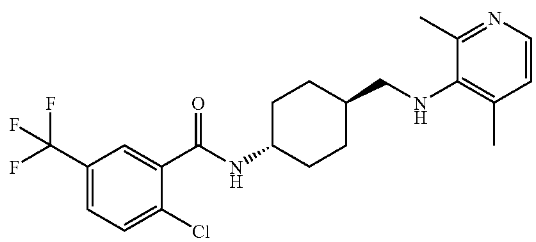 | Trans-2-chloro-N-(4-((2,4-dimethylpyridin-3-ylamino)methyl)cyclohexyl)-5-(trifluoromethyl)benzamide | 440.47 | δH (400 MHz, DMSO); 8.49 (1 H, d), 7.80 (4 H, m), 6.92 (1 H, d), 3.89 (1 H, m), 3.71 (1 H, m), 2.80 (2 H, m), 2.42 (3 H, s), 2.22 (3 H, s), 1.92 (4 H, m), 1.43 (1 H, m), 1.26 (2 H, m), 1.10 (2 H, m). |
| 19.47 | 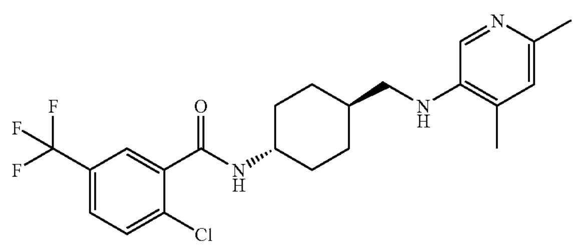 | Trans-2-chloro-N-(4-((4,6-dimethylpyridin-3-ylamino)methyl)cyclohexyl)-5-(trifluoromethyl)benzamide | 440.46 | δH (400 MHz, DMSO); 8.50 (1 H, d), 7.81 (1 H, m), 7.75 (1 H, m), 7.70 (2 H, m), 6.81 (1 H, s), 4.80 (1 H, t), 3.71 (1 H, m), 2.97 (2 H, m), 2.28 (3 H, s), 2.08 (3 H, s), 1.92 (4 H, m), 1.60 (1 H, m), 1.27 (2 H, m), 1.09 (2 H, m). |
| 19.48 | 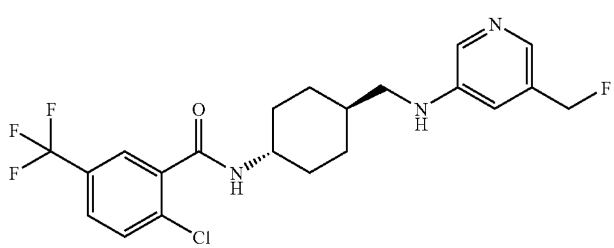 | Trans-2-chloro-N-(4-((5-(fluoromethyl)pyridin-3-ylamino)methyl)cyclohexyl)-5-(trifluoromethyl)benzamide | 444.45 | δH (400 MHz, DMSO); 8.50 (1 H, d), 7.98 (1 H, s), 7.78 (4 H, m), 6.91 (1 H, s), 6.05 (1 H, t), 5.34 (2 H, d, 50 Hz), 3.71 (1 H, m), 2.91 (2 H, t), 1.95 (2 H, m), 1.89 (2 H, m), 1.51 (1 H, m), 1.24 (2 H, m), 1.09 (2 H, m). |
| 19.49 | 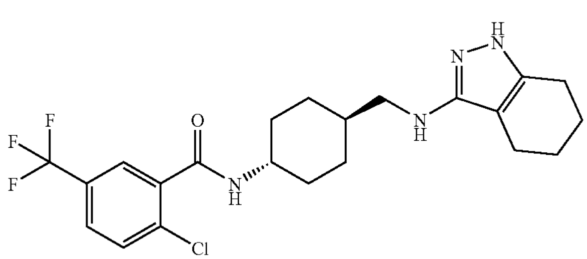 | Trans-2-chloro-N-(4-((4,5,6,7-tetrahydro-1H-indazol-3-ylamino)methyl)cyclohexyl)-5-(trifluoromethyl)benzamide | 455.48 | δH (400 MHz, DMSO); 10.80 (1 H br), 8.47 (d 1 H), 7.79 (m 1 H), 7.74 (m 2 H), 4.55 (br 1 H), 3.70 (br 1 H), 2.89 (t 2 H), 2.41 (m 2 H), 2.33 (m 2 H), 1.91 (m 2 H), 1.82 (m 2 H), 1.63 (br m 4 H), 1.52 (br 1 H), 1.22 (m 2 H), 0.98 (m 2 H) |

TABLE 9-continued

| Ex. | Structure | IUPAC Name | [M + H]+ | NMR Data |
|---|---|---|---|---|
| 19.50 | 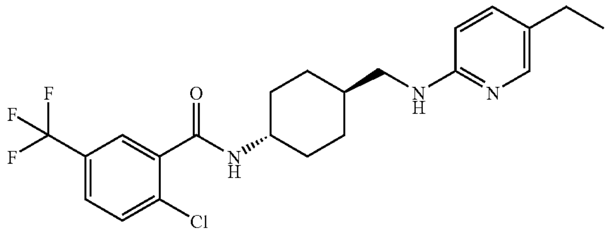 | Trans-2-chloro-N-(4-((5-ethylpyridin-2-ylamino)methyl)cyclohexyl)-5-(trifluoromethyl)benzamide | 440.47 | δH (400 MHz, DMSO); 8.48 (1 H, d, J 7.92 Hz), 7.81-7.73 (4 H, m). 7.22 (1 H, dd, J 2.3, 8.5 Hz), 6.41 (1 H, d, J 8.5 Hz), 6.28 (1 H, br t, 5.6 Hz), 3.70 (1 H, m), 3.07 (2 H, t, J 6.2 Hz), 2.40 (2 H, q, J 7.5 Hz), 1.93 (2 H, m), 1.83 (2 H, m), 1.50 (1 H, m), 1.23 (2 H, m), 1.12-0.83 (5 H, m). |
| 19.51 | 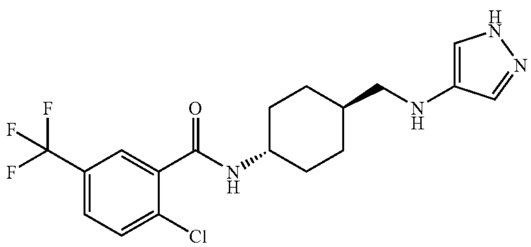 | Trans-N-(4-((1H-pyrazol-4-ylamino)methyl)cyclohexyl)-2-chloro-5-(trifluoromethyl)benzamide | 401.41 | δH (400 MHz, DMSO); 11.99 (1 H, s), 8.49 (1 H, d), 7.81 (1 H, m), 7.73 (2 H, m), 7.02 (2 H, s), 4.23 (1 H, m), 3.70 (1 H, m), 2.70 (2 H, t), 1.92 (2 H, m), 1.85 (2 H, m), 1.46 (1 H, m), 1.25 (2 H, m), 1.03 (2 H, m). |
| 19.52 | 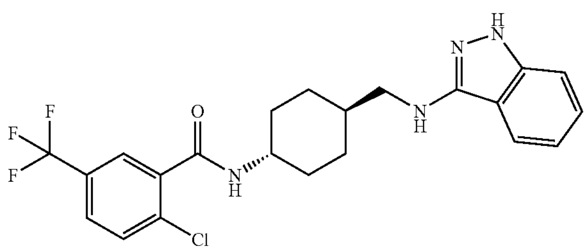 | Trans-N-(4-((1H-indazol-3-ylamino)methyl)cyclohexyl)-2-chloro-5-(trifluoromethyl)benzamide | 541.42 | δH (400 MHz, DMSO); 11.30 (1 H, s), 8.50 (1 H, d), 7.80 (1 H, m), 7.72 (3 H, m), 7.20 (2 H, m), 6.87 (1 H, m), 5.97 (1 H, t), 3.72 (1 H, m), 3.11 (2 H, t), 1.91 (4 H, m), 1.68 (1 H, m), 1.25 (2 H, m), 1.09 (2 H, m). |
| 19.53 | 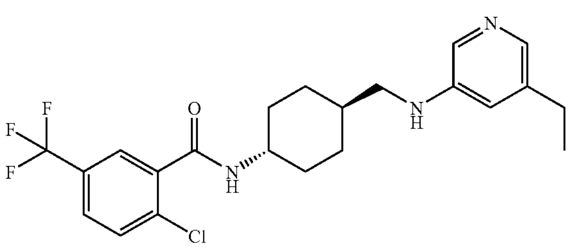 | Trans-2-chloro-N-(4-((5-ethylpyridin-3-ylamino)methyl)cyclohexyl)-5-(trifluoromethyl)benzamide | 440.45 | δH (400 MHz, DMSO); 8.49 (1 H, d, J 7.9 Hz), 7.83-7.74 (4 H, m), 7.61 (1 H, d, J 1.5 Hz), 6.73 (1 H, s), 5.77 (1 H, t, J 5.6 Hz), 3.71 (1 H, m), 2.89 (2 H, t, J 6.0 Hz), 2.49 (2 H, q, partially obscured by residual DMSO), 1.96-1.87 (4 H, m), 1.51 (1 H, m), 1.30-1.22 (2 H, m), 1.16 (3 H, t, J 7.6 Hz), 1.1-1.04 (2 H, m). |
| 19.54 | 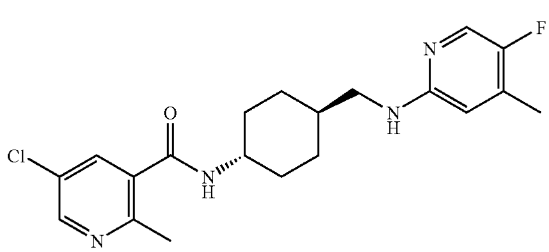 | Trans-5-chloro-N-(4-((5-fluoro-4-methylpyridin-2-ylamino)methyl)cyclohexyl)-2-methylnicotinamide | 391.39 | δH (400 MHz, DMSO); 8.52 (d 1 H), 8.38 (d 1 H), 7.78 (m 2 H), 6.38 (t 1 H), 6.36 (d 1 H), 3.66 (m 1 H), 3.04 (t 2 H), 2.46 (s 3 H), 2.14 (s 3 H), 1.86 (m 4 H), 1.48 (m 1 H), 1.16 (m 4 H). |

TABLE 9-continued

| Ex. | Structure | IUPAC Name | [M + H]+ | NMR Data |
|---|---|---|---|---|
| 19.55 | 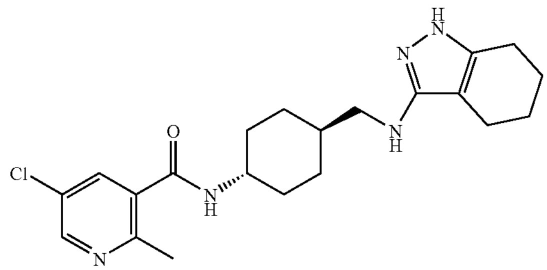 | Trans-5-chloro-2-methyl-N-(4-((4,5,6,7-tetrahydro-1H-indazol-3-ylamino)methyl)cyclohexyl)nicotinamide | 402.47 | δH (400 MHz, DMSO); 10.82 (br s 1 H), 8.54 (d 1 H), 8.36 (d 1 H), 7.80 (d 1 H), 4.54, 4.24 (2 x br s 1 H), 2.36 (t 2 H), 2.46 (s 3 H), 2.42 (m 2 H), 2.22 (m 2 H), 1.88 (m 4 H), 1.64 (m 4 H), 1.54 (m 1 H), 1.22 (m 2 H), 0.98 (m 2 H). |
| 19.56 | 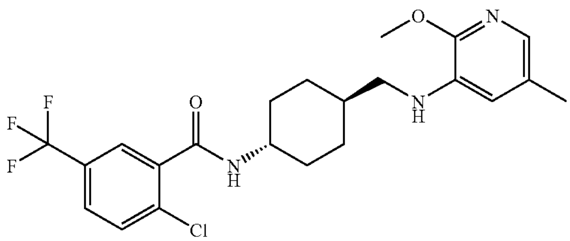 | Trans-2-chloro-N-(4-((2-methoxy-5-methylpyridin-3-ylamino)methyl)cyclohexyl)-5-(trifluoromethyl)benzamide | 456.42 | δH (400 MHz, DMSO); 8.49 (1 H, d), 7.80 (1 H, m), 7.72 (2 H, m), 7.11 (1 H, s), 6.58 (1 H, s), 5.00 (1 H, t), 3.83 (3 H, s), 3.70 (1 H, m), 2.91 (2 H, t), 2.13 (3 H, s), 1.92 (2 H, m), 1.82 (2 H, m), 1.58 (1 H, m), 1.25 (2 H, m), 1.07 (2 H, m). |
| 19.57 | 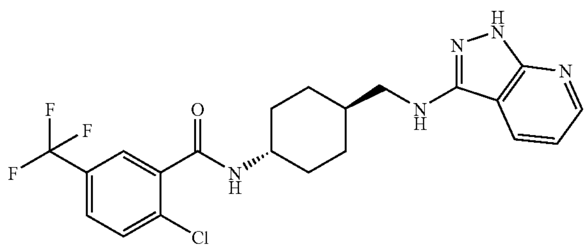 | Trans-N-(4-((1H-pyrazolo[3,4-b]pyridin-3-ylamino)methyl)cyclohexyl)-2-chloro-5-(trifluoromethyl)benzamide | 452.39 | δH (400 MHz, DMSO) 11.9 (1 H, s), 8.49 (1 H, d), 8.33 (1 H, dd), 8.16 (1 H, dd), 7.82-7.70 (3 H, m), 6.93 (1 H, dd), 6.21 (1 H, t), 3.71 (1 H, m), 3.12 (2 H, t), 1.96-1.88 (4 H, m), 1.52 (1 H, m), 1.30-0.87 (4 H, m). |
| 19.58 | 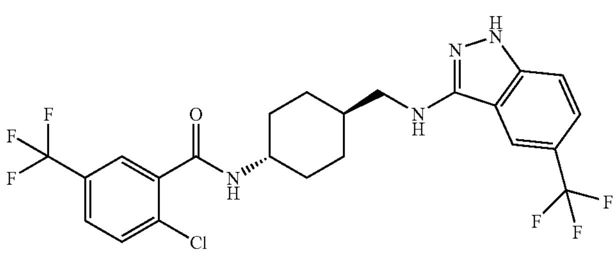 | Trans-2-chloro-5-(trifluoromethyl)-N-(4-((5-trifluoromethyl)-1H-indazol-3-ylamino)methyl)cyclohexyl)benzamide | 519.46 | δH (400 MHz, DMSO) 11.81 (1 H, br s), 8.48 (1 H, d), 8.28 (1 H, s), 7.82-7.74 (3 H, m), 7.47 (1 H, d), 7.39 (1 H, d), 6.30 (1 H, t), 3.72 (1 H, m), 3.14 (2 H, t), 1.97-1.66 (5 H, m), 1.31-1.13 (4 H, m). |
| 19.59 | 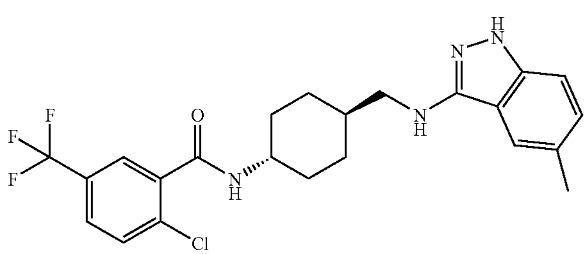 | Trans-2-chloro-N-(4-((5-methyl-1H-indazol-3-ylamino)methyl)cyclohexyl)-5-(trifluoromethyl)benzamide | 465.44 | δH (400 MHz, DMSO) 11.14 (1 H, br s), 8.48 (1 H, d), 7.80 (1 H, dd), 7.74 (2 H, m), 7.50 (1 H, m), 7.11 (1 H, d), 7.05 (1 H, dd), 5.79 (1 H, t), 3.72 (1 H, m), 3.10 (2 H, t), 2.34 (3 H, s), 1.92 (4 H, m), 1.65 (1 H, m), 1.25 (2 H, m), 1.08 (2 H, m). |
| 19.60 | 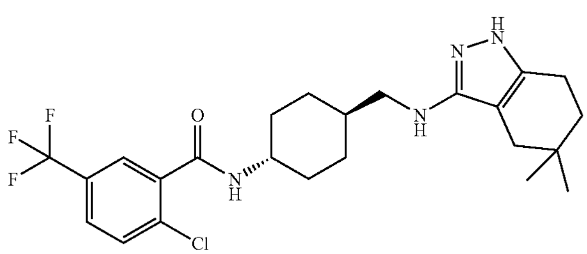 | Trans-2-chloro-N-(4-((5,5-dimethyl-4,5,6,7-tetrahydro-1H-indazol-3-ylamino)methyl)cyclohexyl)-5-(trifluoromethyl)benzamide | 483.41 | δH (400 MHz, DMSO) 8.46 (1 H, d), 7.79 (1H d), 7.75 (1 H d), 7.73 (1 H d), 4.49 (1 H br), 3.68 (1 H s), 2.88 (2 H t), 2.41 (2 H t), 2.02 (2 H s), 1.91 (2 H m), 1.81 (2 H m), 1.54 (1 H br), 1.44 (2 H t), 1.24 (2 H m), 1.01 (2 H m), 0.93 (6 H s) |

TABLE 9-continued

| Ex. | Structure | IUPAC Name | [M + H]+ | NMR Data |
|---|---|---|---|---|
| 19.61 | 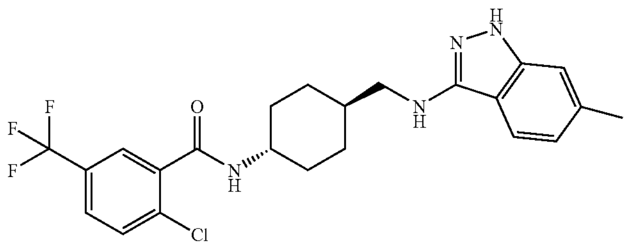 | Trans-2-chloro-N-(4-((6-methyl-1H-indazol-3-ylamino)methyl)cyclohexyl)-5-(trifluoromethyl)benzamide | 465.39 | δH (400 MHz, DMSO); 11.12 (1 H, s), 8.50 (1 H, d), 7.80 (1 H, m), 7.72 (2 H, m), 6.98 (1 H, s), 6.71 (1 H, d), 5.82 (1 H, t), 3.70 (1 H, m), 3.10 (2 H, t), 2.36 (3 H, s), 1.91 (4 H, m), 1.62 (1 H, m), 1.22 (2 H, m), 1.08 (2 H, m). |
| 19.62 | 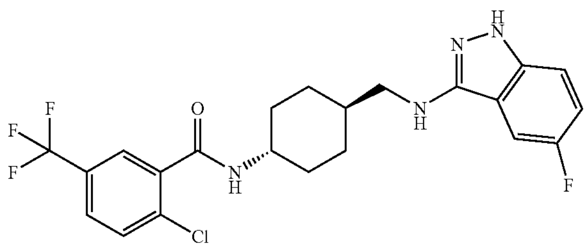 | Trans-2-chloro-N-(4-((5-fluoro-1H-indazol-3-ylamino)methyl)cyclohexyl)-5-(trifluoromethyl)benzamide | 469.36 | δH (400 MHz, DMSO); 11.39 (1 H, br s), 8.48 (1 H, d), 7.80 (1 H, dd), 7.74 (2 H, m), 7.52 (1 H, dd), 7.23 (1 H, dd), 7.11 (1 H, dt), 5.89 (1 H, t), 3.72 (1 H, m), 3.11 (2 H, t), 1.93 (4 H, m), 1.65 (1 H, m), 1.25 (2 H, m), 1.08 (2 H, m). |
| 19.63 | 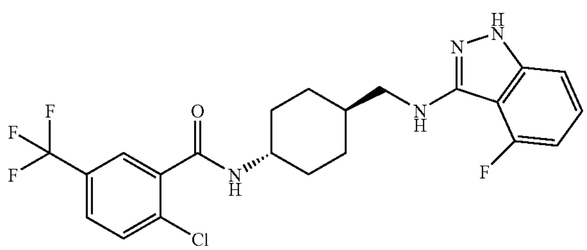 | Trans-2-chloro-N-(4-((4-fluoro-1H-indazol-3-ylamino)methyl)cyclohexyl)-5-(trifluoromethyl)benzamide | 469.33 | δH (400 MHz, DMSO); 11.70 (1 H, s), 8.49 (1 H, d), 7.81 (1 H, m), 7.73 (2 H, m), 7.19 (1 H, m), 7.03 (1 H, d), 6.60 (1 H, m), 5.48 (1 H, t), 3.70 (1 H, m), 3.11 (2 H, t), 1.91 (4 H, m), 1.70 (1 H, m), 1.23 (2 H, m), 1.08 (2 H, m). |
| 19.64 | 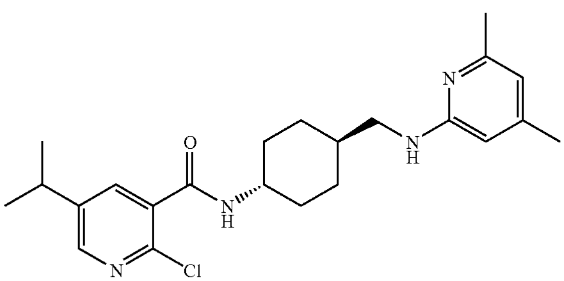 | Trans-2-chloro-N-(4-((4,6-dimethylpyridin-2-ylamino)methyl)cyclohexyl)-5-isopropyl-nicotinamide | 415.44 | δH (400 MHz, DMSO); 8.42 (1 H, d), 8.35 (1 H, d), 7.72 (1 H, d), 6.20 (1 H, t), 6.15 (1 H, s), 6.07 (1 H, s), 3.69 (1 H, m), 3.05 (2 H, t), 2.99 (2 H, t), 2.19 (3 H, s), 2.09 (3 H, s), 1.92 (2 H, m), 1.83 (2 H, m), 1.49 (1 H, m), 1.22 (8 H, m), 1.05 (2 H, m). |
| 19.65 | 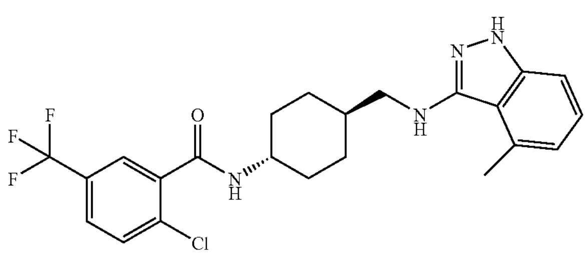 | Trans-2-chloro-N-(4-((4-methyl-1H-indazol-3-ylamino)methyl)cyclohexyl)-5-(trifluoromethyl)benzamide | 465.3 | δH (400 MHz, DMSO) 11.39 (1 H, br s), 8.49 (1 H, d), 7.81 (1 H, dd), 7.74 (2 H, m), 7.05 (2 H, m), 6.60 (1 H, d), 5.12 (1 H, t), 3.72 (1 H, m), 3.11 (2 H, t), 2.61 (3 H, s), 1.93 (4 H, m), 1.70 (1 H, m), 1.25 (2 H, m), 1.08 (2 H, m). |
| 19.66 | 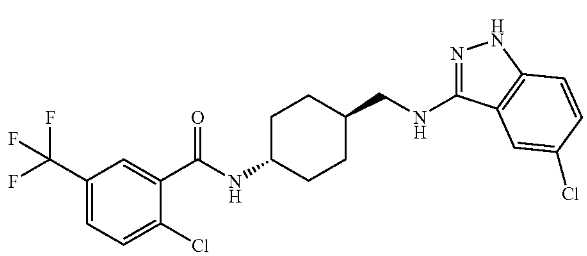 | Trans-2-chloro-N-(4-((5-chloro-1H-indazol-3-ylamino)methyl)cyclohexyl)-5-(trifluoromethyl)benzamide | 485.2 | δH (400 MHz, DMSO) 11.52 (1 H, s), 8.49 (1 H, d), 7.86-7.74 (4 H, m), 7.24 (2 H, m), 6.02 (1 H, t), 3.74 (1 H, m), 3.11 (2 H, t), 1.93 (4 H, m), 1.64 (1 H, m), 1.25 (2 H, m), 1.11 (2 H, m). |

TABLE 9-continued

| Ex. | Structure | IUPAC Name | [M + H]+ | NMR Data |
|---|---|---|---|---|
| 19.67 | 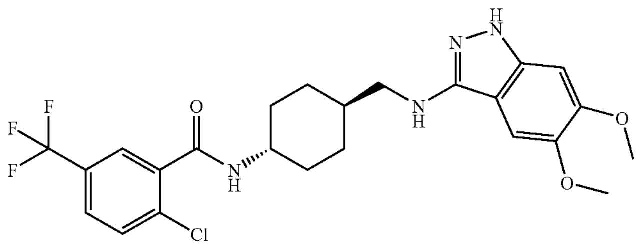 | Trans-2-chloro-N-(4-((5,6-dimethoxy-1H-indazol-3-ylamino)methyl)cyclohexyl)-5-(trifluoromethyl)benzamide | 511.43 | δH (400 MHz, DMSO); 10.95 (1 H, s), 8.50 (1 H, d), 7.80 (1 H, m), 7.73 (2 H, m), 7.21 (1 H, s), 6.70 (1 H, s), 5.63 (1 H, t), 3.79 (3 H, s) 3.71 (4 H, s + m), 3.09 (2 H, t), 1.91 (4 H, m), 1.62 (1 H, m), 1.25 (2 H, m), 1.10 (2 H, m). |
| 19.68 | 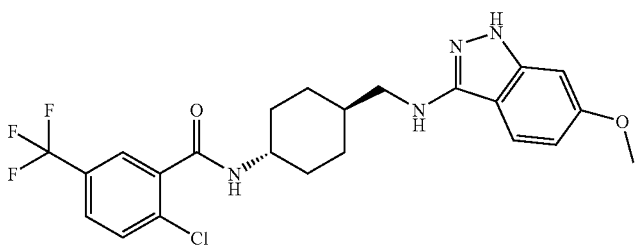 | Trans-2-chloro-N-(4-((6-methoxy-1H-indazol-3-ylamino)methyl)cyclohexyl)-5-(trifluoromethyl)benzamide | 481.36 | δH (400 MHz, DMSO); 11.10 (1 H, s), 8.49 (1 H, d), 7.80 (1 H, m), 7.71 (2 H, m), 7.58 (1 H, d), 6.62 (1 H, d), 6.50 (1 H, d of d), 5.83 (1 H, t), 3.78 (3 H, s), 3.71 (1 H, m), 3.09 (2 H, t), 1.91 (4 H, m), 1.65 (1 H, m), 1.25 (2 H, m), 1.09 (2 H, m). |
| 19.69 | 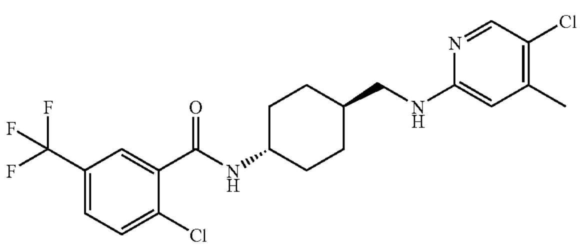 | Trans-2-chloro-N-(4-((5-chloro-4-methylpyridin-2-ylamino)methyl)cyclohexyl)-5-(trifluoromethyl)benzamide | 460.31 | δH (400 MHz, DMSO); 8.49 (1 H, d), 7.89 (1 H, s), 7.80 (1 H, m), 7.71 (2 H, m), 6.63 (1 H, t), 6.42 (1 H, s), 3.70 (1 H, m), 3.08 (2 H, t), 1.93 (2 H, m), 1.81 (2 H, m), 1.49 (1 H, m), 1.21 (2 H, m), 1.04 (2 H, m). |
| 19.70 | 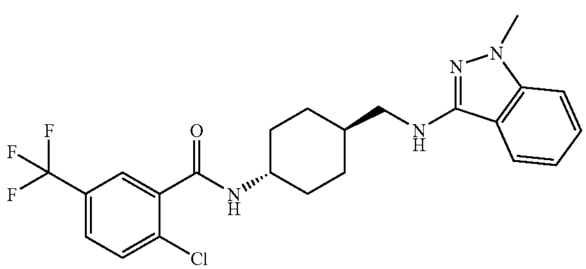 | Trans-2-chloro-N-(4-((1-methyl-1H-indazol-3-ylamino)methyl)cyclohexyl)-5-(trifluoromethyl)benzamide | 465.29 | δH (400 MHz, DMSO); 8.49 (1 H, d), 7.80 (1 H, m), 7.73 (3 H, m), 7.27 (2 H, m), 6.89 (1 H, m), 6.00 (1 H, t), 3.72 (3 H, s and 1 H, m), 3.11 (2 H, t), 1.92 (4 H, m), 1.65 (1 H, m), 1.28 (2 H, m), 1.09 (2 H, m). |
| 19.71 | 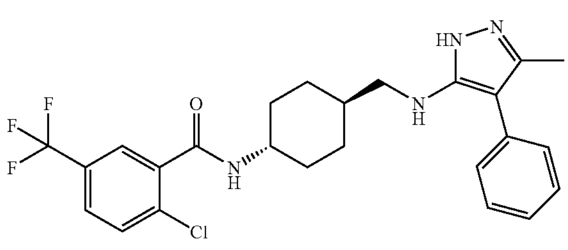 | Trans-2-chloro-N-(4-((3-methyl-4-phenyl-1H-pyrazol-5-ylamino)methyl)cyclohexyl)-5-(trifluoromethyl)benzamide | 491.29 | δH (400 MHz, DMSO); 11.40 (1 H, s), 8.48 (1 H, d), 7.80 (1 H, m), 7.73 (2 H, m), 7.38 (4 H, m), 7.20 (1 H, t), 4.49 (1 H, m), 3.68 (1 H, m), 2.92 (2 H, t), 2.17 (3 H, s), 1.91 (2 H, m), 1.81 (2 H, m), 1.59 (1 H, m), 1.20 (2 H, m), 1.00 (2 H, m). |

TABLE 9-continued

| Ex. | Structure | IUPAC Name | [M + H]+ | NMR Data |
|---|---|---|---|---|
| 19.72 | 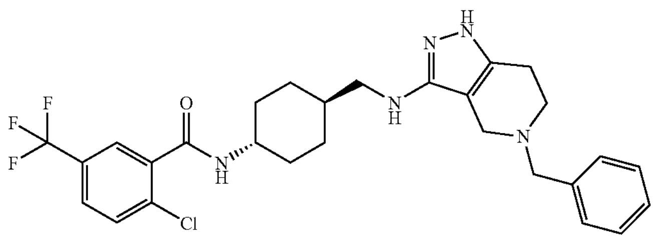 | Trans-N-(4-((5-benzyl-4,5,6,7-tetrahydro-1H-pyrazolo[4,3-c]pyridin-3-ylamino)methyl)cyclohexyl)-2-chloro-5-(trifluoromethyl)benzamide | 546.44 | δH (400 MHz, DMSO); 11.20 (1 H, br), 8.48 (1 H, d), 7.80 (1 H, m), 7.73 (2 H, m), 7.32 (5 H, m), 7.23 (1 H, m), 4.78 (0.5 H, br), 4.33 (0.5 H, br), 3.65 (3 H, m), 3.18 (2 H, s), 2.82 (1 H, m), 2.64 (3 H, m), 1.91 (4 H, m), 1.80 (2 H, m), 1.45 (1 H, m), 1.20 (3 H, m), 0.98 (2 H, m). |
| 19.73 | 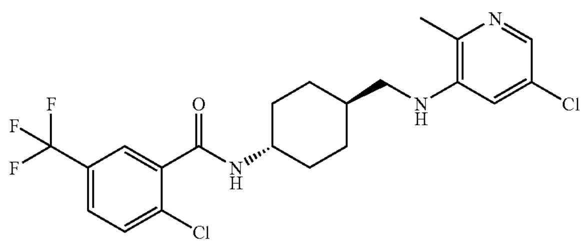 | Trans-2-chloro-N-(4-((5-chloro-2-methylpyridin-3-ylamino)methyl)cyclohexyl)-5-(trifluoromethyl)benzamide | 460.28 | δH (400 MHz, DMSO); 8.49 (1 H, d), 7.80 (1 H, m), 7.73 (2 H, m), 7.51 (1 H, d), 6.82 (1 H, d), 5.50 (1 H, t), 3.70 (1 H, m), 2.95 (2 H, t), 2.28 (3 H, s), 1.92 (2 H, m), 1.87 (2 H, m), 1.58 (1 H, m), 1.22 (2 H, m), 1.06 (2 H, m). |
| 19.74 | 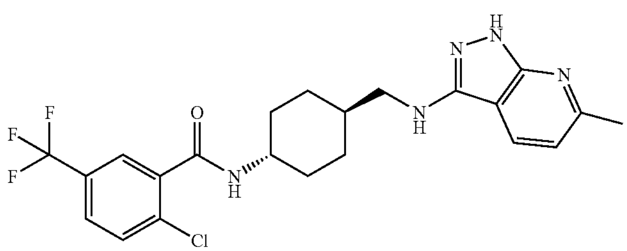 | Trans-2-chloro-N-(4-((6-methyl-1H-pyrazolo[3,4-b]pyridin-3-ylamino)methyl)cyclohexyl)-5-(trifluoromethyl)benzamide | 466.35 | δH (400 MHz, DMSO); 11.70 (1 H, s), 8.49 (1 H, d), 8.02 (1 H, d), 7.80 (1 H, m), 7.73 (2 H, m), 6.82 (1 H, d), 6.12 (1 H, t), 3.70 (1 H, m), 3.10 (2 H, t), 2.50 (3 H, s), 1.91 (4 H, m), 1.62 (1 H, m), 1.25 (2 H, m), 1.10 (2 H, m). |
| 19.75 | 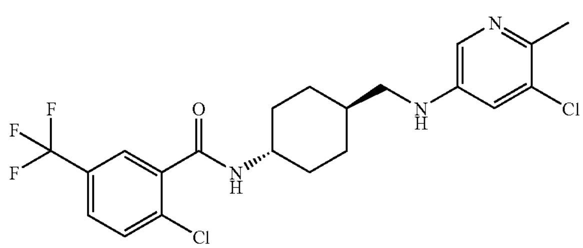 | Trans-2-chloro-N-(4-((5-chloro-6-methylpyridin-3-ylamino)methyl)cyclohexyl)-5-(trifluoromethyl)benzamide | 460.31 | δH (400 MHz, DMSO) 8.49 (1 H, d), 7.81 (2 H, m), 7.73 (2 H, m), 6.95 (1 H, d), 5.99 (1 H, t), 3.70 (1 H, m), 2.90 (2 H, t), 2.34 (3 H, s), 1.93 (2 H, m), 1.87 (2 H, m), 1.49 (1 H, m), 1.23 (2 H, m), 1.08 (2 H, m). |
| 19.76 | 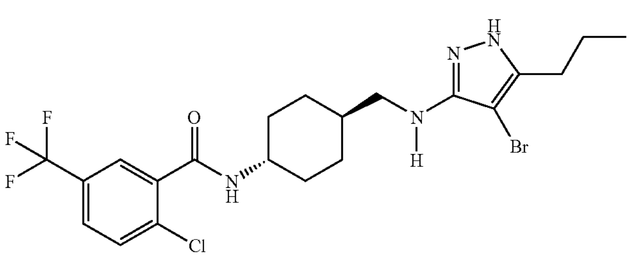 | Trans-N-(4-((4-bromo-5-propyl-1H-pyrazol-3-ylamino)methyl)cyclohexyl)-2-chloro-5-(trifluoromethyl)benzamide | 521.3 | δH (400 MHz, DMSO) 8.50 (1 H, d), 7.81 (1 H, m) 7.73 (2 H, m), 6.45 (1 H, v br), 3.70 (1 H, m), 3.00 (2 H, d), 2.52 (2 H, m), 1.92 (2 H, m), 1.81 (2 H, m), 1.59 (3 H, m), 1.22 (2 H, m), 1.02 (2 H, m), 0.89 (3 H, t). |

TABLE 9-continued

| Ex. | Structure | IUPAC Name | [M + H]+ | NMR Data |
|---|---|---|---|---|
| 19.77 | 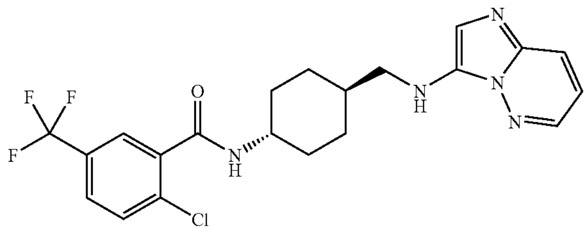 | Trans-2-chloro-N-(4-((imidazo[1,2-b]pyridazin-3-ylamino)methyl)cyclohexyl)-5-(trifluoromethyl)benzamide | 452.3 | δH (400 MHz, DMSO) 8.49 (1 H, d), 8.37 (1 H, dd), 7.88 (1 H, dd), 7.81 (1 H, m), 7.75 (2 H, m), 7.09 (1 H, s), 6.87 (1 H, dd), 5.63 (1 H, br t), 3.71 (1 H, m), 3.08 (2 H, m), 1.92 (4 H, m), 1.64 (1 H, m), 1.26 (2 H, m), 1.09 (2 H, m). |
| 19.78 | 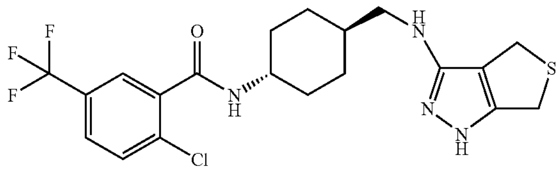 | Trans-2-chloro-N-(4-((4,6-dihydro-1H-thieno[3,4-c]pyrazol-3-ylamino)methyl)cyclohexyl)-5-(trifluoromethyl)benzamide | 459.29 | δH (400 MHz, DMSO), 11.28 (br 1 H), 8.51 (d 1 H), 7.82 (d 1 H), 7.77 (d 1 H), 7.74 (m 2 H), 5.40 (br 1 H), 3.74 (s 2 H), 3.70 (br m 1 H), 3.65 (s 2 H), 2.86 (s 2 H), 1.96 (m 2 H), 1.84 (m 2 H), 1.43 (m 1 H), 1.24 (m 2 H), 1.0 (m 2 H) |
| 19.79 | 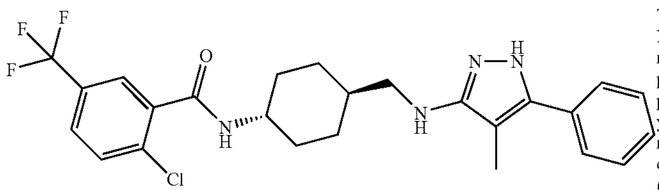 | Trans-2-chloro-N-(4-((4-methyl-5-phenyl-1H-pyrazol-3-ylamino)methyl)cyclohexyl)-5-(trifluoromethyl)benzamide | 491.33 | δH (400 MHz, DMSO) 11.55 (1 H, br s), 8.5 (1 H, d), 7.82 (1 H, d), 7.75 (2 H, m), 7.51 (2 H, m), 7.45 (2 H, m), 7.33 (1 H, m), 4.75 (1 H, br s), 3.72 (1 H, m), 2.96 (2 H, m), 1.98 (3 H, s), 1.92 (4 H, m), 1.60 (1 H, m), 1.25 (2 H, m), 1.03 (2 H, m). |
| 19.80 | 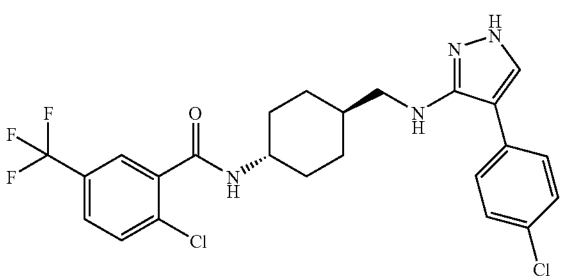 | Trans-2-chloro-N-(4-((4-(4-chlorophenyl)-1H-pyrazol-3-ylamino)methyl)cyclohexyl)-5-(trifluoromethyl)benzamide | 511.2 | 1H NMR (400 MHz, MeOD). δ 8.6 (~0.5 H, d. Slow exchange of amide proton), 8.0 (1 H, s), 7.7 (3 H, m), 7.5 (4 H, s), 3.8 (1 H, m), 3.2 (2 H, d), 2.1 (2 H, d), 1.9 (2 H, d), 1.7 (1 H, m), 1.4 (2 H, m), 1.2 (2 H, m). |
| 19.81 | 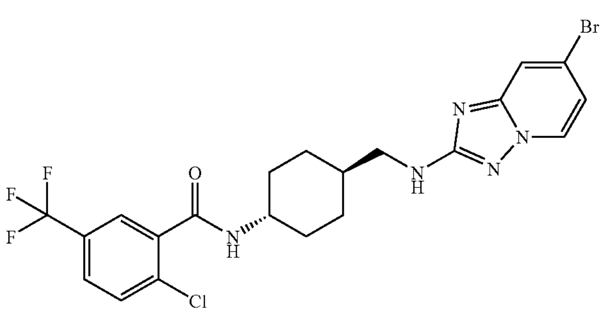 | Trans-N-(4-((7-bromo-[1,2,4]triazolo[1,5-a]pyridin-2-ylamino)methyl)cyclohexyl)-2-chloro-5-(trifluoromethyl)benzamide | 532.1 | 1H NMR (400 MHz, MeOD). δ 8.4 (1 H, d), 7.7 (3 H, m), 7.6 (1 H, s), 7.1 (1 H, d), 3.9 (1 H, m), 3.2 (2 H, d), 2.1 (2 H, d), 2.0 (2 H, d), 1.7 (1 H, m), 1.4 (2 H, m), 1.2 (2 H, m). |

TABLE 9-continued

| Ex. | Structure | IUPAC Name | [M + H]+ | NMR Data |
|---|---|---|---|---|
| 19.82 | 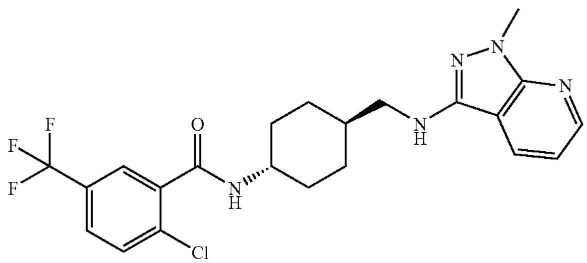 | Trans-2-chloro-N-(4-((1-methyl-1H-pyrazolo[3,4-b]pyridin-3-ylamino)methyl)cyclohexyl)-5-(trifluoromethyl)benzamide | 466.35 | δH (400 MHz, DMSO); 8.50 (1 H, d), 8.38 (1 H, m), 8.17 (1 H, m), 7.80 (1 H, m), 7.75 (2 H, m), 6.95 (1 H, m), 6.32 (1 H, t), 3.78 (3 H, s), 3.71 (1 H, m), 3.11 (2 H, t), 1.92 (4 H, m), 1.62 (1 H, m), 1.25 (2 H, m), 1.10 (2 H, m). |
| 19.83 | 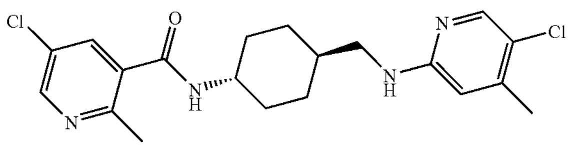 | Trans-5-chloro-N-(4-((5-chloro-4-methylpyridin-2-ylamino)methyl)cyclohexyl)-2-methyl-nicotinamide | 407.37 | δH (400 MHz, DMSO): 8.53 (1 H, d), 8.38 (1 H, d), 7.88 (1 H, s), 7.79 (1 H, d), 6.64 (1 H, t), 6.41 (1 H, s), 3.68 (1 H, m), 3.05 (2 H, t), 2.45 (3 H, s), 2.17 (3 H, s), 1.92 (2 H, m), 1.80 (2 H, m), 1.50 (1 H, m), 1.22 (2 H, m), 1.05 (2 H, m). |
| 19.84 | 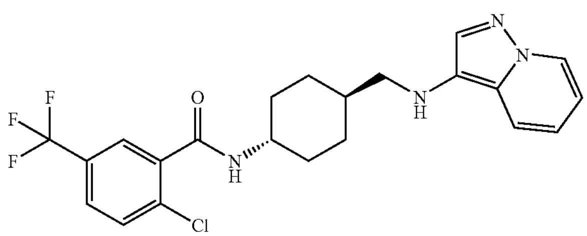 | Trans-2-chloro-N-(4-((pyrazolo[1,5-a]pyridin-3-ylamino)methyl)cyclohexyl)-5-(trifluoromethyl)benzamide | 451.4 | δH (400 MHz, DMSO) 8.49 (1 H, d), 8.34 (1 H, d), 7.81 (1 H, m), 7.75 (2 H, m), 7.62 (1 H, d), 7.53 (1 H, s), 6.86 (1 H, m), 6.63 (1 H, m), 4.71 (1 H, t), 3.72 (1 H, m), 2.91 (2 H, t), 1.94 (4 H, m), 1.53 (1 H, m), 1.25 (2 H, m), 1.09 (2 H, m). |
| 19.85 | 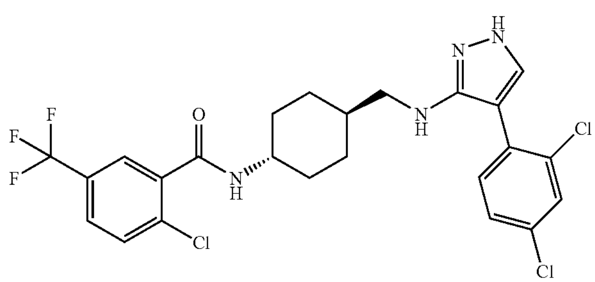 | Trans-2-chloro-N-(4-((4-(2,4-dichlorophenyl)-1H-pyrazol-3-ylamino)methyl)cyclohexyl)-5-(trifluoromethyl)benzamide | 545.1 | 1H NMR (400 MHz, MeOD). δ 8.6 (0.5 H, d, amide proton slow exchange in MeOD), 8.0 (1 H, s), 7.75 (1 H, d), 7.70 (2 H, d), 7.45 (1 H, s), 7.4 (2 H, t), 3.9 (1 H, m), (2 H, d), 2.1 (2 H, d), 1.9 (2 H, d), 1.6 (1 H, m), 1.35 (2 H, q), 1.1 (2 H, q). |
| 19.86 | 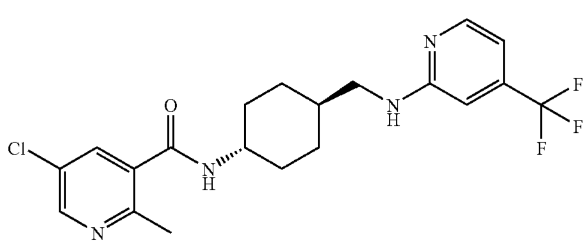 | Trans-5-chloro-2-methyl-N-(4-((4-(trifluoromethyl)pyridin-2-ylamino)methyl)cyclohexyl)nicotinamide | 427.4 | δH (400 MHz, DMSO); 8.53 (1 H, d), 8.40 (1 H, d), 8.18 (1 H, d), 7.80 6.77 (1 H, s), 6.69 (1 H, d), 3.70 (1 H, m), 3.18 (2 H, t), 2.48 (3 H, s), 1.92 (2 H, m), 1.81 (2 H, m), 1.51 (1 H, m), 1.24 (2 H, m), 1.08 (2 H, m). |

TABLE 9-continued

| Ex. | Structure | IUPAC Name | [M + H]+ | NMR Data |
|---|---|---|---|---|
| 19.87 | 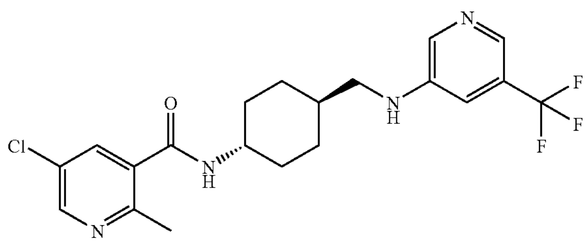 | Trans-5-chloro-2-methyl-N-(4-((5-(trifluoromethyl)pyridin-3-ylamino)methyl)cyclohexyl)nicotinamide | 427.4 | δH (400 MHz, DMSO); 8.54 (1 H, d), 8.40 (1 H, d), 8.22 (1 H, d), 8.02 (1 H, d), 7.80 (1 H, d), 7.11 (1 H, s), 6.45 (1 H, t), 3.70 (1 H, m), 2.98 (2 H, t), 2.48 (3 H, s), 1.91 (4 H, m), 1.51 (1 H, m), 1.28 (2 H, m), 1.10 (2 H, m). |
| 19.88 | 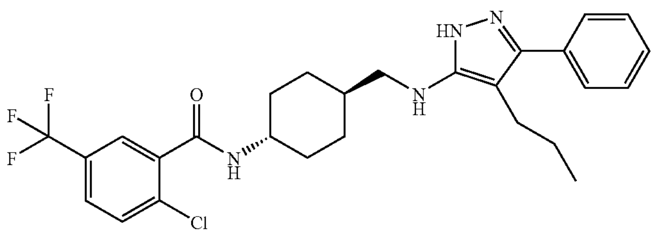 | Trans-2-chloro-N-(4-((3-phenyl-1H-propyl-1H-pyrazol-5-ylamino)methyl)cyclohexyl)-5-(trifluoromethyl)benzamide | 519.43 | δH (400 MHz, DMSO); 11.50 (1 H, s), 8.50 (1 H, d), 7.81 (1 H, m), 7.73 (2 H, m), 7.45 (4 H, m), 7.32 (1 H, m), 4.70 (1 H, m), 3.71 (1 H, m), 2.99 (2 H, t), 2.40 (2 H, t), 1.91 (4 H, m), 1.61 (1 H, m), 1.43 (2 H, m), 1.24 (2 H, m), 1.02 (2 H, m). |
| 19.89 | 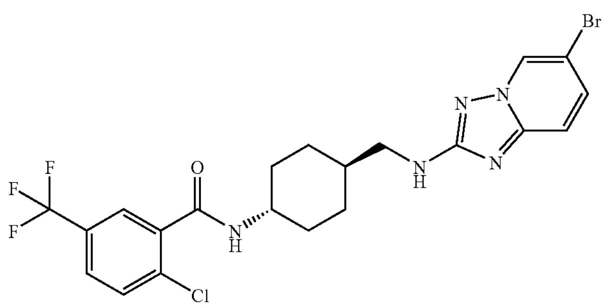 | Trans-N-(4-((6-bromo-[1,2,4]triazolo[1,5-a]pyridin-2-ylamino)methyl)cyclohexyl)-2-chloro-5-(trifluoromethyl)benzamide | 530.1 | 1H NMR (400 MHz, DMSO-d6). δ 9.0 (1 H, s), 8.5 (1 H, d), 7.8 (1 H, d), 7.75 (2 H, d), 7.6 (1 H, d), 7.4 (1 H, d), 6.8 (1 H, t), 3.7 (1 H, m), 3.1 (2 H, t), 2.0 (2 H, d), 1.9 (2 H, d), 1.6 (1 H, m), 1.2 (2 H, q), 1.0 (2 H, q). |
| 19.90 | 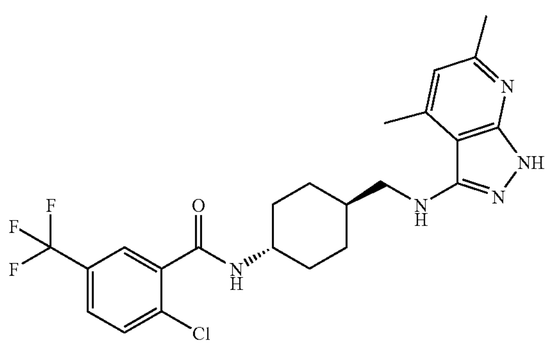 | Trans-2-chloro-N-(4-((4,6-dimethyl-1H-pyrazolo[3,4-b]pyridin-3-ylamino)methyl)cyclohexyl)-5-(trifluoromethyl)benzamide | 480.2 | NO NMR DATA |
| 19.91 | 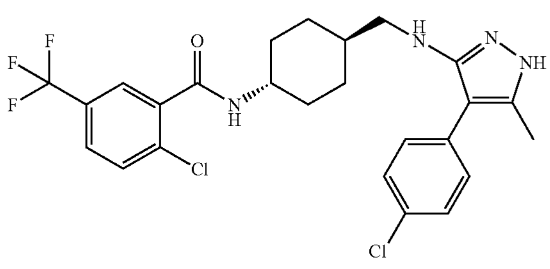 | Trans-2-chloro-N-(4-((4-(4-chlorophenyl)-5-methyl-1H-pyrazol-3-ylamino)methyl)cyclohexyl)-5-(trifluoromethyl)benzamide | 527.54 | δH (400 MHz, DMSO), 11.48 (1 H s), 8.47 (1H d), 7.82 (1H d), 7.76 (d, 7.72) 1 H (s, 7.43) 2 H (d, 7.34) 2 H (d, 4.61) 1 H (br s), 3.69 (1 H m), 2.94 (2 H t), 2.17 (3 H s), 1.94 (2 H m), 1.82 (2 H m), 1.59 (1 H m), 1.22 (2 H m), 0.99 (2 H m). |

TABLE 9-continued

| Ex. | Structure | IUPAC Name | [M + H]+ | NMR Data |
|---|---|---|---|---|
| 19.92 | 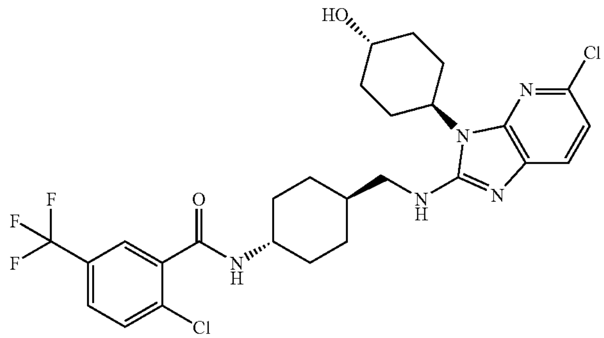 | Trans-2-chloro-N-(4-((5-chloro-3-(4-hydroxy-cyclohexyl)-3H-imidazo[4,5-b]pyridin-2-ylamino)methyl)cyclohexyl)-5-(trifluoromethyl)benzamide | 584.2 | δH (400 MHz, MeOD), 8.6 (~1 H, d, NH slow exchange), 7.7 (4 H, m), 7.3 (1 H, d), 4.4 (1 H, m), 3.9 (1 H, m), 3.8 (1 H, m), 3.4 (2 H, d), 2.7 (2 H, q), 2.2 (4 H, d), 2.0 (4 H, q), 1.8 (1 H, m), 1.5 (4 H, m), 1.3 (2 H, q). |
| 19.93 | 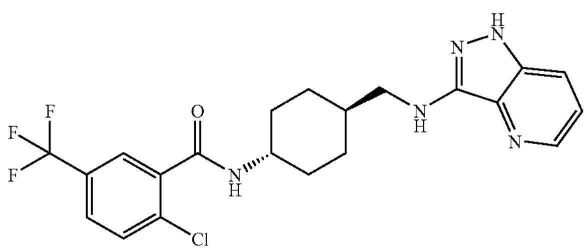 | Trans-N-(4-((1H-pyrazolo[4,3-b]pyridin-3-ylamino)methyl)cyclohexyl)-2-chloro-5-(trifluoromethyl)benzamide | 452.2 | δH (400 MHz, MeOD), 8.6 (~1 H, d, NH slow exchange), 8.4 (1 H, d), 7.9 (1 H, d), 7.7 (3 H, m), 7.5 (1 H, m), 3.9 (1 H, m), 2.1 (4 H, dd), 1.8 (1 H, m), 1.3 (4 H, m). |
| 19.94 | 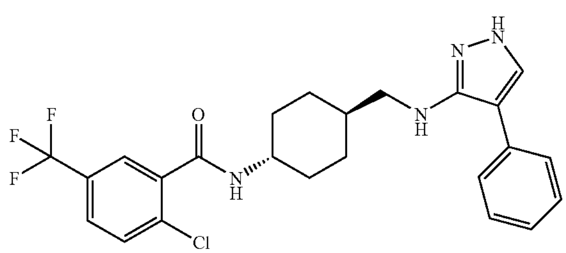 | Trans-2-chloro-N-(4-((4-phenyl-1H-pyrazol-3-ylamino)methyl)cyclohexyl)-5-(trifluoromethyl)benzamide | 477.2 | δH (400 MHz, MeOD). 8.6 (~1 H, d, NH slow exchange), 7.9 (1 H, s), 7.7 (3 H, m), 7.5 (4 H, m), 7.3 (1 H, m, 3.9 (1 H, m), 3.1 (2 H, d), 2.1 (2 H, d), 1.95 (2 H, d), 1.7 (1 H, m), 1.4 (2 H, q), 1.2 (2 H, q). |
| 19.95 | 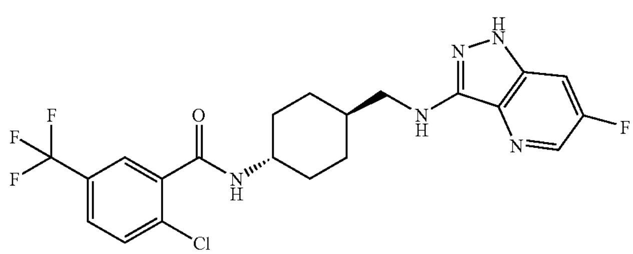 | Trans-2-chloro-N-(4-((6-fluoro-1H-pyrazolo[4,3-b]pyridin-3-ylamino)methyl)cyclohexyl)-5-(trifluoromethyl)benzamide | 470.2 | δH (400 MHz, MeOD). δ 8.6 (1 H, d, NH slow exchange), 8.2 (1 H, s), 7.7 (3 H, m), 7.5 (1 H, d), 3.9 (1 H, m), 3.3 (2 H, d), 2.1 (4 H, dd), 1.7 (1 H, m), 1.3 (4 H, m). |
| 19.96 | 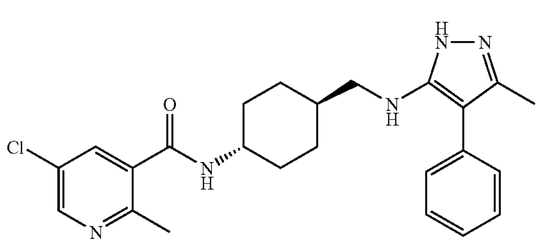 | Trans-2-chloro-2-methyl-N-(4-((3-methyl-4-phenyl-1H-pyrazol-5-ylamino)methyl)cyclohexyl)nicotinamide | 438.47 | δH (400 MHz, DMSO); 11.10 (1 H, br), 8.53 (1 H, d), 8.40 (1 H, d), 7.80 (1 H, d), 7.36 (4 H, m), 7.19 (1 H, m), 4.59 (1 H, t), 3.68 (1 H, m), 2.95 (2 H, t), 2.50 (3 H, s), 2.14 (3 H, s), 1.90 (2 H, m), 1.80 (2 H, m), 1.58 (1 H, m), 1.21 (2 H, m), 0.99 (2 H, m). |

TABLE 9-continued

| Ex. | Structure | IUPAC Name | [M + H]+ | NMR Data |
|---|---|---|---|---|
| 19.97 | 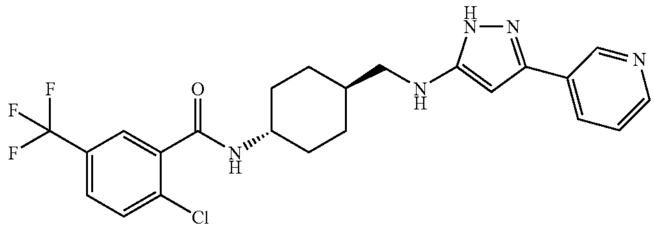 | Trans-2-chloro-N-(4-((3-(pyridin-3-yl)-1H-pyrazol-5-ylamino)methyl)cyclohexyl)-5-(trifluoromethyl)benzamide | 478.3 | δH (400 MHz, DMSO); 11.90 (1 H, br d), 8.90 (1 H, s), 8.48 (2 H, m), 8.03 (1 H, m), 7.81 (1 H, m), 7.74 (2 H, m), 7.40 (1 H, m), 3.70 (3 H, s), 2.91 (2 H, t), 1.95 (2 H, m), 1.88 (2 H, m), 1.51 (1 H, m), 1.23 (2 H, m), 1.08 (2 H, m). |
| 19.98 | 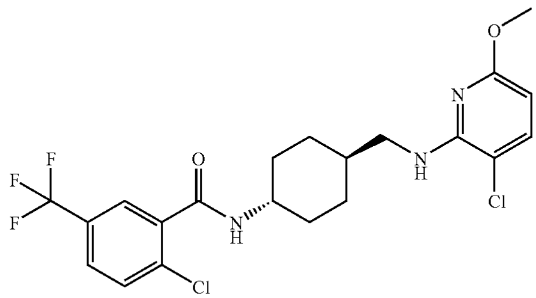 | Trans-2-Chloro-N-{4-[(3-chloro-6-methoxy-pyridin-2-ylamino)-methyl]-cyclohexyl}-5-trifluoromethyl-benzamide | 476.25 | δH (400 MHz, DMSO); 8.49 (1 H, d), 7.80 (1 H, m), 7.73 (2 H, m), 7.42 (1 H, d), 6.47 (1 H, t), 5.91 (1 H, d), 3.79 (3 H, s), 3.70 (1 H, m), 3.22 (2 H, t), 1.93 (2 H, m), 1.80 (2 H, m), 1.62 (1 H, m), 1.22 (2 H, m), 1.07 (2 H, m). |
| 19.99 | 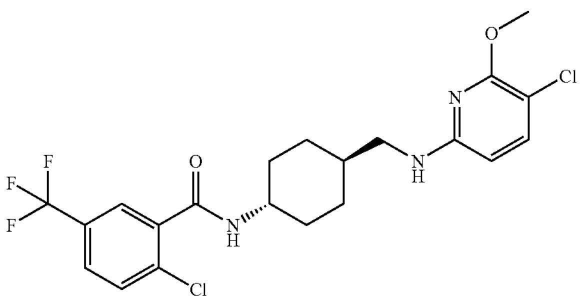 | Trans-2-Chloro-N-{4-[(5-chloro-6-methoxy-pyridin-2-ylamino)-methyl]-cyclohexyl}-5-trifluoromethyl-benzamide | 476.24 | δH (400 MHz, DMSO); 8.49 (1 H, d), 7.81 (1 H, m), 7.73 (2 H, m), 7.33 (1 H, d), 6.78 (1 H, t), 6.03 (1 H, d), 3.83 (3 H, s), 3.70 (1 H, m), 3.10 (2 H, t), 1.95 (2 H, m), 1.81 (2 H, m), 1.51 (1 H, m), 1.22 (2 H, m), 1.08 (2 H, m). |
| 19.100 | 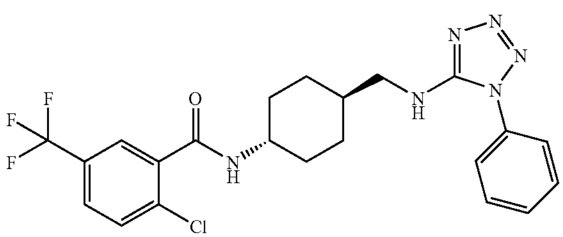 | Trans-2-Chloro-N-{4-[(1-phenyl-1H-tetrazol-5-ylamino)-methyl]-cyclohexyl}-5-trifluoromethyl-benzamide | 479.2 | δH (400 MHz, MeOD); 7.6 (8 H, m), 4.4 (1 H, m), 3.25 (2 H, d), 2.1 (2 H, d), 1.9 (2 H, d), 1.2 (1 H, m), 1.4 (2 H, q), 1.2 (2 H, q). (Tab; NMR product. Hardcopy; av43563). |
| 19.101 | 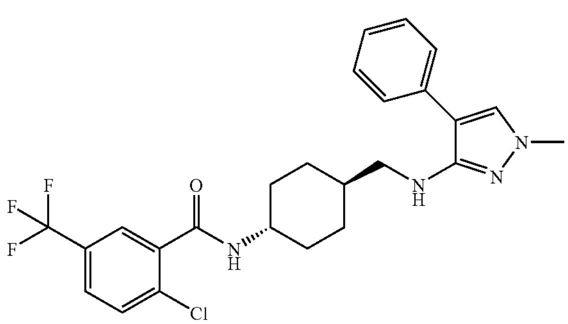 | Trans-2-Chloro-N-{4-[(1-methyl-4-phenyl-1H-pyrazol-3-ylamino)-methyl]-cyclohexyl}-5-trifluoromethyl-benzamide | 491.2 | δH (400 MHz, MeOD); 8.6 (~1 H, d, NH slow exchange), 7.9 (1 H, s), 7.7 (4 H, m), 7.4 (4 H, m), 7.3 (1 H, m, 3.8 (1 H, m), 3.1 (2 H, d), 2.1 (2 H, d), 1.95 (2 H, d), 1.7 (1 H, m), 1.4 (2 H, q), 1.2 (2 H, q). |

TABLE 9-continued

| Ex. | Structure | IUPAC Name | [M + H]+ | NMR Data |
|---|---|---|---|---|
| 19.102 | 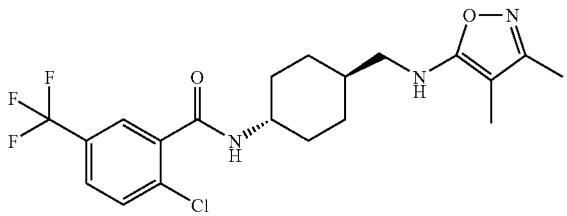 | Trans-2-Chloro-N-{4-[(3,4-dimethyl-isoxazol-5-ylamino)-methyl]-cyclohexyl}-5-trifluoromethyl-benzamide | 430.38 | δH (400 MHz, DMSO); 8.50 (1 H, d), 7.80 (1 H, m), 7.73 (2 H, m), 7.42 (1 H, d), 6.60 (1 H, t), 3.70 (1 H, m), 3.02 (2 H, t), 1.96 (3 H, s), 1.92 (2 H, m), 1.80 (2 H, m), 1.70 (3 H, s), 1.43 (1 H, m), 1.22 (2 H, m), 1.04 (2 H, m). |
| 19.103 | 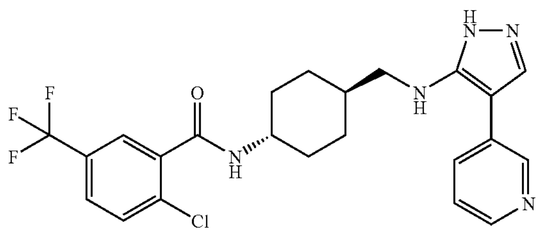 | Trans-2-Chloro-N-{4-[(4-pyridin-3-yl-2H-pyrazol-3-ylamino)-methyl]-cyclohexyl}-5-trifluoromethyl-benzamide | 478.31 | δH (400 MHz, DMSO); 11.90 (1 H, br d), 8.72 (1 H, s), 8.49 (1 H, d), 8.31 (1 H, m), 7.77 (5 H, m), 7.32 (1 H, m), 3.70 (3 H, s), 3.00 (2 H, t), 1.90 (4 H, m), 1.61 (1 H, m), 1.21 (2 H, m), 1.03 (2 H, m). |
| 19.104 | 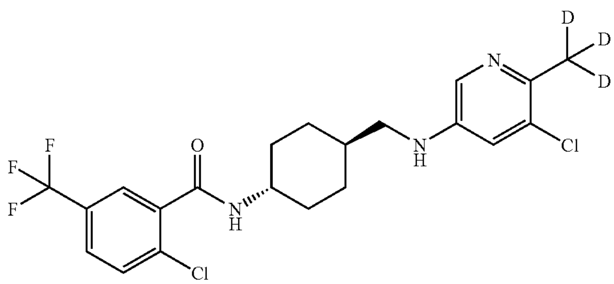 | Trans-2-Chloro-N-{4-[(5-chloro-6-d3-methyl-pyridin-3-ylamino)-methyl]-cyclohexyl}-5-trifluoromethyl-benzamide | 463.3 | δH (400 MHz, DMSO); 8.49 (1 H, d), 7.81 (2 H, m), 7.73 (2 H, m), 6.95 (1 H, d), 5.99 (1 H, t), 3.70 (1 H, m), 2.90 (2 H, t), 1.93 (2 H, m), 1.87 (2 H, m), 1.49 (1 H, m), 1.23 (2 H, m), 1.08 (2 H, m). |
| 19.105 | 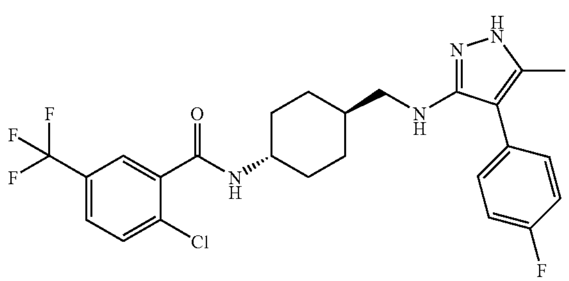 | Trans-2-Chloro-N-(4-{[[4-(4-fluoro-phenyl)-5-methyl-1H-pyrazol-3-ylamino]-methyl}-cyclohexyl)-5-trifluoromethyl-benzamide | 509.4 | δH (400 MHz, DMSO); 8.48 (1 H, d), 7.82 (1 H, m), 7.72 (2 H, m), 7.36 (2 H, m), 7.25 (2 H, m), 3.67 (1 H br), 2.65 (2 H, d), 2.17 (2 H, m), 1.80 (2 H, m), 1.56 (1 H, br), 1.24 (2 H, m), 1.02 (2 H, m). |
| 19.106 | 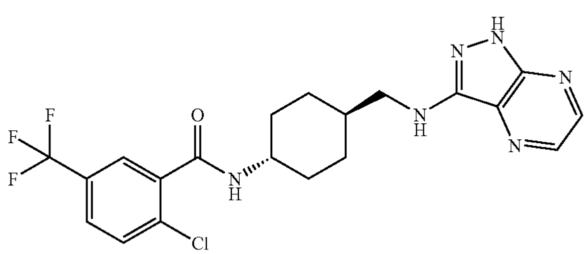 | Trans-2-Chloro-N-{4-[(1H-pyrazolo[3,4-b]pyrazin-3-ylamino)-methyl]-cyclohexyl}-5-trifluoromethyl-benzamide | 453.29 | δH (400 MHz, DMSO); 12.33 (1 H, s), 8.50 (1 H, d), 8.41 (1 H, s), 8.32 (1 H, s), 7.81 (1 H, m), 7.72 (2 H, m), 6.38 (1 H, t), 3.70 (1 H, m), 3.20 (2 H, t), 1.91 (4 H, m), 1.70 (1 H, m), 1.23 (2 H, m), 1.10 (2 H, m). |
| 19.107 | 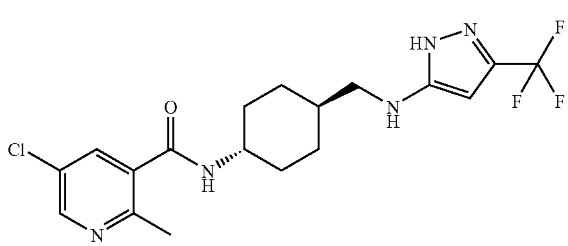 | Trans-5-Chloro-2-methyl-N-{4-[(5-trifluoromethyl-2H-pyrazol-3-ylamino)-methyl]-cyclohexyl}-nicotinamide | 416.4 | δH (400 MHz, DMSO); 1.0 (2 H, m), 1.2 (2 H, m), 1.45 (1 H, m), 1.82 (2 H, m), 1.95 (2 H, m), 2.45 (3 H, s), 2.88 (2 H, t), 3.68 (1 H, m), 5.58 (1 H, s), 5.95 (1 H, t), 7.79 (1 H, s), 8.38 (1 H, d), 8.55 (1 H, d), 12.2 (1 H, s). |

TABLE 9-continued

| Ex. | Structure | IUPAC Name | [M + H]+ | NMR Data |
|---|---|---|---|---|
| 19.108 | 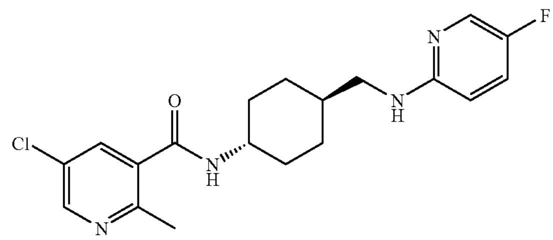 | Trans-5-Chloro-N-{4-[(5-fluoro-pyridin-2-ylamino)-methyl]-cyclohexyl}-2-methyl-nicotinamide | 377.32 | δH (400 MHz, DMSO); 8.52 (1 H, d), 8.39 (1 H, d), 7.90 (1 H, d), 7.79 (1 H, d), 7.31 (1 H, m), 6.52 (1 H, t), 6.49 (1 H, d of d), 3.69 (1 H, m), 3.08 (2 H, t), 2.49 (3 H, s), 1.91 (2 H, m), 1.82 (2 H, m), 1.49 (1 H, m), 1.23 (2 H, m), 1.03 (2 H, m). |
| 19.109 | 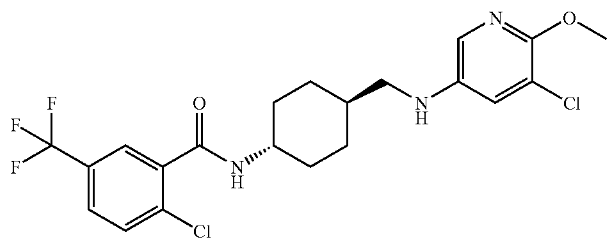 | Trans-2-Chloro-N-{4-[(5-chloro-6-methoxy-pyridin-3-ylamino)-methyl]-cyclohexyl}-5-trifluoromethyl-benzamide | 476.31 | δH (400 MHz, DMSO); 8.50 (1 H, d), 7.81 (1 H, m), 7.75 (2 H, m), 7.48 (1 H, d), 7.19 (1 H, d), 5.58 (1 H, t), 3.80 (3 H, s), 3.70 (1 H, m), 2.87 (2 H, t), 1.97 (2 H, m), 1.87 (2 H, m), 1.49 (1 H, m), 1.26 (2 H, m), 1.09 (2 H, m). |
| 19.110 | 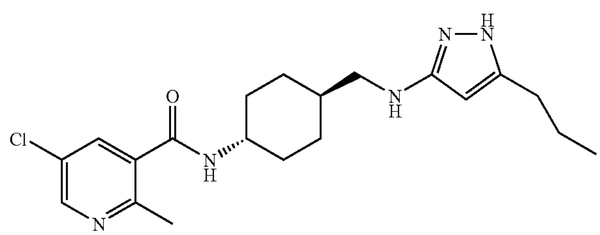 | Trans-2-Chloro-2 methyl-N-{4-[(5-propyl-1H-pyrazol-3-ylamino)-methyl]-cyclohexyl}-nicotinamide | 390.41 | δH (400 MHz, DMSO); 11.02 (1 H, s), 8.52 (1 H, d), 8.39 (1 H, d), 7.80 (1 H, d), 5.20 (1 H, s), 3.68 (1 H, m), 2.81 (2 H, t), 2.48 (3 H, s), 2.39 (2 H, m), 1.90 (2 H, m), 1.81 (2 H, m), 1.53 (2 H, m), 1.46 (1 H, m), 1.21 (2 H, m), 1.00 (2 H, m), 0.89 (3 H, t). |
| 19.111 | 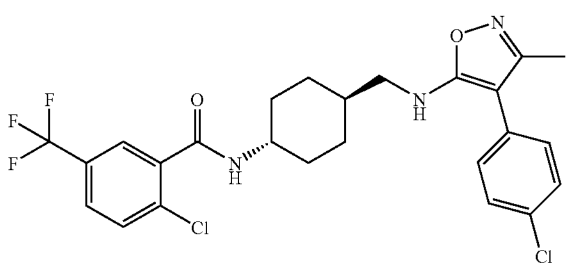 | Trans-2-Chloro-N-(4-{[(4-chloro-phenyl)-3-methyl-isoxazol-5-ylamino]-methyl}-cyclohexyl)-5-trifluoromethyl-benzamide | 526.2 | δH (400 MHz, MeOD); 8.60 (1 H, d), 7.72 (3 H, m), 7.43 (2 H, d), 7.31 (2 H, d), 3.84 (1 H, m), 3.16 (2 H, d), 2.15 (3 H, s), 2.09 (2 H, d), 1.88 (2 H, d), 1.60 (1 H, m), 1.34 (2 H, q), 1.13 (2 H, q) |
| 19.112 | 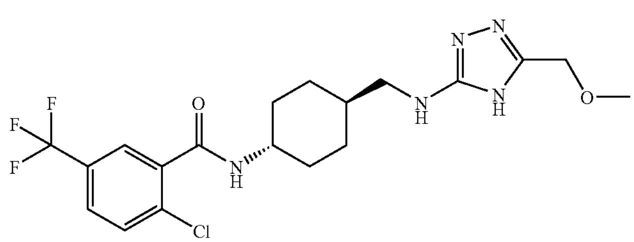 | Trans-2-Chloro-N-{4-[(5-methoxymethyl-4H-[1,2,4]triazol-3-ylamino)-methyl]-cyclohexyl}-5-trifluoromethyl-benzamide | 446.2 | δH (400 MHz, MeOD); 7.73 (3 H, m), 4.47 (3 H, s), 3.86 (1 H, m), 3.43 (2 H, s), 3.21 (2 H, d), 2.13 (2 H, d), 1.96 (2 H, d), 1.65 (1 H, m), 1.39 (2 H, q), 1.22 (2 H, q) |
| 19.113 | 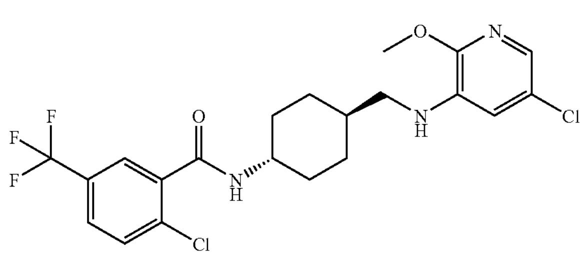 | Trans-2-Chloro-N-{4-[(5-chloro-2-methoxy-pyridin-3-ylamino)-methyl]-cyclohexyl}-5-trifluoromethyl-benzamide | 476.31 | δH (400 MHz, DMSO); 8.49 (1 H, d), 7.80 (1 H, m), 7.72 (2 H, m), 7.29 (1 H, d), 6.76 (1 H, d), 5.53 (1 H, t), 3.88 (3 H, s), 3.69 (1 H, m), 2.94 (2 H, t), 1.92 (2 H, m), 1.80 (2 H, m), 1.56 (1 H, m), 1.22 (2 H, m), 1.03 (2 H, m). |

TABLE 9-continued

| Ex. | Structure | IUPAC Name | [M + H]+ | NMR Data |
|---|---|---|---|---|
| 19.114 | 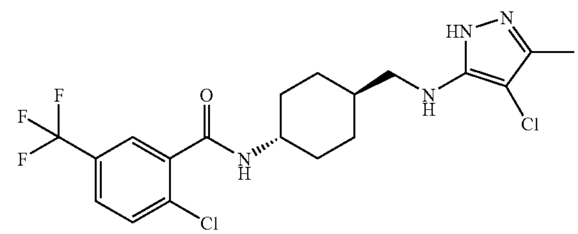 | Trans-2-Chloro-N-{4-[(4-chloro-5-methyl-2H-pyrazol-3-ylamino)-methyl]-cyclohexyl}-5-trifluoromethyl-benzamide | 449.2 | δH (400 MHz, MeOD); 7.72 (3 H, m), 3.85 (1 H, m), 3.07 (2 H, d), 2.16 (3 H, s), 2.09 (2 H, d), 1.96 (2 H, d), 1.63 (1 H, m), 1.35 (2 H, q), 1.16 (2 H, q) |
| 19.115 | 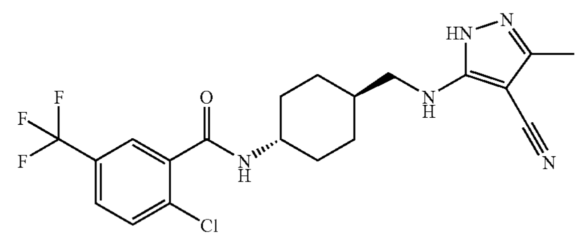 | Trans-2-Chloro-N-{4-[(4-cyano-5-methyl-2H-pyrazol-3-ylamino)-methyl]-cyclohexyl}-5-trifluoromethyl-benzamide | 440.2 | δH (400 MHz, MeOD); 8.61 (1 H, d), 7.72 (3 H, m), 3.86 (1 H, m), 3.10 (2 H, d), 2.26 (3 H, s), 2.10 (2 H, d), 1.96 (2 H, d), 1.63 (1 H, m), 1.36 (2 H, q), 1.15 (2 H, q) |
| 19.116 | 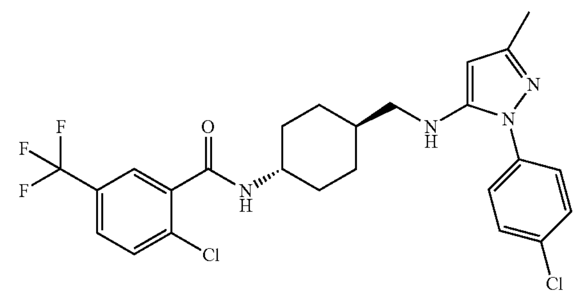 | Trans-2-Chloro-N-(4-{[2-(4-chloro-phenyl)-5-methyl-2H-pyrazol-3-ylamino]-methyl}-cyclohexyl)-5-trifluoromethyl-benzamide | 525.2 | δH (400 MHz, MeOD); 8.61 (1 H, d), 7.56-7.76 (7 H, m), 3.84 (1 H, m), 3.07 (2 H, d), 2.33 (3 H, s), 2.10 (2 H, d), 1.90 (2 H, d), 1.63 (1 H, m), 1.34 (2 H, q), 1.15 (2 H, q) |
| 19.117 | 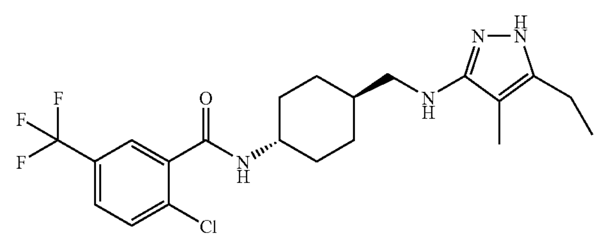 | Trans-2-Chloro-N-{4-[(5-ethyl-4-methyl-1H-pyrazol-3-ylamino)-methyl]-cyclohexyl}-5-trifluoromethyl-benzamide | 443.43 | δH (400 MHz, DMSO); 10.87 (1 H, s), 8.49 (1 H, d), 7.80 (1 H, m), 7.72 (2 H, m), 4.47 (1 H, m), 3.69 (1 H, m), 2.90 (2 H, t), 2.40 (2 H, q), 1.92 (2 H, m), 1.83 (2 H, m), 1.72 (3 H, s), 1.53 (1 H, m), 1.22 (2 H, m), 1.10 (3 H, t), 1.00 (2 H, m). |
| 19.118 | 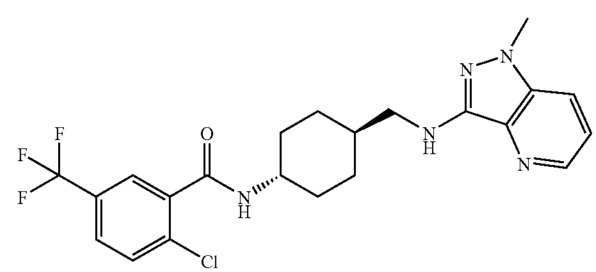 | Trans-2-Chloro-N-{4-[(1-methyl-1H-pyrazolo[4,3-b]pyridin-3-ylamino)-methyl]-cyclohexyl}-5-trifluoromethyl-benzamide | 466.2 | δH (400 MHz, MeOD); 8.3 (1 H, d), 7.8 (1 H, d), 7.7 (3 H, m), 7.4 (1 H, m), 3.9 (1 H, m), 3.8 (3 H, s), 3.3 (2 H, m), 2.1 (2 H, d), 2.05 (2 H, d), 1.75 (1 H, m), 1.4 (2 H, q), 1.25 (2 H, q). |
| 19.119 | 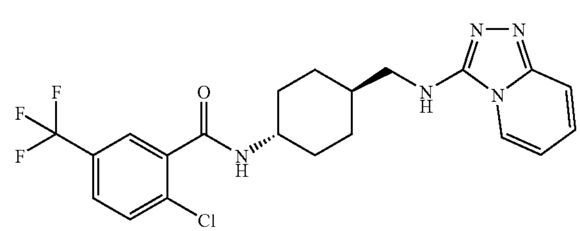 | Trans-2-Chloro-N-[4-([1,2,4]triazolo[4,3-a]pyridin-3-ylaminomethyl)-cyclohexyl]-5-trifluoromethyl-benzamide | 452.2 | δH (400 MHz, MeOD); 1.2 (2 H, m), 1.4 (2 H, m), 1.80 (1 H, m), 2.0 (2 H, m), 2.12 (2 H, m), 3.90 (1 H, m), 6.80 (1 H, t), 7.25 (1 H, dd), 7.45 (1 H, d), 7.6 (3 H, m), 8.05 (1 H, d). |

TABLE 9-continued

| Ex. | Structure | IUPAC Name | [M + H]+ | NMR Data |
|---|---|---|---|---|
| 19.120 | 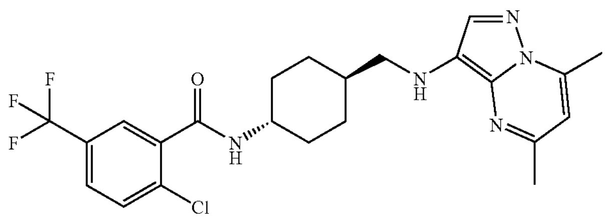 | Trans-2-Chloro-N-{4-[(5,7-dimethyl-pyrazolo[1,5-a]pyrimidin-3-ylamino)-methyl]-cyclohexyl}-5-trifluoromethyl-benzamide | 480.3 | δH (400 MHz, CDCl3) 1.3 (4 H, m), 1.80 (1 H, m), 2.12 (2 H, m), 2.22 (2 H, m), 2.55 (3 H, s), 2.70 (3 H, s), 3.25 (2 H, m), 4.0 (1 H, m), 6.02 (1 H, d), 6.50 (1 H, s), 7.50 (1 H, d), 7.62 (1 H, d), 7.88 (1 H, s), 8.0 (1 H, m) |
| 19.121 | 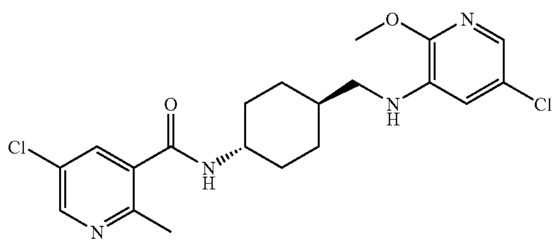 | Trans-5-Chloro-N-{4-[(Trans-5-Chloro-2-methoxy-pyridin-3-ylamino)-methyl]-cyclohexyl}-2-methyl-nicotinamide | 423.4 | δH (d6-DMSO, 400 MHz); 8.53 (1 H, d), 8.40 (1 H, d), 7.80 (1 H, m), 7.30 (1 H, d), 6.77 (1 H, d), 5.55 (1 H, t), 3.89 (3 H, s), 3.69 (1 H, m), 2.95 (2 H, t), 2.49 (3 H, s), 1.91 (2 H, m), 1.80 (2 H, m), 1.57 (1 H, m), 1.25 (2 H, m), 1.06 (2 H, m). |
| 19.122 | 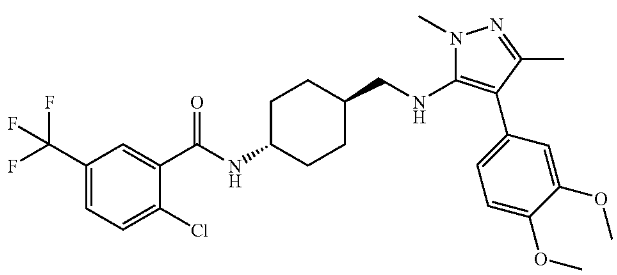 | Trans-2-Chloro-N-(4-{[4-(3,4-dimethoxy-phenyl)-2,5-dimethyl-2H-pyrazol-3-ylamino]-methyl}-cyclohexyl)-5-trifluoromethyl-benzamide | 565.3 | δH (CDCl3, 400 MHz) 7.89 (1 H, s), 7.62 (1 H, d), 7.54 (1 H, d), 6.93 (1 H, d), 6.80 (2 H, d), 5.99 (1 H, d), 3.93 (3 H, s), 3.90 (3 H, s), 3.73 (3 H, s), 3.30 (1 H, br), 2.79 (2 H, d), 2.20 (3 H, s), 2.12 (2 H, d), 1.73 (2 H, d), 1.33 (1 H, m), 1.15 (2 H, q), 1.05 (2 H, q) |
| 19.123 | 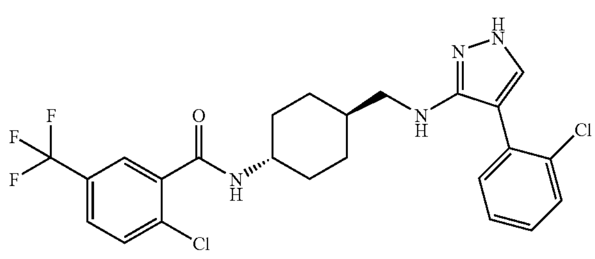 | Trans-2-Chloro-N-(4-{[4-(Trans-2-Chloro-phenyl)-1H-pyrazol-3-ylamino]-methyl}-cyclohexyl)-5-trifluoromethyl-benzamide | 511.29 | δH (400 MHz, MeOD). 7.8 (3 H, m), 7.5 (3 H, m), 7.4 (2 H, m), 3.8 (1 H, m), 3.0 (2 H, d), 2.1 (2 H, d), 1.9 (2 H, d), 1.6 (1 H, m), 1.3 (2 H, m), 1.1 (2 H, m). |
| 19.124 | 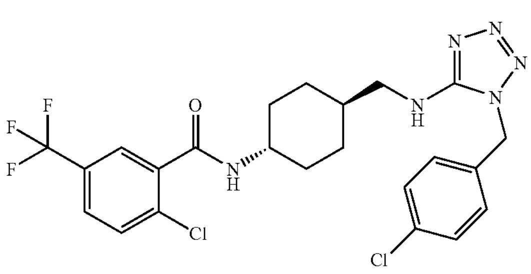 | Trans-2-Chloro-N-(4-{[1-(4-chloro-benzyl-1H-tetrazol-5-ylamino]-methyl}-cyclohexyl)-5-trifluoromethyl-benzamide | 527.4 | δH (400 MHz, DMSO-d6). 8.5 (1 H, d), 7.8 (1 H, d), 7.7 (2 H, d), δ7.4 (2 H, d), 7.2 (2 H, m), 7.0 (1 H, m), 5.4 (2 H, m + DCM), 3.7 (1 H, m), 3.1 (2 H, t), 1.9 (2 H, d), 1.7 (2 H, d), 1.5 (1 H, m), 1.2 (2 H, m), 1.0 (2 H, m). |

TABLE 9-continued

| Ex. | Structure | IUPAC Name | [M + H]+ | NMR Data |
|---|---|---|---|---|
| 19.125 | 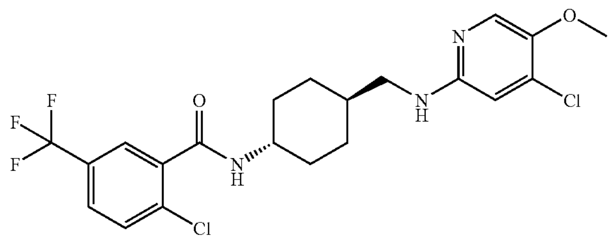 | Trans-2-Chloro-N-{4-[(4-chloro-5-methoxy-pyridin-2-ylamino)-methyl]-cyclohexyl}-5-trifluoromethyl-benzamide | 476.3 | δH (d6-DMSO, 400 MHz); 8.49 (1 H, d), 7.81 (2 H, m), 7.74 (2 H, m), 6.68 (1 H, t), 6.17 (1 H, s), 3.81 (3 H, s), 3.69 (1 H, m), 3.09 (2 H, t), 1.92 (2 H, m), 1.80 (2 H, m), 1.50 (1 H, m), 1.23 (2 H, m), 1.03 (2 H, m). |

The compounds of the following tabulated Examples (Table 10) are prepared according from trans-(4-amino-cyclohexylmethyl)phenylamine (Ex. 5.1 step 5) according to the following general procedure:

In each reaction: carboxylic acid (0.147 mmol, 1.47 eq), trans-(4-amino-cyclohexylmethyl)phenylamine (Step 5) (0.1 mmol, 1 eq, 21 mg), HATU (0.147 mmol, 1.47 eq, 56 mg), PS-DIEA 3.4 mmol/g loading (0.2 mmol, 2 eq, 60 mg) are used.

A stock solution of trans-(4-amino-cyclohexylmethyl)phenylamine is made up in DMF (1.428 g in 13.6 mL). A stock solution of HATU is made up in DMF (3.808 g in 20.4 mL DMF). Ca. 60 mg PS-DIEA is added to each pre-weighed carboxylic acid. 200 ul Trans-(4-amino-cyclohexylmethyl)phenylamine solution is pipetted into each vial, followed by 300 µl of HATU solution. Vials are sealed and shaken at RT for 16 hr. Crude reactions are purified by loading onto a 1 g SCX-2 cartridge pre-wetted with MeOH, crude is washed with 3 mL MeOH before compounds are eluted with 2×2 mL 2M ammonia in MeOH. Compounds are analyzed and evaporated in vacuo. Crude mixtures are purified further by prep HPLC (Waters Sunfire C18 5 micron column, 19×50 mm, mobile phases 0.1% TFA in water, 0.1% TFA in acetonitrile, 6 minute gradient dependant on retention time from analytics). Successful purifications are turned into free-based amines by passing prep fraction through a SCX-2 cartridge pre-wetted with MeOH, washed with 5 mL MeOH, and eluted with 2×2 mL 3.5M ammonia in MeOH. Compounds are evaporated in vacuo.

TABLE 10

| Ex. | Structure | IUPAC Name | [M + H]+ | NMR Data |
|---|---|---|---|---|
| 20.1 | 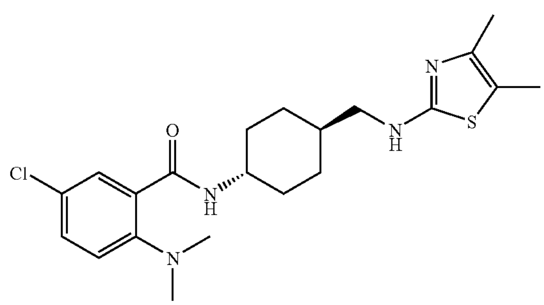 | 5-chloro-2-(dimethylamino)-N-(4-((4,5-dimethylthiazol-2-ylamino)methyl)cyclohexyl)benzamide | 421.47 | δH (400 MHz, DMSO); 8.75 (d 1H), 7.47 (d 1H), 7.43 (dd 1H), 7.24 (t 1H), 7.13 (d 1H), 3.74 (m 1H), 3.03 (t 2H), 2.78 (s 6 H), 2.17 (s 3H), 2.04 (s 3H), 1.96 (m 2H), 1.86 (m 2H), 1.49 (m 1H), 1.30(m 2H), 1.20 (m 2H) |
| 20.2 | 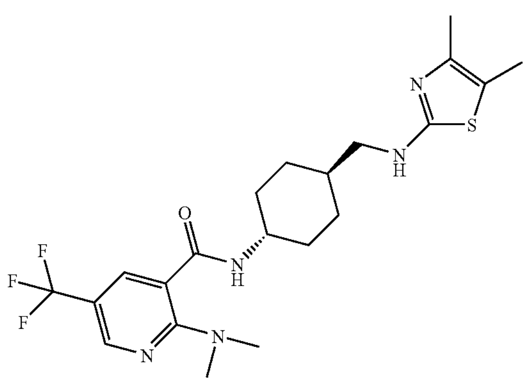 | 2-(dimethylamino)-N-(4-((4,5-dimethylthiazol-2-ylamino)methyl)cyclohexyl)-5-(trifluoromethyl)nicotinamide | 456.42 | δH (400 MHz, DMSO); 8.42 (2H, m), 7.64 (1H, s), 7.18 (1H, t), 3.63 (1H, m), 3.04 (6 H, s), 3.01 (2H, t), 2.10 (3H, s), 1.98 (3H, s), 1.90 (2H, m), 1.80 (2H, m), 1.51 (1H, m), 1.23 (2H, m), 1.02 (2H, m) |

TABLE 10-continued

| Ex. | Structure | IUPAC Name | [M + H]+ | NMR Data |
|---|---|---|---|---|
| 20.3 | 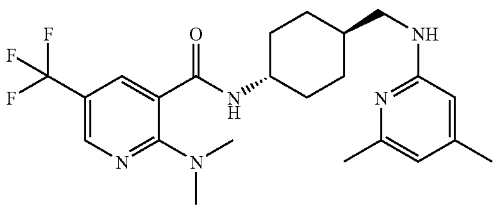 | 2-(dimethylamino)-N-{-4-((4,6-dimethylpyridin-2-ylamino)methyl)cyclohexyl}-5-(trifluoromethyl)nicotinamide | 450.58 | δH (400 MHz, DMSO); 8.42 (2H, m), 7.64 (1H, s), 6.30 (1H, br s), 6.20 (1H, s), 6.12 (1H, br s), 3.63 (1H, m), 3.05 (2H, m), 2.20 (3H, s), 2.11 93H, s), 1.92 (2H, m), 1.82 (2H, m), 1.48 (1H, m), 1.23 (2H, m), 1.05 (2H, m) |

The compounds of the following tabulated Examples (Table 11), or tautomers thereof, are prepared by a similar method to that of Example 6 by replacing 1-(1H-pyrazol-3-yl)imidazolidin-2-one with the appropriate intermediate.

TABLE 11

| Ex. | Structure | IUPAC Name | [M + H]+ | NMR Data |
|---|---|---|---|---|
| 21.1 | 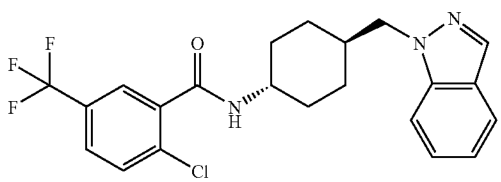 | N-(4-((1H-indazol-1-yl)methyl)cyclohexyl)-2-chloro-5-(trifluoromethyl)benzamide | 436.26 | δH (400 MHz, DMSO) 8.48 (1H, d), 8.07 (1H, s), 7.30 (5 H, m), 7.39 (1H, t), 7.11 (1H, t), 4.29 (2H, d), 3.69 (1H, m), 1.88 (3H, m), 1.55 (2H, m), 1.20 (4H, m) |
| 21.2 | 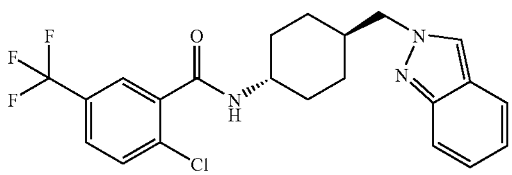 | 2-Chloro-N-(4-indazol-2-ylmethyl-cyclohexyl)-5-trifluorometnyl-benzamide | 436.29 | δH (400 MHz, DMSO) 8.50 (1H, d), 8.34 (1H, s), 7.80 (1H, m) 7.71 (3H, m), 7.60 (1H, m), 7.21 (1H, t), 7.02 (1H, t), 4.30 (2H, d), 3.70 (1H, m), 1.93 (3H, m), 1.58 (2H, m), 1.20 (4H, m). |
| 21.3 | 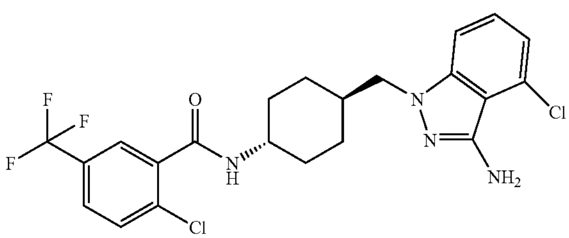 | N-[4-(3-Amino-4-chloro-indazol-1-yl methyl)-cyclohexyl]-2-chloro-5-trifluoromethyl-benzamide | 485.2 | δH (400 MHz, DMSO) 8.48 (1H, d), 7.80 (1H, m), 7.73 (2H, m), 7.38 (1H, d), 7.21 (1H, m), 6.90 (1H, d), 5.27 (2H, br s), 3.98 (2H, d), 3.67 (1H, m), 1.89 (2H, m(, 1.81 (1H, m), 1.56 (2H, m), 1.16 (4H, m). |
| 21.4 | 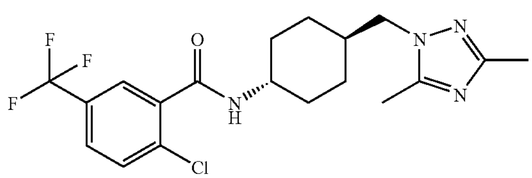 | 2-Chloro-N-[4-(3,5-dimethyl-[1,2,4]triazol-1-ylmethyl)-cyclohexyl]-5-trifluoromethyl-benzamide | 415.4 | δH (400 Mhz, DMSO) 8.50 (1H, d), 7.81 (1H, m), 7.74 (2H, m), 3.84 (2H, d), 3.69 (1H, m), 2.32 (3H, s), 2.16 (3H, s), 1.91 (2H, m), 1.74 (1H, m), 1.59 (2H, m), 1.18 (4H, m). |
| 21.5 | 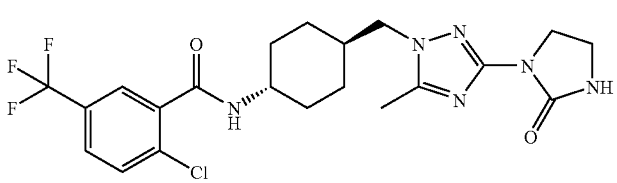 | 2-Chloro-N-{4-[5-methyl-3-(2-oxo-imidazolidin-1-yl)-pyrazol-1-ylmethyl]-cyclohexyl}-5-trifluoromethyl-benzamide | 484.26 | δH (400 MHz, DMSO) 8.50 (1H, d), 7.81 (1H, m), 7.73 (2H, m), 6.75 (1H, s), 6.22 (1H, s), 3.73 (4H, m), 3.70 (1H, m), 2.20 (3H, s), 1.90 (2H, d), 1.75 (1H, m), 1.58 (2H, m), 1.15 (4H, m). |

TABLE 11-continued

| Ex. | Structure | IUPAC Name | [M + H]+ | NMR Data |
|---|---|---|---|---|
| 21.6 | 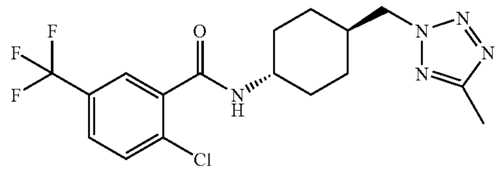 | 2-Chloro-N-[4-(5-methyl-tetrazol-2-ylmethyl)-cyclohexyl]-5-trifluoromethyl-benzamide | 402.1 | δH (400 MHz, MeOD) 7.7 (3H, m), 4.5 (2H, d), 3.9 (1H, m), 2.5 (3H, s), 2.1 (3H, m), 1.7 (2H, d), 1.3 (4H, m). |
| 21.7 | 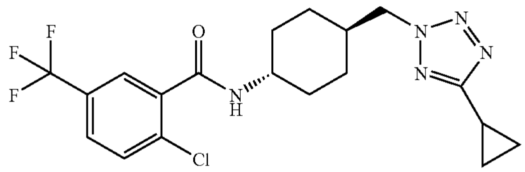 | 2-Chloro-N-[4-(5-cyclopropyl-tetrazol-2-ylmethyl)-cyclohexyl]-5-trifluoromethyl-benzamide | 428.2 | δH (400 MHz, MeOD) 8.6 (~0.5 H, d, NH slow exchange), 7.7 (3H, m), 4.5 (2H, d), 3.85 (1H, m), 2.2 (1H, m), 2.0 (3H, m), 1.7 (2H, d), 1.3 (4H, m), 1.1 (2H, m), 1.0 (2H, m). |
| 21.8 | 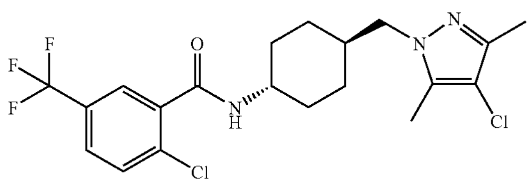 | 2-Chloro-N-[4-(4-chloro-3,5-dimethyl-pyrazol-1-ylmethyl)-cyclohexyl]-5-trifluoromethyl-benzamide | 448.33 | δH (400 MHz, DMSO) 8.50 (1H, d), 7.80 (1H, m), 7.72 (2H, m), 3.82 (2H, d), 3.70 (1H, m), 2.20 (3H, s), 2.10 (3H, s), 1.91 (2H, m), 1.72 (1H, m), 1.58 (2H, m), 1.18 (4H, m). |
| 21.9 | 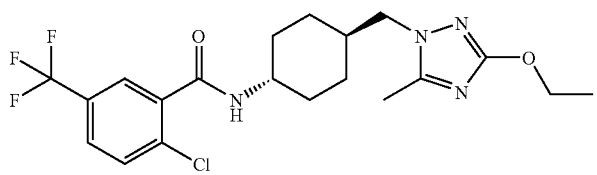 | 2-Chloro-N-[4-(3-ethoxy-5-methyl-[1,2,4]triazol-1-ylmethyl)-cyclohexyl]-5-trifluoromethyl-benzamide | 445.4 | δH (400 MHz, DMSO) 8.50 (1H, d), 7.81 (1H, m), 7.74 (2H, m), 4.15 (2H, q), 3.78 (2H, d), 3.69 (1H, m), 2.30 (3H, s), 1.92 (2H, m), 1.74 (1H, m), 1.60 (2H, m), 1.28 (3H, t), 1.18 (4H, m). |
| 21.10 | 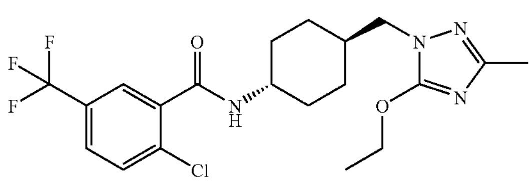 | 2-Chloro-N-[4-(5-ethoxy-3-methyl-[1,2,4]triazol-1-ylmethyl)-cyclohexyl]-5-trifluoromethyl-benzamide | 445.4 | δH (400 MHz, DMSO) 8.49 (1H, d), 7.81 (1H, m), 7.74 (2H, m), 4.36 (2H, q), 3.69 (1H, m), 3.64 (2H, d), 2.12 (3H, s), 1.91 (2H, m), 1.69 (1H, m), 1.60 (2H, m), 1.33 (3H, t), 1.22 (2H, m), 1.08 (2H, m). |
| 21.11 | 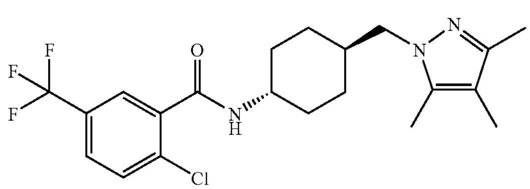 | 2-Chloro-5-trifluoromethyl-N-[4-(3,4,5-trimethyl-pyrazol-1-ylmethyl)-cyclohexyl]-benzamide | 428.44 | δH (400 MHZ, DMSO) 8.48 (1H, d), 7.80 (1H, m), 7.72 (2H, m), 3.75 (2H, d), 3.69 (1H, m), 2.10 (3H, s), 2.01 (3H, s), 1.90 (2H, m), 1.82 (3H, s), 1.70 (1H, m), 1.58 (2H, m), 1.20 (2H, m), 1.10 (2H, m). |

TABLE 11-continued

| Ex. | Structure | IUPAC Name | [M + H]+ | NMR Data |
|---|---|---|---|---|
| 21.12 | 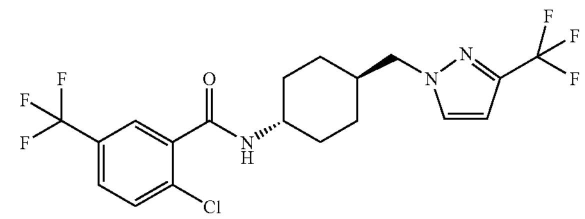 | 2-Chloro-5-trifluoromethyl-N-[4-(3-trifluoromethyl-pyrazol-1-ylmethyl)-cyclohexyl]-benzamide | 454.35 | δH (400 MHZ, DMSO) 8.50 (1H, d), 7.98 (1H, s), 7.80 (1H, m), 7.72 (2H, m), 6.70 (1H, d), 4.09 (2H, d), 3.68 (1H, m), 1.91 (2H, m), 1.80 (1H, m), 1.55 (2H, m), 1.22 (2H, m), 1.11 (2H, m). |

The compounds of the following tabulated Examples (Table 12), or tautomers thereof, are prepared by a similar method to that of Example 12 using the appropriate acid chloride.

TABLE 12

| Ex. | Structure | IUPAC Name | [M + H]+ | NMR Data |
|---|---|---|---|---|
| 22.1 | 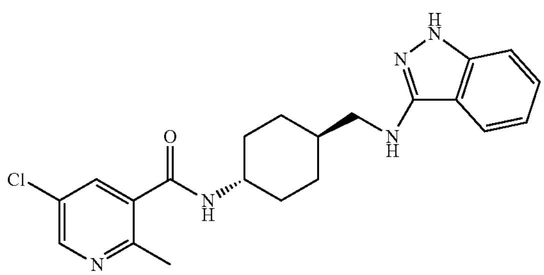 | 5-Chloro-N-{4-[(1H-indazol-3-ylamino)-methyl]-cyclohexyl}-2-methyl-nicotinamide | 398.35 | δH (400 MHz, DMSO) 11.30 (1H, s), 8.52 (1H, d), 8.40 (1H, d), 8.22 (1H, d), 7.80 (1H, d), 7.72 (1H, d), 7.21 (2H, m), 6.89 (1H, m), 5.93 (1H, t), 3.72 (1H, m), 3.11 (2H, t), 2.48 (3H, s), 1.92 (4H, m), 1.68 (1H, m), 1.26 (2H, m), 1.10 (2H, m). |
| 22.2 | 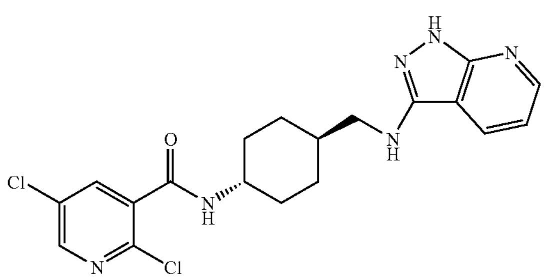 | 5-Chloro-2-methyl-N-{4-[(1H-pyrazolo[3,4-b]pyridin-3-ylamino)-methyl]-cyclohexyl}-nicotinamide | 399.38 | δH (400 MHz, DMSO) 11.90 (1H, s), 8.53 (1H, d), 8.40 (1H, d), 8.32 (1H, d), 8.18 (1H, d), 7.80 (1H, d), 6.93 (1H, m), 6.21 (1H, t), 3.72 (1H, m), 3.12 (2H, t), 2.48 (3H, s), 1.91 (4H, m), 1.67 (1H, m), 1.25 (2H, m), 1.11 (2H, m). |
| 22.3 | 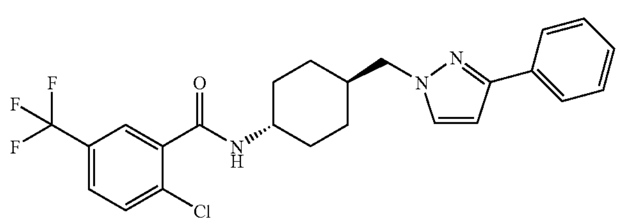 | 2-Chloro-N-[4-(3-phenyl-pyrazol-1-ylmethyl)-cyclohexyl]-5-trifluoromethyl-benzamide | 462.34 | δH (400 MHz, DMSO) 8.50 (1H, d), 7.78 (6 H, m), 7.40 (2H, t), 7.29 (1H, t), 4.01 (2H, d), 3.70 (1H, m), 1.93 (2H, m), 1.72 (1H, m), 1.62 (2H, m), 1.20 (4H, m). |
| 22.4 | 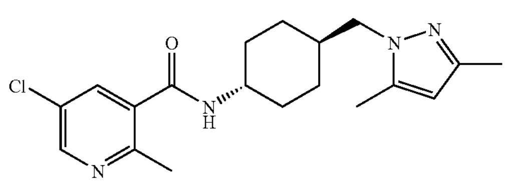 | 5-Chloro-N-[4-(3,5-dimethyl-pyrazol-1-ylmethyl)-cyclohexyl]-2-methyl-nicotinamide | 361.3 | δH (400 MHz, CDCl3) 8.50 (1H, d), 7.62 (1H, d), 5.82 (1H, s), 5.70 (1H, s), 3.94 (1H, m), 3.86 (2H, d), 2.62 (3H, s), 2.27 (3H, s), 2.25 (3H, s), 2.14 (2H, m), 2.02 (1H, m), 1.76 (2H, m), 1.23 (4H, m). |

TABLE 12-continued

| Ex. | Structure | IUPAC Name | [M + H]+ | NMR Data |
|---|---|---|---|---|
| 22.5 | 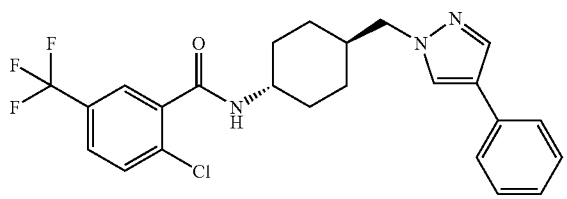 | 2-Chloro-N-[4-(4-phenyl-pyrazol-1-ylmethyl)-cyclohexyl]-5-trifluoromethyl-benzamide | 462.33 | δH (400 MHz, DMSO) 8.50 (1H, d), 8.17 (1H, s), 7.90 (1H, s), 7.80 (1H, m), 7.72 (2H, m), 7.58 (2H, d), 7.35 (2H, t), 7.19 (1H, t), 4.00 (2H, d), 3.70 (1H, m), 1.91 (2H, m), 1.81 (1H, m), 1.62 (2H, m), 1.23 (2H, m), 1.12 (2H, m). |
| 22.6 | 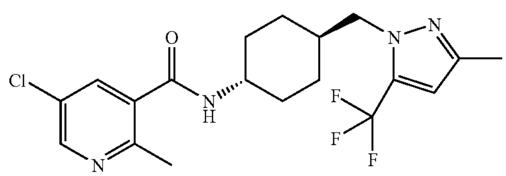 | Trans-5-Chloro-2-methyl-N-[4-(3-methyl-5-trifluoromethyl-pyrazol-1-ylmethyl)-cyclohexyl]-nicotinamide | 415.4 | δH (400 MHz, CDCl3) 8.48 (1H, d), 7.62 (1H, d), 6.36 (1H, s), 5.64 (1H, br d), 3.98 (2H, d), 3.93 (1H, m), 2.61 (3H, s), 2.28 (3H, s), 2.13 (2H, m), 2.02 (1H, m), 1.72 (2H, m), 1.22 (4H, m). |
| 22.7 | 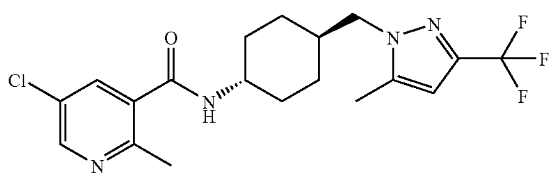 | Trans-5-Chloro-2-methyl-N-[4-(5-methyl-3-trifluoromethyl-pyrazol-1-ylmethyl)-cyclohexyl]-nicotinamide | 415.4 | δH (400 MHz, CDCl3) 8.48 (1H, d), 7.63 (1H, d), 6.26 (1H, s), 5.67 (1H, br), 3.93 (1H, m), 3.91 (2H, d), 2.62 (3H, s), 2.30 (3H, s), 2.13 (2H, m), 1.99 (1H, m), 1.72 (2H, m), 1.22 (4H, m). |
| 22.8 | 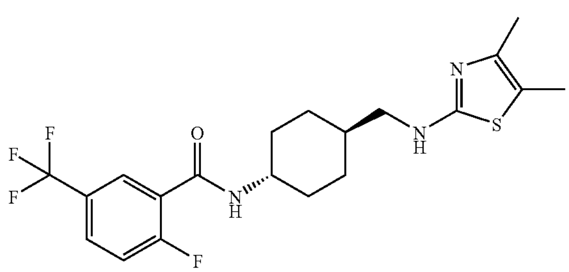 | Trans-N-{4-[(4,5-Dimethyl-thiazol-2-ylamino)-methyl]-cyclohexyl}-2-fluoro-5-trifluoromethyl-benzamide | 430.4 | No Data |
| 22.9 | 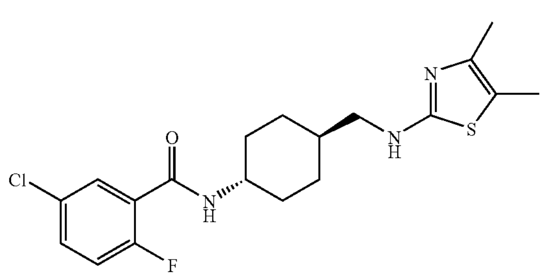 | Trans-5-Chloro-N-{4-[(4,5-Dimethyl-thiazol-2-ylamino)-methyl]-cyclohexyl}-2-fluoro-benzamide | 393.3 | No Data |

TABLE 13

CRF-1 $IC_{50}$ data and $^1H$ NMR data for representative compounds of the invention

| Example No. | $IC_{50}$ (micro molar) | NMR data (400 MHz, DMSO unless stated otherwise) |
|---|---|---|
| 1 | 0.038 | 8.48 (1H, d), 7.85-7.73 (4H, m), 7.18 (1H, d), 6.40 (1H, dd), 5.82 (1H, t), 3.70 (1H, m), 3.20 (2H, t), 2.04 (3H, s), 1.93 (2H, m), 1.83 (2H, m), 1.61 (1H, m), 1.21 (2H, m), 1.05 (2H, m). |
| 1.13 | 0.019 | 8.50 (1H, d), 7.81 (1H, d), 7.73 (2H, m), 7.64 (1H, m), 6.98 (1H, m), 6.80 (1H, m), 5.11 (1H, t), 3.70 (1H, m), 2.93 (2H, m), 2.30 (3H, s), 1.90 (4H, m), 1.60 (1H, m), 1.25 (2H, m), 1.06 (2H, m). |
| 1.18 | 0.031 | 8.57 (1H, s), 8.52 (1H, d), 8.09 (1H, s), 7.18 (1H, t), 3.65 (1H, m), 3.00 (2H, t), 2.10 (3H, s), 1.98 (3H, s), 1.92 (2H, m), 1.79 (2H, m), 1.50 (1H, m), 1.20 (2H, m), 1.02 (2H, m). |
| 1.33 | 6.425 | 12.29 (1H, s), 8.53 (1H, d), 8.48 (1H, d), 7.78 (4H, m) 7.35 (1H, m), 6.50 (1H, d), 3.71 (1H, m), 3.19 (2H, m), 1.96 (2H, m), 1.83 (2H, m), 1.52 (1H, m), 1.23 (2H, m), 1.08 (2H, m). |
| 1.34 | 1.241 | 11.75 (1H, s), 8.51 (1H, d), 8.10 (1H, s), 7.92 (1H, br), 7.80 (1H, m), 7.81 (1H, m), 7.74 (2H, m), 7.05 (1H, br s), 4.20 (2H, m), 3.71 (1H, m), 3.27 (2H, m), 2.70 (6H, d), 1.92 (4H, m), 1.59 (1H, m), 1.28 (2H, m), 1.12 (2H, m). |
| 1.35a^ | 0.199 | 11.81 (1H, br s), 8.42 (1H, d), 7.80 (1H, m), 7.71 (4H, m), 7.20 (1H, m), 5.78 (1H, br s), 5.27 (1H, br), 3.96 (1H, m), 2.91 (2H, m), 2.12 (1H, m), 1.94 (1H, m), 1.74 (1H, m), 1.61 (1H, m), 1.45 (1H, m), 1.24 (3H, m), 0.92 (3H, d). |
| 2.5 | 0.036 | 8.49 (1H, d), 7.81 (1H, d), 7.75 (2H, d), 7.30 (1H, t), 6.61 (1H, s), 3.69 (1H, m), 3.02 (2H, t), 2.19 (3H, s), 1.92 (2H, m), 1.79 (2H, m), 1.51 (1H, m), 1.22 (2H, m), 1.03 (2H, m). |
| 2.6 | 0.215 | 8.48 (1H, d), 7.80 (1H, m), 7.72 (2H, m), 6.20 (1H, t), 6.14 (1H, s), 6.04 (1H, s), 3.69 (1H, m), 3.03 (2H, m), 2.19 (3H, s), 2.09 (3H, s), 1.92 (2H, m), 1.81 (2H, m), 1.48 (1H, m), 1.22 (2H, m), 1.03 (2H, m). |
| 2.8 | 0.066 | 8.48 (1H, d), 7.80 (1H, m), 7.72 (2H, m), 7.18 (1H, d of d), 6.39 (1H, d), 6.23 (1H, t), 3.69 (1H, m), 3.05 (2H, m), 2.06 (3H, m), 1.91 (2H, m), 1.81 (2H, m), 1.49 (1H, m), 1.22 (2H, m), 1.02 (2H, m). |
| 2.9 | 0.039 | 8.47 (1H, d), 7.80 (1H, m), 7.72 (2H, m), 7.20 (1H, t), 6.30 (2H, m), 6.22 (1H, d), 3.68 (1H, m), 3.05 (2H, m), 2.20 (3H, s), 1.92 (2H, m), 1.82 (2H, m), 1.49 (1H, m), 1.23 (2H, m), 1.04 (2H, m). |
| 2.26 | 0.063 | 8.48 (1H, d), 7.82-7.73 (3H, m), 6.91 (1H, t), 6.13-6.04 (3H, m), 5.56 (1H, t), 4.48 (1H, m), 3.71 (1H, m), 2.84 (2H, t), 1.95-1.86 (4H, m), 1.49 (1H, m), 1.39-1.21 (8H, m), 1.20-1.02 (2H, m). |
| 2.35 | 0.346 | 8.47 (1H, d), 7.87-7.73 (5H, m), 7.56-7.48 (3H, m), 6.99 (1H, s), 3.75 (2H, s), 3.66 (1H, m), 2.39 (2H, d), 2.19 (1H, br s), 1.93-1.83 (4H, m), 1.37 (1H, m), 1.28-1.20 (2H, m), 1.04-0.95 (2H, m). |
| 3 | 0.060 | 8.47 (1H, d), 7.81 (1H, d), 7.72 (2H, d), 7.18 (1H, t), 3.68 (1H, m), 2.99 (2H, t), 2.09 (3H, s), 1.98 (3H, s), 1.92 (2H, m), 1.79 (2H, m), 1.50 (1H, m), 1.22 (2H, m), 1.03 (2H, m). |
| 4.11 | 0.061 | 11.40-12.00 (1H, very broad d), 7.70 (5H, m) 7.20 (2H, m), 5.77 (1H, br), 5.00-5.60 (1H, very broad d), 3.70 (1H, m), 2.90 (2H, m), 1.90 (4H, m), 1.82 (2H, m), 1.49 (1H, m), 1.22 (2H, m), 1.03 (2H, m). |
| 4.15 | 0.061 | 11.05 (1H, br s), 8.47 (1H, d), 7.82-7.73 (3H, m), 5.20 (1H, br s), 4.89 (1H, br s), 3.70 (1H, m), 2.83 (2H, m), 2.39 (2H, t), 1.92 (2H, m), 1.83 (2H, m), 1.59-1.46 (3H, m), 1.22 (2H, m), 1.00 (2H, m), 0.89 (3H, t),. |
| 4.16 | 0.063 | 11.06 (1H, br s), 8.48 (1H, d), 7.82-7.73 (3H, m), 5.20 (1H, br s), 4.86 (1H, br s), 3.69 (1H, m), 2.83 (2H, t), 2.76 (1H, m), 1.92 (2H, m), 1.83 (2H, m), 1.47 (1H, m), 1.24 (2H, m), 1.15 (6H, d), 1.01 (2H, m). |
| 4.21 | 0.076 | 8.50 (1H, d), 7.96 (1H, d), 7.81 (1H, m), 7.72 (3H, m), 7.03 (1H, m), 6.88 (1H, m), 5.89 (1H, t), 3.71 (1H, m), 2.90 (2H, t), 1.90 (4H, m), 1.50 (1H, m), 1.25 (2H, m), 1.10 (2H, m). |
| 4.33 | 0.050 | 8.50 (1H, d), 7.80 (1H, m), 7.72 (2H, d), 7.05 (2H, t), 6.55 (2H, d), 6.48 (1H, t), 5.58 (1H, m), 3.70 (1H, m), 2.86 (2H, t), 1.90 (4H, m), 1.50 (1H, m), 1.23 (2H, m), 1.07 (2H, m). |
| 5.14 | 0.066 | 8.54 (1H, d), 8.38 (1H, d), 7.79 (1H, d), 7.18 (1H, t), 3.70 (1H, m), 3.00 (2H, t), 2.47 (3H, s), 2.10 (3H, s), 1.97 (3H, s), 1.90 (2H, m), 1.80 (2H, m), 1.50 (1H, m), 1.22 (2H, m), 1.03 (2H, m). |
| 6 | 0.090 | 8.49 (1H, d), 7.81 (1H, m), 7.74 (2H, d), 7.30 (1H, t), 6.80 (1H, s), 6.39 (1H, s), 3.83 (2H, d), 3.79 (2H, t), 3.69 (1H, m), 3.40 (2H, t), 1.91 (2H, m), 1.73 (1H, m), 1.58 (2H, m), 1.21 (2H, m), 1.09 (2H, m). |
| 7 | 0.022 | See Example 7.0 |
| 8 | 0.047 | 11.08 (1H, br s), 8.47 (1H, d), 7.82-7.73 (3H, m), 5.08 (1H, br s), 4.95 (1H, br s), 3.69 (1H, m), 2.80 (2H, m), 1.92 (2H, m), 1.82 (2H, m), 1.72 (1H, m), 1.45 (1H, m), 1.23 (2H, m), 1.02 (2H, m), 0.81 (2H, m), 0.58 (2H, m). |
| 9 | 0.050 | 8.50 (1H, d), 7.81 (1H, m), 7.75 (2H, m), 7.04 (1H, q), 6.38 (1H, d), 6.30 (1H, m), 6.24 (1H, m), 5.98 (1H, m), 3.71 (1H, m), 2.86 (2H, t), 1.91 (4H, m), 1.50 (1H, m), 1.25 (2H, m), 1.08 (2H, m). |
| 10 | 0.041 | 8.50 (1H, d), 7.78 (4H, m), 7.59 (1H, s), 6.70 (1H, s), 5.79 (1H, t), 3.70 (1H, m), 2.89 (2H, m), 2.18 (3H, s), 1.91 (4H, m), 1.51 (1H, m), 1.28 (2H, m), 1.09 (2H, m). |
| 11 | 0.174 | 12.99-12.68 (1H 2 × br s), 8.40 (1H, d), 7.77 (2H, br m), 7.54-7.29 (6H, m), 6.56 (1H, s), 3.63 (1H, m), 3.52 (2H, m), 2.15 (3H, s), 2.13 (3H, s), 1.88 (4H, m), 1.46 (1H, m), 1.30-1.21 (2H, m), 0.95-0.87 (2H, m). |
| 12 | 0.137 | 8.34 (1H, d), 7.88 (1H, m), 7.80 (1H, m), 7.58 (1H, m), 7.49 (1H, m), 7.05 (2H, m), 6.55 (2H, d), 6.48 (1H, t), 5.58 (1H, t), 3.75 (1H, m), 2.86 (2H, m), 1.89 (4H, m), 1.52 (1H, m), 1.33 (2H, m), 1.07 (2H, m). |
| 13 | 0.070 | 8.78 (1H, dd), 8.68 (1H, d), 8.51 (1H, d), 8.17 (2H, m), 7.89 (1H, d), 7.71 (1H, m), 7.50 (1H, m), 7.38 (1H, dd), 7.19 (1H, d), 6.54 (1H, d), 6.42 (1H, br t), 3.82 (1H, m), 3.10 (2H, t), 1.95 (4H, m), 1.76 (1H, m), 1.37 (2H, m), 1.15 (2H, m). |
| 14 | 3.225 | 11.70 (1H, br), 8.50 (1H, d), 7.80 (1H, d), 7.75 (1H, d), 7.70 (2H, t), 7.20 (2H, t), 5.75 (1H, br), 5.30 (1H, br), 4.00 (1H, br), 2.95 (2H, t), 1.70 (3H, m), 1.55 (4H, m), 1.45 (2H, m). |
| 14.1 | 2.205 | 8.51 (1H, d), 8.01 (1H, d), 7.94 (1H, s), 7.82 (1H, dd), 7.76 (2H, m), 7.64 (1H, d), 6.33 (1H, br t), 4.02 (1H, br m), 3.09 (2H, br t), 2.34 (3H, s), 1.76 (3H, m), 1.59 (4H, m), 1.47 (2H, m). |
| 15$^a$ | 0.108 | 7.81 (1H, d), 6.94 (1H, m), 6.90 (2H, m), 6.80 (1H, m), 6.72 (1H, m), 6.66 (2H, m), 3.05 (1H, m), 2.82 (1H, m), 1.35 (1H, m), 1.10 (2H, m), 0.91 (1H, m), 0.60 (4H, m), 0.49 (3H, d). |
| 16$^b$ | 0.051 | 8.47 (1H, d), 7.82 (1H, d), 7.73 (2H, m), 7.07 (2H, t), 6.56 (2H, d), 6.49 (1H, t), 5.55 (1H, m), 3.93 (1H, m), 2.86 (2H, m), 2.23 (2H, m), 1.88 (1H, m), 1.78 (1H, m), 1.70 (1H, m), 1.59 (2H, m), 1.31 (1H, m), 1.11 (1H, m), 0.92 (3H, d). |
| 17 | 0.070 | 8.53 (1H, d), 8.39 (1H, d), 7.78 (1H, d), 3.83 (2H, d), 3.67 (1H, m), 2.47 (3H, s), 2.20 (3H, s), 2.09 (3H, s), 1.89 (2H, m), 1.73 (1H, m), 1.57 (2H, m), 1.16 (4H, m) |

TABLE 13-continued

CRF-1 $IC_{50}$ data and $^1H$ NMR data for representative compounds of the invention

| Example No. | $IC_{50}$ (micro molar) | NMR data (400 MHz, DMSO unless stated otherwise) |
|---|---|---|
| 18 | 0.577 | 8.54 (1H, d), 8.39 (1H, d), 7.79 (1H, d), 3.74 (2H, d), 3.67 (1H, m), 2.47 (3H, s), 2.10 (3H, s), 2.02 (3H, s), 1.88 (2H, m), 1.83 (3H, m), 1.70 (1H, m), 1.57 (2H, m), 1.14 (4H, m). |
| 19.1 | 0.026 | See Table 9 |
| 19.2 | 0.023 | See Table 9 |
| 19.26 | 0.013 | See Table 9 |
| 19.49 | 0.031 | See Table 9 |
| 19.53 | 0.028 | See Table 9 |
| 19.54 | 0.062 | See Table 9 |
| 19.55 | 0.143 | See Table 9 |
| 19.56 | 0.084 | See Table 9 |
| 19.57 | 0.088 | See Table 9 |
| 19.59 | 0.087 | See Table 9 |
| 19.62 | 0.09 | See Table 9 |
| 19.63 | 0.017 | See Table 9 |
| 19.65 | 0.053 | See Table 9 |
| 19.66 | 0.062 | See Table 9 |
| 19.68 | 0.032 | See Table 9 |
| 19.69 | 0.022 | See Table 9 |
| 19.70 | 0.029 | See Table 9 |
| 19.71 | 0.14 | See Table 9 |
| 19.73 | 0.019 | See Table 9 |
| 19.74 | 0.054 | See Table 9 |
| 19.75 | 0.054 | See Table 9 |
| 19.76 | 0.078 | See Table 9 |
| 19.79 | 0.037 | See Table 9 |
| 19.80 | 0.015 | See Table 9 |
| 19.83 | 0.038 | See Table 9 |
| 19.91 | 0.057 | See Table 9 |
| 19.93 | 0.069 | See Table 9 |
| 19.94 | 0.059 | See Table 9 |
| 19.98 | 0.052 | See Table 9 |
| 19.100 | 0.029 | See Table 9 |
| 19.101 | 0.069 | See Table 9 |
| 19.102 | 0.076 | See Table 9 |
| 19.103 | 0.037 | See Table 9 |
| 19.104 | 0.08 | See Table 9 |
| 19.107 | 0.118 | See Table 9 |
| 19.108 | 0.072 | See Table 9 |
| 19.110 | 0.097 | See Table 9 |
| 19.113 | 0.153 | See Table 9 |
| 19.114 | 0.034 | See Table 9 |
| 19.116 | 0.059 | See Table 9 |
| 19.117 | 0.043 | See Table 9 |
| 21.1 | 0.114 | See Table 11 |
| 21.2 | 0.338 | See Table 11 |
| 21.4 | 0.299 | See Table 11 |
| 21.5 | 0.157 | See Table 11 |
| 21.8 | 0.113 | See Table 11 |
| 21.11 | 0.14 | See Table 11 |
| 22.3 | 0.234 | See Table 12 |
| 22.4 | 0.35 | See Table 12 |
| 22.7 | 0.187 | See Table 12 |

*Data shown is for most active isomer (retention time = 10.48 min from SFC separation) in which the 1,4 substituents are equatorial and methyl substituent is axial..
$^a$$IC_{50}$ for racemate; NMR spectrum recorded in d4-MeOH.
$^b$$IC_{50}$ for racemate; the two separated enantiomers have a trans-1,4-diequatorial arrangement with the 2-methyl substituent axial; $IC_{50}$ of each enantiomer is identical to racemate.

The invention claimed is:

1. A compound of Formula XI;

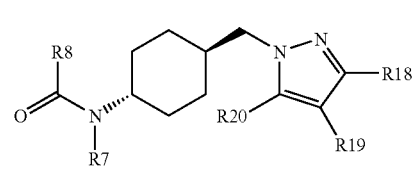

in which

R$^7$ is hydrogen or alkyl C1 to 6;

R$^8$ is phenyl or a heteroaryl, each of which may be optionally substituted by one or more substituents selected from the group alkyl C1 to 6, haloalkyl C1 to 6, halogen, alkoxy C1 to 6, nitrile and dialkyl amino C1 to 6 or two adjacent substituents may together form a saturated or unsaturated carbocyclic or heterocyclic ring;

R$^{18}$, R$^{19}$ and R$^{20}$, which may be the same or different, are each hydrogen, alkyl C1 to 10, alkoxy C1 to 10, halogen, haloalkyl C1 to 10, halogenated alkoxy, morpholinyl, or imidazolinyl, or phenyl or phenoxy that is optionally substituted by one or more substituents selected from the group carboxy, alkyl C1 to 6, halogen and hydroxy; or R$^{18}$ and R$^{19}$ or R$^{19}$ and R$^{20}$ may together form a saturated or unsaturated carbocyclic or heterocyclic ring;

in free form or in salt form.

2. A pharmaceutical composition comprising a compound of claim 1 in free form or in pharmaceutically acceptable salt form, in association with a pharmaceutically acceptable adjuvant, diluent or carrier.

3. A pharmaceutical composition comprising a compound of claim 1 in free form or in pharmaceutically acceptable salt form, in combination with another therapeutically active ingredient.

4. The compound of claim 1, wherein R$^8$ is disubstituted phenyl or disubstituted 3-pyridyl.

5. The compound of claim 1, wherein R$^8$ is 2,5-disubstituted phenyl or 2,5-disubstituted 3-pyridyl.

6. The compound of claim 1, which is selected from the group consisting of:

Trans-2-Chloro-N-[4-(3-methyl-5-trifluoromethyl-pyrazol-1-ylmethyl)-cyclohexyl]-5-trifluoromethyl-benzamide;

Trans-2-Chloro-N-[4-(5-methyl-3-trifluoromethyl-pyrazol-1-ylmethyl)-cyclohexyl]-5-trifluoromethyl-benzamide;

Trans-2-Chloro-N-[4-(3,5-di-(d3)-methyl-pyrazol-1-ylmethyl)-cyclohexyl]-5-trifluoromethyl-benzamide;

Trans-2-Chloro-N-[4-(5-methyl-pyrazol-1-ylmethyl)-cyclohexyl]-5-trifluoromethyl-benzamide;

Trans-2-Chloro-N-[4-(3-methyl-pyrazol-1-ylmethyl)-cyclohexyl]-5-trifluoromethyl-benzamide;

Trans-2-Chloro-N-{4-[5-(4-methoxy-phenyl)-pyrazol-1-ylmethyl]-cyclohexyl}-5-trifluoromethyl-benzamide;

Trans-2-Chloro-N-{4-[3-(4-methoxy-phenyl)-pyrazol-1-ylmethyl]-cyclohexyl}-5-trifluoromethyl-benzamide;

N-(4-((1H-indazol-1-yl)methyl)cyclohexyl)-2-chloro-5-(trifluoromethyl)benzamide 2-Chloro-N-(4-indazol-2-ylmethyl-cyclohexyl)-5-trifluoromethyl-benzamide;

N-[4-(3-Amino-4-chloro-indazol-1-ylmethyl)-cyclohexyl]-2-chloro-5-trifluoromethyl-Benzamide;

2-Chloro-N-{4-[5-methyl-3-(2-oxo-imidazolidin-1-yl)-pyrazol-1-ylmethyl]-cyclohexyl}-5-trifluoromethyl-benzamide;

2-Chloro-N-[4-(4-chloro-3,5-dimethyl-pyrazol-1-ylm-ethyl)-cyclohexyl]-5-trifluoromethyl-benzamide;
2-Chloro-5-trifluoromethyl-N-[4-(3,4,5-trimethyl-pyrazol-1-ylmethyl)-cyclohexyl]-benzamide;
2-Chloro-5-trifluoromethyl-N-[4-(3-trifluoromethyl-pyrazol-1-ylmethyl)-cyclohexyl]-benzamide;
5-Chloro-N-{4-[(1H-indazol-3-ylamino)-methyl]-cyclohexyl}-2-methyl-nicotin amide;
2-Chloro-N-[4-(3-phenyl-pyrazol-1-ylmethyl)-cyclohexyl]-5-trifluoromethyl-benzamide;
5-Chloro-N-[4-(3,5-dimethyl-pyrazol-1-ylmethyl)-cyclohexyl]-2-methyl-nicotinamide;
2-Chloro-N-[4-(4-phenyl-pyrazol-1-ylmethyl)-cyclohexyl]-5-trifluoromethyl-benzamide;
Trans-5-Chloro-2-methyl-N-[4-(3-methyl-5-trifluoromethyl-pyrazol-1-ylmethyl)-cyclohexyl]-nicotinamide;
Trans-5-Chloro-2-methyl-N-[4-(5-methyl-3-trifluoromethyl-pyrazol-1-ylmethyl)-cyclohexyl]-nicotinamide;
Trans-5-Chloro-N-[4-(4-chloro-3,5-dimethyl-pyrazol-1-ylmethyl)-cyclohexyl]-2-methyl-nicotinamide;
Trans-5-Chloro-2-methyl-N-[4-(3,4,5-trimethyl-pyrazol-1-ylmethyl)-cyclohexyl]-nicotinamide;
Trans-5-Chloro-2-methyl-N-[4-(3-methyl-5-trifluoromethyl-pyrazol-1-ylmethyl)-cyclohexyl]-nicotinamide; and
Trans-5-Chloro-2-methyl-N-[4-(5-methyl-3-trifluoromethyl-pyrazol-1-ylmethyl)-cyclohexyl]-nicotinamide;
or a pharmaceutically acceptable salt thereof.

7. The compound of claim 1, which is selected from the group consisting of:

2-Chloro-5-trifluoromethyl-N-[4-(3,4,5-trimethyl-pyrazol-1-ylmethyl)-cyclohexyl]-benzamide;
2-Chloro-5-trifluoromethyl-N-[4-(3-trifluoromethyl-pyrazol-1-ylmethyl)-cyclohexyl]-benzamide;
2-Chloro-N-[4-(3-phenyl-pyrazol-1-ylmethyl)-cyclohexyl]-5-trifluoromethyl-benzamide;
5-Chloro-N-[4-(3,5-dimethyl-pyrazol-1-ylmethyl)-cyclohexyl]-2-methyl-nicotinamide;
2-Chloro-N-[4-(4-phenyl-pyrazol-1-ylmethyl)-cyclohexyl]-5-trifluoromethyl-benzamide;
Trans-5-Chloro-2-methyl-N-[4-(3-methyl-5-trifluoromethyl-pyrazol-1-ylmethyl)-cyclohexyl]-nicotinamide; and
Trans-5-Chloro-2-methyl-N-[4-(5-methyl-3-trifluoromethyl-pyrazol-1-ylmethyl)-cyclohexyl]-nicotinamide;
and the pharmaceutically acceptable salts thereof.

8. A pharmaceutical composition comprising a compound of claim 6 in free form or in pharmaceutically acceptable salt form, in combination with another therapeutically active ingredient.

9. A pharmaceutical composition comprising a compound of claim 7 in free form or in pharmaceutically acceptable salt form, in combination with another therapeutically active ingredient.

10. The compound of claim 1, wherein $R^7$ is H.

11. The compound of claim 4, wherein the substituents for $R^8$ are selected from halo, haloalkyl 1-10, alkyl C1-6, alkoxy C1-6, trifluoroalkoxy C1-6 and dimethylamino.

* * * * *